(12) United States Patent
Wang et al.

(10) Patent No.: US 10,975,093 B2
(45) Date of Patent: Apr. 13, 2021

(54) FUSED 1,4-DIAZEPINES AS BET PROTEIN DEGRADERS

(71) Applicant: THE REGENTS OF THE UNIVERSITY OF MICHIGAN, Ann Arbor, MI (US)

(72) Inventors: Shaomeng Wang, Superior Township, MI (US); Yang Hu, Ann Arbor, MI (US); Chong Qin, Ann Arbor, MI (US); Fuming Xu, Ypsilanti, MI (US); Jiantao Hu, Ann Arbor, MI (US); Weiguo Xiang, Ypsilanti, MI (US); Bing Zhou, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/332,544

(22) PCT Filed: Sep. 13, 2017

(86) PCT No.: PCT/US2017/051286
§ 371 (c)(1),
(2) Date: Mar. 12, 2019

(87) PCT Pub. No.: WO2018/052949
PCT Pub. Date: Mar. 22, 2018

(65) Prior Publication Data
US 2019/0263827 A1 Aug. 29, 2019

Related U.S. Application Data

(60) Provisional application No. 62/393,923, filed on Sep. 13, 2016.

(51) Int. Cl.
  C07D 495/14  (2006.01)
  C07K 5/06    (2006.01)
  A61K 45/06   (2006.01)
  A61P 35/00   (2006.01)

(52) U.S. Cl.
CPC .......... *C07D 495/14* (2013.01); *A61K 45/06* (2013.01); *A61P 35/00* (2018.01); *C07K 5/06* (2013.01)

(58) Field of Classification Search
CPC ........ A61K 45/06; C07D 495/14; C07K 5/06; A61P 35/00
See application file for complete search history.

(56) References Cited

U.S. PATENT DOCUMENTS

| | | | |
|---|---|---|---|
| 8,044,042 B2 | 10/2011 | Adachi et al. | |
| 8,114,995 B2 | 2/2012 | Hansen et al. | |
| 8,476,260 B2 | 7/2013 | Miyoshi et al. | |
| 8,557,984 B2 | 10/2013 | Bouillot et al. | |
| 8,580,957 B2 | 11/2013 | Demont et al. | |
| 2006/0003995 A1* | 1/2006 | Cook | C07D 243/24 514/221 |
| 2010/0286127 A1 | 11/2010 | Miyoshi et al. | |
| 2012/0059002 A1 | 3/2012 | Hansen et al. | |
| 2012/0157428 A1 | 6/2012 | Albrecht et al. | |
| 2012/0202799 A1 | 8/2012 | Crowe et al. | |
| 2012/0208800 A1 | 8/2012 | Chung et al. | |
| 2012/0252781 A1 | 10/2012 | Bailey et al. | |
| 2012/0273468 A1 | 11/2012 | Arjakine et al. | |
| 2013/0079335 A1 | 3/2013 | Bailey | |
| 2013/0184264 A1 | 7/2013 | Bradner et al. | |
| 2013/0252331 A1 | 9/2013 | Bradner et al. | |
| 2013/0281399 A1 | 10/2013 | McLure et al. | |
| 2013/0281450 A1 | 10/2013 | Pratt et al. | |
| 2013/0331382 A1 | 12/2013 | Hubbard et al. | |
| 2014/0005169 A1 | 1/2014 | Albrecht et al. | |
| 2014/0011862 A1 | 1/2014 | Bradner et al. | |
| 2014/0213575 A1 | 7/2014 | Schmees et al. | |
| 2014/0256706 A1 | 9/2014 | Wang et al. | |
| 2015/0246923 A1 | 9/2015 | Wang et al. | |
| 2015/0291562 A1 | 10/2015 | Crew et al. | |

FOREIGN PATENT DOCUMENTS

| | | |
|---|---|---|
| CA | 2265645 A1 | 3/1998 |
| WO | WO-1998011111 A1 | 3/1998 |
| WO | WO-2006129623 A1 | 12/2006 |
| WO | WO-2008092231 A1 | 8/2008 |
| WO | WO-2009084693 A1 | 7/2009 |

(Continued)

OTHER PUBLICATIONS

Walser, et al, Thienotriazolodiazepines as platelet-activating factor antagonists. Steric limitations for the substituent in position 2, J. of Med. Chem., 34(4), 1440-6 (1991). (Year: 1991).*
Walser, et al., J. Med. Chem. 34:1440-1446 (1991) (Year: 1991).*
International Application No. PCT/US2017/051286, International Preliminary Report on Patentability, dated Mar. 19, 2019.

(Continued)

*Primary Examiner* — Erich A Leeser
(74) *Attorney, Agent, or Firm* — Marshall, Gerstein & Borun LLP

(57) ABSTRACT

The present disclosure provides compounds represented by Formula I: I, and the pharmaceutically acceptable salts, hydrates, and solvates thereof, wherein $R^1$, $R^{2a}$, $R^{2b}$, $R^3$, $R^4$, Ar, L, X, Y, and B are as defined as set forth in the specification. The present disclosure also provides compounds of Formula I for use to treat a condition or disorder responsive to degradation of BET bromodomains such as cancer.

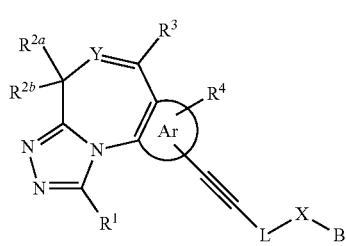

19 Claims, No Drawings

(56) References Cited

FOREIGN PATENT DOCUMENTS

| WO | WO-2009158404 A1 | 12/2009 |
|---|---|---|
| WO | WO-2010123975 A1 | 10/2010 |
| WO | WO-2011/054864 A1 | 5/2011 |
| WO | WO-2011054843 A1 | 5/2011 |
| WO | WO-2011054844 A1 | 5/2011 |
| WO | WO-2011054845 A1 | 5/2011 |
| WO | WO-2011054846 A1 | 5/2011 |
| WO | WO-2011054848 A1 | 5/2011 |
| WO | WO-2011143651 A1 | 11/2011 |
| WO | WO-2011143660 A2 | 11/2011 |
| WO | WO-2011143669 A2 | 11/2011 |
| WO | WO-2011161031 A1 | 12/2011 |
| WO | WO-2012075383 | 6/2012 |
| WO | WO-2012116170 A1 | 8/2012 |
| WO | WO-2012151512 A2 | 11/2012 |
| WO | WO-2012174487 | 12/2012 |
| WO | WO-2013024104 | 2/2013 |
| WO | WO-2013027168 | 2/2013 |
| WO | WO-2013030150 A1 | 3/2013 |
| WO | WO-2013033268 | 3/2013 |
| WO | WO-2013097601 A1 | 7/2013 |
| WO | WO-2014159392 A1 | 10/2014 |
| WO | WO-2014164596 A1 | 10/2014 |

OTHER PUBLICATIONS

Bondeson, D. P., et al., "Catalytic in Vivo Protein Knockdown by Small-Molecule PROTACs," Nature *Chemical Biology* 11, No. 8 (2015), pp. 611-617.

Buckley, D. L., "Targeting the von Hippel-Lindau E3 Ubiquitin Ligase Using Small Molecules to Disrupt the VHL/HIF-1α Interaction," *Journal of the American Chemical Society* 134, No. 10 (2012): 4465-4468.

Buckley, D. L., et al., "Small-Molecule Inhibitors of the Interaction Between the E3 Ligase VHL and HIF1α," *Angewandte Chemie International Edition* 51, No. 46 (2012), pp. 11463-11467.

Delmore, J.E., et al., "BET Bromodomain Inhibition as a Therapeutic Strategy to Target c-Myc.," *Cell*, vol. 146, No. 6 (2011), pp. 904-917.

Ito, T., et al., "Identification of a Primary Target of Thalidomide Teratogenicity," *Science* 327, No. 5971 (2010), pp. 1345-1350.

Lipkowitz, S., et al., "RINGs of Good and Evil: RING Finger Ubiquitin Ligases at the Crossroads of Tumour Suppression and Oncogenesis," *Nature Reviews Cancer* 11, No. 9 (2011), pp. 629-643.

Seal, J., et al., "Identification of a Novel Series of BET Family Bromodomain Inhibitors: Binding Mode and Profile of I-BET151 (GSK1210151A)," *Bioorganic & Medicinal Chemistry Letters*, vol. 22, No. 8 (2012), pp. 2968-2972.

Van Hagen, M., et al., "RNF4 and VHL Regulate the Proteasomal Degradation of SUMO-Conjugated Hypoxia-Inducible Factor-2α," *Nucleic Acids Research* 38, No. 6 (2009), pp. 1922-1931.

Walser, A., et al., "Pentacyclic Triazolodiazepines as PAF ❒ Antagonists," *Journal of Heterocyclic Chemistry* 28, No. 4 (1991), pp. 1121-1125.

Walser, A., et al., "Thienotriazolodiazepines as Platelet-Activating Factor Antagonists. Steric Limitations for the Substituent in Position 2," *Journal of Medicinal Chemistry* 34, No. 4 (1991), pp. 1440-1446.

Walser, A., et al., "Triazolobenzo- and Triazolothienodiazepines as Potent Antagonists of Platelet Activating Factor," *Journal of Medicinal Chemistry* 34, No. 3 (1991), pp. 1209-1221.

Winter, G. E., et al., "Phthalimide Conjugation as a Strategy for in Vivo Target Protein Degradation," *Science* 348, No. 6241 (2015), pp. 1376-1381.

Zengerle, M., et al., "Selective Small Molecule Induced Degradation of the BET Bromodomain Protein BRD4," *ACS Chemical Biology* 10, No. 8 (2015), pp. 1770-1777.

International Search Report for PCT Application No. PCT/US2017/051286, dated Nov. 29, 2017.

\* cited by examiner

FUSED 1,4-DIAZEPINES AS BET PROTEIN DEGRADERS

BACKGROUND OF THE INVENTION

Field of the Invention

The present disclosure provides BET bromodomain protein inhibitors and degraders and therapeutic methods of treating conditions and diseases wherein inhibition and/or degradation of one or more BET bromodomains provides a benefit.

Background

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octamer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins ("BET bromodomains" or "BET bromodomain proteins") includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864. A discussion of BET bromodomain inhibitors, e.g., I-BET-151 and I-BET-762, can be found in Delmore et al., *Cell* 146: 904-917 (2011) and Seal et al., *Bioorg. Med. Chem. Lett.* 22:2968-2972 (2012).

Small molecule inhibitors of BET bromodomains have therapeutic potential for the treatment of diseases and conditions in which BET bromodomains have a role, including cancer. BET bromodomain inhibitors are disclosed in the following U.S. patents: U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, US 20100286127, US 20140256706, and US 2015/0246923; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, WO 2013097601, and WO 2014164596.

Phthalimide-based drugs, e.g., thalidomide or lenalidomide, bind to protein-degradation machinery, e.g., cereblon (CRBN; part of an ubiquitin E3 ligase complex). This may promote the recruitment of two transcription factors (IKZF1 and IKZF3) that are essential to disease progression, resulting in drug-induced ubiquitylation and degradation by the proteasome. See, e.g., Ito et al., *Science* 327:1345-1350 (2010) and Winter et al., *Science* 348:1376-1381 (2015).

A high-affinity VHL ligand, see Bondeson et al., *Nat. Chem. Biol.* 11:611-617 (2015), may recruit a target protein to an E3 ubiquitin ligase, resulting in drug induced ubiquitination and degradation. See, e.g., van Hagen et al., *Nucleic Acids Research* 38: 1922-1931 (2010); Buckley et al., *J. Am. Chem. Soc.* 134:4465-4468 (2012); Buckley et al., *Angew. Chem. Int. Ed. Engl.* 51:11463-11467 (2012); Lipkowitz and Weissman, *Nat Rev Cancer* 11:629-643 (2011); and Zengerle et al., *ACS Chem. Biol.* 10:1770-1777 (2015).

There is an ongoing need for new agents, e.g., small molecules, for treating and/or preventing cancer and other diseases responsive to deregulation, e.g., inhibition, of BET bromodomain activity and/or degradation of BET bromodomain proteins.

BRIEF SUMMARY OF THE INVENTION

In one aspect, the present disclosure provides compounds represented by any one of Formulae I-IX or XV-XXIV, below, and the pharmaceutically acceptable salts and solvates thereof, collectively referred to as "Compounds of the Disclosure." Compounds of the Disclosure having any one of Formulae I-IX or XV-XVII are BET bromodomain protein degraders and thus are useful in treating or preventing diseases or conditions wherein degradation of BET bromodomains, e.g., BRD2, BRD3, BRD4, BRD-t, or an isoform or mutant thereof, provides a benefit. Compounds of the Disclosure having any one of Formulae XVIII-XXIV are: 1) BET bromodomain protein inhibitors and thus are useful in treating or preventing diseases or conditions wherein inhibition of BET bromodomains, e.g., BRD2, BRD3, BRD4, BRD-t, or an isoform or mutant thereof, provides a benefit; and/or 2) synthetic intermediates used to prepare compounds having Formulae I-IX or XV-XVII.

In another aspect, the present disclosure provides synthetic intermediates represented by Formulae X, XI, XII, or XIV, below, and the pharmaceutically acceptable salts and solvates thereof, collectively referred to as "Intermediates of the Disclosure." Intermediates of the Disclosure can be used to prepare BET bromodomain protein degraders having Formulae I-VIII or XV-XVII.

In another aspect, the present disclosure provides methods of treating or preventing a condition or disease by administering a therapeutically effective amount of a Compound of the Disclosure to an individual, e.g., a human, in need thereof. The disease or condition of interest is treatable or preventable by inhibition or degradation of BET bromodomain proteins, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides methods of treating a patient having cancer, comprising administering a therapeutically effective amount of a Compound of the Disclosure to the patient in need thereof, wherein cells of the patient contain a biomarker, e.g., overexpression of MCL1, overexpression of BCL-XL, or co-overexpression of MCL-1 and BCL-$X_L$.

In another aspect, the present disclosure provides methods of reducing BET bromodomain protein within a cell of an individual in need thereof, the method comprising administering a Compound of the Disclosure to the individual.

In another aspect, the present disclosure provides a method of inhibiting or degrading BET bromodomain proteins in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition or degradation of BET bromodomain proteins provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure having any one of Formulae I-VIII or XV-XVII degrade BET bromodomain proteins. Compounds of the Disclosure having any one of Formulae XVIII-XXIV inhibit BET bromodomain proteins and/or are synthetic intermediates used to prepare BET bromodomain protein degraders.

In one embodiment, Compounds of the Disclosure are compounds represented by Formula I:

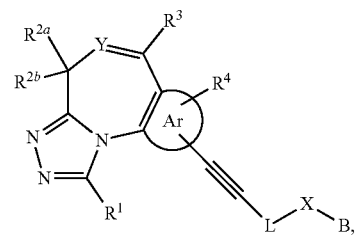

and the pharmaceutically acceptable salts or hydrates thereof, wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, (alkoxycarbonyl)alkyl, and —$CH_2C(=O)NR^{19a}R^{19b}$, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

Y is —N═;
$R^{15}$ is selected from the group consisting of hydrogen, halogen, $C_{1-4}$ alkyl, and alkoxy;
B is a monovalent radical of a ligand for an E3 ubiquitin ligase protein, e.g., B is:
B-1
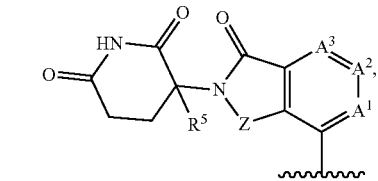
B-2
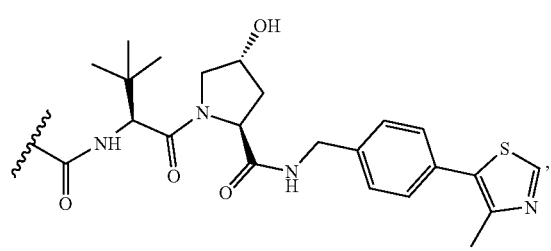
B-3
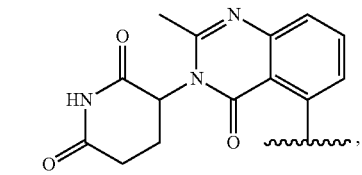
B-4
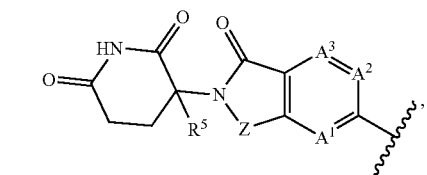
B-5
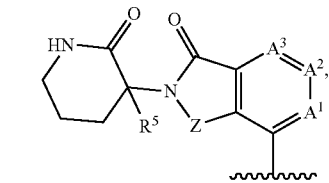
B-6
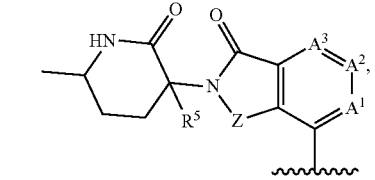
B-7
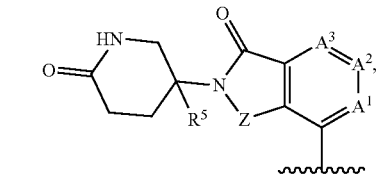
-continued
B-8
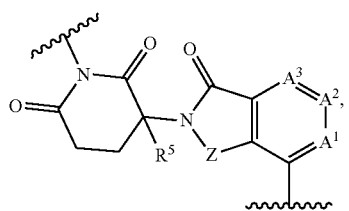
B-9
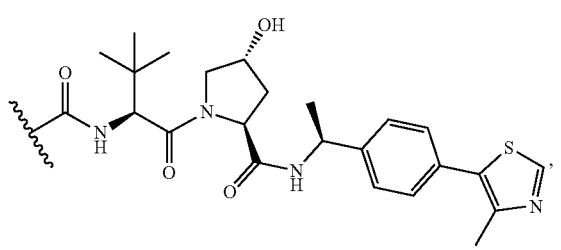
B-10
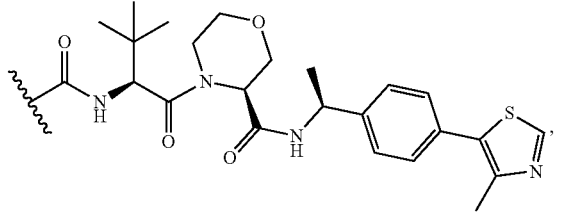
B-11
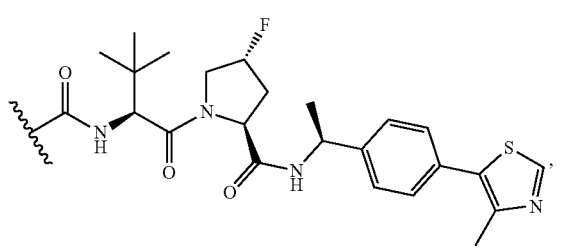
B-12
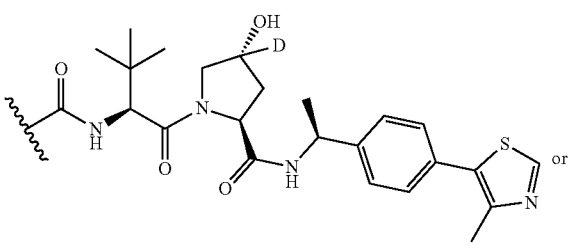
or
B-13
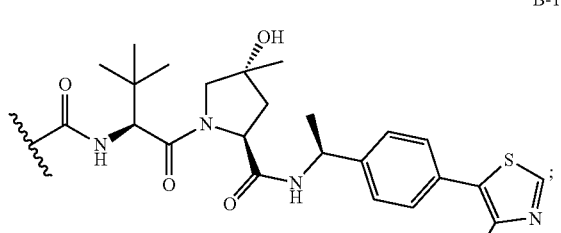
L is selected from the group consisting of alkylenyl, heteroalkylenyl, -A-$(CH_2)_m$—W—$(CH_2)_n$—, —$(CH_2)_m$—W—$(CH_2)_u$—O—$(CH_2)_v$—, and —$(CH_2)_m$—W—[$(CH_2)_w$—O]$_x$—$(CH_2)_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

each w is independently 2, 3, or 4;

x is 2, 3, or 4;

X is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2f}$)C(=O)CH$_2$N(R$^{2g}$)—; or X is absent;

wherein the carboxamide nitrogen atom of —N(R$^{2e}$)C(=O)CH$_2$O— and —N(R$^{2f}$)C(=O)CH$_2$N(R$^{2g}$)—, and the carbon atom of —C(=O)N(R$^{2d}$)— is attached to L;

R$^{2c}$, R$^{2d}$, R$^{2e}$, R$^{2f}$, and R$^{2g}$ are each independently selected from the group consisting of hydrogen and C$_{1-4}$ alkyl;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)= and —N=;

A$^2$ is selected from the group consisting of —C(R$^{16b}$)= and —N=;

A$^3$ is selected from the group consisting of —C(R$^{16c}$)= and —N=;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl;

R$^{16c}$ is selected from the group consisting of hydrogen, halo, and C$_{1-4}$ alkyl; and R$^{19a}$ and R$^{19b}$ are independently selected from the group consisting of hydrogen, C$_{1-6}$ alkyl and optionally substituted aryl; or R$^{19a}$ and R$^{19b}$ taken together with the nitrogen atom to which they are attached form a 4- to 8-membered optionally substituted heterocyclo.

In one embodiment, Compounds of the Disclosure are compounds represented by Formula I, and the pharmaceutically acceptable salts or hydrates thereof, wherein R$^{2a}$ and R$^{2b}$ are each independently selected from the group consisting of hydrogen, optionally substituted C$_{1-4}$ alkyl, and (alkoxycarbonyl)alkyl; B is selected from the group consisting of B-1, B-2, and B-3, and L is selected from the group consisting of alkylenyl, heteroalkylenyl, -A-(CH$_2$)$_m$—W—(CH$_2$)$_n$—, and —(CH$_2$)$_m$—W—(CH$_2$)$_u$—O—(CH$_2$)$_v$—.

In another embodiment, Compounds of the Disclosure are compounds represented by Formula II

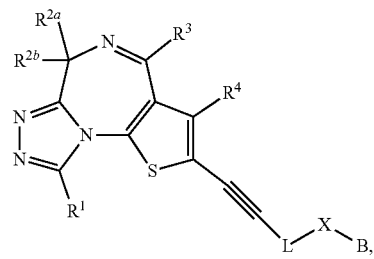

and the pharmaceutically acceptable salts or hydrates thereof, wherein R$^1$, R$^{2a}$, R$^{2b}$, R$^3$, R$^4$, L, X, and B are as defined in connection with Formula I.

In another embodiment, Compounds of the Disclosure are compounds represented by Formula I or Formula II, and the pharmaceutically acceptable salts or hydrates thereof, wherein R$^3$ is optionally substituted phenyl.

In another embodiment, Compounds of the Disclosure are compounds represented by Formula I or Formula II, and the pharmaceutically acceptable salts or hydrates thereof, wherein R$^1$ is C$_{1-4}$ alkyl. In another embodiment, R$^1$ is methyl.

In another embodiment, Compounds of the Disclosure are compounds represented by Formula I or Formula II, and the pharmaceutically acceptable salts or hydrates thereof, wherein R$^{2a}$ and R$^{2b}$ are each independently selected from the group consisting of hydrogen and C$_{1-4}$ alkyl.

In another embodiment, Compounds of the Disclosure are compounds represented by Formula III:

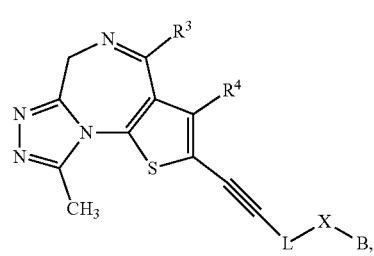

and the pharmaceutically acceptable salts or hydrates thereof, wherein R$^3$, R$^4$, L, X, and B are as defined in connection with Formula I.

In another embodiment, Compounds of the Disclosure are compounds represented by Formula IV:

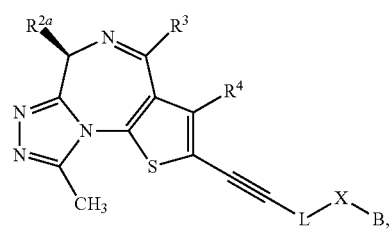

and the pharmaceutically acceptable salts or hydrates thereof, wherein R$^{2a}$ is C$_{1-4}$ alkyl, and R$^3$, R$^4$, L, X, and B are as defined in connection with Formula I.

In another embodiment, Compounds of the Disclosure are compounds represented by Formula V:

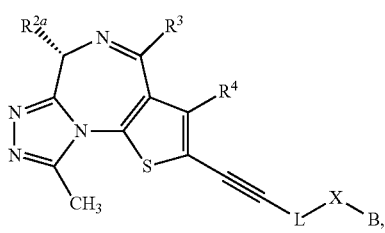

and the pharmaceutically acceptable salts or hydrates thereof, wherein $R^{2a}$ is $C_{1-4}$ alkyl, and $R^3$, $R^4$, L, X, and B are as defined in connection with Formula I.

In another embodiment, Compounds of the Disclosure are compounds represented by any one of Formula I-V, and the pharmaceutically acceptable salts or hydrates thereof, wherein $R^4$ is $C_{1-4}$ alkyl. In another embodiment, $R^4$ is methyl. In another embodiment, $R^4$ is hydrogen.

In another embodiment, Compounds of the Disclosure are compounds represented by Formula VI:

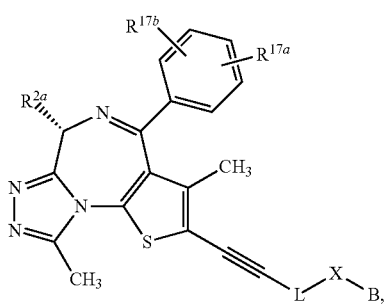

and the pharmaceutically acceptable salts and hydrates thereof, wherein $R^{2a}$ is selected from the group consisting of hydrogen and $C_{1-3}$ alkyl; $R^{17a}$ and $R^{17b}$ are each independently selected from the group consisting of hydrogen, $C_{1-4}$ alkyl, haloalkyl, $C_{1-4}$ alkoxy, and halo; and L, X, and B are as defined in connection with Formula I. In another embodiment, $R^{17a}$ and $R^{17b}$ are each independently selected from the group consisting of hydrogen and halo.

In another embodiment, Compounds of the Disclosure are compounds represented by any one of Formulae I-VI, and the pharmaceutically acceptable salts or solvates thereof, wherein L is $C_{1-12}$ alkylenyl. In another embodiment, L is selected from the group consisting of —$CH_2$—, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, and —$CH_2(CH_2)_6CH_2$—.

In another embodiment, Compounds of the Disclosure are compounds represented by any one of Formulae I-VI, and the pharmaceutically acceptable salts or solvates thereof, wherein, L is 3- to 12-membered heteroalkylenyl. In another embodiment, L is —$(CH_2)_oO$—$(CH_2CH_2O)_p$—$(CH_2)_q$—; o is 1, 2, or 3; p is 0, 1, 2, 3, 4, or 5; and q is 1, 2, or 3.

In another embodiment, Compounds of the Disclosure are compounds represented by any one of Formulae I-VI, and the pharmaceutically acceptable salts or solvates thereof, wherein L is selected from the group consisting of: —$CH_2OCH_2CH_2$—, —$CH_2CH_2OCH_2CH_2$—, —$CH_2O(CH_2CH_2O)CH_2CH_2$—, —$CH_2O(CH_2CH_2O)_2CH_2CH_2$—, —$CH_2O(CH_2CH_2O)_3CH_2CH_2$—, —$CH_2CH_2O(CH_2CH_2O)_6CH_2CH_2CH_2$—, —$CH_2CH_2O(CH_2CH_2O)_6$ $CH_2CH_2$—, —$CH_2CH_2CH_2OCH_2CH_2OCH_2CH_2$—, —$CH_2CH_2CH_2O(CH_2CH_2O)_2CH_2CH_2CH_2$—, and —$CH_2CH_2CH_2O(CH_2)_4OCH_2CH_2CH_2$—.

In another embodiment, Compounds of the Disclosure are compounds represented by any one of Formulae I-VI, and the pharmaceutically acceptable salts or solvates thereof, wherein L is —$(CH_2)_m$—W—$(CH_2)_n$—, i.e., A is absent. In another embodiment, W is phenylenyl. In another embodiment, W is 5-membered heteroarylenyl. In another embodiment, W is 6-membered heteroarylenyl. In another embodiment, wherein m is 0. In another embodiment, wherein n is 1, 2, 3, 4, or 5.

In another embodiment, Compounds of the Disclosure are compounds represented by any one of Formulae I-VI, and the pharmaceutically acceptable salts or solvates thereof, wherein L is -A-$(CH_2)_m$—W—$(CH_2)_n$—, wherein A is selected from the group consisting of 5-membered heteroarylenyl and 6-membered heteroarylenyl. In another embodiment, W is phenylenyl. In another embodiment, W is 5-membered heteroarylenyl. In another embodiment, W is 6-membered heteroarylenyl. In another embodiment, W is heterocyclenyl. In another embodiment, W is cycloalkylenyl In another embodiment, wherein m is 1, 2, or 3. In another embodiment, wherein n is 1, 2, 3, or 4.

In another embodiment, Compounds of the Disclosure are compounds represented by any one of Formulae I-VI, and the pharmaceutically acceptable salts or solvates thereof, and Intermediates of the Disclosure are compounds represented by Formula XI, and the pharmaceutically acceptable salts or solvates thereof, wherein L is —$(CH_2)_m$—W—$(CH_2)_u$—O—$(CH_2)_v$—. In another embodiment, W is phenylenyl. In another embodiment, W is 5-membered heteroarylenyl. In another embodiment, W is 6-membered heteroarylenyl.

In another embodiment, Compounds of the Disclosure are compounds represented by any one of Formula I-VI, and the pharmaceutically acceptable salts or solvates thereof, and Intermediates of the Disclosure are compounds represented by Formula IX, and the pharmaceutically acceptable salts or solvates thereof, wherein L is —$(CH_2)_m$—W—$[(CH_2)_w$—O$]_x$—$(CH_2)_v$—. In another embodiment, W is phenylenyl. In another embodiment, W is 5-membered heteroarylenyl. In another embodiment, W is 6-membered heteroarylenyl.

In another embodiment, Compounds of the Disclosure are compounds represented by any one of Formulae I-VI, and the pharmaceutically acceptable salts or solvates thereof, wherein L is selected from the group consisting of:

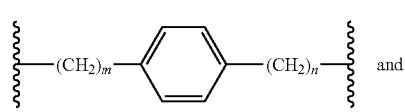

L-1

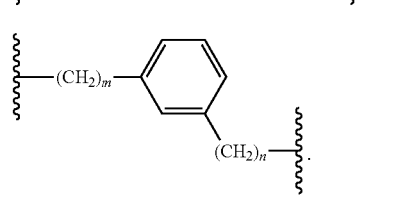

L-2

In another embodiment, m is 0. In another embodiment, n is 1, 2, 3, 4, or 5. In another embodiment, L is L-1. In another embodiment, L is L-2.

In another embodiment, Compounds of the Disclosure are compounds represented by any one of Formulae I-VI, and the pharmaceutically acceptable salts or solvates thereof, wherein L is selected from the group consisting of:

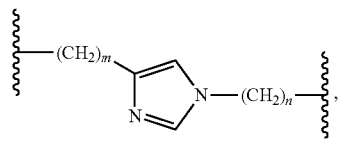
L-3

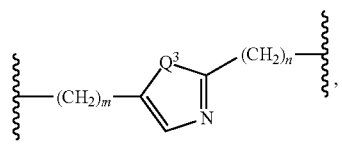
L-4

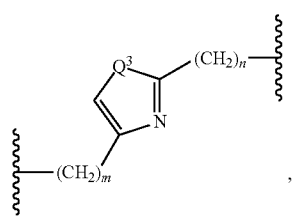
L-5

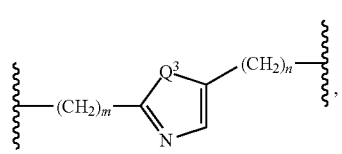
L-6

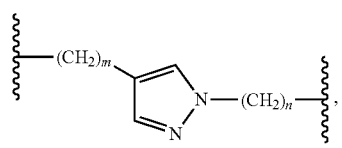
L-7

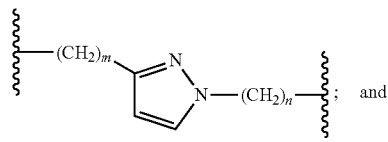
L-8; and

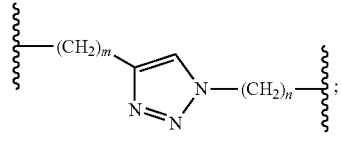
L-9

$Q^3$ is selected from the group consisting of —O—, —S—, and —N($R^6$)—; and $R^6$ is selected from the group consisting of hydrogen and $C_{1-4}$ alkyl. In another embodiment, m is 0. In another embodiment, n is 1, 2, 3, 4, or 5. In another embodiment, n is 2, 3, or 4. In another embodiment, L is L-3. In another embodiment, L is L-4. In another embodiment, L is L-5. In another embodiment, L is L-6. In another embodiment, L is L-7. In another embodiment, L is L-8. In another embodiment, L is L-9.

In another embodiment, Compounds of the Disclosure are compounds represented by any one of Formulae I-VI, and the pharmaceutically acceptable salts or solvates thereof, wherein L is selected from the group consisting of:

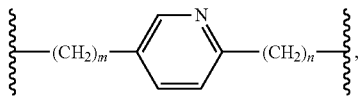
L-10

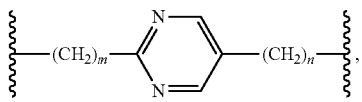
L-11

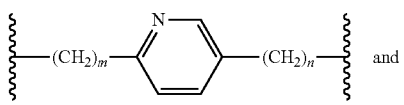
L-12 and

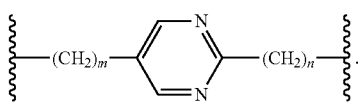
L-13

In another embodiment, m is 0. In another embodiment, n is 1, 2, 3, 4, or 5. In another embodiment, n is 2, 3, or 4. In another embodiment, L is L-10. In another embodiment, L is L-11. In another embodiment, L is L-12. In another embodiment, L is L-13.

In another embodiment, Compounds of the Disclosure are compounds represented by any one of Formulae I-VI, and the pharmaceutically acceptable salts or solvates thereof, wherein L is selected from the group consisting of:

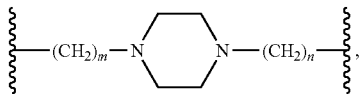
L-14

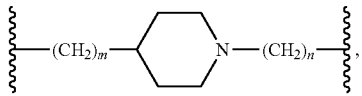
L-15

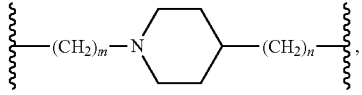
L-16

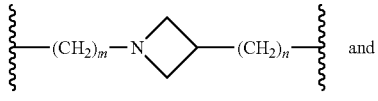
L-17 and

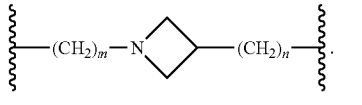
L-18

In another embodiment, m is 1, 2, or 3. In another embodiment, n is 0, 1, 2, 3, or 4. In another embodiment, n is 0, 1, or 2. In another embodiment, L is L-14. In another embodiment, L is L-15. In another embodiment, L is L-16. In another embodiment, L is L-17. In another embodiment, L is L-18.

In another embodiment, Compounds of the Disclosure are compounds represented by any one of Formulae I-VI, and the pharmaceutically acceptable salts or solvates thereof, wherein L is selected from the group consisting of:

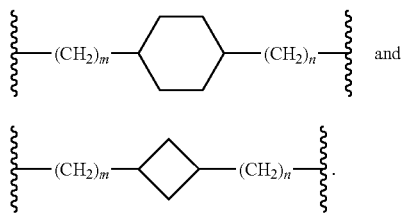

L-19

L-20

In another embodiment, m is 1, 2, or 3. In another embodiment, n is 0, 1, 2, 3, or 4. In another embodiment, n is 1 or 2. In another embodiment, L is L-19. In another embodiment, L is L-20.

In another embodiment, Compounds of the Disclosure are compounds represented by any one of Formulae I-VI, and the pharmaceutically acceptable salts or solvates thereof, wherein L is selected from the group consisting of:

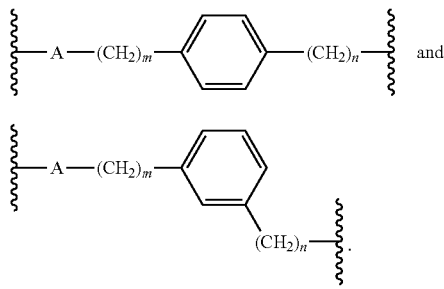

L-21

L-22

In another embodiment, m is 1, 2, or 3. In another embodiment, n is 1, 2, 3, 4, or 5. In another embodiment, L is L-21. In another embodiment, L is L-22. In another embodiment, A is 5-membered heteroarylenyl. In another embodiment, A is 6-membered heteroarylenyl.

In another embodiment, Compounds of the Disclosure are compounds represented by any one of Formulae I-VI, and the pharmaceutically acceptable salts or solvates thereof, wherein L is selected from the group consisting of:

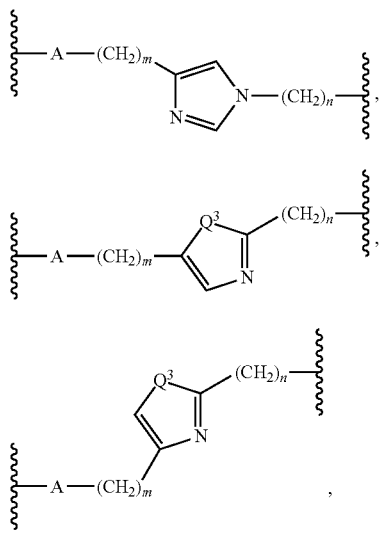

L-23

L-24

L-25

L-26

L-27

L-28

L-29

$Q^3$ is selected from the group consisting of —O—, —S—, and —N($R^6$)—; and $R^6$ is selected from the group consisting of hydrogen and $C_{1-4}$ alkyl. In another embodiment, m is 1, 2, or 3. In another embodiment, n is 1, 2, 3, or 4. In another embodiment, n is 2, 3, or 4. In another embodiment, L is L-23. In another embodiment, L is L-24. In another embodiment, L is L-25. In another embodiment, L is L-26. In another embodiment, L is L-27. In another embodiment, L is L-28. In another embodiment, L is L-29. In another embodiment, A is 5-membered heteroarylenyl. In another embodiment, A is 6-membered heteroarylenyl.

In another embodiment, Compounds of the Disclosure are compounds represented by any one of Formulae I-VI, and the pharmaceutically acceptable salts or solvates thereof, wherein L is selected from the group consisting of:

L-30

L-31

L-32

L-33

In another embodiment, m is 1, 2, or 3. In another embodiment, n is 1, 2, 3, or 4. In another embodiment, n is 2, 3, or 4. In another embodiment, L is L-30. In another embodiment, L is L-31. In another embodiment, L is L-32. In another embodiment, L is L-33. In another embodiment, A is 5-membered heteroarylenyl. In another embodiment, A is 6-membered heteroarylenyl.

In another embodiment, Compounds of the Disclosure are compounds represented by any one of Formulae I-VI, and the pharmaceutically acceptable salts or solvates thereof, wherein L is selected from the group consisting of:

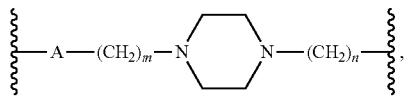
L-34

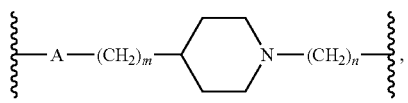
L-35

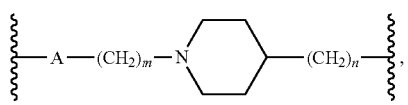
L-36

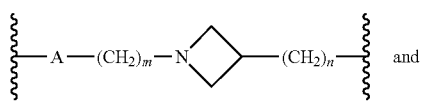
L-37 and

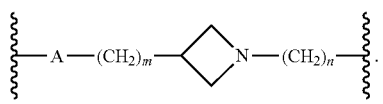
L-38

In another embodiment, m is 1, 2, or 3. In another embodiment, n is 0, 1, 2, 3, or 4. In another embodiment, n is 0, 1, or 2. In another embodiment, L is L-34. In another embodiment, L is L-35. In another embodiment, L is L-36. In another embodiment, L is L-37. In another embodiment, L is L-38. In another embodiment, A is 5-membered heteroarylenyl. In another embodiment, A is 6-membered heteroarylenyl.

In another embodiment, Compounds of the Disclosure are compounds represented by any one of Formulae I-VI, and the pharmaceutically acceptable salts or solvates thereof, wherein L is selected from the group consisting of:

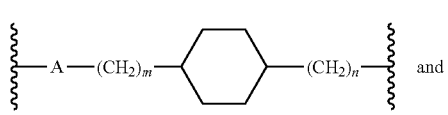
L-39 and

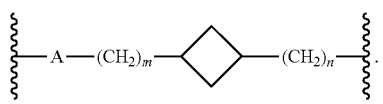
L-40

In another embodiment, m is 1, 2, or 3. In another embodiment, n is 0, 1, 2, 3, or 4. In another embodiment, n is 1 or 2. In another embodiment, L is L-39. In another embodiment, L is L-40. In another embodiment, A is 5-membered heteroarylenyl. In another embodiment, A is 6-membered heteroarylenyl.

In another embodiment, Compounds of the Disclosure are compounds represented by any one of Formulae I-VI, and the pharmaceutically acceptable salts or solvates thereof, wherein L is —$(CH_2)_m$—W—$(CH_2)_u$—O—$(CH_2)_v$—; W is selected from the group consisting of 5-membered heteroarylenyl and optionally substituted 6-membered heteroarylenyl; m is 0, 1, 2, 3, 4, 5, 6, or 7; u is 0; and v is 1, 2, 3, or 4. In another embodiment, m is 0.

In another embodiment, Compounds of the Disclosure are compounds represented by Formula VII:

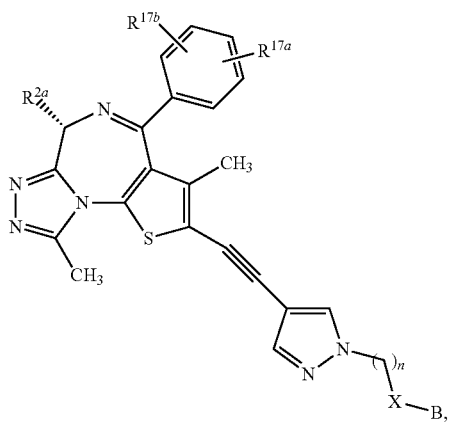
VII and the pharmaceutically acceptable salts or solvates thereof, wherein n is 2, 3, 4, or 5, and $R^{2a}$, $R^{17a}$, $R^{17b}$, X, and B are as defined in connection with Formula VI.

In another embodiment, Compounds of the Disclosure are compounds represented by Formula VIII:

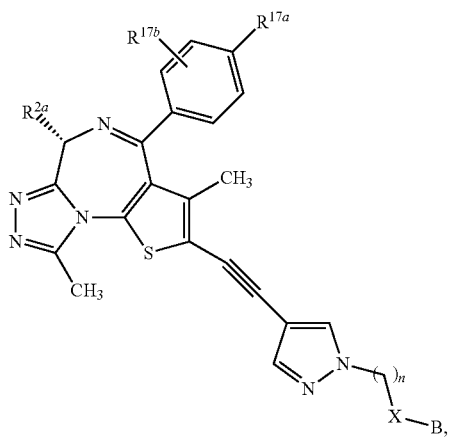
VIII and the pharmaceutically acceptable salts or solvates thereof, wherein n is 2, 3, 4, or 5, and $R^{2a}$, $R^{17a}$, $R^{17b}$, X, and B are as defined in connection with Formula VI.

In another embodiment, Compounds of the Disclosure are compounds represented by Formula IX:

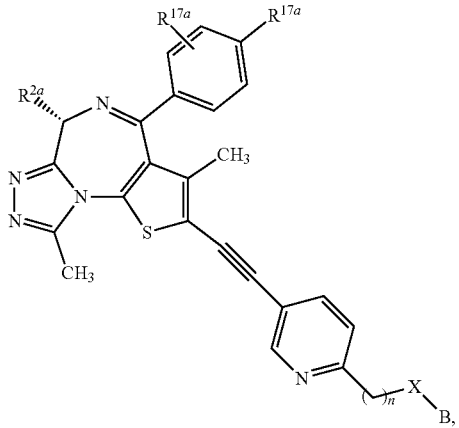

IX and the pharmaceutically acceptable salts or solvates thereof, wherein n is 2, 3, 4, or 5, and $R^{2a}$, $R^{17a}$, $R^{17b}$, X, and B are as defined in connection with Formula VI.

In another embodiment, Compounds of the Disclosure are compounds represented by Formula XV:

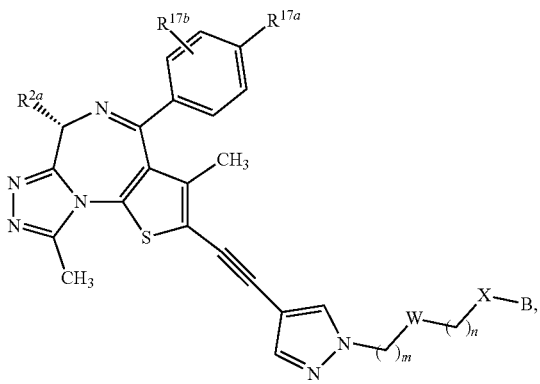

XV and the pharmaceutically acceptable salts or solvates thereof, wherein m is 2, 3, or 4, n is 0, 1, or 2, W is 5-membered heteroarylenyl, 6-membered heteroarylenyl, heterocyclenyl, or cycloalkylenyl, and $R^{2a}$, $R^{17a}$, $R^{17b}$, X, and B are as defined in connection with Formula VI. In another embodiment, W is 5-membered heteroarylenyl. In another embodiment, W is 6-membered heteroarylenyl. In another embodiment, W is heterocyclenyl. In another embodiment, W is cycloalkylenyl.

In another embodiment, Compounds of the Disclosure are compounds represented by Formula XVI:

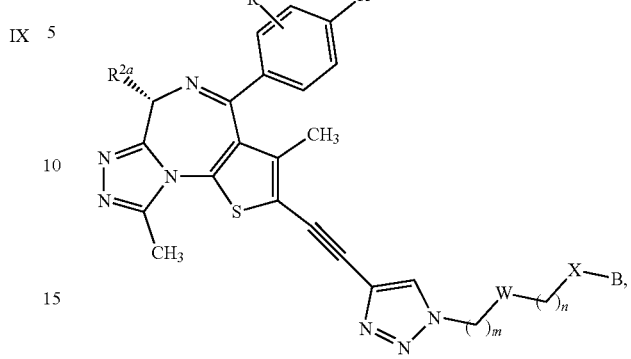

XVI and the pharmaceutically acceptable salts or solvates thereof, wherein m is 2, 3, or 4, n is 0, 1, or 2, W is 5-membered heteroarylenyl, 6-membered heteroarylenyl, heterocyclenyl, or cycloalkylenyl, and $R^{2a}$, $R^{17a}$, $R^{17b}$, X, and B are as defined in connection with Formula VI. In another embodiment, W is 5-membered heteroarylenyl. In another embodiment, W is 6-membered heteroarylenyl. In another embodiment, W is heterocyclenyl. In another embodiment, W is cycloalkylenyl.

In another embodiment, Compounds of the Disclosure are compounds represented by Formula XVII:

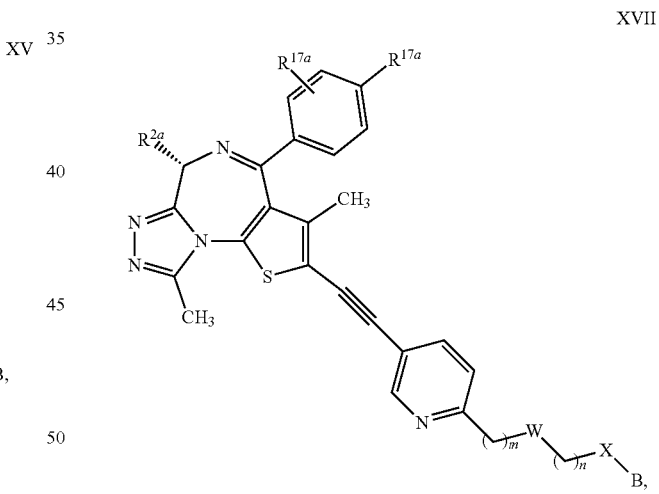

XVII and the pharmaceutically acceptable salts or solvates thereof, wherein m is 2, 3, or 4, n is 0, 1, or 2, W is 5-membered heteroarylenyl, 6-membered heteroarylenyl, heterocyclenyl, or cycloalkylenyl, and $R^{2a}$, $R^{17a}$, $R^{17b}$, X, and B are as defined in connection with Formula VI. In another embodiment, W is 5-membered heteroarylenyl. In another embodiment, W is 6-membered heteroarylenyl. In another embodiment, W is heterocyclenyl. In another embodiment, W is cycloalkylenyl.

In another embodiment, Compounds of the Disclosure are compounds represented by Formula XXV:

XXV

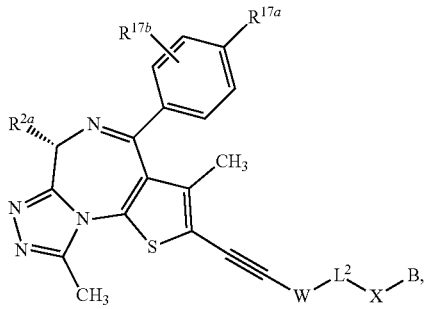

and the pharmaceutically acceptable salts or solvates thereof, wherein $L^2$ is heteroalkylenyl, W is selected from the group consisting of 5-membered heteroarylenyl and 6-membered heteroarylenyl, and $R^{2a}$, $R^{17a}$, $R^{17b}$, X, and B are as defined in connection with Formula VI.

In another embodiment, Compounds of the Disclosure are compounds represented by any one of Formulae VII-IX, XV-XVII, or XXV, and the pharmaceutically acceptable salts or solvates thereof, wherein $R^{2a}$ is hydrogen. In another embodiment, $R^{2a}$ is methyl.

In another embodiment, Compounds of the Disclosure are compounds represented by any one of Formulae VII-IX, XV-XVII, or XXV, and the pharmaceutically acceptable salts or solvates thereof, wherein $R^{2a}$ is —CH$_2$C(=O)NR$^{19a}$R$^{19b}$. In another embodiment, $R^{19a}$ and $R^{19b}$ are independently selected from the group consisting of hydrogen and $C_{1-6}$ alkyl; or $R^{19a}$ and $R^{19b}$ taken together with the nitrogen atom to which they are attached form a 6-membered optionally substituted heterocyclo.

In another embodiment, Compounds of the Disclosure are compounds represented by any one of Formulae VII-IX, XV-XVII, or XXV, and the pharmaceutically acceptable salts or solvates thereof, wherein X is selected from the group consisting of —C≡C—, —CH$_2$—, —O—, and —N(H)—. In another embodiment, X is —C≡C—. In another embodiment, X is —CH$_2$—. In another embodiment, X is —O—. In another embodiment, X is —N(H)—.

In another embodiment, Compounds of the Disclosure are compounds represented by any one of Formula I-IX, XV-XVII, or XXV, and the pharmaceutically acceptable salts or solvates thereof, wherein B is B-1. In another embodiment, $A^1$ is —C(R$^{16a}$)= and R$^{16a}$ is selected from the group consisting of hydrogen and halo. In another embodiment, $A^2$ is —C(R$^{16b}$)= and R$^{16b}$ is selected from the group consisting of hydrogen and halo. In another embodiment, $A^3$ is —C(R$^{16c}$)= and R$^{16c}$ is selected from the group consisting of hydrogen and halo. In another embodiment, $A^1$ is —N=, $A^2$ is —C(R$^{16b}$)=, and $A^3$ is —C(R$^{16c}$)=. In another embodiment, $A^1$ is —C(R$^{16a}$)=, $A^2$ is —N=, and $A^3$ is —C(R$^{16c}$)=. In another embodiment, $A^1$ is —C(R$^{16a}$)=, $A^2$ is —C(R$^{16b}$)= and $A^3$ is —N=. In another embodiment, Z is —CH$_2$—. In another embodiment, Z is —C(=O)—. In another embodiment, $R^5$ is hydrogen. In another embodiment, B-1 is selected from the group consisting of:

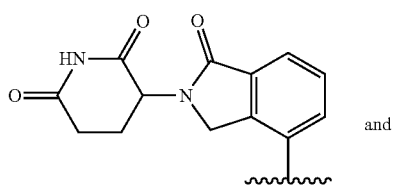

and

-continued

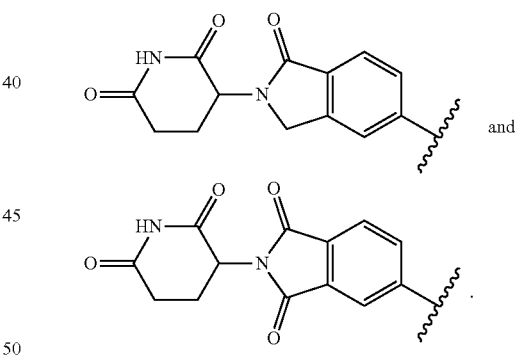

In another embodiment, Compounds of the Disclosure are compounds represented by any one of Formula I-IX, XV-XVII, or XXV, and the pharmaceutically acceptable salts or solvates thereof, wherein B is B-2.

In another embodiment, Compounds of the Disclosure are compounds represented by any one of Formula I-IX, XV-XVII, or XXV, and the pharmaceutically acceptable salts or solvates thereof, wherein B is B-3.

In another embodiment, Compounds of the Disclosure are compounds represented by any one of Formula I-IX, XV-XVII, or XXV, and the pharmaceutically acceptable salts or solvates thereof, wherein B is B-4. In another embodiment, $A^1$ is —C(R$^{16a}$)= and R$^{16a}$ is selected from the group consisting of hydrogen and halo. In another embodiment, $A^2$ is —C(R$^{16b}$)= and R$^{16b}$ is selected from the group consisting of hydrogen and halo. In another embodiment, $A^3$ is —C(R$^{16c}$)= and R$^{16c}$ is selected from the group consisting of hydrogen and halo. In another embodiment, $A^1$ is —N=, $A^2$ is —C(R$^{16b}$)=, and $A^3$ is —C(R$^{16c}$)=. In another embodiment, $A^1$ is —C(R$^{16a}$)=, $A^2$ is —N=, and $A^3$ is —C(R$^{16c}$)=. In another embodiment, $A^1$ is —C(R$^{16a}$)=, $A^2$ is —C(R$^{16b}$)= and $A^3$ is —N=. In another embodiment, Z is —CH$_2$—. In another embodiment, Z is —C(=O)—. In another embodiment, $R^5$ is hydrogen. In another embodiment, B-4 is selected from the group consisting of:

In another embodiment, Compounds of the Disclosure are compounds represented by any one of Formula I-IX, XV-XVII, or XXV, and the pharmaceutically acceptable salts or solvates thereof, wherein B is B-5. In another embodiment, $A^1$ is —C(R$^{16a}$)= and R$^{16a}$ is selected from the group consisting of hydrogen and halo. In another embodiment, $A^2$ is —C(R$^{16b}$)= and R$^{16b}$ is selected from the group consisting of hydrogen and halo. In another embodiment, $A^3$ is —C(R$^{16c}$)= and R$^{16c}$ is selected from the group consisting of hydrogen and halo. In another embodiment, $A^1$ is —N=, $A^2$ is —C(R$^{16b}$)=, and $A^3$ is —C(R$^{16c}$)=. In another embodiment, $A^1$ is —C(R$^{16a}$)=, $A^2$ is —N=, and $A^3$ is —C(R$^{16c}$)=. In another embodiment, $A^1$ is —C(R$^{16a}$)=, $A^2$ is —C(R$^{16b}$)= and $A^3$ is —N=. In another embodiment, Z is —CH$_2$—. In another embodiment, Z is —C(=O)—. In another embodiment, $R^5$ is hydrogen.

In another embodiment, Compounds of the Disclosure are compounds represented by any one of Formula I-IX, XV-XVII, or XXV, and the pharmaceutically acceptable salts or solvates thereof, wherein B is B-6. In another embodiment, $A^1$ is —C($R^{16a}$)═ and $R^{16a}$ is selected from the group consisting of hydrogen and halo. In another embodiment, $A^2$ is —C($R^{16b}$)═ and $R^{16b}$ is selected from the group consisting of hydrogen and halo. In another embodiment, $A^3$ is —C($R^{16c}$)═ and $R^{16c}$ is selected from the group consisting of hydrogen and halo. In another embodiment, $A^1$ is —N═, $A^2$ is —C($R^{16b}$)═, and $A^3$ is —C($R^{16c}$)═. In another embodiment, $A^3$ is —C($R^{16a}$)═, $A^2$ is —N═, and $A^3$ is —C($R^{16c}$)═. In another embodiment, $A^1$ is —C($R^{16a}$)═, $A^2$ is —C($R^{16b}$)═ and $A^3$ is —N═. In another embodiment, Z is —CH$_2$—. In another embodiment, Z is —C(═O)—. In another embodiment, $R^5$ is hydrogen.

In another embodiment, Compounds of the Disclosure are compounds represented by any one of Formula I-IX, XV-XVII, or XXV, and the pharmaceutically acceptable salts or solvates thereof, wherein B is B-7. In another embodiment, $A^1$ is —C($R^{16a}$)═ and $R^{16a}$ is selected from the group consisting of hydrogen and halo. In another embodiment, $A^2$ is —C($R^{16b}$)═ and $R^{16b}$ is selected from the group consisting of hydrogen and halo. In another embodiment, $A^3$ is —C($R^{16c}$)═ and $R^{16c}$ is selected from the group consisting of hydrogen and halo. In another embodiment, $A^1$ is —N═, $A^2$ is —C($R^{16b}$)═, and $A^3$ is —C($R^{16c}$)═. In another embodiment, $A^1$ is —C($R^{16a}$)═, $A^2$ is —N═, and $A^3$ is —C($R^{16c}$)═. In another embodiment, $A^1$ is —C($R^{16a}$)═, $A^2$ is —C($R^{16b}$)═ and $A^3$ is —N═. In another embodiment, Z is —CH$_2$—. In another embodiment, Z is —C(═O)—. In another embodiment, $R^5$ is hydrogen.

In another embodiment, Compounds of the Disclosure are compounds represented by any one of Formula I-IX, XV-XVII, or XXV, and the pharmaceutically acceptable salts or solvates thereof, wherein B is B-8. In another embodiment, $A^1$ is —C($R^{16a}$)═ and $R^{16a}$ is selected from the group consisting of hydrogen and halo. In another embodiment, $A^2$ is —C($R^{16b}$)═ and $R^{16b}$ is selected from the group consisting of hydrogen and halo. In another embodiment, $A^3$ is —C($R^{16c}$)═ and $R^{16c}$ is selected from the group consisting of hydrogen and halo. In another embodiment, $A^1$ is —N═, $A^2$ is —C($R^{16b}$)═, and $A^3$ is —C($R^{16c}$)═. In another embodiment, $A^1$ is —C($R^{16a}$)═, $A^2$ is —N═, and $A^3$ is —C($R^{16c}$)═. In another embodiment, $A^1$ is —C($R^{16a}$)═, $A^2$ is —C($R^{16b}$)═ and $A^3$ is —N═. In another embodiment, Z is —CH$_2$—. In another embodiment, Z is —C(═O)—. In another embodiment, $R^5$ is hydrogen.

In another embodiment, Compounds of the Disclosure are compounds represented by any one of Formula I-IX, XV-XVII, or XXV, and the pharmaceutically acceptable salts or solvates thereof, wherein B is B-9.

In another embodiment, Compounds of the Disclosure are compounds represented by any one of Formula I-IX, XV-XVII, or XXV, and the pharmaceutically acceptable salts or solvates thereof, wherein B is B-10.

In another embodiment, Compounds of the Disclosure are compounds represented by any one of Formula I-IX, XV-XVII, or XXV, and the pharmaceutically acceptable salts or solvates thereof, wherein B is B-11.

In another embodiment, Compounds of the Disclosure are compounds represented by any one of Formula I-IX, XV-XVII, or XXV, and the pharmaceutically acceptable salts or solvates thereof, wherein B is B-12.

In another embodiment, Compounds of the Disclosure are compounds represented by any one of Formula I-IX, XV-XVII, or XXV, and the pharmaceutically acceptable salts or solvates thereof, wherein B is B-13.

In another embodiment, Compounds of the Disclosure are compounds represented by Formula XVIII:

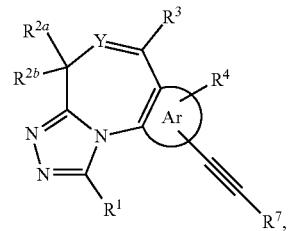

XVIII and the pharmaceutically acceptable salts or hydrates thereof, wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, and (alkoxycarbonyl)alkyl, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

Y is —N═;

$R^{15}$ is selected from the group consisting of hydrogen, halogen, $C_{1-4}$ alkyl, and alkoxy; and $R^7$ is selected from the group consisting of optionally substituted alkyl, hydroxyalkyl, optionally substituted aryl, and optionally substituted heteroaryl.

In another embodiment, Compounds of the Disclosure are compounds represented by Formula XIX:

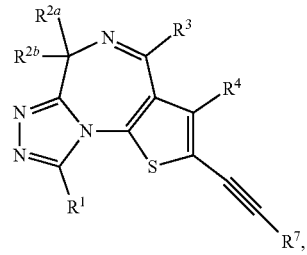

XIX and the pharmaceutically acceptable salts or hydrates thereof, wherein $R^1$, $R^{2a}$, $R^{2b}$, $R^3$, $R^4$, and $R^7$ are as defined in connection with Formula XVIII.

In another embodiment, Compounds of the Disclosure are compounds represented by Formula XVIII or Formula XIX, and the pharmaceutically acceptable salts or hydrates thereof, wherein $R^3$ is optionally substituted phenyl.

In another embodiment, Compounds of the Disclosure are compounds represented by Formula XVIII or Formula XIX, and the pharmaceutically acceptable salts or hydrates thereof, wherein $R^1$ is $C_{1-4}$ alkyl. In another embodiment, $R^1$ is methyl.

In another embodiment, Compounds of the Disclosure are compounds represented by Formula XVIII or Formula XIX, and the pharmaceutically acceptable salts or hydrates thereof, wherein $R^{2a}$ and $R^{2b}$ are each independently selected from the group consisting of hydrogen and $C_{1-4}$ alkyl.

In another embodiment, Compounds of the Disclosure are compounds represented by Formula XX:

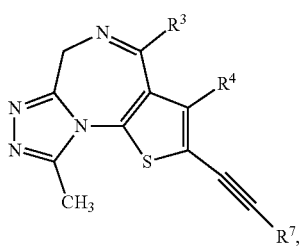

XX and the pharmaceutically acceptable salts or hydrates thereof, wherein $R^3$, $R^4$, and $R^7$ are as defined in connection with Formula XVIII.

In another embodiment, Compounds of the Disclosure are compounds represented by Formula XXI:

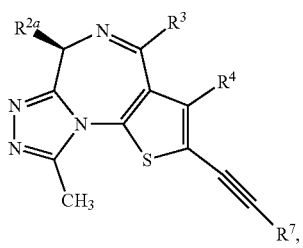

XXI and the pharmaceutically acceptable salts or hydrates thereof, wherein $R^{2a}$ is $C_{1-4}$ alkyl, and $R^3$, $R^4$, and $R^7$ are as defined in connection with Formula XVIII.

In another embodiment, Compounds of the Disclosure are compounds represented by Formula XXII:

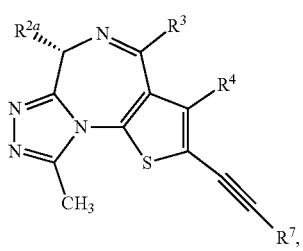

XXII and the pharmaceutically acceptable salts or hydrates thereof, wherein $R^{2a}$ is $C_{1-4}$ alkyl, and $R^3$, $R^4$, and $R^7$ are as defined in connection with Formula XVIII.

In another embodiment, Compounds of the Disclosure are compounds represented by any one of Formula XVIII-XXII, and the pharmaceutically acceptable salts or hydrates thereof, wherein $R^4$ is $C_{1-4}$ alkyl. In another embodiment, $R^4$ is methyl. In another embodiment, $R^4$ is hydrogen.

In another embodiment, Compounds of the Disclosure are compounds represented by Formula XXIII:

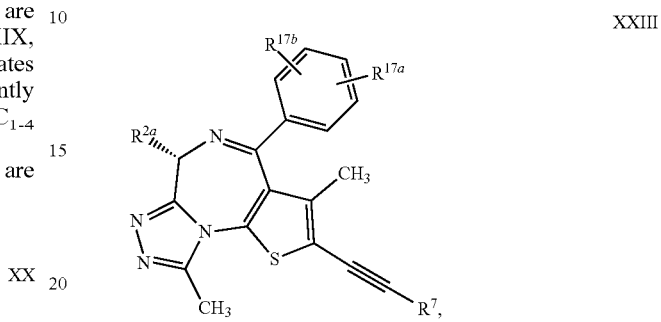

XXIII and the pharmaceutically acceptable salts and hydrates thereof, wherein $R^{2a}$ is selected from the group consisting of hydrogen and $C_{1-3}$ alkyl; $R^{17a}$ and $R^{17b}$ are each independently selected from the group consisting of hydrogen, $C_{1-4}$ alkyl, haloalkyl, $C_{1-4}$ alkoxy, and halo; and $R^7$ is as defined in connection with Formula XVII. In another embodiment, $R^{17a}$ and $R^{17b}$ are each independently selected from the group consisting of hydrogen and halo.

In another embodiment, Compounds of the Disclosure are compounds represented by Formula XXIV:

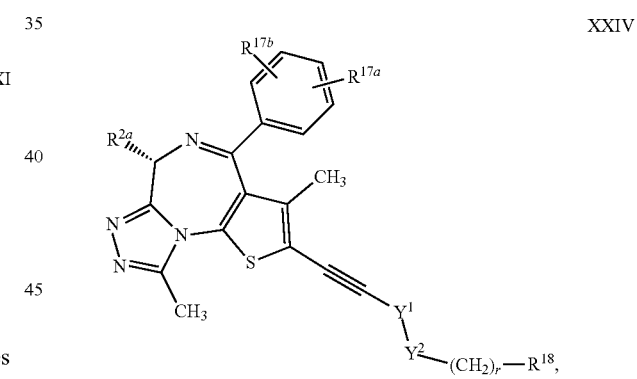

XXIV and the pharmaceutically acceptable salts and hydrates thereof, wherein:

$R^{2a}$ is selected from the group consisting of hydrogen and $C_{1-3}$ alkyl;

$R^{17a}$ and $R^{17b}$ are each independently selected from the group consisting of hydrogen, $C_{1-4}$ alkyl, haloalkyl, $C_{1-4}$ alkoxy, and halo;

$Y^1$ is selected from the group consisting of phenylenyl and heteroarylenyl;

$Y^2$ is selected from the group consisting of —O— and —N(H)—; or $Y^2$ is absent;

$R^{18}$ is selected from the group consisting of —C≡CH, —CHO, —CO$_2$H, —OH, and halo; and r is 2, 3, 4, 5, or 6.

In another embodiment, Compounds of the Disclosure are compounds represented by Formula XXIV, and the pharmaceutically acceptable salts and solvates thereof, wherein $R^{17a}$ and $R^{17b}$ are each independently selected from the group consisting of hydrogen and halo. In another embodiment, $Y^1$ is heteroarylenyl.

In another embodiment, Compounds of the Disclosure are compounds of Table 1, and the pharmaceutically acceptable salts and solvates thereof.

In another embodiment, Compounds of the Disclosure are compounds of Table 1A, and the pharmaceutically acceptable salts and solvates thereof.

In another embodiment, Compounds of the Disclosure are compounds of Tables 1 and 1A, and the pharmaceutically acceptable salts and solvates thereof.

TABLE 1

| Cpd. No. | Structure | Name |
|---|---|---|
| 1 | 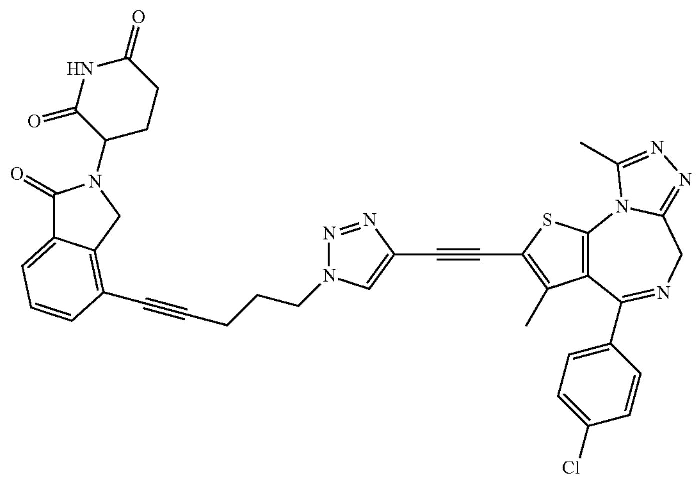 [SMILES: Cc1c(C#Cc2cn(CCCC#Cc3cccc4c3CN(C3CCC(=O)NC3=O)C4=O)nn2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione |
| 2 | 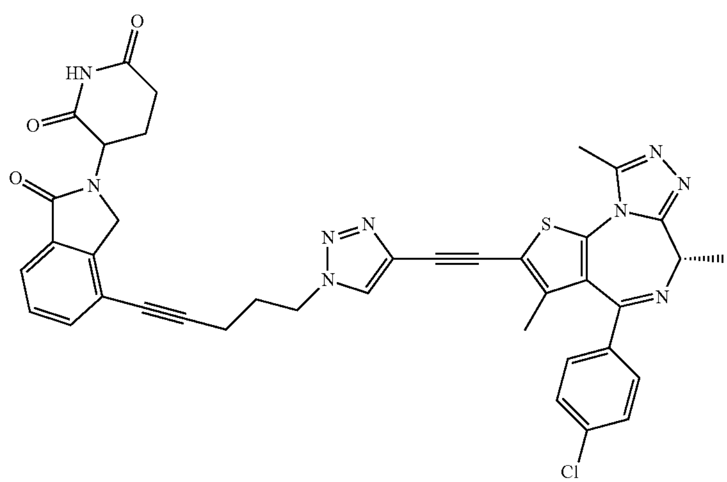 [SMILES: Cc1c(C#Cc2cn(CCCC#Cc3cccc4c3CN(C3CCC(=O)NC3=O)C4=O)nn2)sc2c1C(c1ccc(Cl)cc1)=N[C@@H](C)c1nnc(C)n1-2] | 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione |
| 3 | 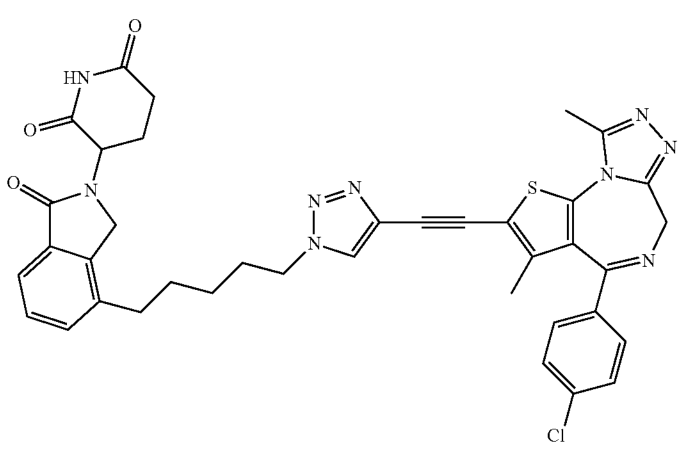 [SMILES: Cc1c(C#Cc2cn(CCCCCc3cccc4c3CN(C3CCC(=O)NC3=O)C4=O)nn2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione |

TABLE 1-continued

| Cpd. No. | Structure | Name |
|---|---|---|
| 4 | 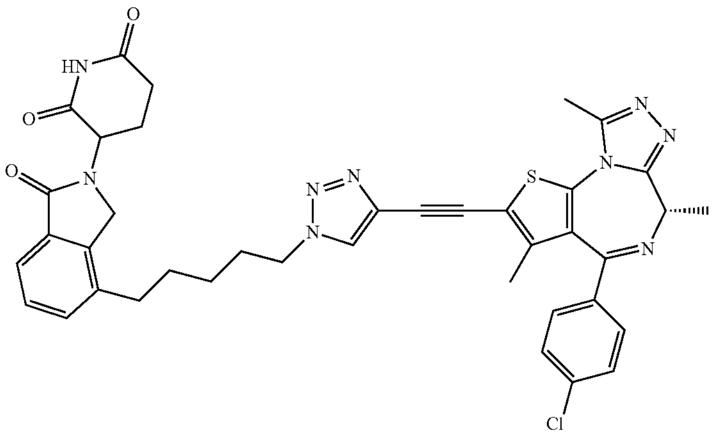 [SMILES: Cc1c(C#Cc2cn(CCCCCc3cccc4c3CN(C3CCC(=O)NC3=O)C4=O)nn2)sc2c1C(c1ccc(Cl)cc1)=N[C@@H](C)c1nnc(C)n1-2] | 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione |
| 5 | 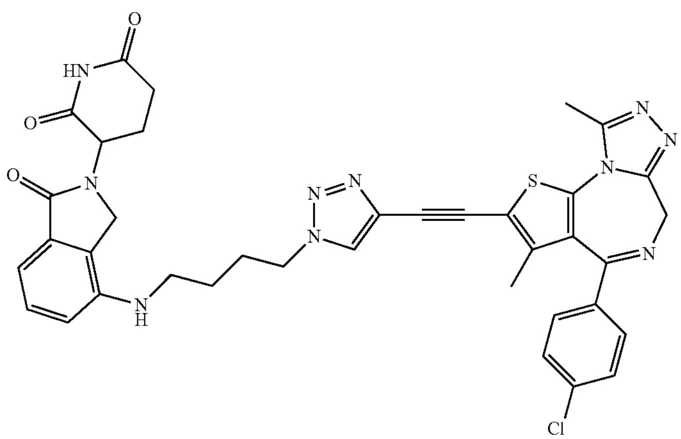 [SMILES: Cc1c(C#Cc2cn(CCCCNc3cccc4c3CN(C3CCC(=O)NC3=O)C4=O)nn2)sc2c1C(c1ccc(Cl)cc1)=NCc1nnc(C)n1-2] | 3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione |
| 6 | 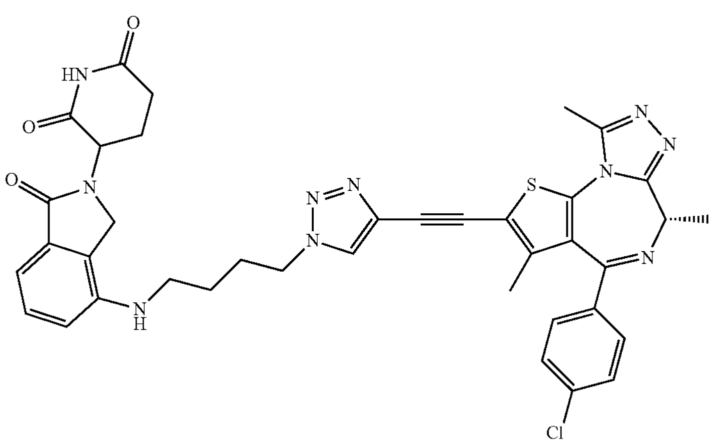 [SMILES: Cc1c(C#Cc2cn(CCCCNc3cccc4c3CN(C3CCC(=O)NC3=O)C4=O)nn2)sc2c1C(c1ccc(Cl)cc1)=N[C@@H](C)c1nnc(C)n1-2] | 3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione |

TABLE 1-continued

| Cpd. No. | Structure | Name |
|---|---|---|
| 7 | 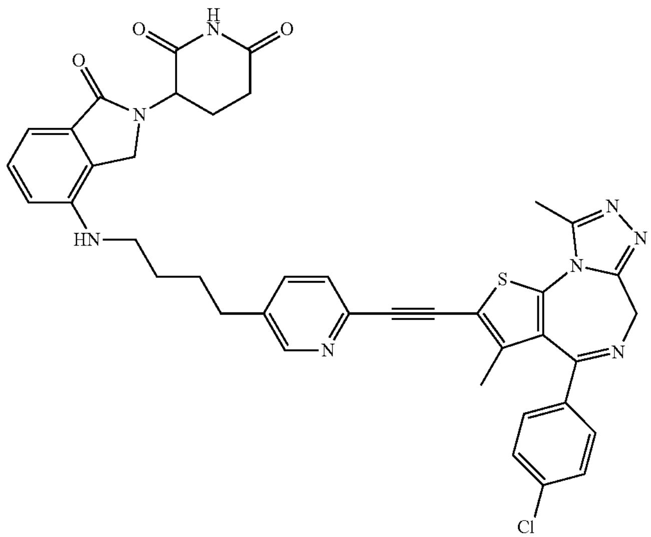 [SMILES: Cc1c(C#Cc2ccc(CCCCNc3cccc4c3CN(C3CCC(=O)NC3=O)C4=O)cn2)sc2c1C(c1ccc(Cl)cc1)=NCc1nnc(C)n1-2] | 3-(4-((4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione |
| 8 | 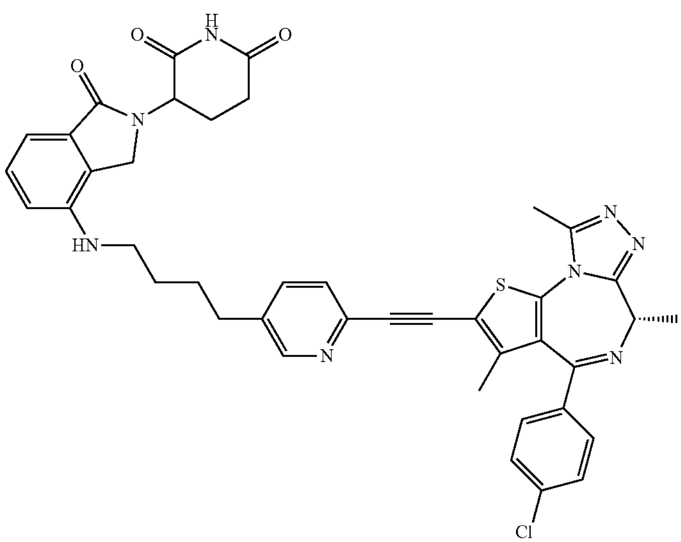 [SMILES: Cc1c(C#Cc2ccc(CCCCNc3cccc4c3CN(C3CCC(=O)NC3=O)C4=O)cn2)sc2c1C(c1ccc(Cl)cc1)=N[C@@H](C)c1nnc(C)n1-2] | 3-(4-((4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione |
| 9 | 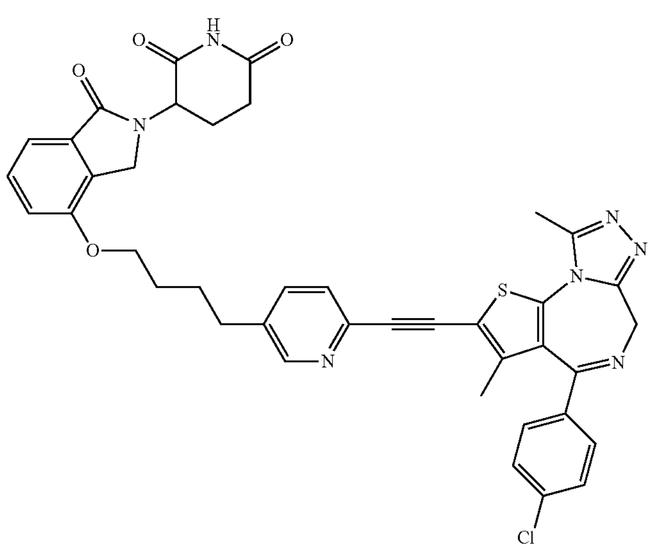 [SMILES: Cc1c(C#Cc2ccc(CCCCOc3cccc4c3CN(C3CCC(=O)NC3=O)C4=O)cn2)sc2c1C(c1ccc(Cl)cc1)=NCc1nnc(C)n1-2] | 4-(4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione |

TABLE 1-continued

| Cpd. No. | Structure | Name |
| --- | --- | --- |
| 10 | 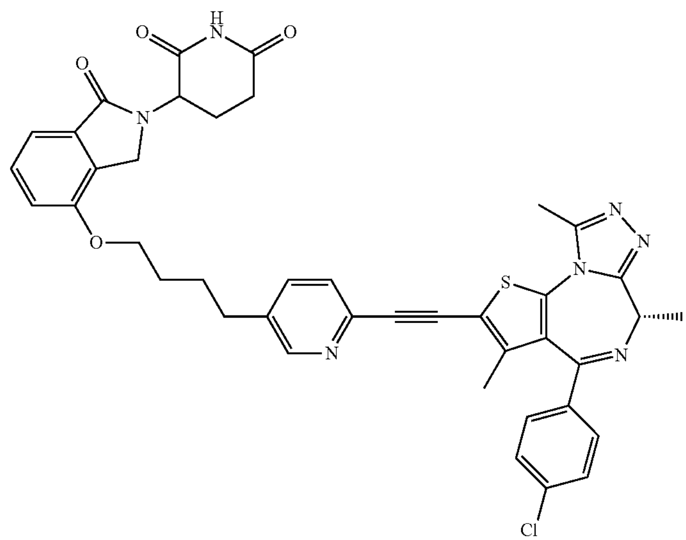 [SMILES: Cc1c(C#Cc2ccc(CCCCOc3cccc4c3CN(C3CCC(=O)NC3=O)C4=O)cn2)sc2c1C(c1ccc(Cl)cc1)=N[C@@H](C)c1nnc(C)n1-2] | 4-(4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione |
| 11 | 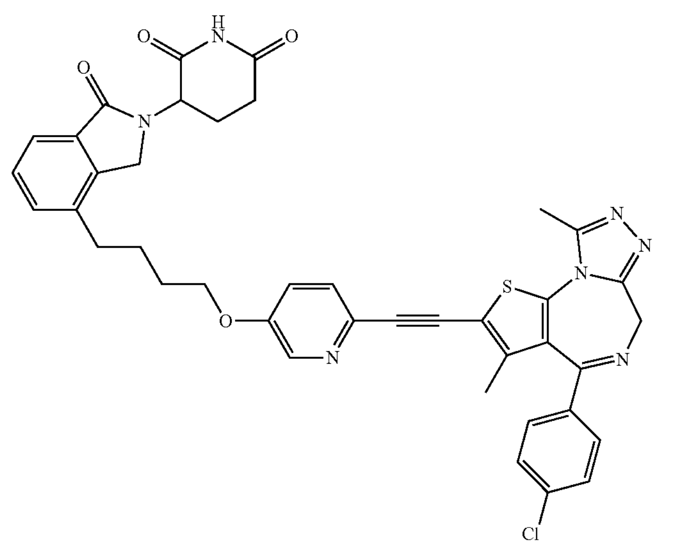 [SMILES: Cc1c(C#Cc2ccc(OCCCCc3cccc4c3CN(C3CCC(=O)NC3=O)C4=O)cn2)sc2c1C(c1ccc(Cl)cc1)=NCc1nnc(C)n1-2] | 3-(4-(4-((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperridine-2,6-dione |
| 12 | 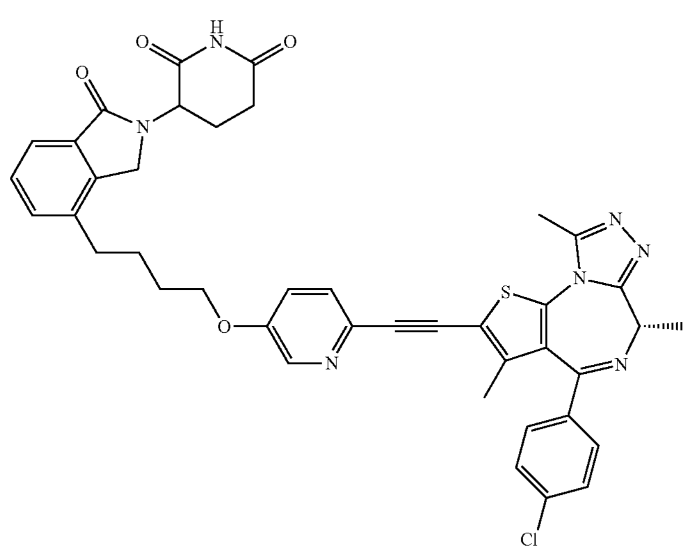 [SMILES: Cc1c(C#Cc2ccc(OCCCCc3cccc4c3CN(C3CCC(=O)NC3=O)C4=O)cn2)sc2c1C(c1ccc(Cl)cc1)=N[C@@H](C)c1nnc(C)n1-2] | 3-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperidine-2,6-dione |

TABLE 1-continued
| Cpd. No. | Structure | Name |
|---|---|---|
| 13 | 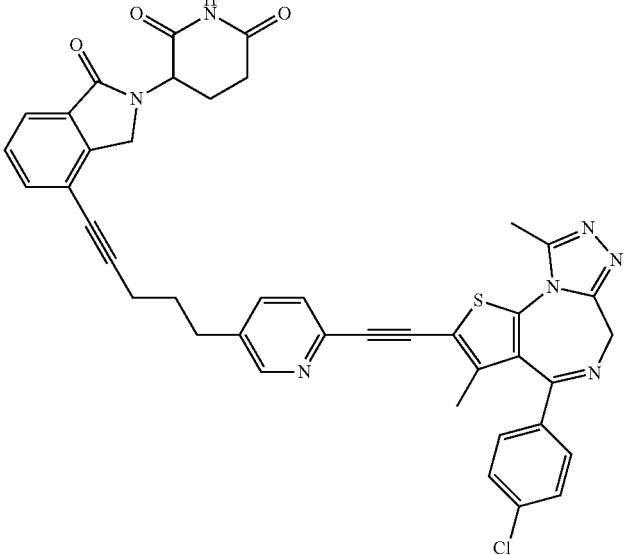 | 3-(4-(5-(6-((4-(4-chlorophenyl)-3,9-dimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione |
| 14 | 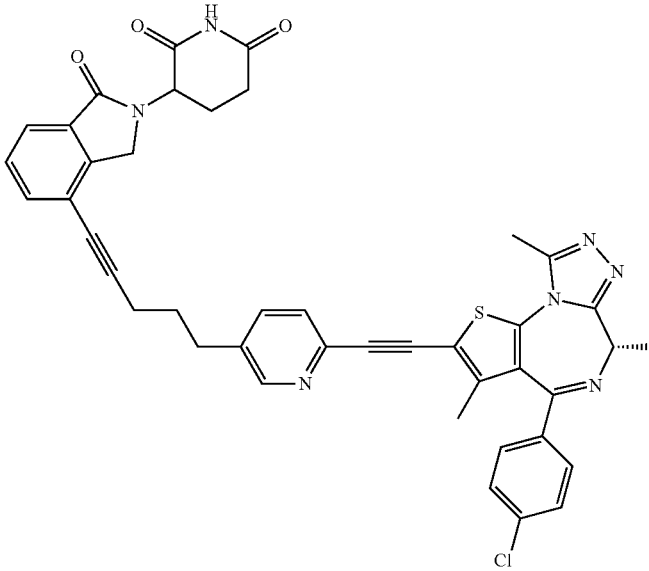 | 3-(4-(5-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione |

TABLE 1-continued
| Cpd. No. | Structure | Name |
|---|---|---|
| 15 | 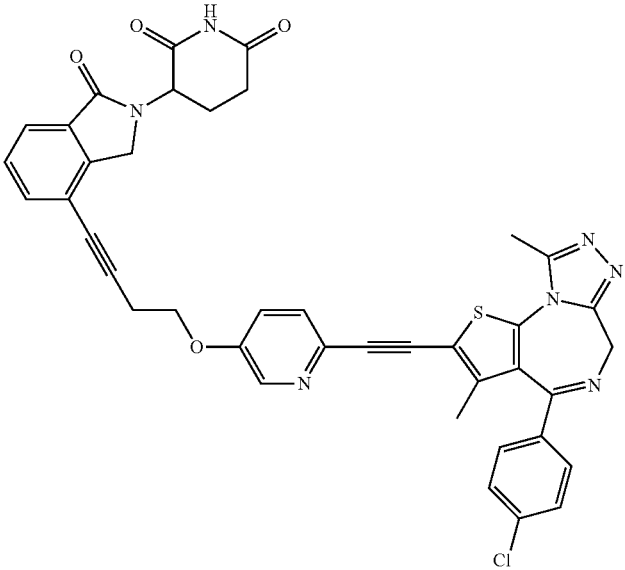 [SMILES: Cc1c(C#Cc2ccc(OCCC#Cc3cccc4c3CN(C3CCC(=O)NC3=O)C4=O)cn2)sc2c1C(c1ccc(Cl)cc1)=NCc1nnc(C)n1-2] | 3-(4-(4-((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione |
| 16 | 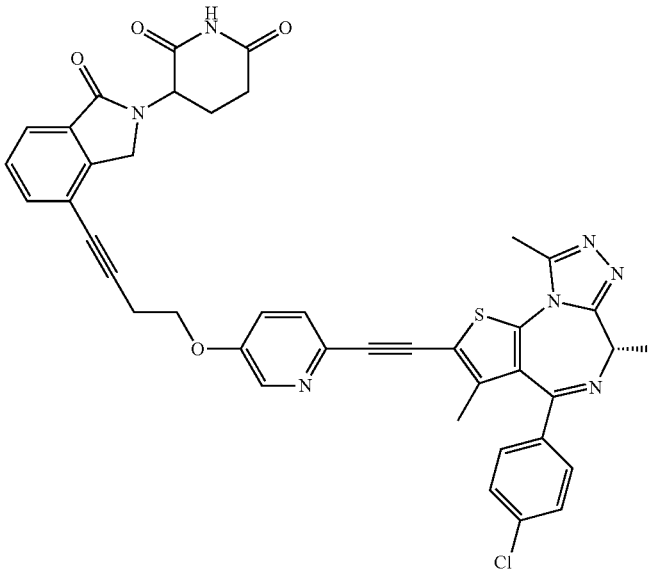 | 3-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione |

TABLE 1-continued

| Cpd. No. | Structure | Name |
|---|---|---|
| 17 | 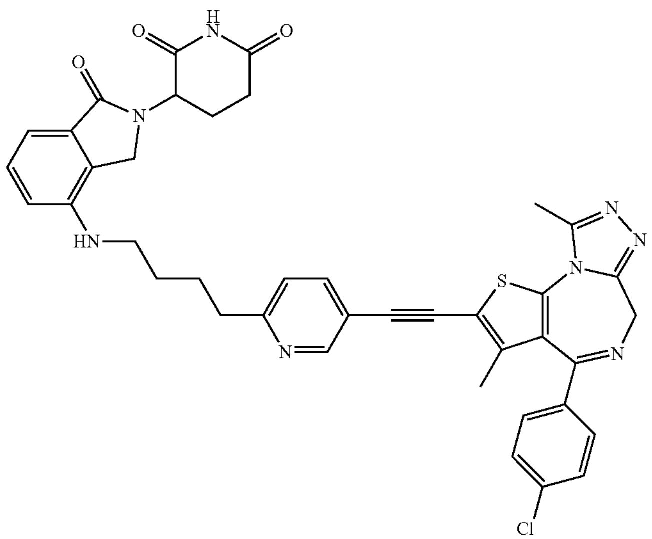 [SMILES: Cc1c(C#Cc2ccc(CCCCNc3cccc4c3CN(C3CCC(=O)NC3=O)C4=O)nc2)sc2c1C(c1ccc(Cl)cc1)=NCc1nnc(C)n1-2] | 3-(4-((4-(5-((4-(4-chlorophenyl)-3,9-dimethyl-6H-thieno[3,2-f][1,2,4]triazolo[4,3-a][1,4]diazepin-2-yl)ethynyl)pyridin-2-yl)butyl)amino)-1-oxoisoindolin-2-yl)piperidine-2,6-dione |
| 18 | 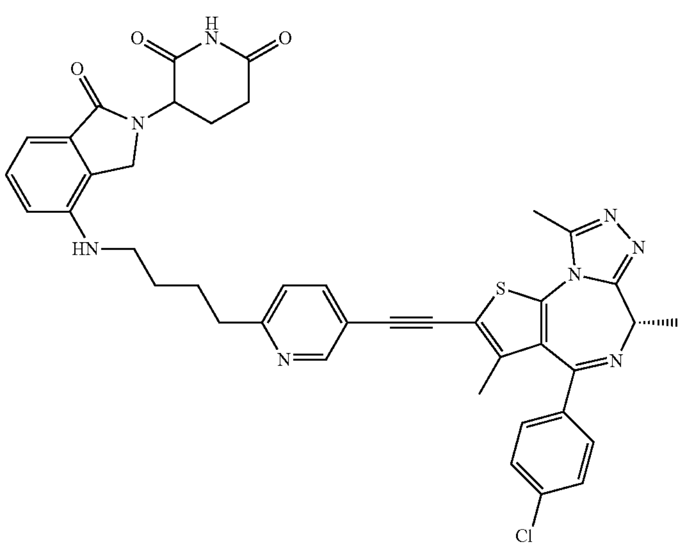 [SMILES: Cc1c(C#Cc2ccc(CCCCNc3cccc4c3CN(C3CCC(=O)NC3=O)C4=O)nc2)sc2c1C(c1ccc(Cl)cc1)=N[C@@H](C)c1nnc(C)n1-2] | 3-(4-((4-(5-(((S)-4-(4-chlorophenyl)-3,6,9-trimethyl-6H-thieno[3,2-f][1,2,4]triazolo[4,3-a][1,4]diazepin-2-yl)ethylyl)pyridin-2-yl)butyl)amino)-1-oxoisoindolin-2-yl)piperidine-2,6-dione |

TABLE 1-continued

| Cpd. No. | Structure | Name |
|---|---|---|
| 19 | 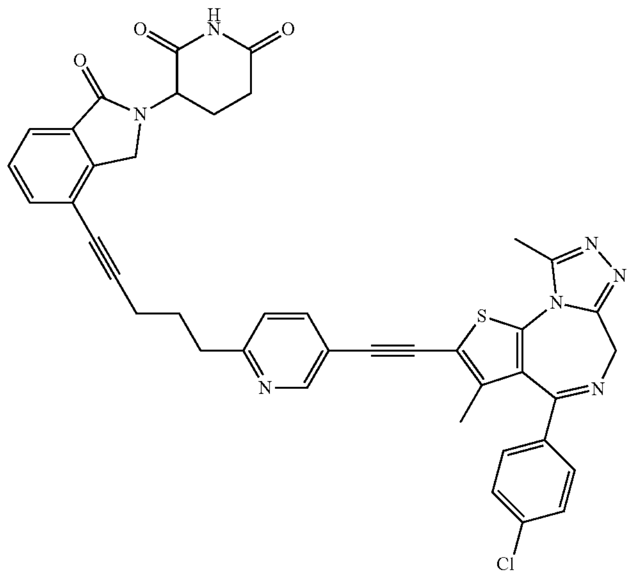 [SMILES: Cc1c(C#Cc2ccc(CCCC#Cc3cccc4c3CN(C3CCC(=O)NC3=O)C4=O)nc2)sc2c1C(c1ccc(Cl)cc1)=NCc1nnc(C)n1-2] | 3-(4-(5-(5-((4-(4-chlorophenyl)-3,9-dimethyl-6H-thieno[3,2-f][1,2,4]triazolo[4,3-a][1,4]diazepin-2-yl)ethynyl)pyridin-2-yl)pent-1-yn-1-yl)-1-oxoisoindolin-2-yl)piperidine-2,6-dione |
| 20 | 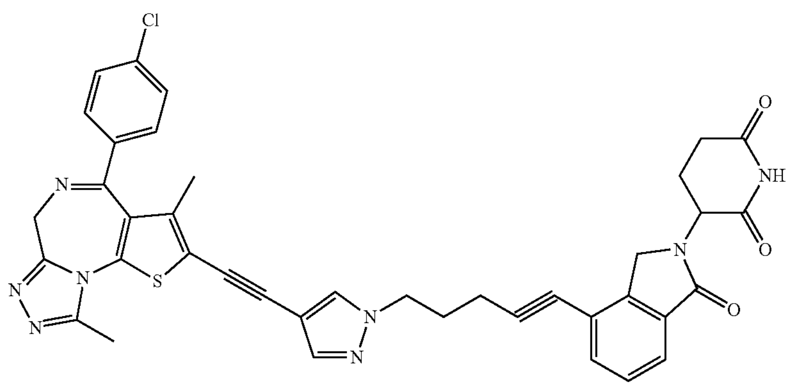 [SMILES: Cc1c(C#Cc2cnn(CCCC#Cc3cccc4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione |
| 21 | 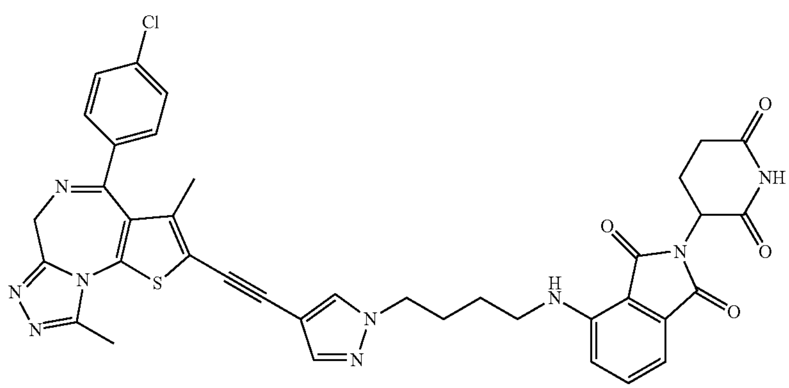 [SMILES: Cc1c(C#Cc2cnn(CCCCNc3cccc4c3C(=O)N(C3CCC(=O)NC3=O)C4=O)c2)sc2c1C(c1ccc(Cl)cc1)=NCc1nnc(C)n1-2] | 4-((4-(4-((4-(4-chlorophenyl)-3,9-dimethyl-6H-thieno[3,2-f][1,2,4]triazolo[4,3-a][1,4]diazepin-2-yl)ethynyl)-1H-pyraol-1-yl)butyl)amino)-2-(2,6-dioxopiperidin-3-yl)isoindoline-1,3-dione |

TABLE 1-continued

| Cpd. No. | Structure | Name |
|---|---|---|
| 22 | 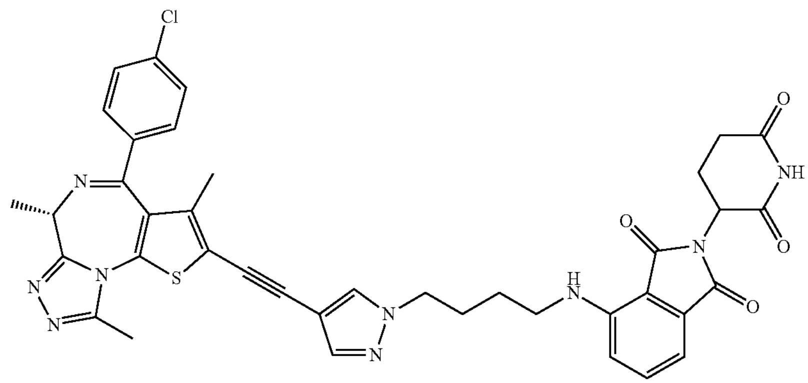 [SMILES: Cc1c(C#Cc2cnn(CCCCNc3cccc4c3C(=O)N(C3CCC(=O)NC3=O)C4=O)c2)sc2c1C(c1ccc(Cl)cc1)=N[C@@H](C)c1nnc(C)n1-2] | 4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-2-(2,6-dioxopiperidin-3-yl)isoindoline-1,3-dione |
| 23 | 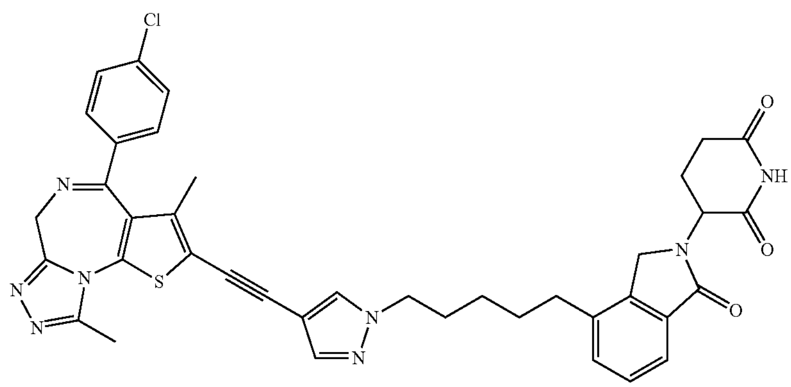 [SMILES: Cc1c(C#Cc2cnn(CCCCCc3cccc4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione |
| 24 | 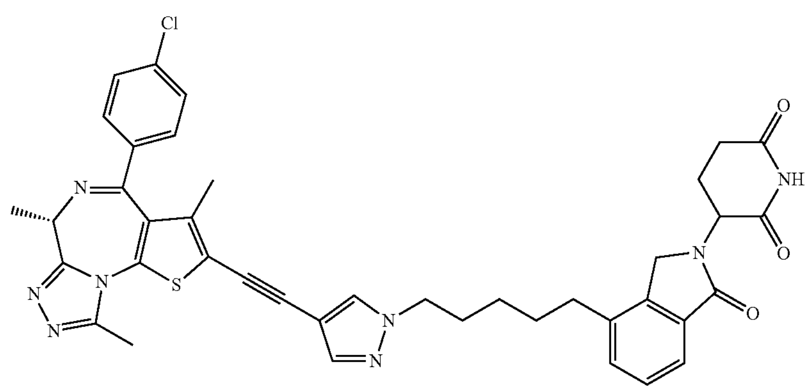 [SMILES: Cc1c(C#Cc2cnn(CCCCCc3cccc4c3CN(C3CCC(=O)NC3=O)C4=O)c2)sc2c1C(c1ccc(Cl)cc1)=N[C@@H](C)c1nnc(C)n1-2] | 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione |
| 25 | 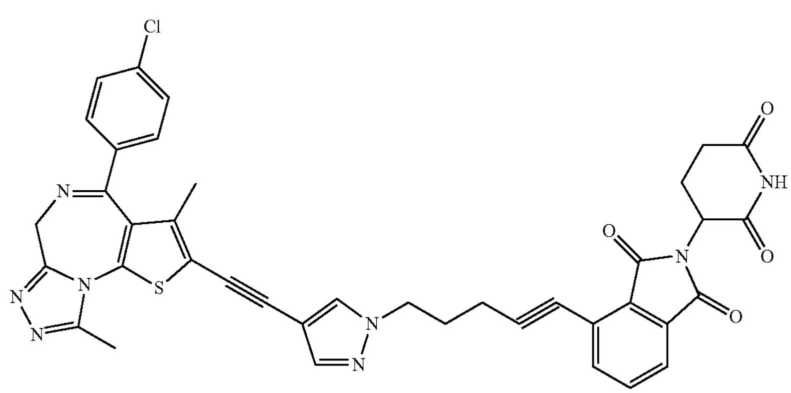 [SMILES: Cc1c(C#Cc2cnn(CCCC#Cc3cccc4c3C(=O)N(C3CCC(=O)NC3=O)C4=O)c2)sc2c1C(c1ccc(Cl)cc1)=NCc1nnc(C)n1-2] | 4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione |

TABLE 1-continued

| Cpd. No. | Structure | Name |
|---|---|---|
| 26 | 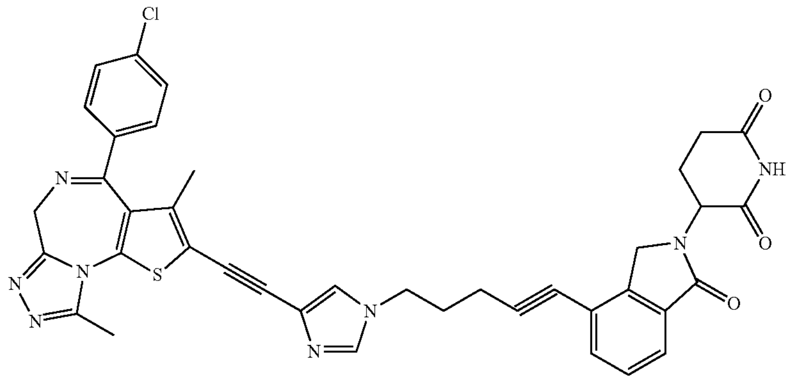 [SMILES: Cc1c(C#Cc2cn(CCCC#Cc3cccc4c3CN(C3CCC(=O)NC3=O)C4=O)cn2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione |
| 27 | 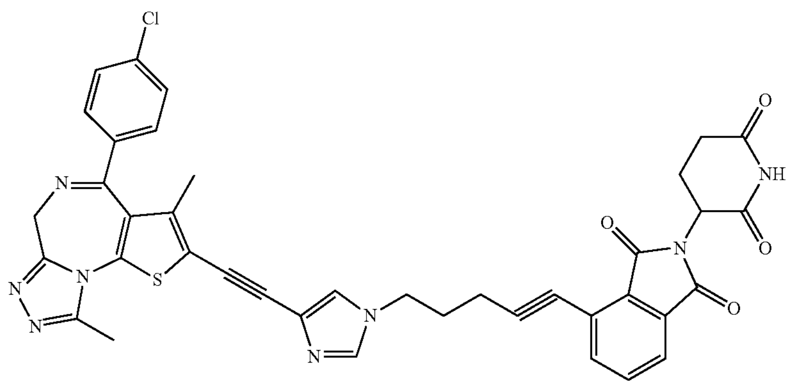 [SMILES: Cc1c(C#Cc2cn(CCCC#Cc3cccc4c3C(=O)N(C3CCC(=O)NC3=O)C4=O)cn2)sc2c1C(c1ccc(Cl)cc1)=NCc1nnc(C)n1-2] | 4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-2-(2,6-dioxopiperidin-3-yl)isoindoline-1,3-dione |
| 28 | 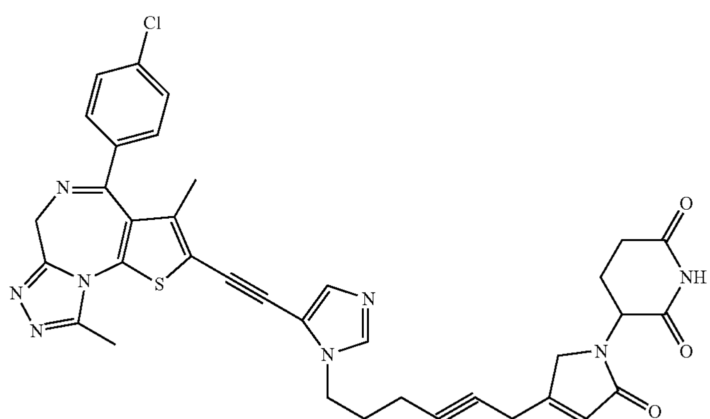 | 3-(4-(5-(5-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione |

TABLE 1-continued

| Cpd. No. | Structure | Name |
|---|---|---|
| 29 | 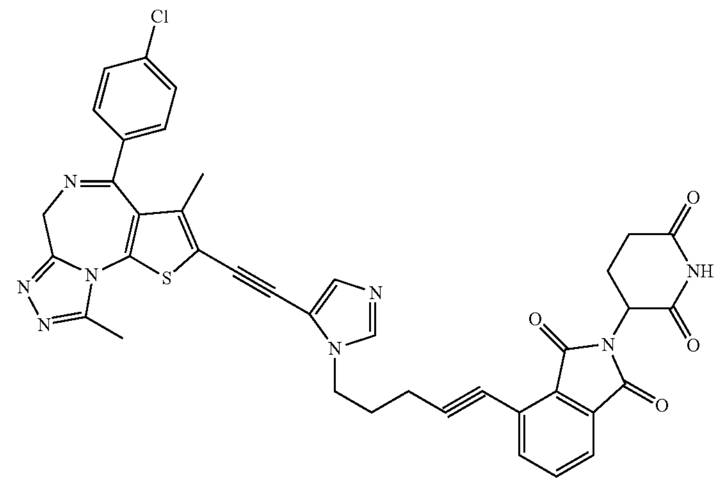 [SMILES: Cc1c(C#Cc2cncn2CCCC#Cc2cccc3c2C(=O)N(C2CCC(=O)NC2=O)C3=O)sc2c1C(c1ccc(Cl)cc1)=NCc1nnc(C)n1-2] | 4-(5-(5-((4-(4-chlorophenyl)-3,9-dimethyl-6H-thieno[3,2-f][1,2,4]triazolo[4,3-a]diazepin-2-yl)ethynyl)-1H-imidazol-1-yl)pent-1-yn-1-yl)-2-(2,6-dioxopiperidin-3-yl)isoindoline-1,3-dione |
| 30 | 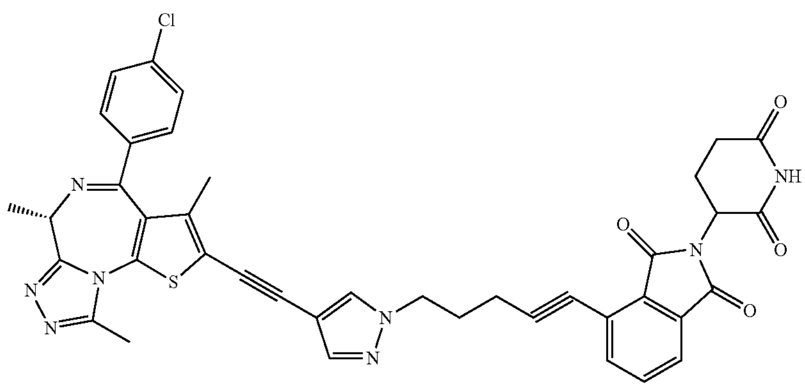 [SMILES: Cc1c(C#Cc2cnn(CCCC#Cc3cccc4c3C(=O)N(C3CCC(=O)NC3=O)C4=O)c2)sc2c1C(c1ccc(Cl)cc1)=N[C@@H](C)c1nnc(C)n1-2] | 4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione |
| 31 | 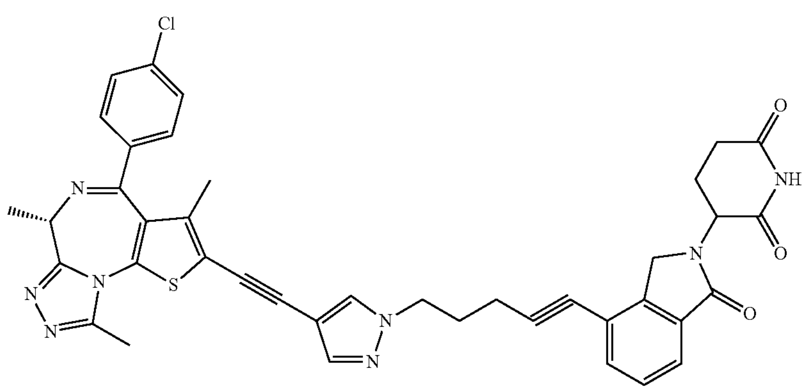 [SMILES: Cc1c(C#Cc2cnn(CCCC#Cc3cccc4c3CN(C3CCC(=O)NC3=O)C4=O)c2)sc2c1C(c1ccc(Cl)cc1)=N[C@@H](C)c1nnc(C)n1-2] | 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione |

TABLE 1-continued

| Cpd. No. | Structure | Name |
|---|---|---|
| 32 | 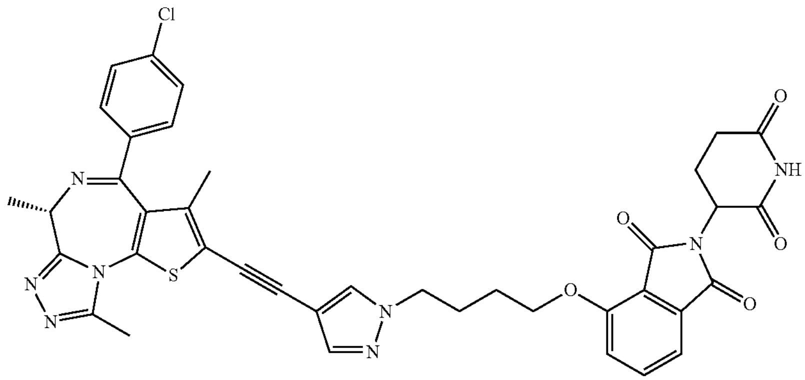 [SMILES: Cc1c(C#Cc2cnn(CCCCOc3cccc4c3C(=O)N(C3CCC(=O)NC3=O)C4=O)c2)sc2c1C(c1ccc(Cl)cc1)=N[C@@H](C)c1nnc(C)n1-2] | 4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione |
| 33 | 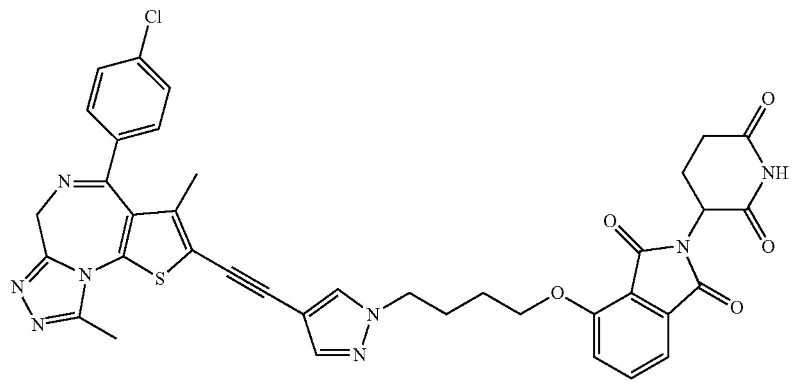 [SMILES: Cc1c(C#Cc2cnn(CCCCOc3cccc4c3C(=O)N(C3CCC(=O)NC3=O)C4=O)c2)sc2c1C(c1ccc(Cl)cc1)=NCc1nnc(C)n1-2] | 4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione |
| 34 | 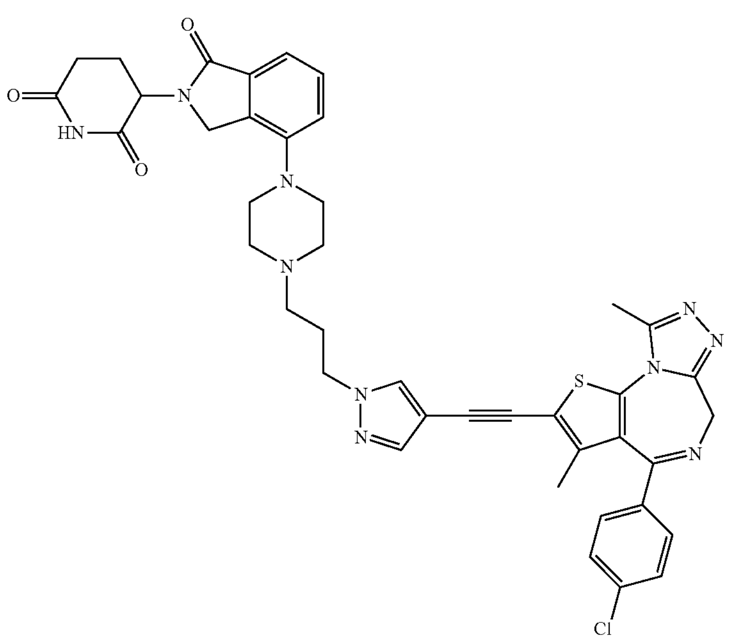 [SMILES: Cc1c(C#Cc2cnn(CCCN3CCN(c4cccc5c4CN(C4CCC(=O)NC4=O)C5=O)CC3)c2)sc2c1C(c1ccc(Cl)cc1)=NCc1nnc(C)n1-2] | 3-(4-(4-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperazin-1-yl)-1-oxoisoindolin-2-yl)piperidine-2,6-dione |

| Cpd. No. | Structure | Name |
|---|---|---|
| 35 | 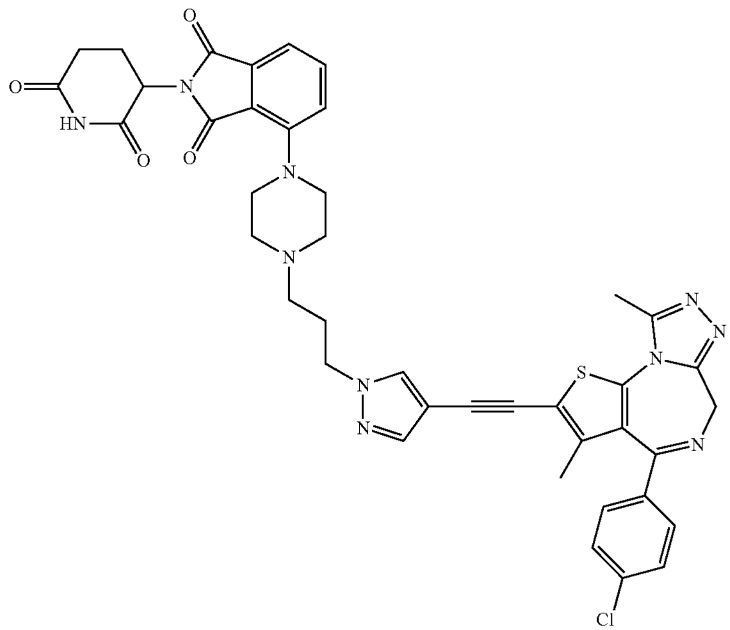 [SMILES: Cc1c(C#Cc2cnn(CCCN3CCN(c4cccc5c4C(=O)N(C4CCC(=O)NC4=O)C5=O)CC3)c2)sc2c1C(c1ccc(Cl)cc1)=NCc1nnc(C)n1-2] | 4-(4-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione |
| 36 | 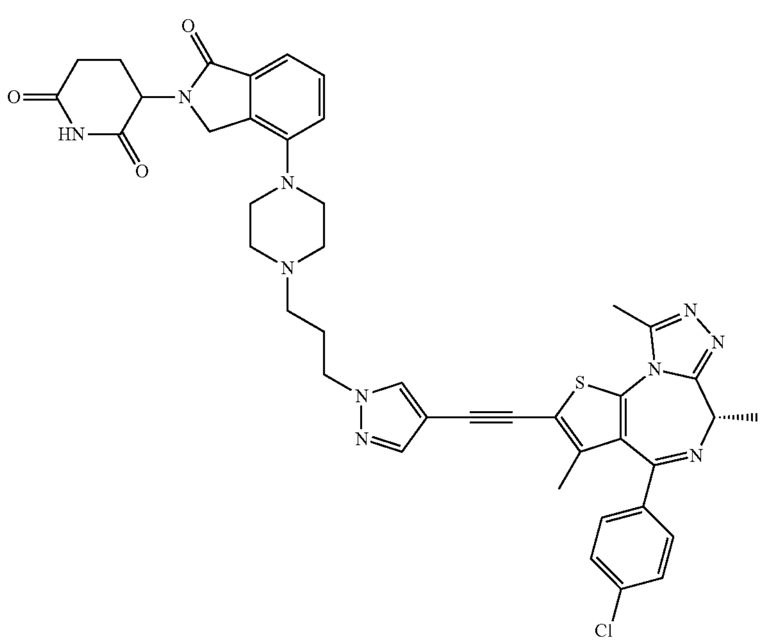 [SMILES: Cc1c(C#Cc2cnn(CCCN3CCN(c4cccc5c4CN(C4CCC(=O)NC4=O)C5=O)CC3)c2)sc2c1C(c1ccc(Cl)cc1)=N[C@@H](C)c1nnc(C)n1-2] | 3-(4-(4-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-1-oxoisoindolin-2-yl)piperidine-2,6-dione |

TABLE 1-continued

| Cpd. No. | Structure | Name |
|---|---|---|
| 37 | 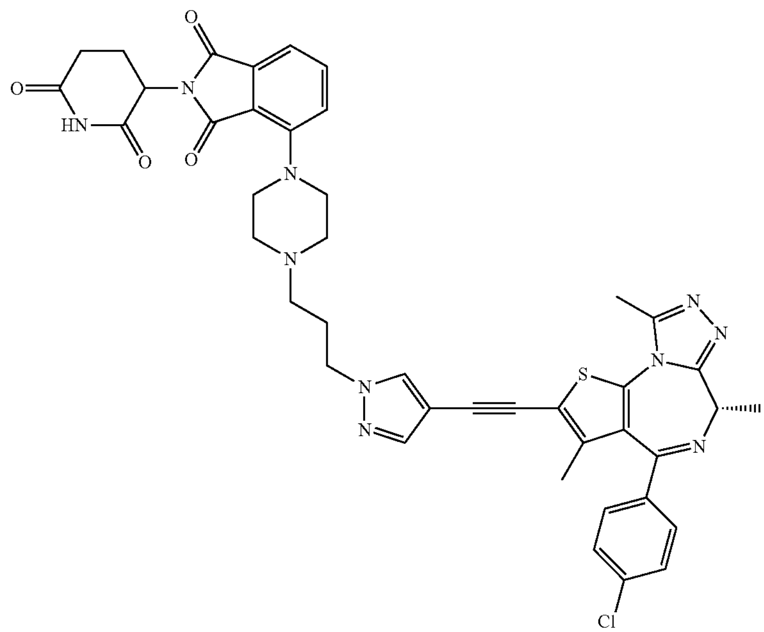 [SMILES: Cc1c(C#Cc2cnn(CCCN3CCN(c4cccc5c4C(=O)N(C4CCC(=O)NC4=O)C5=O)CC3)c2)sc2c1C(c1ccc(Cl)cc1)=N[C@@H](C)c1nnc(C)n1-2] | 4-(4-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione |
| 38 | 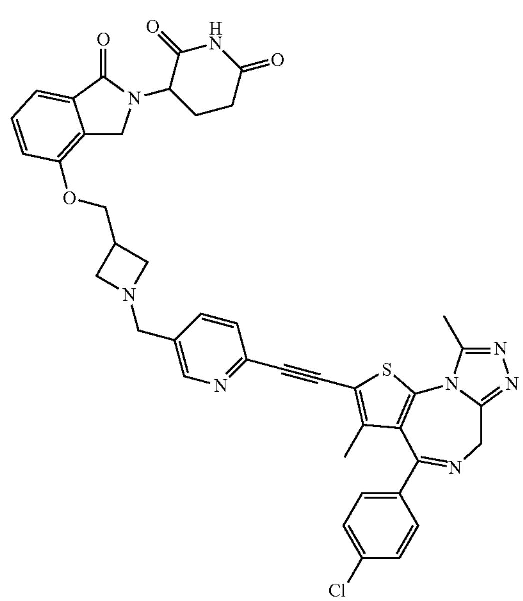 | 3-(4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methoxy)-1-oxoisoindolin-2-yl)piperidine-2,6-dione |

TABLE 1-continued

| Cpd. No. | Structure | Name |
|---|---|---|
| 39 | 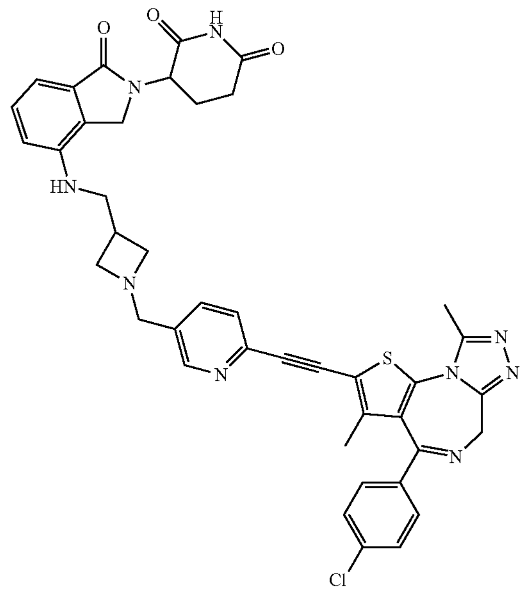 [SMILES: Cc1c(C#Cc2ccc(CN3CC(CNc4cccc5c4CN(C4CCC(=O)NC4=O)C5=O)C3)cn2)sc2c1C(c1ccc(Cl)cc1)=NCc1nnc(C)n1-2] | 3-(4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione |
| 40 | 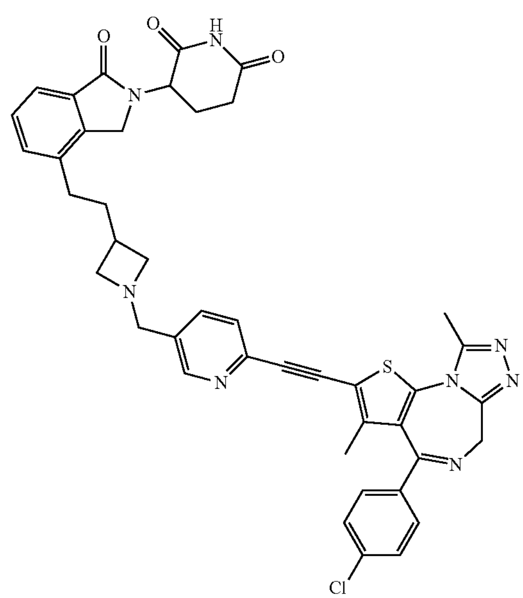 [SMILES: Cc1c(C#Cc2ccc(CN3CC(CCc4cccc5c4CN(C4CCC(=O)NC4=O)C5=O)C3)cn2)sc2c1C(c1ccc(Cl)cc1)=NCc1nnc(C)n1-2] | 3-(4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)ethyl)-1-oxoisoindolin-2-yl)piperidine-2,6-dione |

TABLE 1-continued
| Cpd. No. | Structure | Name |
|---|---|---|
| 41 | 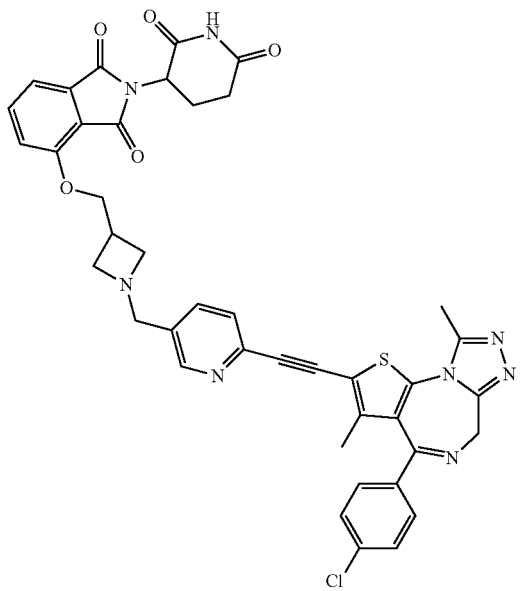 [SMILES: Cc1c(C#Cc2ccc(CN3CC(COc4cccc5c4C(=O)N(C4CCC(=O)NC4=O)C5=O)C3)cn2)sc2c1C(c1ccc(Cl)cc1)=NCc1nnc(C)n1-2] | 4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methoxy)-2-(2,6-dioxopiperidin-3-yl)isoindoline-1,3-dione |
| 42 | 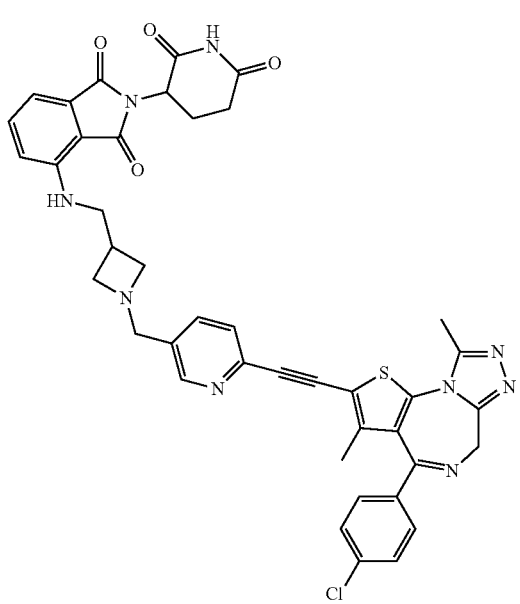 [SMILES: Cc1c(C#Cc2ccc(CN3CC(CNc4cccc5c4C(=O)N(C4CCC(=O)NC4=O)C5=O)C3)cn2)sc2c1C(c1ccc(Cl)cc1)=NCc1nnc(C)n1-2] | 4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methyl)amino)-2-(2,6-dioxopiperidin-3-yl)isoindoline-1,3-dione |

TABLE 1-continued
| Cpd. No. | Structure | Name |
|---|---|---|
| 43 | 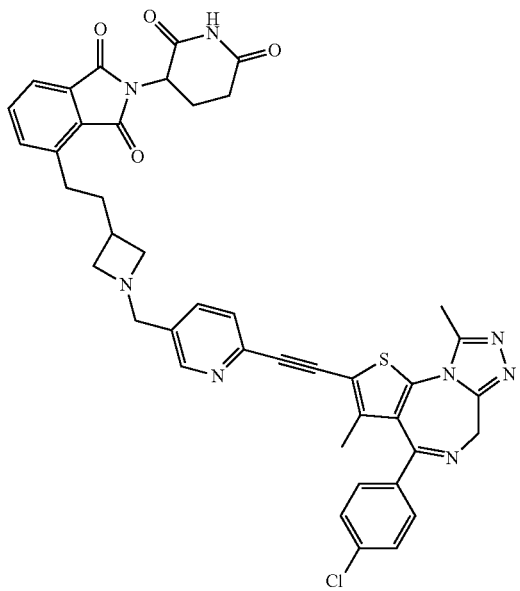 [SMILES: Cc1c(C#Cc2ccc(CN3CC(CCc4cccc5c4C(=O)N(C4CCC(=O)NC4=O)C5=O)C3)cn2)sc2c1C(c1ccc(Cl)cc1)=NCc1nnc(C)n1-2] | 4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)ethyl)-2-(2,6-dioxopiperidin-3-yl)isoindoline-1,3-dione |
| 44 | 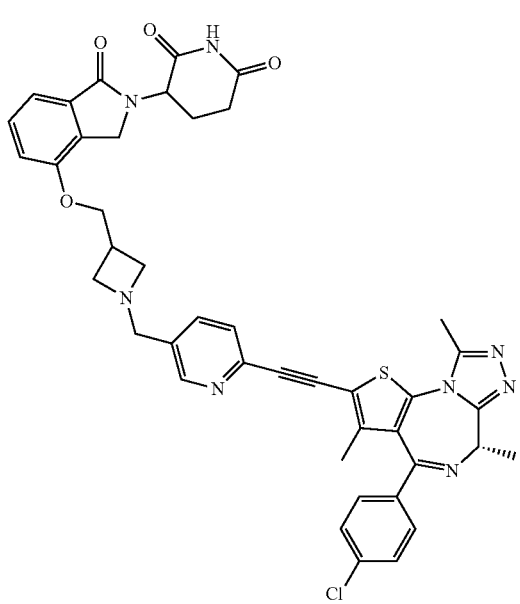 | 3-(4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methoxy)-1-oxoisoindolin-2-yl)piperidine-2,6-dione |

TABLE 1-continued

| Cpd. No. | Structure | Name |
|---|---|---|
| 45 | 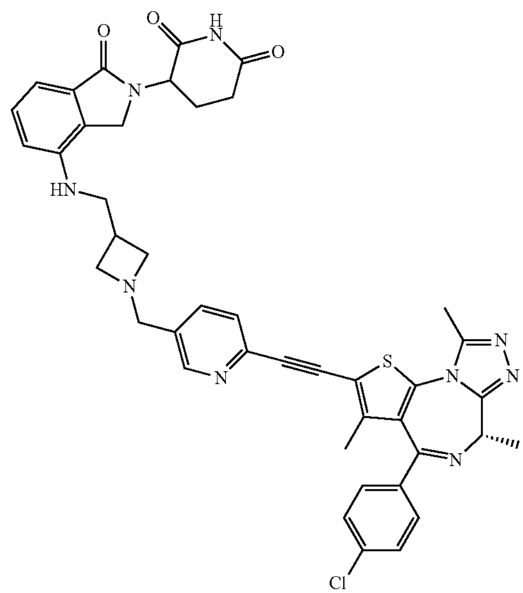 [SMILES: Cc1c(C#Cc2ccc(CN3CC(CNc4cccc5c4CN(C4CCC(=O)NC4=O)C5=O)C3)cn2)sc2c1C(c1ccc(Cl)cc1)=N[C@@H](C)c1nnc(C)n1-2] | 3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione |
| 46 | 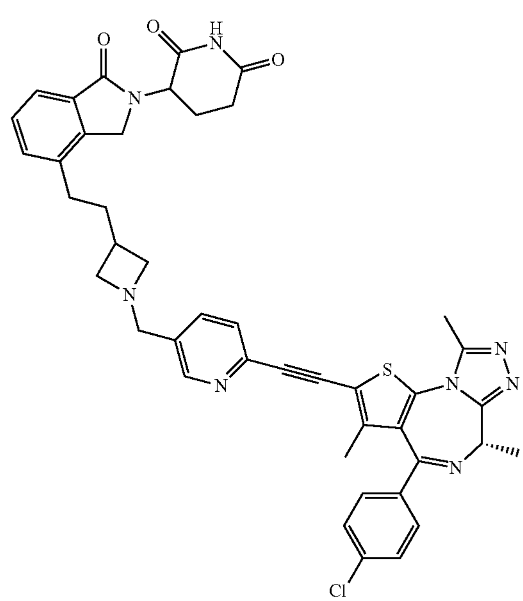 [SMILES: Cc1c(C#Cc2ccc(CN3CC(CCc4cccc5c4CN(C4CCC(=O)NC4=O)C5=O)C3)cn2)sc2c1C(c1ccc(Cl)cc1)=N[C@@H](C)c1nnc(C)n1-2] | 3-(4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)ethyl)-1-oxoisoindolin-2-yl)piperidine-2,6-dione |

TABLE 1-continued
| Cpd. No. | Structure | Name |
|---|---|---|
| 47 | 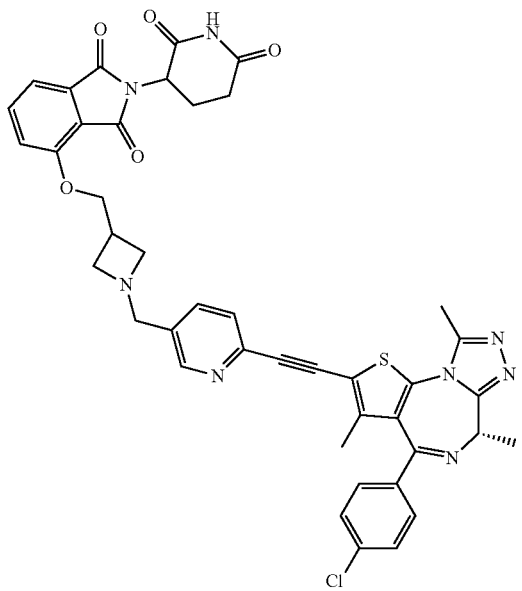 [SMILES: Cc1c(C#Cc2ccc(CN3CC(COc4cccc5c4C(=O)N(C4CCC(=O)NC4=O)C5=O)C3)cn2)sc2c1C(c1ccc(Cl)cc1)=N[C@@H](C)c1nnc(C)n1-2] | 4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methoxy)-2-(2,6-dioxopiperidin-3-yl)isoindoline-1,3-dione |
| 48 | 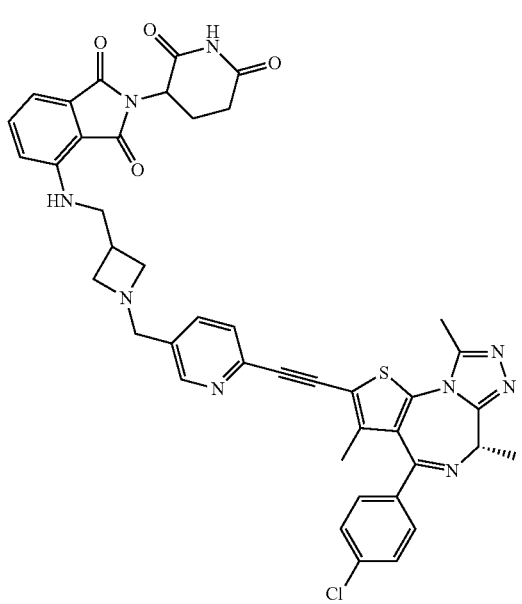 [SMILES: Cc1c(C#Cc2ccc(CN3CC(CNc4cccc5c4C(=O)N(C4CCC(=O)NC4=O)C5=O)C3)cn2)sc2c1C(c1ccc(Cl)cc1)=N[C@@H](C)c1nnc(C)n1-2] | 4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-2-(2,6-dioxopiperidin-3-yl)isoindoline-1,3-dione |

TABLE 1-continued
| Cpd. No. | Structure | Name |
|---|---|---|
| 49 | 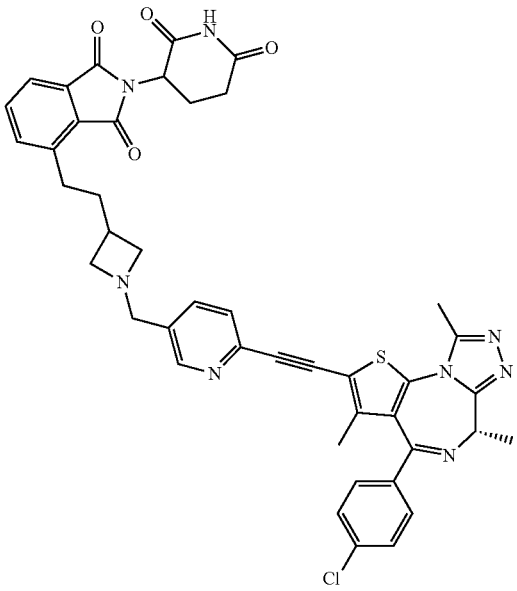 [SMILES: Cc1c(C#Cc2ccc(CN3CC(CCc4cccc5c4C(=O)N(C4CCC(=O)NC4=O)C5=O)C3)cn2)sc2c1C(c1ccc(Cl)cc1)=N[C@@H](C)c1nnc(C)n1-2] | 4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)ethyl)-2-(2,6-dioxopiperidin-3-yl)isoindoline-1,3-dione |
| 50 | 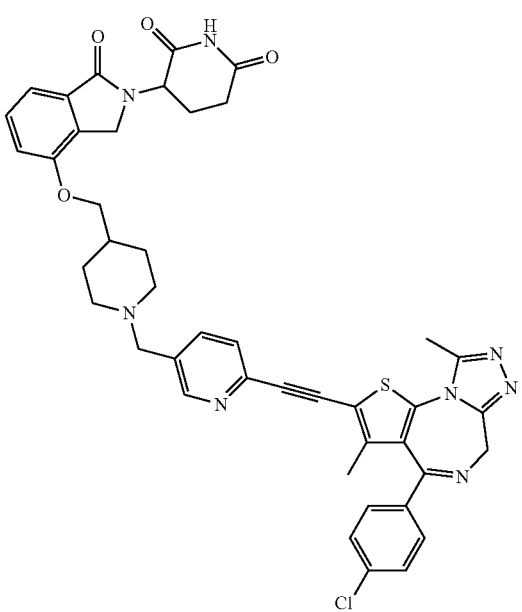 [SMILES: Cc1c(C#Cc2ccc(CN3CCC(COc4cccc5c4CN(C4CCC(=O)NC4=O)C5=O)CC3)cn2)sc2c1C(c1ccc(Cl)cc1)=NCc1nnc(C)n1-2] | 3-(4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methoxy)-1-oxoisoindolin-2-yl)piperidine-2,6-dione |

TABLE 1-continued

| Cpd. No. | Structure | Name |
|---|---|---|
| 51 | 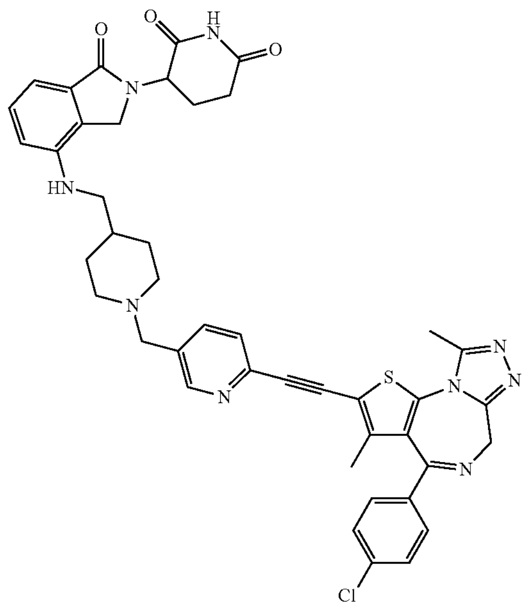 [SMILES: Cc1c(C#Cc2ccc(CN3CCC(CNc4cccc5c4CN(C4CCC(=O)NC4=O)C5=O)CC3)cn2)sc2c1C(c1ccc(Cl)cc1)=NCc1nnc(C)n1-2] | 3-(4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione |
| 52 | 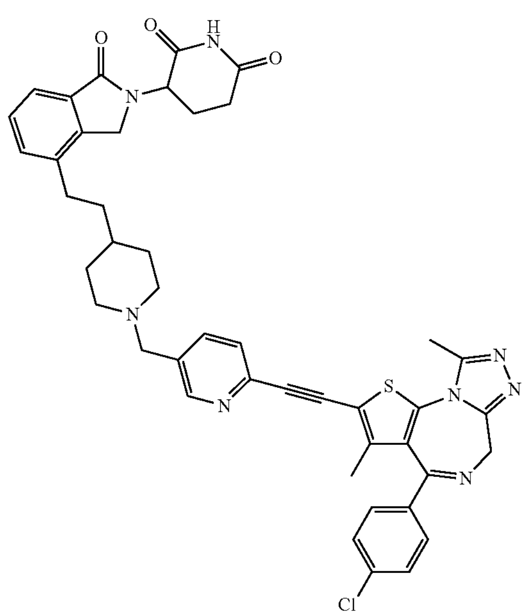 [SMILES: Cc1c(C#Cc2ccc(CN3CCC(CCc4cccc5c4CN(C4CCC(=O)NC4=O)C5=O)CC3)cn2)sc2c1C(c1ccc(Cl)cc1)=NCc1nnc(C)n1-2] | 3-(4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)ethyl)-1-oxoisoindolin-2-yl)piperidine-2,6-dione |

TABLE 1-continued
| Cpd. No. | Structure | Name |
|---|---|---|
| 53 | 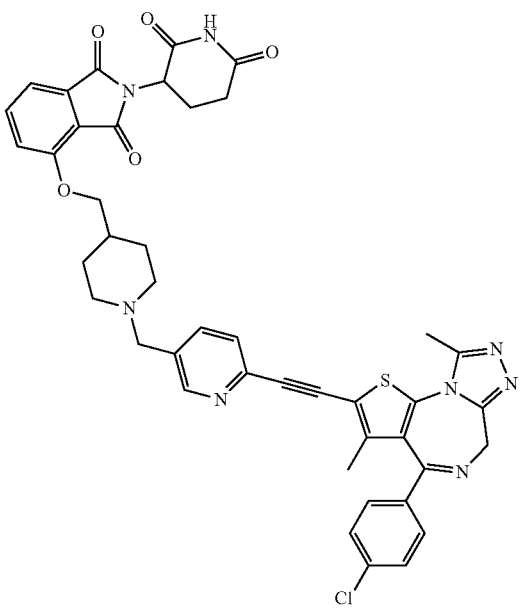 [SMILES: Cc1c(C#Cc2ccc(CN3CCC(COc4cccc5c4C(=O)N(C4CCC(=O)NC4=O)C5=O)CC3)cn2)sc2c1C(c1ccc(Cl)cc1)=NCc1nnc(C)n1-2] | 4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methoxy)-2-(2,6-dioxopiperidin-3-yl)isoindoline-1,3-dione |
| 54 | 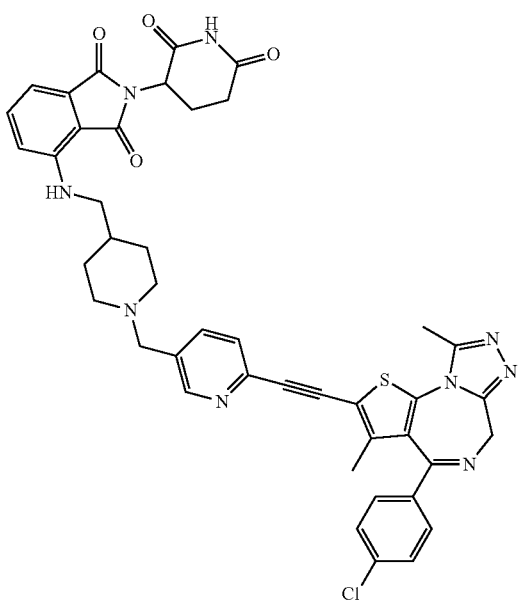 [SMILES: Cc1c(C#Cc2ccc(CN3CCC(CNc4cccc5c4C(=O)N(C4CCC(=O)NC4=O)C5=O)CC3)cn2)sc2c1C(c1ccc(Cl)cc1)=NCc1nnc(C)n1-2] | 4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-2-(2,6-dioxopiperidin-3-yl)isoindoline-1,3-dione |

TABLE 1-continued
| Cpd. No. | Structure | Name |
|---|---|---|
| 55 | 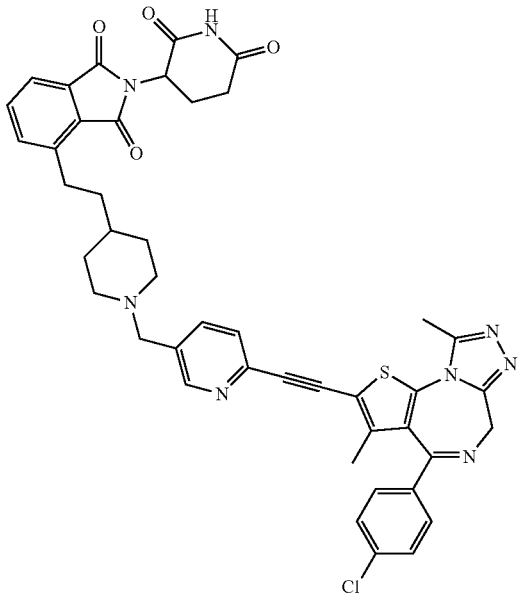 [SMILES: Cc1c(C#Cc2ccc(CN3CCC(CCc4cccc5c4C(=O)N(C4CCC(=O)NC4=O)C5=O)CC3)cn2)sc2c1C(c1ccc(Cl)cc1)=NCc1nnc(C)n1-2] | 4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)ethyl)-2-(2,6-dioxopiperidin-3-yl)isoindoline-1,3-dione |
| 56 | 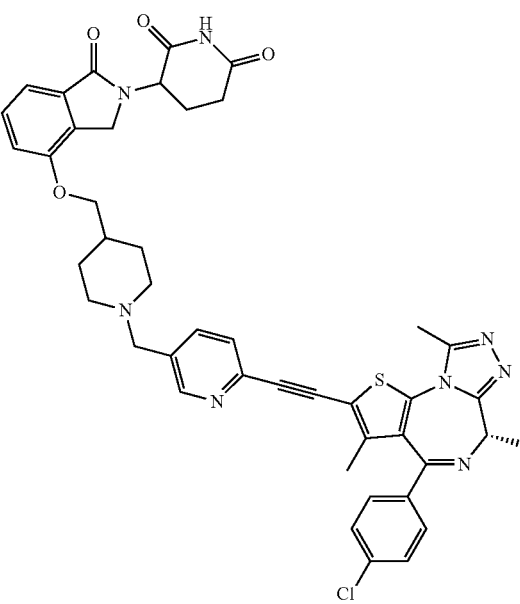 | 3-(4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methoxy)-1-oxoisoindolin-2-yl)piperidine-2,6-dione |

TABLE 1-continued
| Cpd. No. | Structure | Name |
|---|---|---|
| 57 | 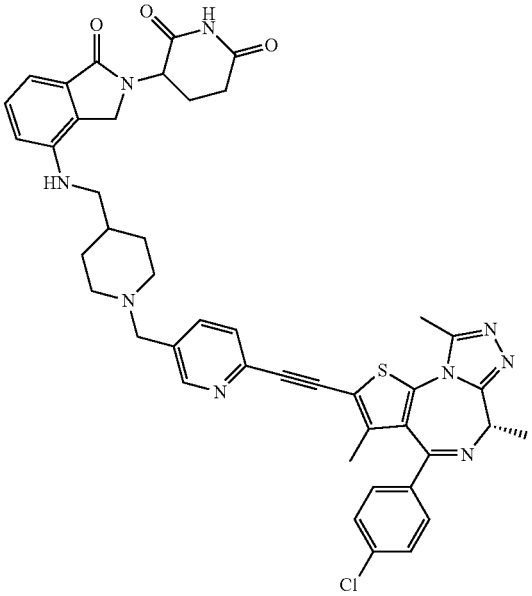 [SMILES: Cc1c(C#Cc2ccc(CN3CCC(CNc4cccc5c4CN(C4CCC(=O)NC4=O)C5=O)CC3)cn2)sc2c1C(c1ccc(Cl)cc1)=N[C@@H](C)c1nnc(C)n1-2] | 3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione |
| 58 | 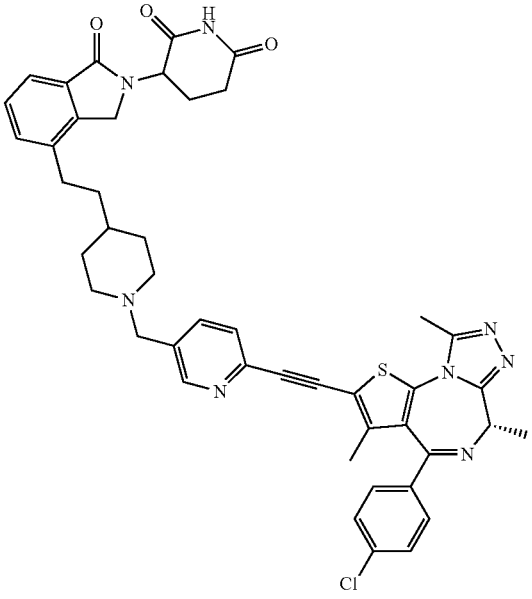 [SMILES: Cc1c(C#Cc2ccc(CN3CCC(CCc4cccc5c4CN(C4CCC(=O)NC4=O)C5=O)CC3)cn2)sc2c1C(c1ccc(Cl)cc1)=N[C@@H](C)c1nnc(C)n1-2] | 3-(4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)ethyl)-1-oxoisoindolin-2-yl)piperidine-2,6-dione |

TABLE 1-continued
| Cpd. No. | Structure | Name |
|---|---|---|
| 59 | 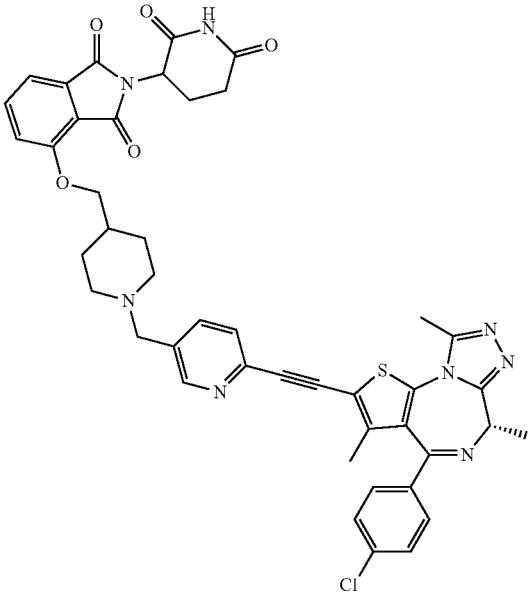 [SMILES: Cc1c(C#Cc2ccc(CN3CCC(COc4cccc5c4C(=O)N(C4CCC(=O)NC4=O)C5=O)CC3)cn2)sc2c1C(c1ccc(Cl)cc1)=N[C@@H](C)c1nnc(C)n1-2] | 4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methoxy)-2-(2,6-dioxopiperidin-3-yl)isoindoline-1,3-dione |
| 60 | 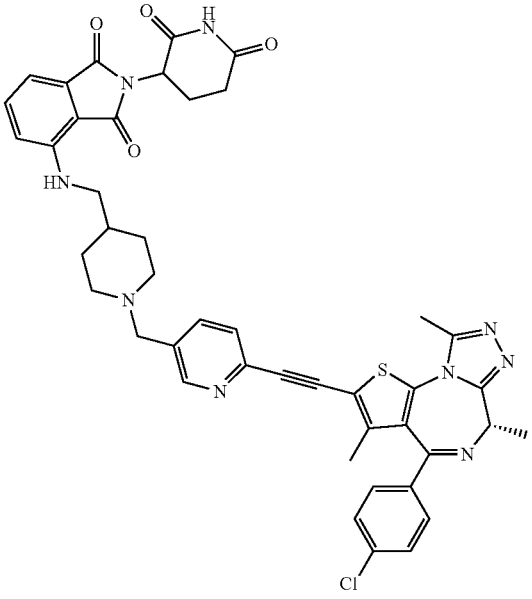 [SMILES: Cc1c(C#Cc2ccc(CN3CCC(CNc4cccc5c4C(=O)N(C4CCC(=O)NC4=O)C5=O)CC3)cn2)sc2c1C(c1ccc(Cl)cc1)=N[C@@H](C)c1nnc(C)n1-2] | 4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-2-(2,6-dioxopiperidin-3-yl)isoindoline-1,3-dione |

TABLE 1-continued

| Cpd. No. | Structure | Name |
|---|---|---|
| 61 | 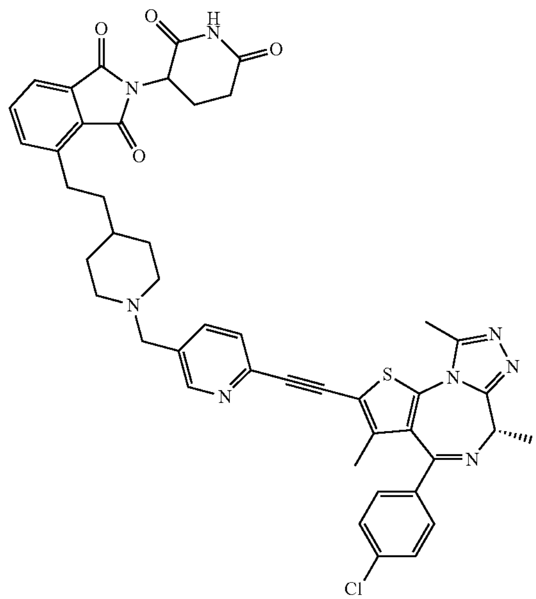 [SMILES: Cc1c(C#Cc2ccc(CN3CCC(CCc4cccc5c4C(=O)N(C4CCC(=O)NC4=O)C5=O)CC3)cn2)sc2c1C(c1ccc(Cl)cc1)=N[C@@H](C)c1nnc(C)n1-2] | 4-(2-(1-(((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)ethyl)-2-(2,6-dioxopiperidin-3-yl)isoindoline-1,3-dione |
| 62 | 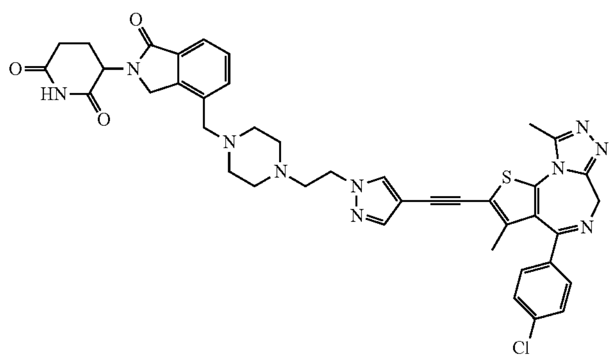 [SMILES: Cc1c(C#Cc2cnn(CCN3CCN(Cc4cccc5c4CN(C4CCC(=O)NC4=O)C5=O)CC3)c2)sc2c1C(c1ccc(Cl)cc1)=NCc1nnc(C)n1-2] | 3-(4-((4-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-1-oxoisoindolin-2-yl)piperidine-2,6-dione |
| 63 | 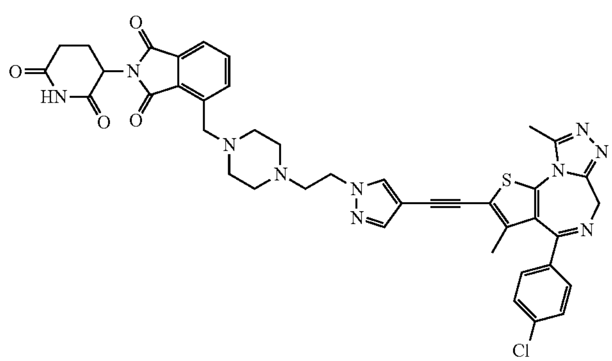 [SMILES: Cc1c(C#Cc2cnn(CCN3CCN(Cc4cccc5c4C(=O)N(C4CCC(=O)NC4=O)C5=O)CC3)c2)sc2c1C(c1ccc(Cl)cc1)=NCc1nnc(C)n1-2] | 4-((4-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-2-(2,6-dioxopiperidin-3-yl)isoindoline-1,3-dione |

TABLE 1-continued

| Cpd. No. | Structure | Name |
|---|---|---|
| 64 | 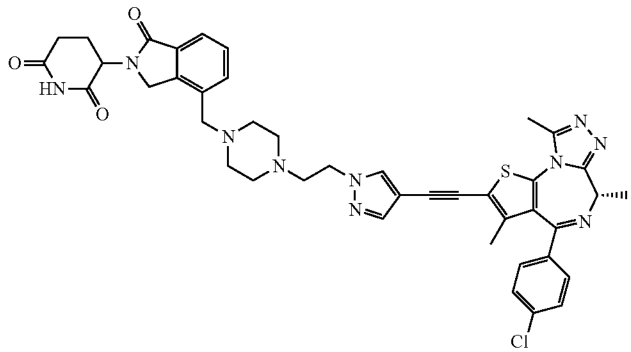 [SMILES: Cc1c(C#Cc2cnn(CCN3CCN(Cc4cccc5c4CN(C4CCC(=O)NC4=O)C5=O)CC3)c2)sc2c1C(c1ccc(Cl)cc1)=N[C@@H](C)c1nnc(C)n1-2] | 3-(4-((4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-1-oxoisoindolin-2-yl)piperidine-2,6-dione |
| 65 | 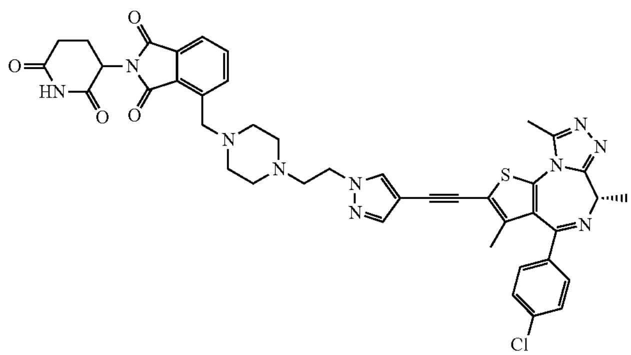 [SMILES: Cc1c(C#Cc2cnn(CCN3CCN(Cc4cccc5c4C(=O)N(C4CCC(=O)NC4=O)C5=O)CC3)c2)sc2c1C(c1ccc(Cl)cc1)=N[C@@H](C)c1nnc(C)n1-2] | 4-((4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-2-(2,6-dioxopiperidin-3-yl)isoindoline-1,3-dione |
| 66 | 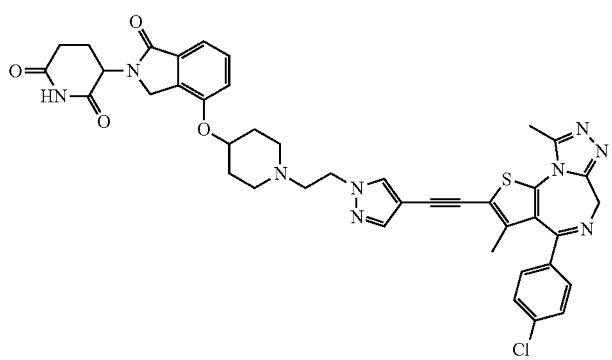 [SMILES: Cc1c(C#Cc2cnn(CCN3CCC(Oc4cccc5c4CN(C4CCC(=O)NC4=O)C5=O)CC3)c2)sc2c1C(c1ccc(Cl)cc1)=NCc1nnc(C)n1-2] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione |
| 67 | 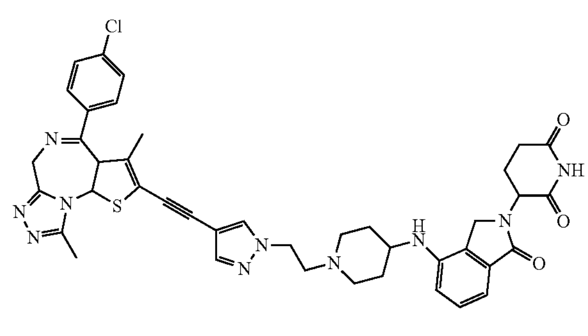 [SMILES: CC1=C(C#Cc2cnn(CCN3CCC(Nc4cccc5c4CN(C4CCC(=O)NC4=O)C5=O)CC3)c2)SC2C1C(c1ccc(Cl)cc1)=NCc1nnc(C)n12] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione |

TABLE 1-continued

| Cpd. No. | Structure | Name |
| --- | --- | --- |
| 68 | 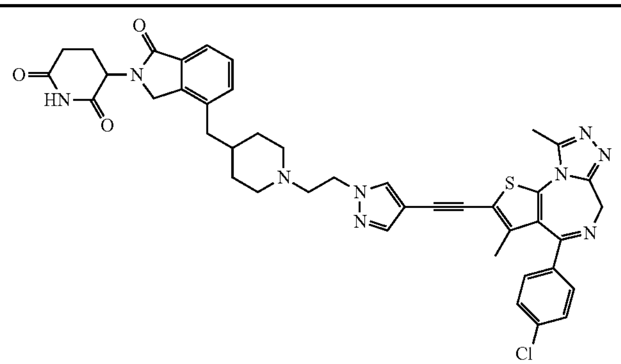 | 3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-1-oxoisoindolin-2-yl)piperidine-2,6-dione |
| 69 | 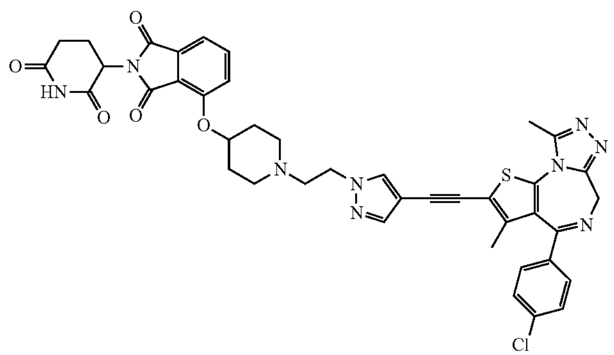 [SMILES: Cc1c(C#Cc2cnn(CCN3CCC(Oc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione |
| 70 | 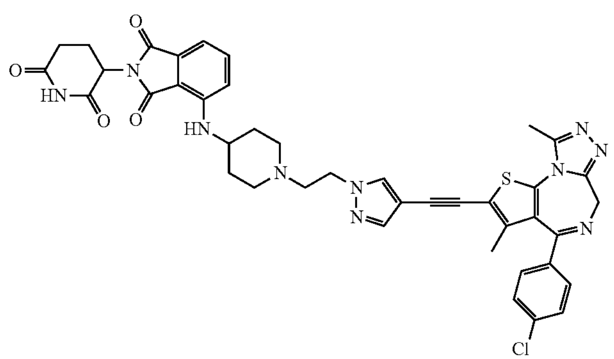 [SMILES: Cc1c(C#Cc2cnn(CCN3CCC(Nc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione |
| 71 | 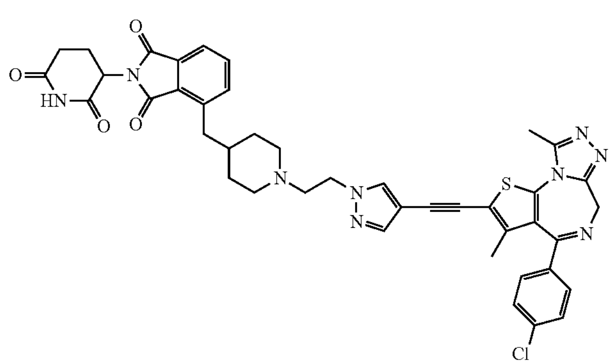 [SMILES: Cc1c(C#Cc2cnn(CCN3CCC(Cc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-2-(2,6-dioxopiperidin-3-yl)isoindoline-1,3-dione |

TABLE 1-continued

| Cpd. No. | Structure | Name |
|---|---|---|
| 72 | 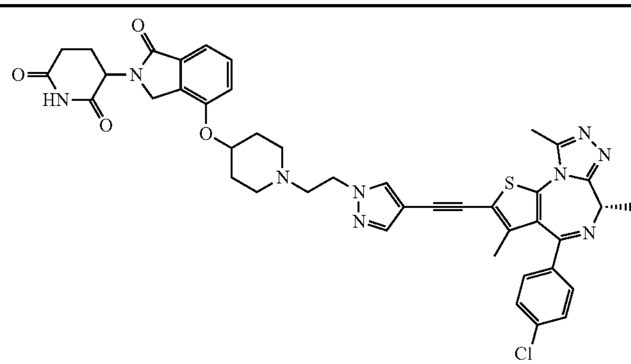 | 3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione |
| 73 | 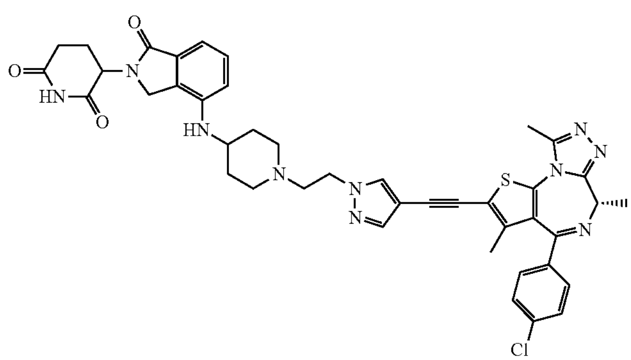 [SMILES: Cc1c(C#Cc2cnn(CCN3CCC(Nc4cccc5c4CN(C4CCC(=O)NC4=O)C5=O)CC3)c2)sc2c1C(c1ccc(Cl)cc1)=N[C@@H](C)c1nnc(C)n1-2] | 3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione |
| 74 | 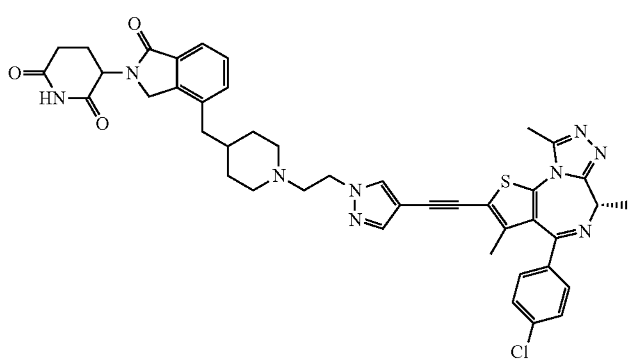 [SMILES: Cc1c(C#Cc2cnn(CCN3CCC(Cc4cccc5c4CN(C4CCC(=O)NC4=O)C5=O)CC3)c2)sc2c1C(c1ccc(Cl)cc1)=N[C@@H](C)c1nnc(C)n1-2] | 3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-1-oxoisoindolin-2-yl)piperidine-2,6-dione |
| 75 | 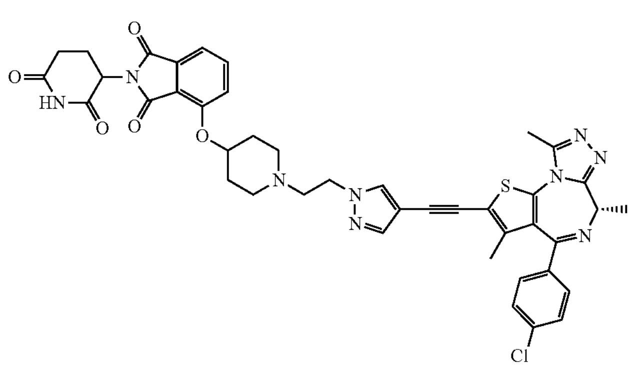 [SMILES: Cc1c(C#Cc2cnn(CCN3CCC(Oc4cccc5c4C(=O)N(C4CCC(=O)NC4=O)C5=O)CC3)c2)sc2c1C(c1ccc(Cl)cc1)=N[C@@H](C)c1nnc(C)n1-2] | 4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione |

TABLE 1-continued

| Cpd. No. | Structure | Name |
|---|---|---|
| 76 | 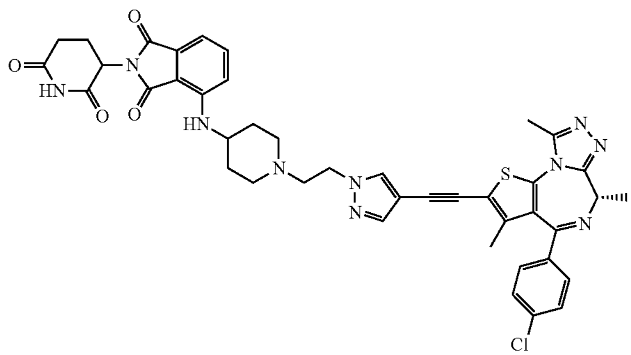 [SMILES: Cc1c(C#Cc2cnn(CCN3CCC(Nc4cccc5c4C(=O)N(C4CCC(=O)NC4=O)C5=O)CC3)c2)sc2c1C(c1ccc(Cl)cc1)=N[C@@H](C)c1nnc(C)n1-2] | 4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione |
| 77 | 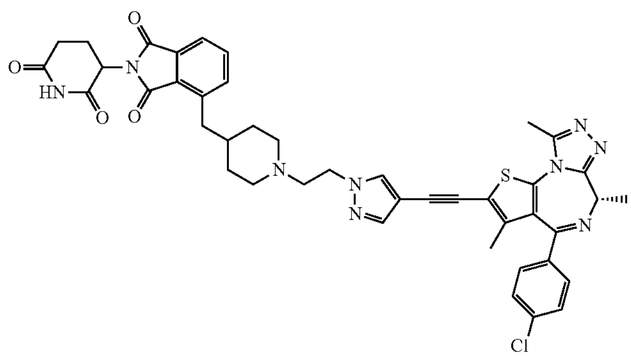 [SMILES: Cc1c(C#Cc2cnn(CCN3CCC(Cc4cccc5c4C(=O)N(C4CCC(=O)NC4=O)C5=O)CC3)c2)sc2c1C(c1ccc(Cl)cc1)=N[C@@H](C)c1nnc(C)n1-2] | 4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-2-(2,6-dioxopiperidin-3-yl)isoindoline-1,3-dione |
| 78 | 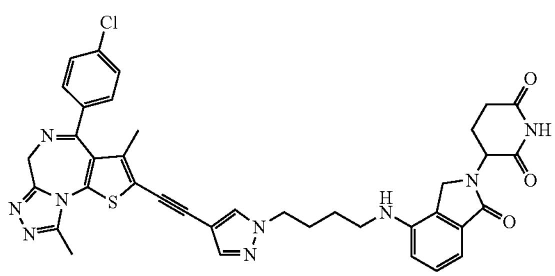 [SMILES: Cc1c(C#Cc2cnn(CCCCNc3cccc4c3CN(C3CCC(=O)NC3=O)C4=O)c2)sc2c1C(c1ccc(Cl)cc1)=NCc1nnc(C)n1-2] | 3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione |
| 79 | 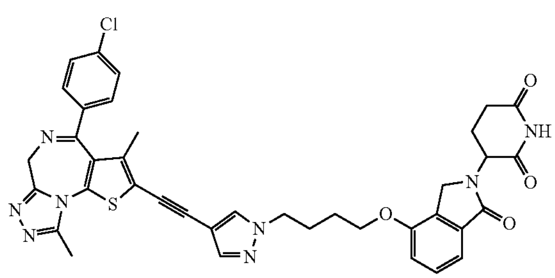 [SMILES: Cc1c(C#Cc2cnn(CCCCOc3cccc4c3CN(C3CCC(=O)NC3=O)C4=O)c2)sc2c1C(c1ccc(Cl)cc1)=NCc1nnc(C)n1-2] | 3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione |
| 80 | 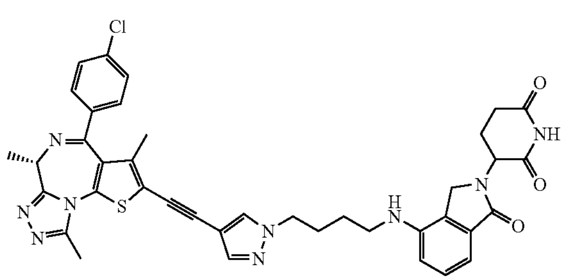 [SMILES: Cc1c(C#Cc2cnn(CCCCNc3cccc4c3CN(C3CCC(=O)NC3=O)C4=O)c2)sc2c1C(c1ccc(Cl)cc1)=N[C@@H](C)c1nnc(C)n1-2] | 3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione |

| Cpd. No. | Structure | Name |
|---|---|---|
| 81 | 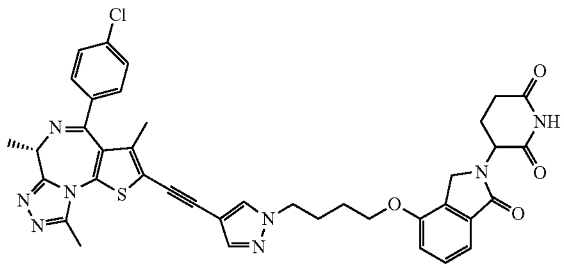 [SMILES: Cc1c(C#Cc2cnn(CCCCOc3cccc4c3CN(C3CCC(=O)NC3=O)C4=O)c2)sc2c1C(c1ccc(Cl)cc1)=N[C@@H](C)c1nnc(C)n1-2] | 3-(4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione |
| 82 | 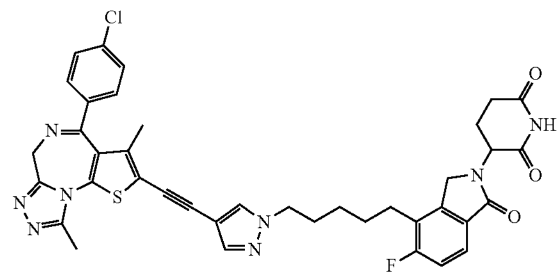 [SMILES: Cc1c(C#Cc2cnn(CCCCCc3c(F)ccc4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-5-fluoro-1-oxoisoindolin-2-yl)piperidine-2,6-dione |
| 83 | 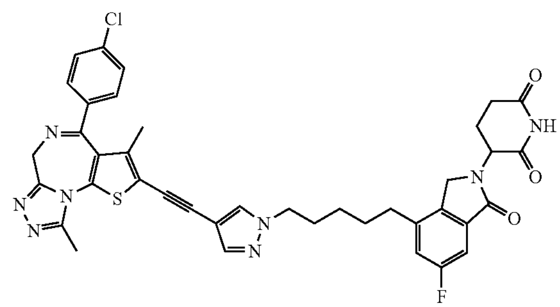 [SMILES: Cc1c(C#Cc2cnn(CCCCCc3cc(F)cc4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-6-fluoro-1-oxoisoindolin-2-yl)piperidine-2,6-dione |
| 84 | 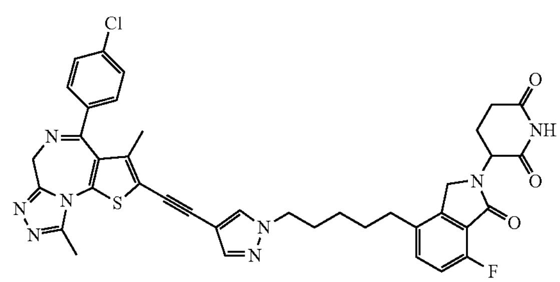 [SMILES: Cc1c(C#Cc2cnn(CCCCCc3ccc(F)c4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-7-fluoro-1-oxoisoindolin-2-yl)piperidine-2,6-dione |
| 85 | 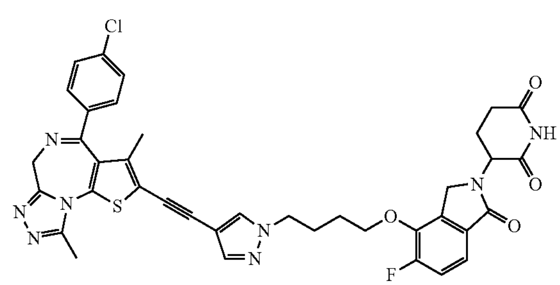 [SMILES: Cc1c(C#Cc2cnn(CCCCOc3c(F)ccc4c3CN(C3CCC(=O)NC3=O)C4=O)c2)sc2c1C(c1ccc(Cl)cc1)=NCc1nnc(C)n1-2] | 3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-5-fluoro-1-oxoisoindolin-2-yl)piperidine-2,6-dione |

TABLE 1-continued

| Cpd. No. | Structure | Name |
|---|---|---|
| 86 | 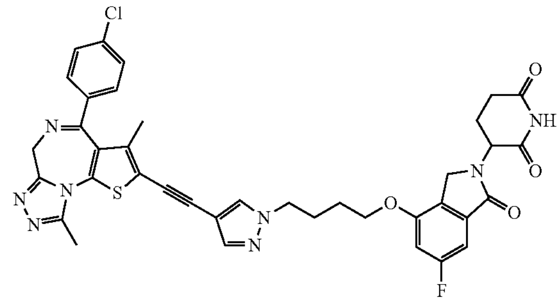 [SMILES: Cc1c(C#Cc2cnn(CCCCOc3cc(F)cc4c3CN(C3CCC(=O)NC3=O)C4=O)c2)sc2c1C(c1ccc(Cl)cc1)=NCc1nnc(C)n1-2] | 3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-6-fluoro-1-oxoisoindolin-2-yl)piperidine-2,6-dione |
| 87 | 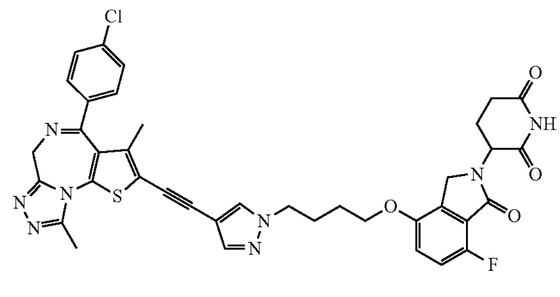 [SMILES: Cc1c(C#Cc2cnn(CCCCOc3ccc(F)c4c3CN(C3CCC(=O)NC3=O)C4=O)c2)sc2c1C(c1ccc(Cl)cc1)=NCc1nnc(C)n1-2] | 3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-7-fluoro-1-oxoisoindolin-2-yl)piperidine-2,6-dione |
| 88 | 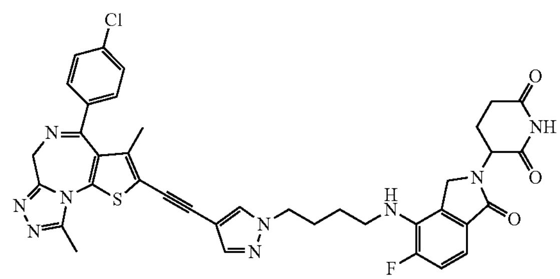 [SMILES: Cc1c(C#Cc2cnn(CCCCNc3c(F)ccc4c3CN(C3CCC(=O)NC3=O)C4=O)c2)sc2c1C(c1ccc(Cl)cc1)=NCc1nnc(C)n1-2] | 3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-5-fluoro-1-oxoisoindolin-2-yl)piperidin-2,6-dione |
| 89 | 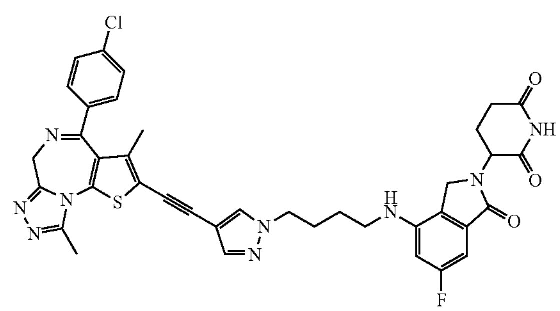 [SMILES: Cc1c(C#Cc2cnn(CCCCNc3cc(F)cc4c3CN(C3CCC(=O)NC3=O)C4=O)c2)sc2c1C(c1ccc(Cl)cc1)=NCc1nnc(C)n1-2] | 3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-6-fluoro-1-oxoisoindolin-2-yl)piperidine-2,6-dione |
| 90 | 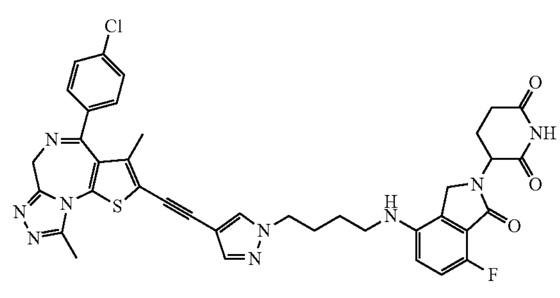 [SMILES: Cc1c(C#Cc2cnn(CCCCNc3ccc(F)c4c3CN(C3CCC(=O)NC3=O)C4=O)c2)sc2c1C(c1ccc(Cl)cc1)=NCc1nnc(C)n1-2] | 3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-7-fluoro-1-oxoisoindolin-2-yl)piperidine-2,6-dione |

TABLE 1-continued

| Cpd. No. | Structure | Name |
|---|---|---|
| 91 | 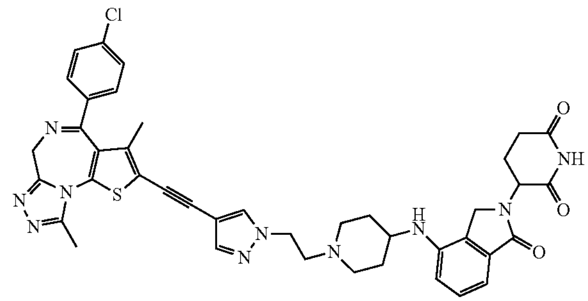 [SMILES: Cc1c(C#Cc2cnn(CCN3CCC(Nc4cccc5c4CN(C4CCC(=O)NC4=O)C5=O)CC3)c2)sc2c1C(c1ccc(Cl)cc1)=NCc1nnc(C)n1-2] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione |
| 92 | 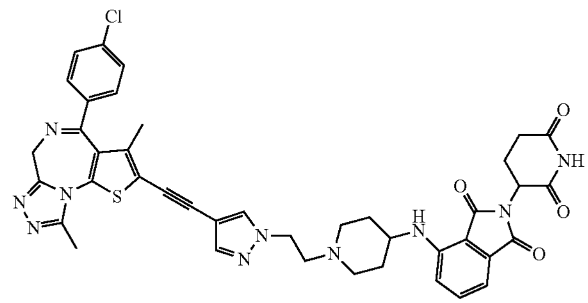 [SMILES: Cc1c(C#Cc2cnn(CCN3CCC(Nc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione |
| 93 | 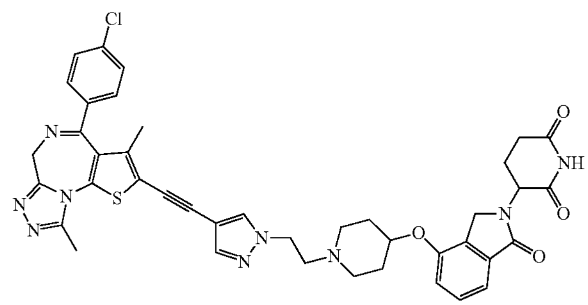 | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione |
| 94 | 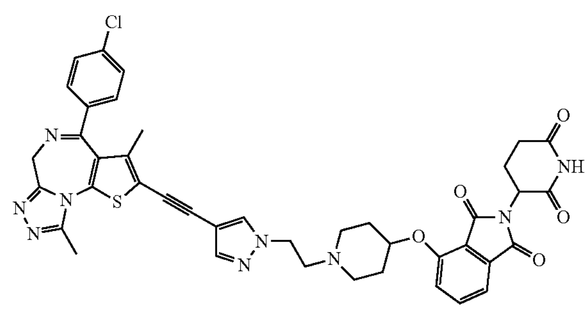 [SMILES: Cc1c(C#Cc2cnn(CCN3CCC(Oc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione |
| 95 | 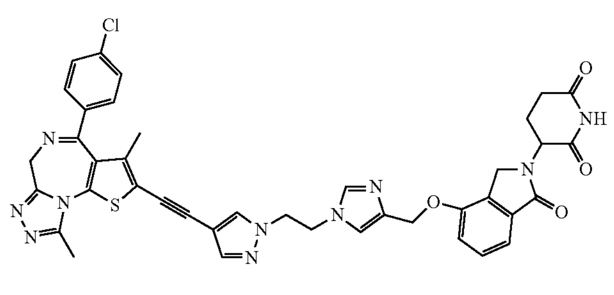 [SMILES: Cc1c(C#Cc2cnn(CCn3cnc(COc4cccc5c4CN(C4CCC(=O)NC4=O)C5=O)c3)c2)sc2c1C(c1ccc(Cl)cc1)=NCc1nnc(C)n1-2] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione |

TABLE 1-continued

| Cpd. No. | Structure | Name |
|---|---|---|
| 96 | 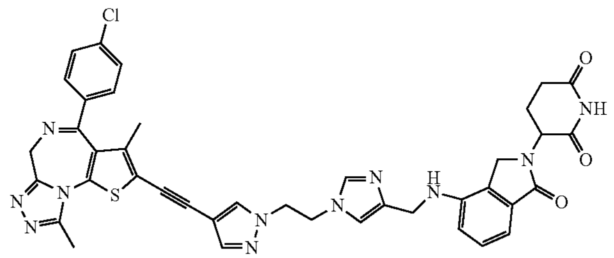 [SMILES: Cc1c(C#Cc2cnn(CCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione |
| 97 | 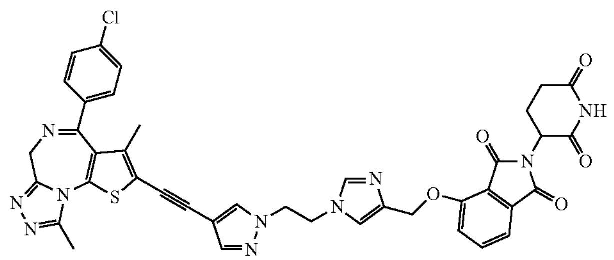 [SMILES: Cc1c(C#Cc2cnn(CCn3cnc(COc4cccc5c4C(=O)N(C4CCC(=O)NC4=O)C5=O)c3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-2-(2,6-dioxopiperidin-3-yl)isoindoline-1,3-dione |
| 98 | 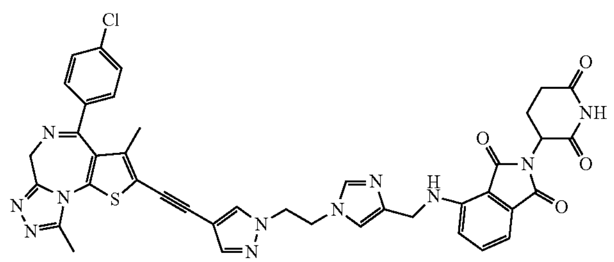 [SMILES: Cc1c(C#Cc2cnn(CCn3cnc(CNc4cccc5c4C(=O)N(C4CCC(=O)NC4=O)C5=O)c3)c2)sc2c1C(c1ccc(Cl)cc1)=NCc1nnc(C)n1-2] | 4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-2-(2,6-dioxopiperidin-3-yl)isoindoline-1,3-dione |
| 99 | 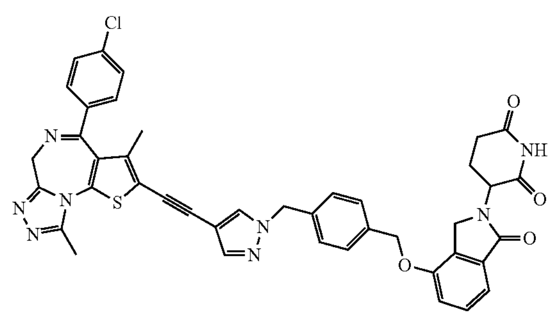 [SMILES: Cc1c(C#Cc2cnn(Cc3ccc(COc4cccc5c4CN(C4CCC(=O)NC4=O)C5=O)cc3)c2)sc2c1C(c1ccc(Cl)cc1)=NCc1nnc(C)n1-2] | 3-(4-((4-((4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)oxy)-1-oxoisoindolin-2-yl)piperidine-2,6-dione |
| 100 | 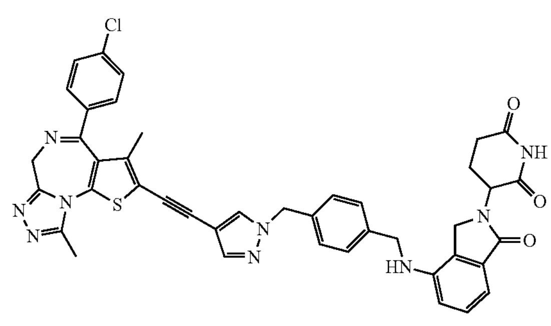 [SMILES: Cc1c(C#Cc2cnn(Cc3ccc(CNc4cccc5c4CN(C4CCC(=O)NC4=O)C5=O)cc3)c2)sc2c1C(c1ccc(Cl)cc1)=NCc1nnc(C)n1-2] | 3-(4-((4-((4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)amino)-1-oxoisoindolin-2-yl)piperidine-2,6-dione |

TABLE 1-continued

| Cpd. No. | Structure | Name |
|---|---|---|
| 101 | 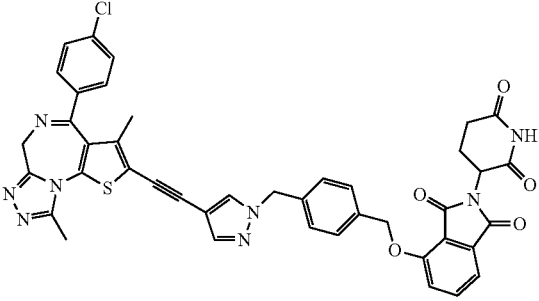 [SMILES: Cc1c(C#Cc2cnn(Cc3ccc(COc4cccc5c4C(=O)N(C4CCC(=O)NC4=O)C5=O)cc3)c2)sc2c1C(c1ccc(Cl)cc1)=NCc1nnc(C)n1-2] | 4-((4-((4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)oxy)-2-(2,6-dioxopiperidin-3-yl)isoindoline-1,3-dione |
| 102 | 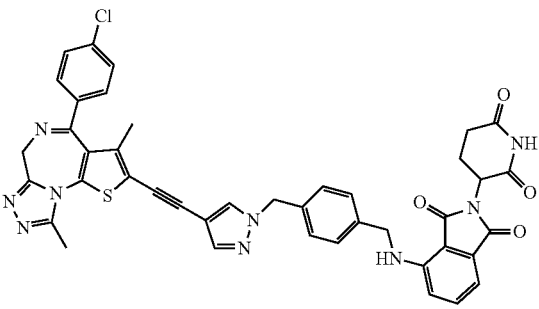 [SMILES: Cc1c(C#Cc2cnn(Cc3ccc(CNc4cccc5c4C(=O)N(C4CCC(=O)NC4=O)C5=O)cc3)c2)sc2c1C(c1ccc(Cl)cc1)=NCc1nnc(C)n1-2] | 4-((4-((4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)amino)-2-(2,6-dioxoipieridin-3-yl)isoindoline-1,3-dione |
| 103 | 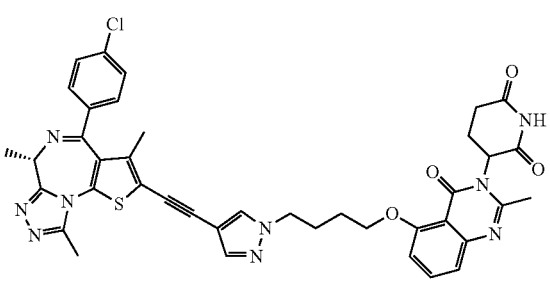 [SMILES: Cc1c(C#Cc2cnn(CCCCOc3cccc4nc(C)n(C5CCC(=O)NC5=O)c(=O)c34)c2)sc2c1C(c1ccc(Cl)cc1)=N[C@@H](C)c1nnc(C)n1-2] | 3-(5-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-2-methyl-4-oxoquinazolin-3(4H)-yl)piperidine-2,6-dione |
| 104 | 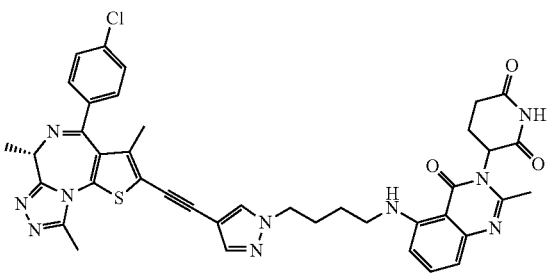 [SMILES: Cc1c(C#Cc2cnn(CCCCNc3cccc4nc(C)n(C5CCC(=O)NC5=O)c(=O)c34)c2)sc2c1C(c1ccc(Cl)cc1)=N[C@@H](C)c1nnc(C)n1-2] | 3-(5-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-2-methyl-4-oxoquinazolin-3(4H)-yl)piperidine-2,6-dione |
| 105 | 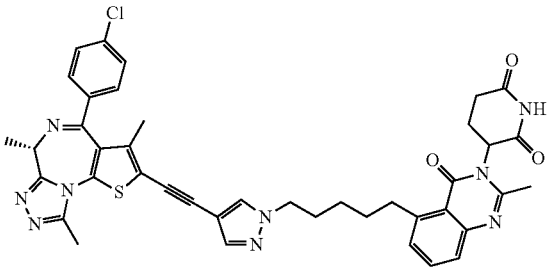 [SMILES: Cc1c(C#Cc2cnn(CCCCCc3cccc4nc(C)n(C5CCC(=O)NC5=O)c(=O)c34)c2)sc2c1C(c1ccc(Cl)cc1)=N[C@@H](C)c1nnc(C)n1-2] | 3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-2-methyl-4-oxoquinazolin-3(4H)-yl)piperidine-2,6-dione |

| Cpd. No. | Structure | Name |
|---|---|---|
| 106 | 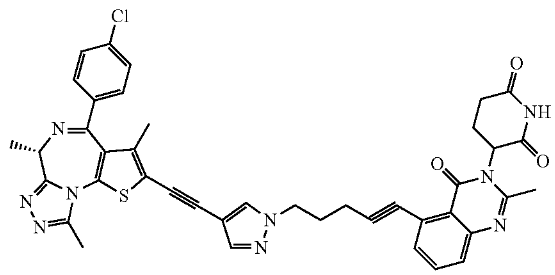 [SMILES: Cc1c(C#Cc2cnn(CCCC#Cc3cccc4nc(C)n(C5CCC(=O)NC5=O)c(=O)c34)c2)sc2c1C(c1ccc(Cl)cc1)=N[C@@H](C)c1nnc(C)n1-2] | 3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-methyl-4-oxoquinazolin-3(4H)-yl)piperidine-2,6-dione |
| 107 | 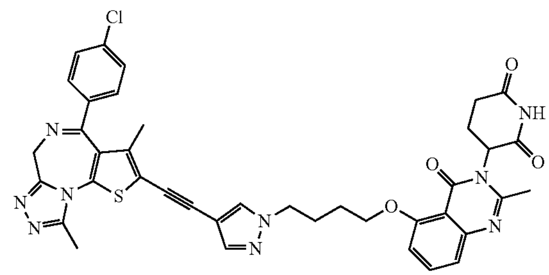 [SMILES: Cc1c(C#Cc2cnn(CCCCOc3cccc4nc(C)n(C5CCC(=O)NC5=O)c(=O)c34)c2)sc2c1C(c1ccc(Cl)cc1)=NCc1nnc(C)n1-2] | 3-(5-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-2-methyl-4-oxoquinazolin-3(4H)-yl)piperidine-2,6-dione |
| 108 | 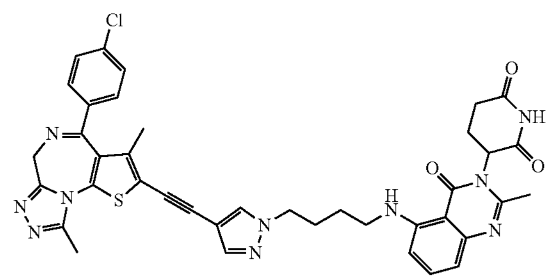 [SMILES: Cc1c(C#Cc2cnn(CCCCNc3cccc4nc(C)n(C5CCC(=O)NC5=O)c(=O)c34)c2)sc2c1C(c1ccc(Cl)cc1)=NCc1nnc(C)n1-2] | 3-(5-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-methyl-4-oxoquinazolin-3(4H)-yl)piperidine-2,6-dione |
| 109 | 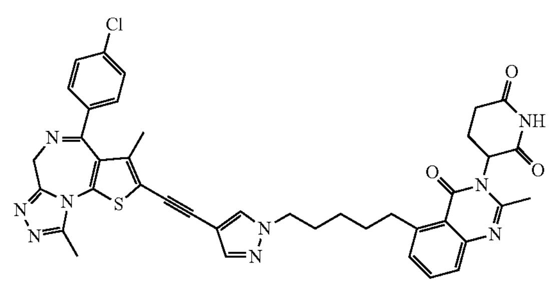 [SMILES: Cc1c(C#Cc2cnn(CCCCCc3cccc4nc(C)n(C5CCC(=O)NC5=O)c(=O)c34)c2)sc2c1C(c1ccc(Cl)cc1)=NCc1nnc(C)n1-2] | 3-(5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-2-methyl-4-oxoquinazolin-3(4H)-yl)piperidine-2,6-dione |
| 110 | 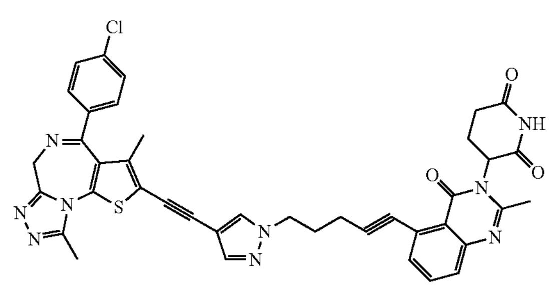 [SMILES: Cc1c(C#Cc2cnn(CCCC#Cc3cccc4nc(C)n(C5CCC(=O)NC5=O)c(=O)c34)c2)sc2c1C(c1ccc(Cl)cc1)=NCc1nnc(C)n1-2] | 3-(5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-methyl-4-oxoquinazolin-3(4H)-yl)piperidine-2,6-dione |

TABLE 1-continued

| Cpd. No. | Structure | Name |
|---|---|---|
| 125 | 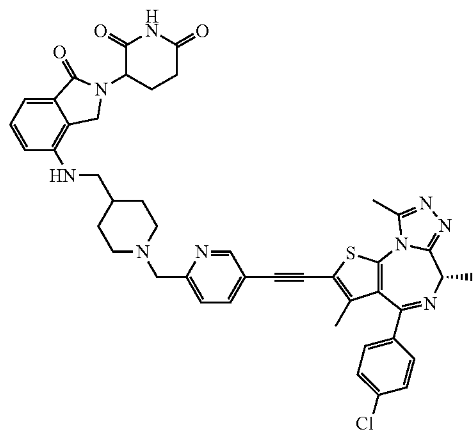 [SMILES: Cc1c(C#Cc2ccc(CN3CCC(CNc4cccc5c4CN(C4CCC(=O)NC4=O)C5=O)CC3)nc2)sc2c1C(c1ccc(Cl)cc1)=N[C@@H](C)c1nnc(C)n1-2] | 3-(4-(((1-((5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)methyl)piperidin-4-yl)methyl)amino)-1-oxoisoindolin-2-yl)piperidine-2,6-dione |
| 126 | 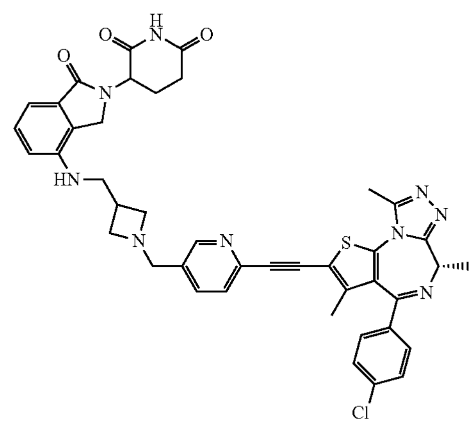 [SMILES: Cc1c(C#Cc2ccc(CN3CC(CNc4cccc5c4CN(C4CCC(=O)NC4=O)C5=O)C3)cn2)sc2c1C(c1ccc(Cl)cc1)=N[C@@H](C)c1nnc(C)n1-2] | 3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione |
| 127 | 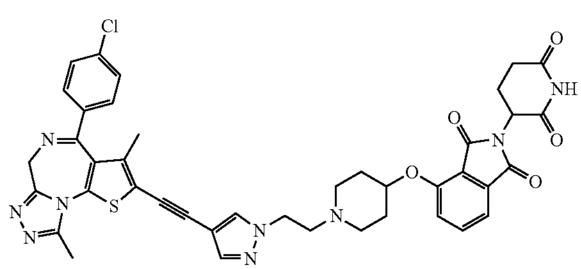 [SMILES: Cc1c(C#Cc2cnn(CCN3CCC(Oc4cccc5c4C(=O)N(C4CCC(=O)NC4=O)C5=O)CC3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione |
| 128 | 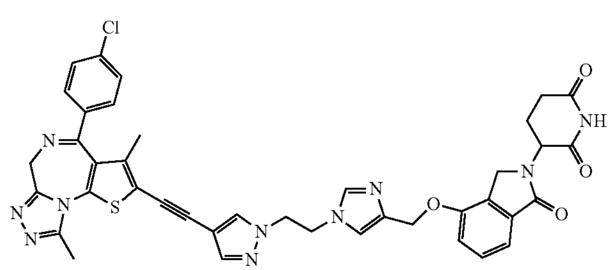 [SMILES: Cc1c(C#Cc2cnn(CCn3cnc(COc4cccc5c4CN(C4CCC(=O)NC4=O)C5=O)c3)c2)sc2c1C(c1ccc(Cl)cc1)=NCc1nnc(C)n1-2] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione |

TABLE 1-continued

| Cpd. No. | Structure | Name |
|---|---|---|
| 129 | 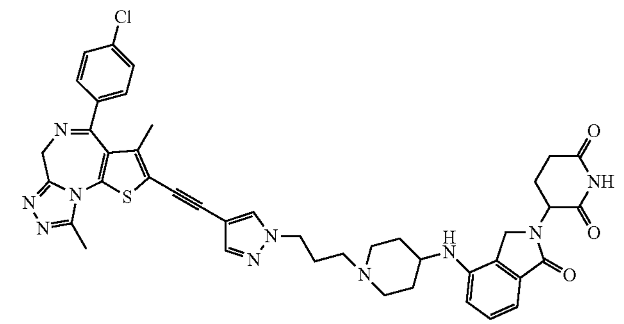 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=NCc1nnc(C)n1-2] | 3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione |
| 130 | 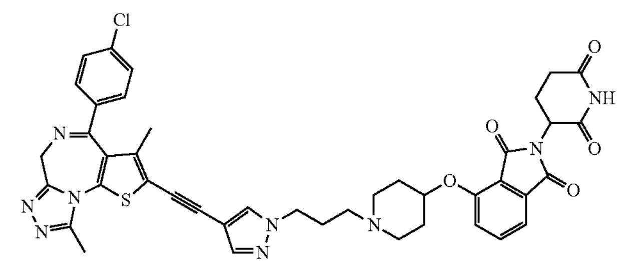 [SMILES: Cc1c(C#Cc2cnn(CCCN3CCC(Oc4cccc5c4C(=O)N(C4CCC(=O)NC4=O)C5=O)CC3)c2)sc2c1C(c1ccc(Cl)cc1)=NCc1nnc(C)n1-2] | 4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)oxy)-2-(2,6-dioxopiperidin-3-yl)isoindoline-1,3-dione |
| 131 | 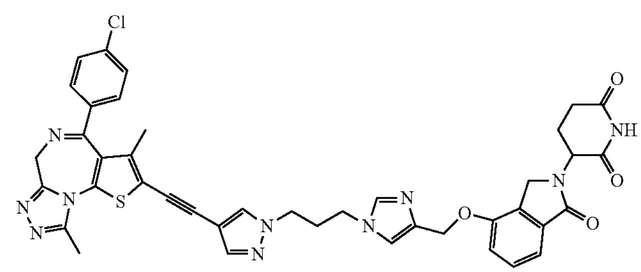 [SMILES: Cc1c(C#Cc2cnn(CCCn3cnc(COc4cccc5c4CN(C4CCC(=O)NC4=O)C5=O)c3)c2)sc2c1C(c1ccc(Cl)cc1)=NCc1nnc(C)n1-2] | 3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methoxy)-1-oxoisoindolin-2-yl)piperidine-2,6-dione |
| 132 | 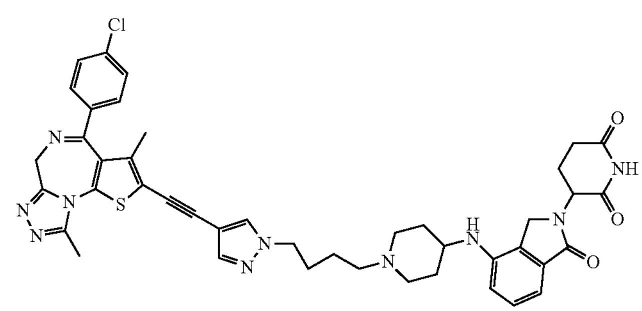 [SMILES: Cc1c(C#Cc2cnn(CCCCN3CCC(Nc4cccc5c4CN(C4CCC(=O)NC4=O)C5=O)CC3)c2)sc2c1C(c1ccc(Cl)cc1)=NCc1nnc(C)n1-2] | 3-(4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)amino)-1-oxoisoindolin-2-yl)piperidine-2,6-dione |
| 133 | 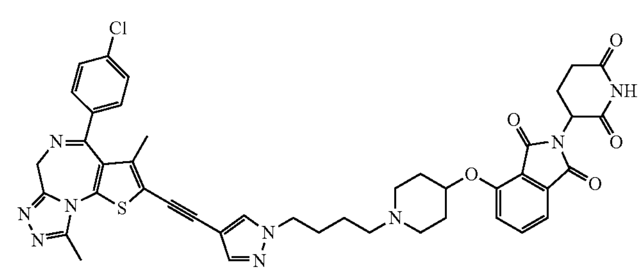 [SMILES: Cc1c(C#Cc2cnn(CCCCN3CCC(Oc4cccc5c4C(=O)N(C4CCC(=O)NC4=O)C5=O)CC3)c2)sc2c1C(c1ccc(Cl)cc1)=NCc1nnc(C)n1-2] | 4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)oxy)-2-(2,6-dioxopiperidin-3-yl)isoindoline-1,3-dione |

TABLE 1-continued

| Cpd. No. | Structure | Name |
|---|---|---|
| 134 | 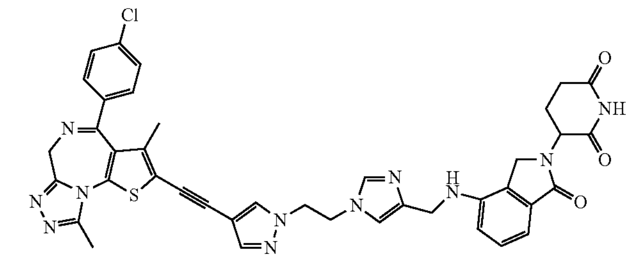 [SMILES: Cc1c(C#Cc2cnn(CCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione |
| 135 | 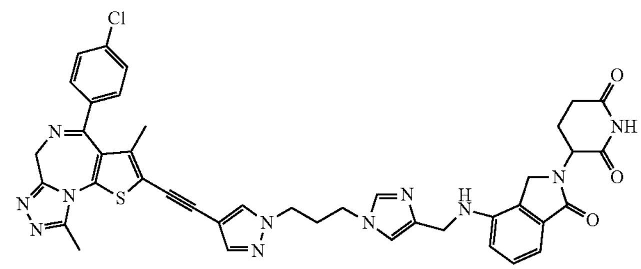 [SMILES: Cc1c(C#Cc2cnn(CCCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-(((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methyl)amino)-1-oxoisoindolin-2-yl)piperidine-2,6-dione |
| 136 | | 3-(4-(((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)-1H-imidazol-4-yl)methyl)amino)-1-oxoisoindolin-2-yl)piperidine-2,6-dione |
| 136 | | 3-(4-((4-((4-(((S)-4-(4-clorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione |
| 137 | 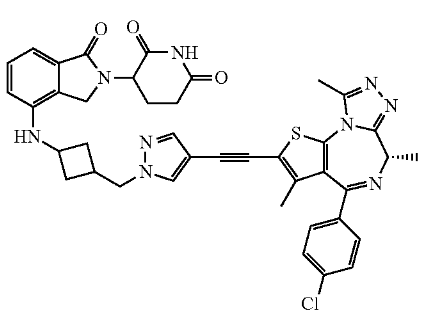 [SMILES: Cc1c(C#Cc2cnn(CC3CC(Nc4cccc5c4CN(C4CCC(=O)NC4=O)C5=O)C3)c2)sc2c1C(c1ccc(Cl)cc1)=N[C@@H](C)c1nnc(C)n1-2] | 3-(4-((3-((4-(((S)-4-(4-chlorophenyl)-3,6,9-trimethyl-6H-thineo[3,2-f][1,2,4]triazolo[4,3-a][1,4]diazepin-2-yl)ethynyl)-1H-pyrazol-1-yl)methyl)cyclobutyl)amino)-1-oxoisoindolin-2-yl)piperidine-2,6-dione |

TABLE 1-continued

| Cpd. No. | Structure | Name |
|---|---|---|
| 138 | 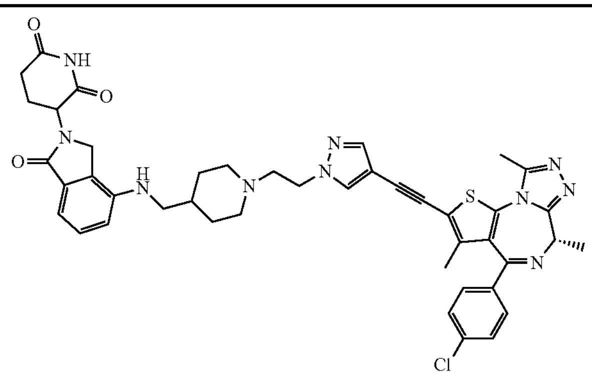 | 3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)amino)-1-oxoisoindolin-2-yl)piperidine-2,6-dione |
| 139 | 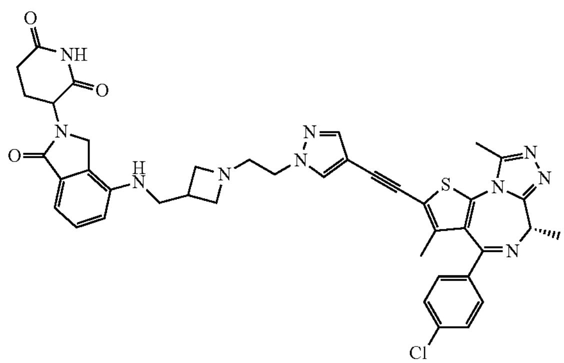 [SMILES: Cc1c(C#Cc2cnn(CCN3CC(CNc4cccc5c4CN(C4CCC(=O)NC4=O)C5=O)C3)c2)sc2c1C(c1ccc(Cl)cc1)=N[C@@H](C)c1nnc(C)n1-2] | 3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)methyl)amino)-1-oxoisoindolin-2-yl)piperidine-2,6-dione |
| 140 | 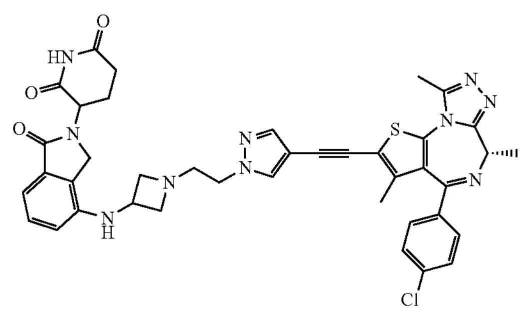 [SMILES: Cc1c(C#Cc2cnn(CCN3CC(Nc4cccc5c4CN(C4CCC(=O)NC4=O)C5=O)C3)c2)sc2c1C(c1ccc(Cl)cc1)=N[C@@H](C)c1nnc(C)n1-2] | 3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)amino)-1-oxoisoindolin-2-yl)piperidine-2,6-dione |
| 141 | 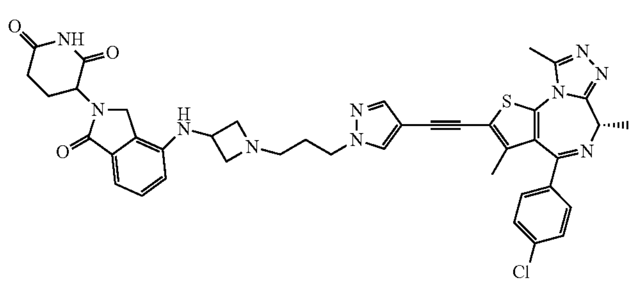 [SMILES: Cc1c(C#Cc2cnn(CCCN3CC(Nc4cccc5c4CN(C4CCC(=O)NC4=O)C5=O)C3)c2)sc2c1C(c1ccc(Cl)cc1)=N[C@@H](C)c1nnc(C)n1-2] | 3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)amino)-1-oxoisoindolin-2-yl)piperidine-2,6-dione |

TABLE 1A

| Cpd. No. | Structure | Name |
|---|---|---|
| 142 | 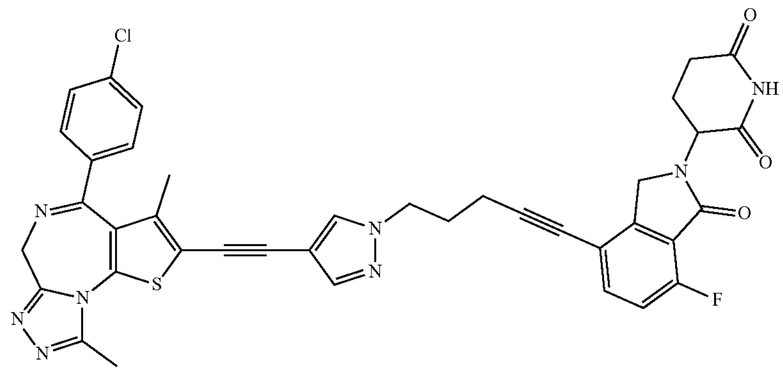 [SMILES: Cc1c(C#Cc2cnn(CCCC#Cc3ccc(F)c4c3CN(C3CCC(=O)NC3=O)C4=O)c2)sc2c1C(c1ccc(Cl)cc1)=NCc1nnc(C)n1-2] | 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-7-fluoro-1-oxoisoindolin-2-yl)piperidine-2,6-dione |
| 143 | 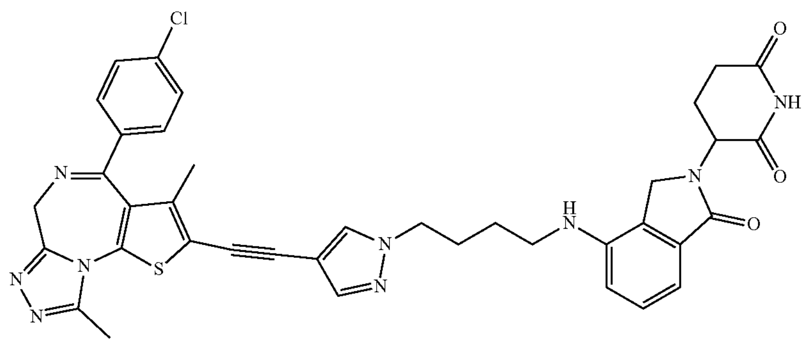 [SMILES: Cc1c(C#Cc2cnn(CCCCNc3cccc4c3CN(C3CCC(=O)NC3=O)C4=O)c2)sc2c1C(c1ccc(Cl)cc1)=NCc1nnc(C)n1-2] | 3-(4-(4-((4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione |

TABLE 1A-continued

| Cpd. No. | Structure | Name |
|---|---|---|
| 144 | 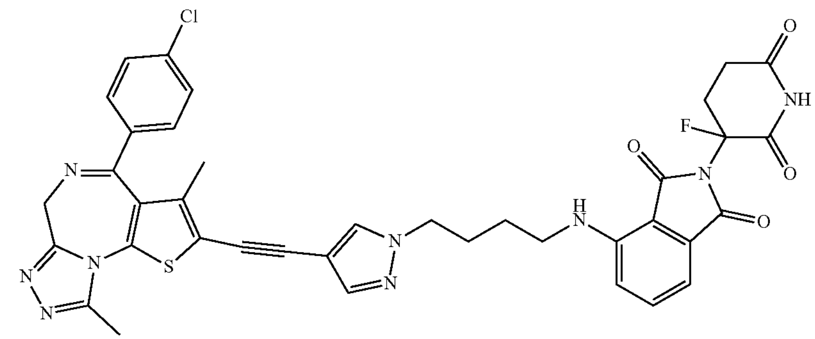 [SMILES: Cc1c(C#Cc2cnn(CCCCNc3cccc4c3C(=O)N(C3(F)CCC(=O)NC3=O)C4=O)c2)sc2c1C(c1ccc(Cl)cc1)=NCc1nnc(C)n1-2] | 4-(4-(4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(3-fluoro-2,6-dioxopiperidin-3-yl)isoindoline-1,3-dione |
| 145 | 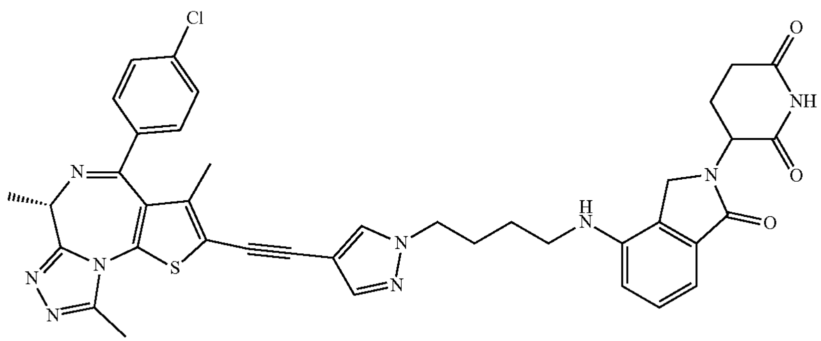 [SMILES: Cc1c(C#Cc2cnn(CCCCNc3cccc4c3CN(C3CCC(=O)NC3=O)C4=O)c2)sc2c1C(c1ccc(Cl)cc1)=N[C@@H](C)c1nnc(C)n1-2] | 3-(4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione |
| 146 | 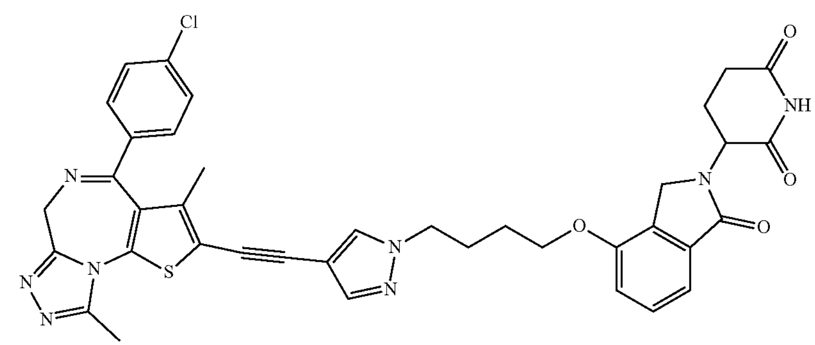 [SMILES: Cc1c(C#Cc2cnn(CCCCOc3cccc4c3CN(C3CCC(=O)NC3=O)C4=O)c2)sc2c1C(c1ccc(Cl)cc1)=NCc1nnc(C)n1-2] | 3-(4-(4-(4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione |

TABLE 1A-continued

| Cpd. No. | Structure | Name |
|---|---|---|
| 147 | 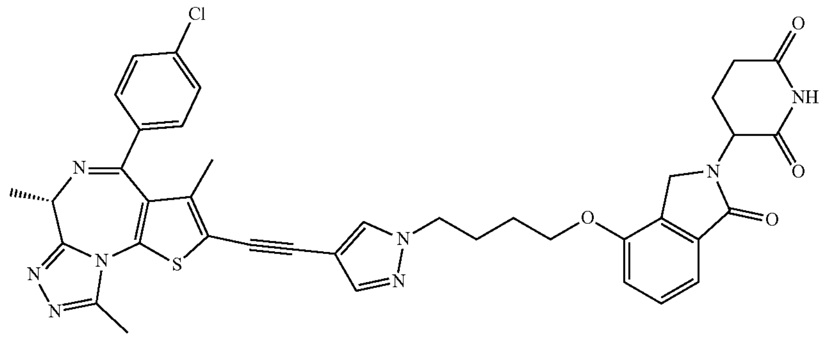 [SMILES: Cc1c(C#Cc2cnn(CCCCOc3cccc4c3CN(C3CCC(=O)NC3=O)C4=O)c2)sc2c1C(c1ccc(Cl)cc1)=N[C@@H](C)c1nnc(C)n1-2] | 3-(4-(4-(4-((S)-4-(4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione |
| 148 | 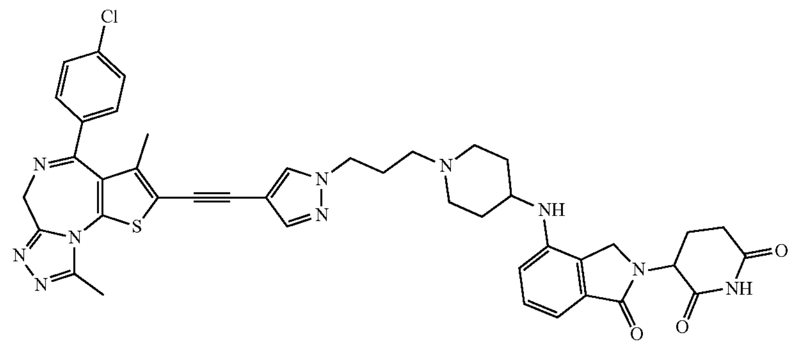 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=NCc1nnc(C)n1-2] | 3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione |
| 149 | 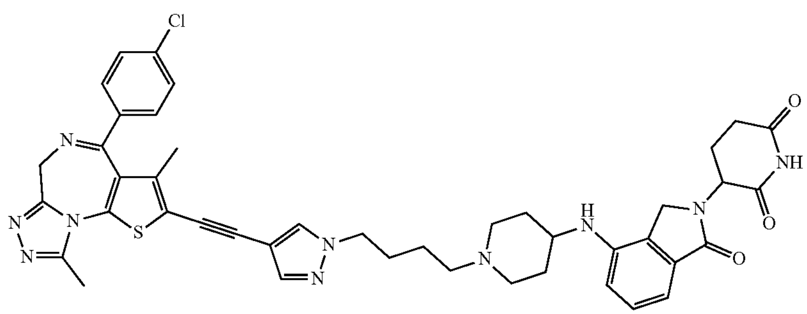 [SMILES: Cc1c(C#Cc2cnn(CCCCN3CCC(Nc4cccc5c4CN(C4CCC(=O)NC4=O)C5=O)CC3)c2)sc2c1C(c1ccc(Cl)cc1)=NCc1nnc(C)n1-2] | 3-(4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)amino)-1-oxoisoindolin-2-yl)piperidine-2,6-dione |

TABLE 1A-continued

| Cpd. No. | Structure | Name |
|---|---|---|
| 150 | 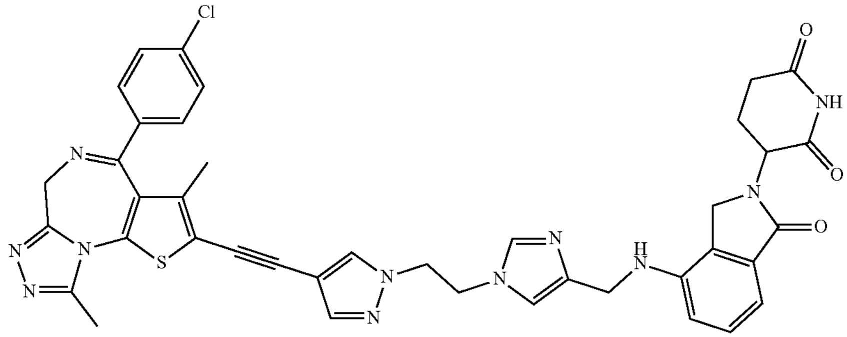 [SMILES: Cc1c(C#Cc2cnn(CCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione |
| 151 | 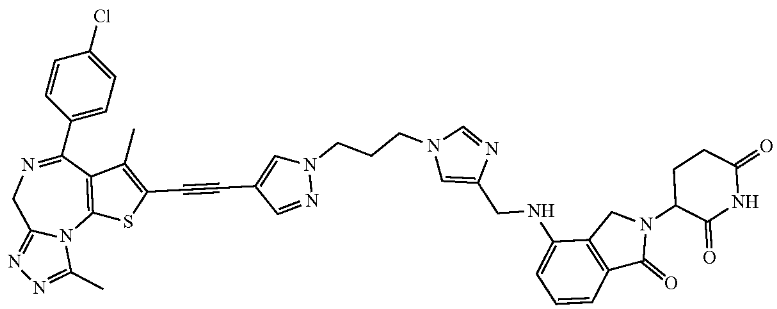 [SMILES: Cc1c(C#Cc2cnn(CCCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-2-yl)methyl)amino)-1-oxoisoindolin-2-yl)piperidine-2,6-dione |
| 152 | 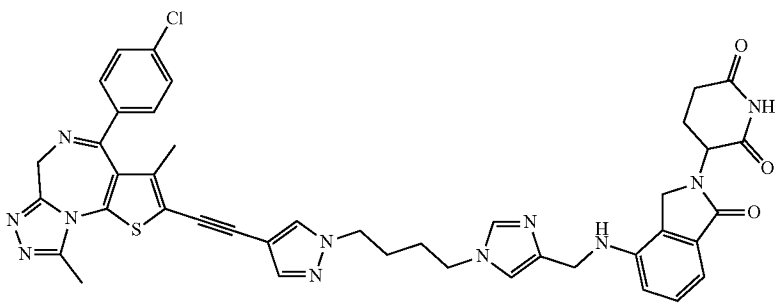 [SMILES: Cc1c(C#Cc2cnn(CCCCn3cnc(CNc4cccc5c4CN(C4CCC(=O)NC4=O)C5=O)c3)c2)sc2c1C(c1ccc(Cl)cc1)=NCc1nnc(C)n1-2] | 3-(4-(((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)-1H-imidazol-4-yl)methyl)amino)-1-oxoisoindolin-2-yl)piperidine-2,6-dione |

| Cpd. No. | Structure | Name |
|---|---|---|
| 153 | 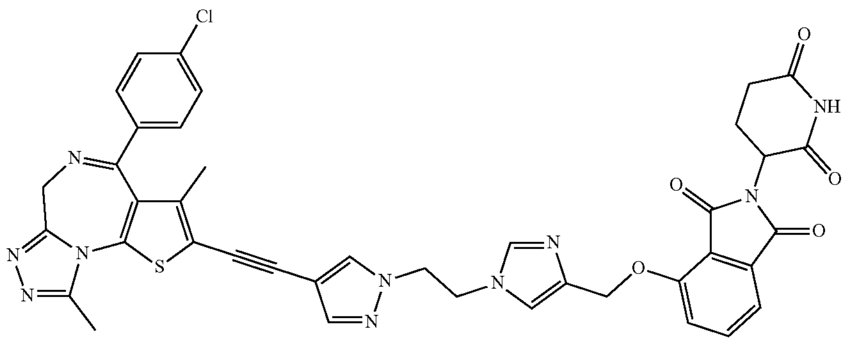 [SMILES: Cc1c(C#Cc2cnn(CCn3cnc(COc4cccc5c4C(=O)N(C4CCC(=O)NC4=O)C5=O)c3)c2)sc2c1C(c1ccc(Cl)cc1)=NCc1nnc(C)n1-2] | 4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-2-(2,6-dioxopiperidin-3-yl)isoindoline-1,3-dione |
| 154 | 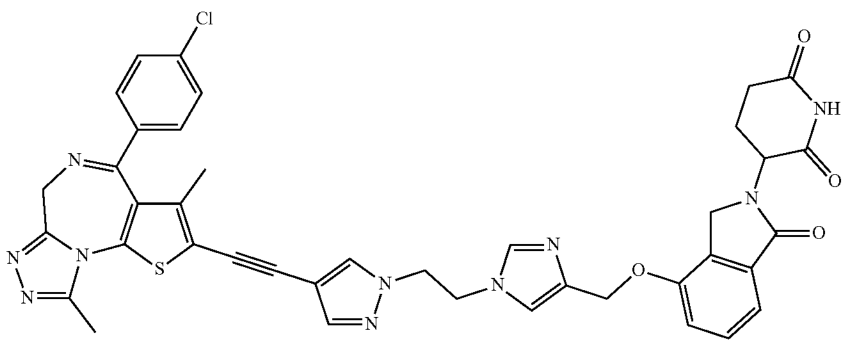 [SMILES: Cc1c(C#Cc2cnn(CCn3cnc(COc4cccc5c4CN(C4CCC(=O)NC4=O)C5=O)c3)c2)sc2c1C(c1ccc(Cl)cc1)=NCc1nnc(C)n1-2] | 3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione |
| 155 | 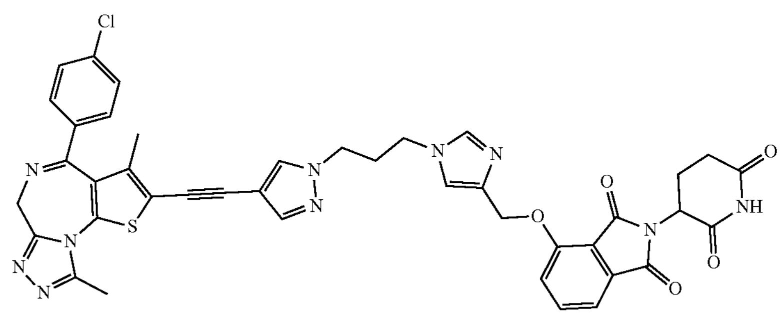 [SMILES: Cc1c(C#Cc2cnn(CCCn3cnc(COc4cccc5c4C(=O)N(C4CCC(=O)NC4=O)C5=O)c3)c2)sc2c1C(c1ccc(Cl)cc1)=NCc1nnc(C)n1-2] | 4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methoxy)-2-(2,6-dioxopiperidin-3-yl)isoindoline-1,3-dione |

TABLE 1A-continued

| Cpd. No. | Structure | Name |
|---|---|---|
| 156 | 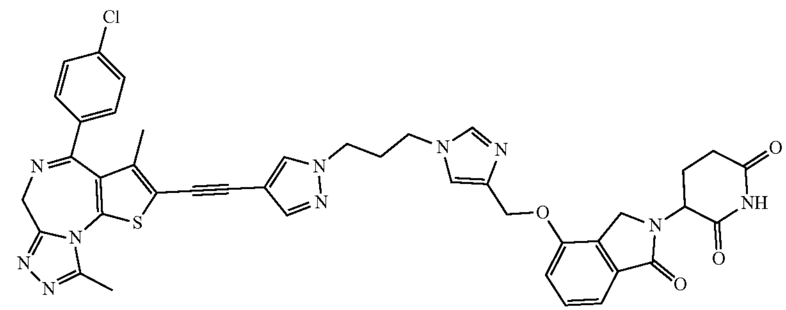 [SMILES: Cc1c(C#Cc2cnn(CCCn3cnc(COc4cccc5c4CN(C4CCC(=O)NC4=O)C5=O)c3)c2)sc2c1C(c1ccc(Cl)cc1)=NCc1nnc(C)n1-2] | 3-(4-((1-(3-(4-((4-(4-chlorophenyl)-3,9-dimethyl-6H-thieno[3,2-f][1,2,4]triazolo[4,3-a][1,4]diazepin-2-yl]-1H-pyrazol-1-yl)propyl)-1H-imidazol-4-yl)methoxy)-1-oxoisoindolin-2-yl)piperidine-2,6-dione |
| 157 | 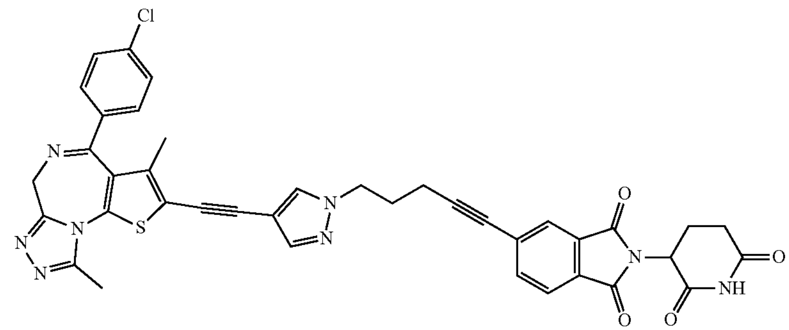 [SMILES: Cc1c(C#Cc2cnn(CCCC#Cc3ccc4c(c3)C(=O)N(C3CCC(=O)NC3=O)C4=O)c2)sc2c1C(c1ccc(Cl)cc1)=NCc1nnc(C)n1-2] | 5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazolo-1-yl)pent-1-yn-1-yl)-2-(2,6-dioxopiperidin-3-yl)isoindoline-1,3-dione |
| 158 | 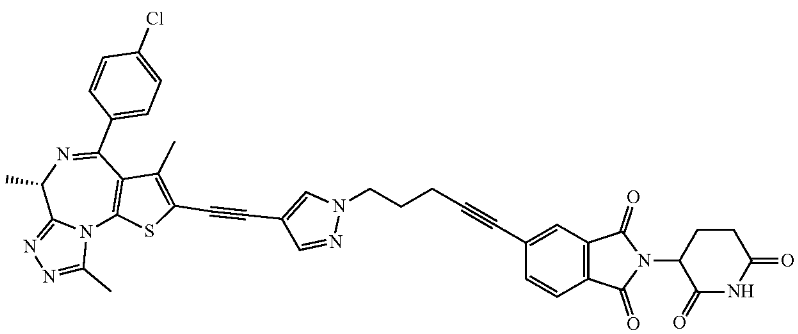 [SMILES: Cc1c(C#Cc2cnn(CCCC#Cc3ccc4c(c3)C(=O)N(C3CCC(=O)NC3=O)C4=O)c2)sc2c1C(c1ccc(Cl)cc1)=N[C@@H](C)c1nnc(C)n1-2] | 5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazolo-1-yl)pent-1-yn-1-yl)-2-(2,6-dioxopiperidin-3-yl)isoindoline-1,3-dione |

TABLE 1A-continued

| Cpd. No. | Structure | Name |
|---|---|---|
| 159 | 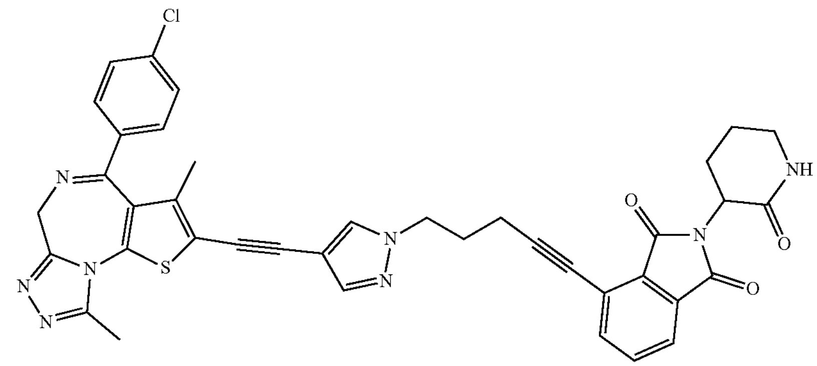 [SMILES: Cc1c(C#Cc2cnn(CCCC#Cc3cccc4c3C(=O)N(C3CCCNC3=O)C4=O)c2)sc2c1C(c1ccc(Cl)cc1)=NCc1nnc(C)n1-2] | 4-(5-(4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2-oxopiperidin-3-yl)isoindoline-1,3-dione |
| 160 | 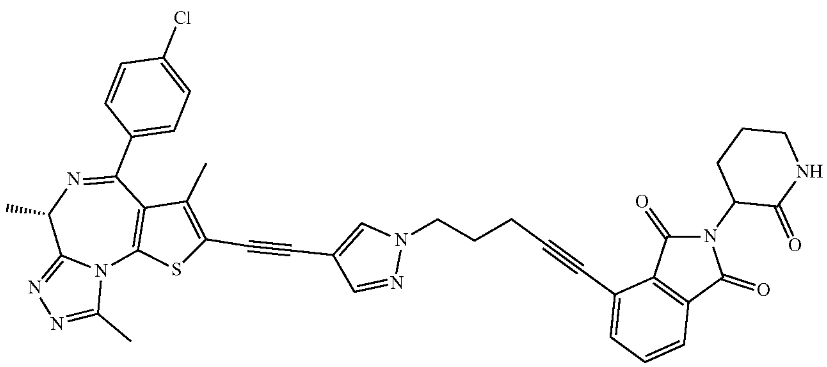 [SMILES: Cc1c(C#Cc2cnn(CCCC#Cc3cccc4c3C(=O)N(C3CCCNC3=O)C4=O)c2)sc2c1C(c1ccc(Cl)cc1)=N[C@@H](C)c1nnc(C)n1-2] | 4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2-oxopiperidin-3-yl)isoindoline-1,3-dione |

TABLE 1A-continued

| Cpd. No. | Structure | Name |
|---|---|---|
| 161 | 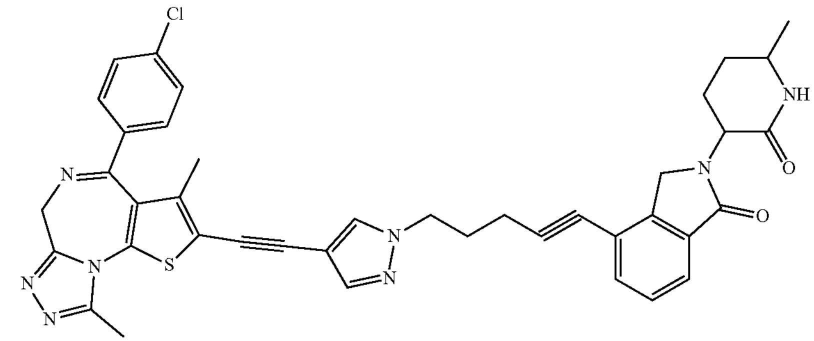 [SMILES: Cc1c(C#Cc2cnn(CCCC#Cc3cccc4c3CN(C3CCC(C)NC3=O)C4=O)c2)sc2c1C(c1ccc(Cl)cc1)=NCc1nnc(C)n1-2] | 4-(5-(4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(6-methyl-2-oxopiperidin-3-yl)isoindolin-1-one |
| 162 | 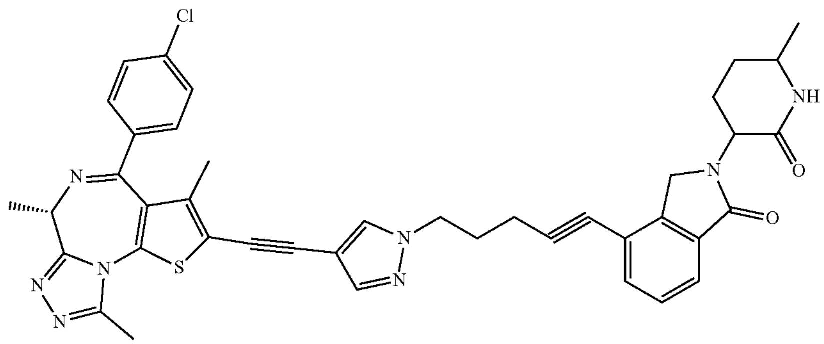 | 4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(6-methyl-2-oxopiperidin-3-yl)isoindolin-1-one |
| 163 | 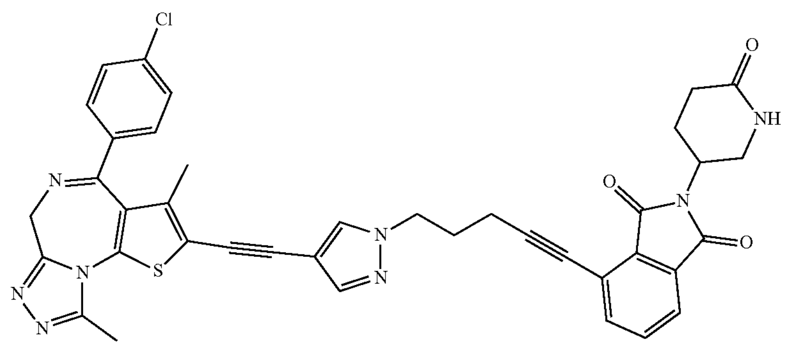 [SMILES: Cc1c(C#Cc2cnn(CCCC#Cc3cccc4c3C(=O)N(C3CCC(=O)NC3)C4=O)c2)sc2c1C(c1ccc(Cl)cc1)=NCc1nnc(C)n1-2] | 4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(6-oxopiperidin-3-yl)isoindoline-1,3-dione |

TABLE 1A-continued
| Cpd. No. | Structure | Name |
|---|---|---|
| 164 | 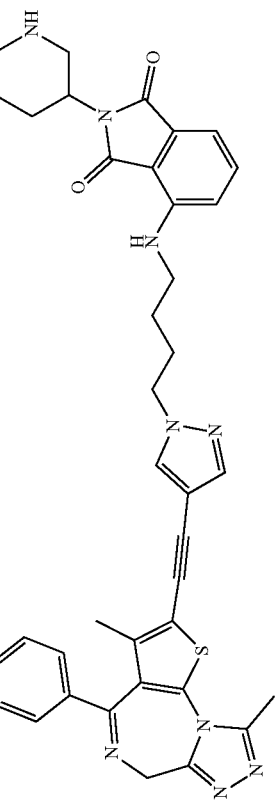 | 4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(6-oxopiperidin-3-yl)isoindoline-1,3-dione |
| 165 | 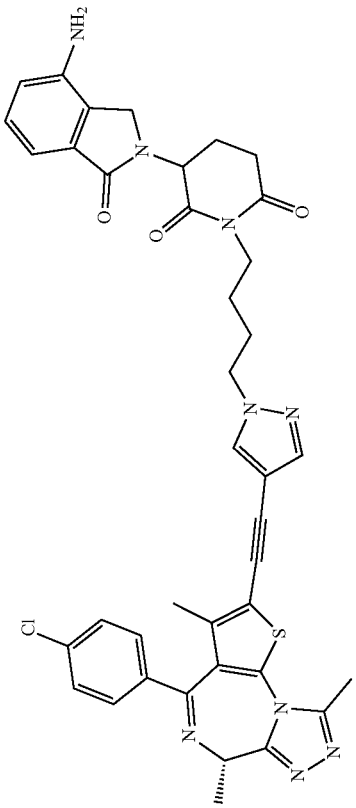 | 3-(4-amino-1-oxoisoindolin-2-yl)-1-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)piperidine-2,6-dione |

TABLE 1A-continued
| Cpd. No. | Structure | Name |
|---|---|---|
| 166 | 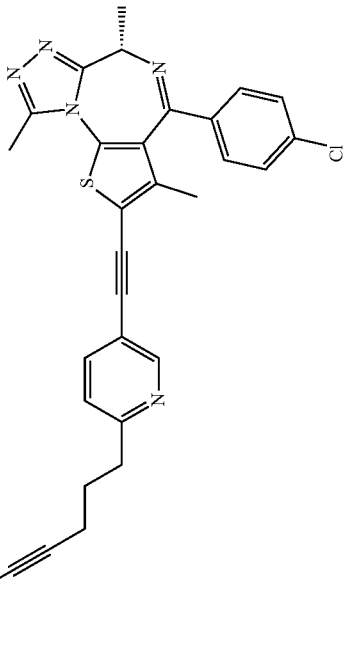 | 3-(4-(5-(5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)pent-1-yn-1-yl)-1-oxoisoindolin-2-yl)piperidine-2,6-dione |

TABLE 1A-continued
| Cpd. No. | Structure | Name |
|---|---|---|
| 167 | 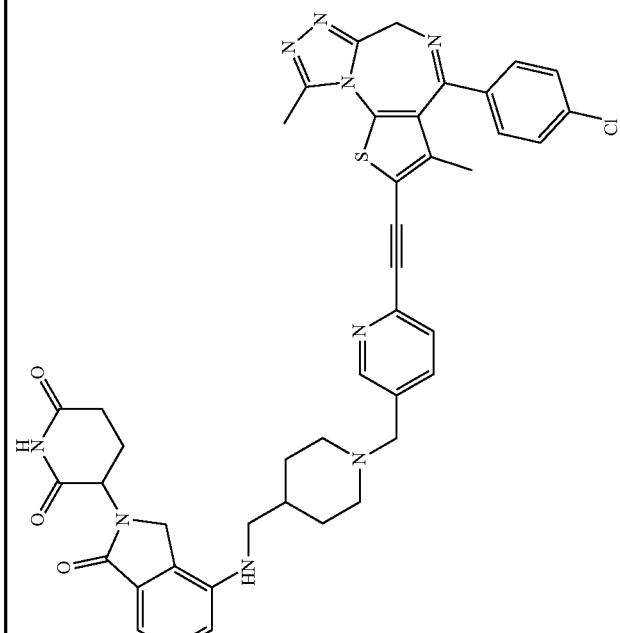 | 3-(4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione |

TABLE 1A-continued
| Cpd. No. | Structure | Name |
|---|---|---|
| 168 | 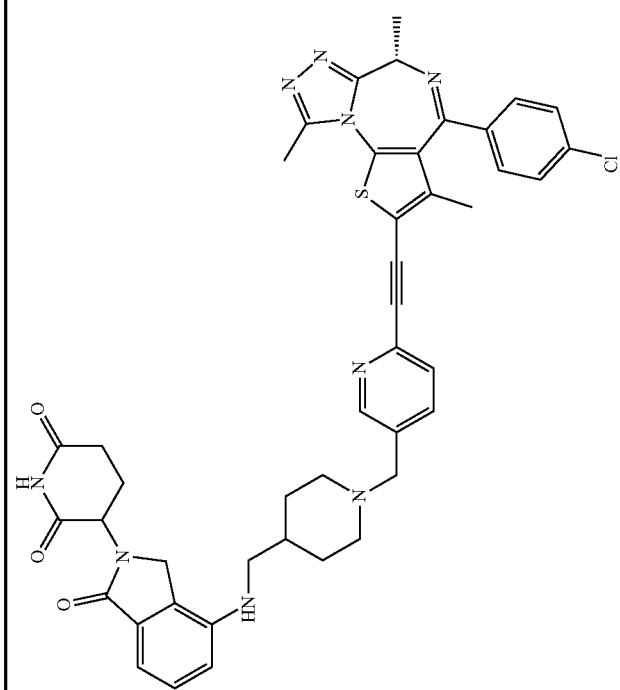 | 3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione |

TABLE 1A-continued
| Cpd. No. | Structure | Name |
|---|---|---|
| 168 | 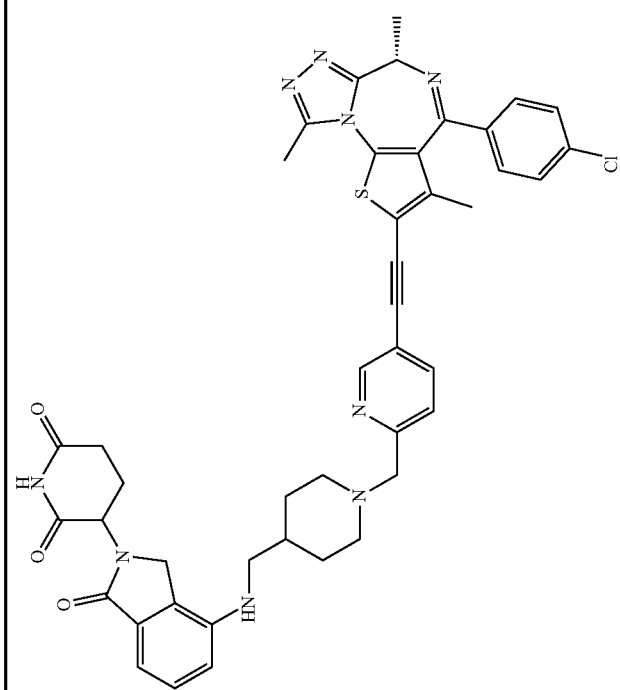 | 3-(4-(((1-((5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)methyl)piperidin-4-yl)methyl)amino)-1-oxoisoindolin-2-yl)piperidine-2,6-dione |

TABLE 1A-continued

| Cpd. No. | Structure | Name |
|---|---|---|
| 170 | 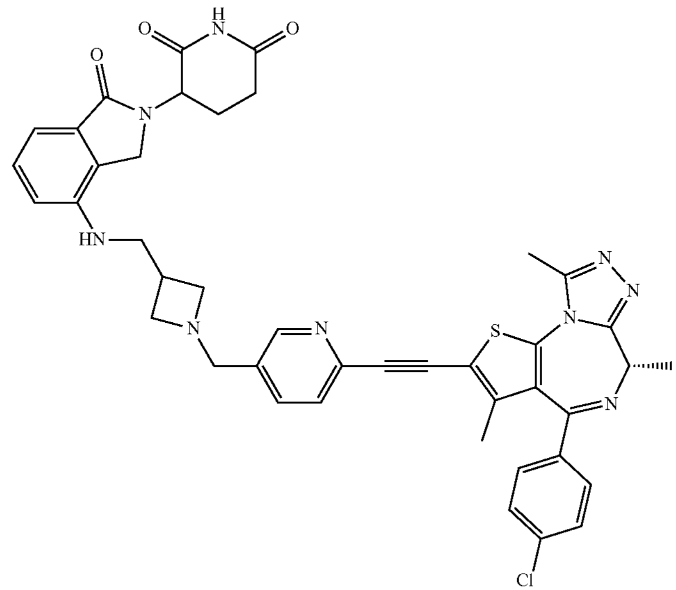 [SMILES: Cc1c(C#Cc2ccc(CN3CC(CNc4cccc5c4CN(C4CCC(=O)NC4=O)C5=O)C3)cn2)sc2c1C(c1ccc(Cl)cc1)=N[C@@H](C)c1nnc(C)n1-2] | 3-(4-(((1-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione |
| 171 | 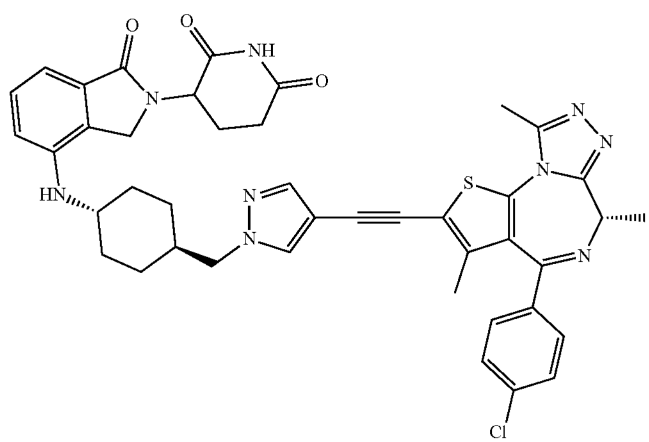 [SMILES: Cc1c(C#Cc2cnn(C[C@H]3CC[C@H](Nc4cccc5c4CN(C4CCC(=O)NC4=O)C5=O)CC3)c2)sc2c1C(c1ccc(Cl)cc1)=N[C@@H](C)c1nnc(C)n1-2] | 3-(4-(((1S,4r)-4-(((4-((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione |

TABLE 1A-continued

| Cpd. No. | Structure | Name |
|---|---|---|
| 172 | 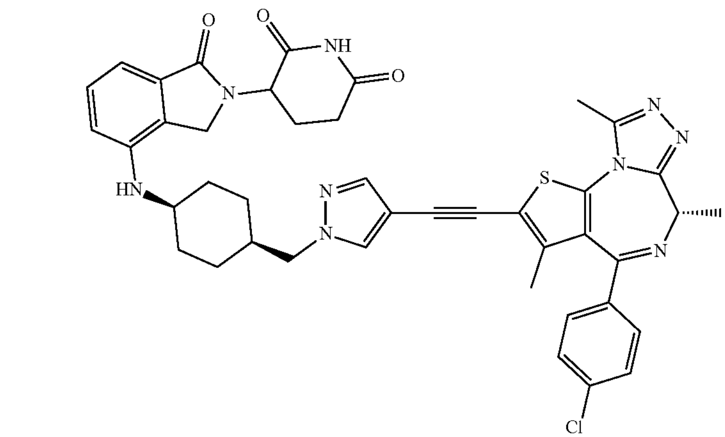 [SMILES: Cc1c(C#Cc2cnn(C[C@H]3CC[C@@H](Nc4cccc5c4CN(C4CCC(=O)NC4=O)C5=O)CC3)c2)sc2c1C(c1ccc(Cl)cc1)=N[C@@H](C)c1nnc(C)n1-2] | 3-(4-(((1R,4s)-4-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione |
| 173 | 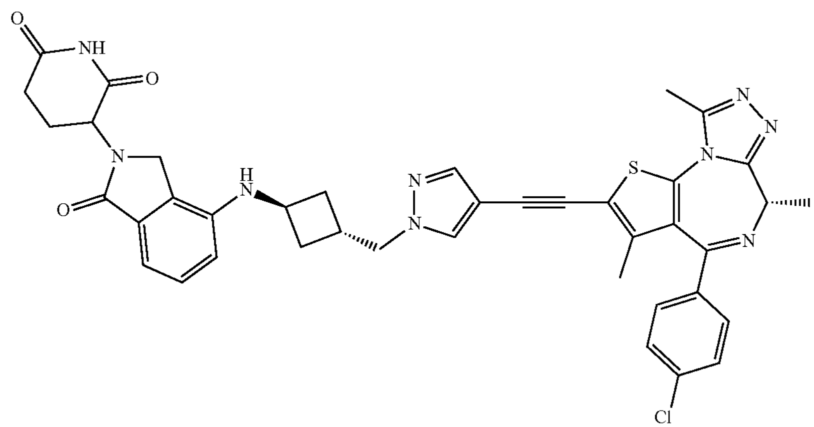 [SMILES: Cc1c(C#Cc2cnn(C[C@H]3C[C@H](Nc4cccc5c4CN(C4CCC(=O)NC4=O)C5=O)C3)c2)sc2c1C(c1ccc(Cl)cc1)=N[C@@H](C)c1nnc(C)n1-2] | 3-(4-(((1S,3r)-3-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclobutyl)amino)-1-oxoisoindolin-2-yl)piperidine-2,6-dione |

TABLE 1A-continued

| Cpd. No. | Structure | Name |
|---|---|---|
| 174 | 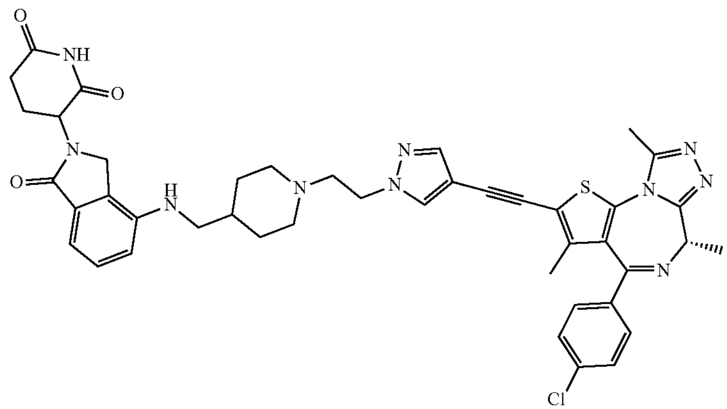 [SMILES: Cc1c(C#Cc2cnn(CCN3CCC(CNc4cccc5c4CN(C4CCC(=O)NC4=O)C5=O)CC3)c2)sc2c1C(c1ccc(Cl)cc1)=N[C@@H](C)c1nnc(C)n1-2] | 3-(4-(((1-(2-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)amino)-1-oxoisoindolin-2-yl)piperidine-2,6-dione |
| 175 | 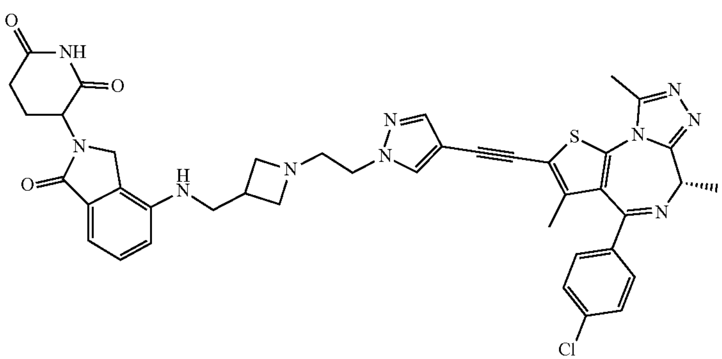 [SMILES: Cc1c(C#Cc2cnn(CCN3CC(CNc4cccc5c4CN(C4CCC(=O)NC4=O)C5=O)C3)c2)sc2c1C(c1ccc(Cl)cc1)=N[C@@H](C)c1nnc(C)n1-2] | 3-(4-(((1-(2-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)methyl)amino)-1-oxoisoindolin-2-yl)piperidine-2,6-dione |

TABLE 1A-continued

| Cpd. No. | Structure | Name |
|---|---|---|
| 176 | 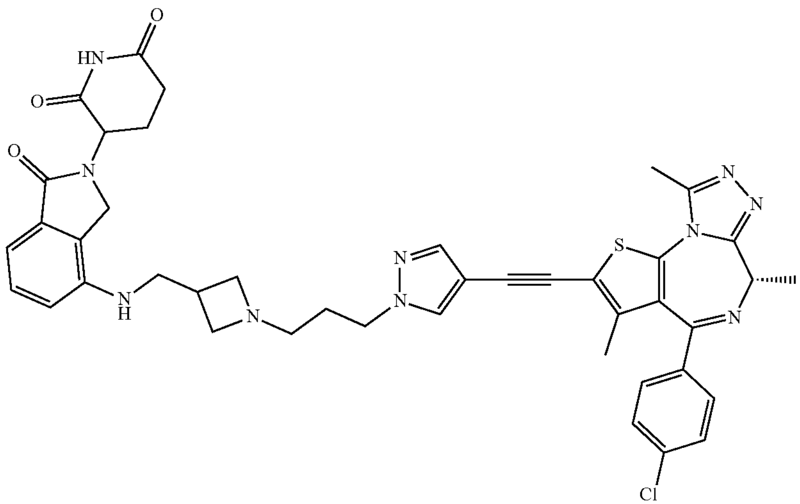 [SMILES: Cc1c(C#Cc2cnn(CCCN3CC(CNc4cccc5c4CN(C4CCC(=O)NC4=O)C5=O)C3)c2)sc2c1C(c1ccc(Cl)cc1)=N[C@@H](C)c1nnc(C)n1-2] | 3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)methyl)amino)-1-oxoisoindolin-2-yl)piperidine-2,6-dione |
| 177 | 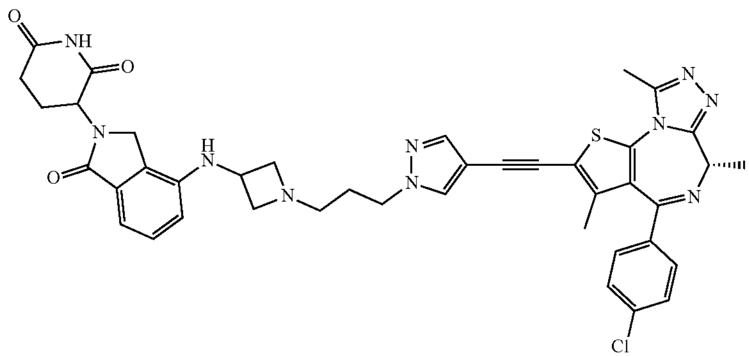 [SMILES: Cc1c(C#Cc2cnn(CCCN3CC(Nc4cccc5c4CN(C4CCC(=O)NC4=O)C5=O)C3)c2)sc2c1C(c1ccc(Cl)cc1)=N[C@@H](C)c1nnc(C)n1-2] | 3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)amino)-1-oxoisoindolin-2-yl)piperidine-2,6-dione |

TABLE 1A-continued
| Cpd. No. | Structure | Name |
|---|---|---|
| 178 | 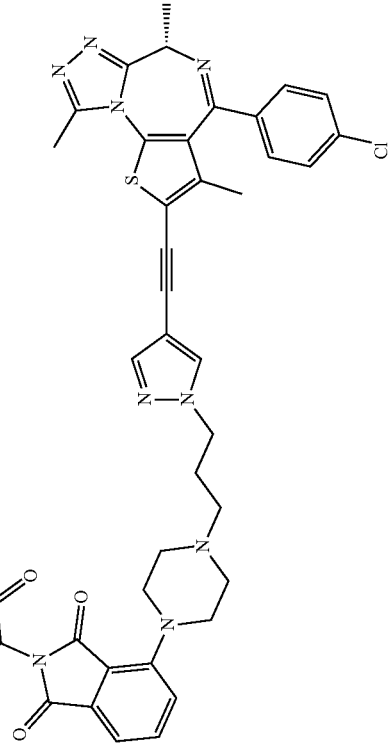 | 4-(4-(3-(4-((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione |
| 179 | 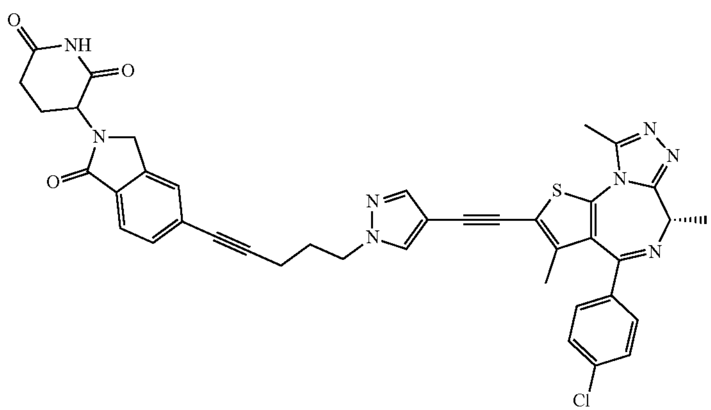 [SMILES: Cc1c(C#Cc2cnn(CCCC#Cc3ccc4c(c3)CN(C3CCC(=O)NC3=O)C4=O)c2)sc2c1C(c1ccc(Cl)cc1)=N[C@@H](C)c1nnc(C)n1-2] | 3-(5-(5-(4-((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione |

TABLE 1A-continued
| Cpd. No. | Structure | Name |
|---|---|---|
| 180 | 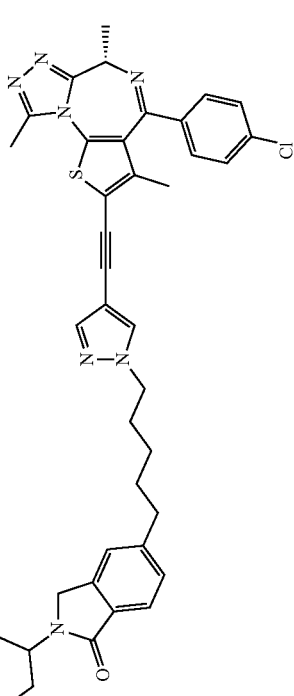 | 3-(5-(5-(4-((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione |
| 181 | 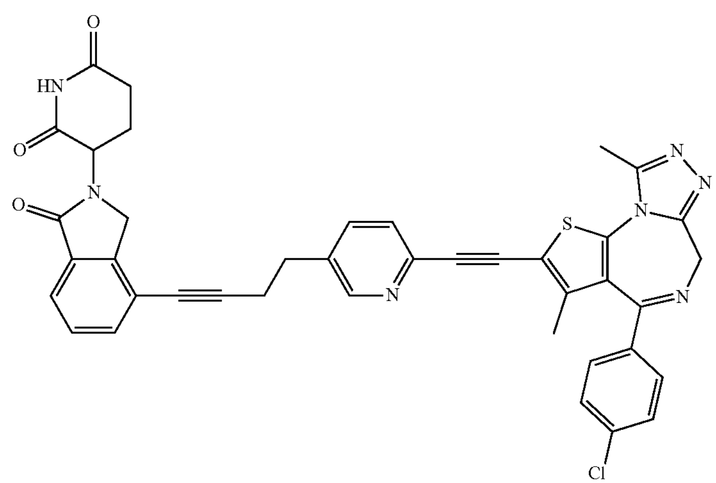 [SMILES: Cc1c(C#Cc2ccc(CCC#Cc3cccc4c3CN(C3CCC(=O)NC3=O)C4=O)cn2)sc2c1C(c1ccc(Cl)cc1)=NCc1nnc(C)n1-2] | 3-(4-(4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)but-1-yn-1-yl)-1-oxoisoindolin-2-yl)piperidine-2,6-dione |

TABLE 1A-continued
| Cpd. No. | Structure | Name |
|---|---|---|
| 182 | 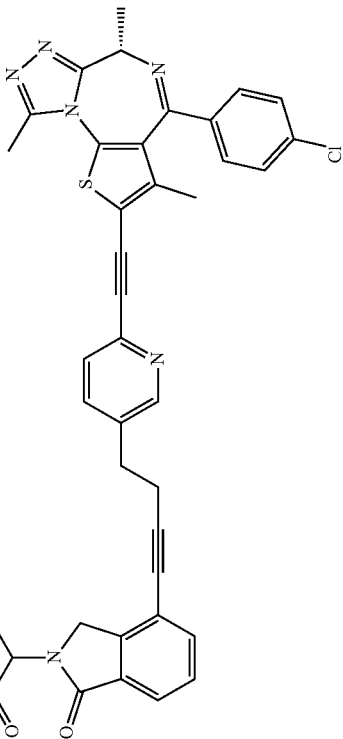 | 3-(4-(4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)but-1-yn-1-yl)-1-oxoisoindolin-2-yl)piperidine-2,6-dione |
| 183 | 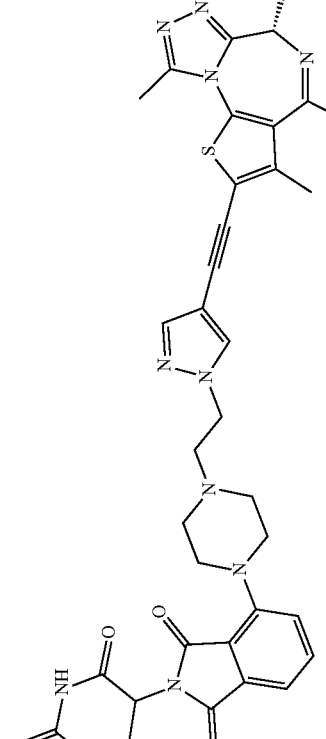 | 4-(4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)-2-(2,6-dioxopiperidin-3-yl)isoindoline-1,3-dione |

TABLE 1A-continued

| Cpd. No. | Structure | Name |
|---|---|---|
| 184 | 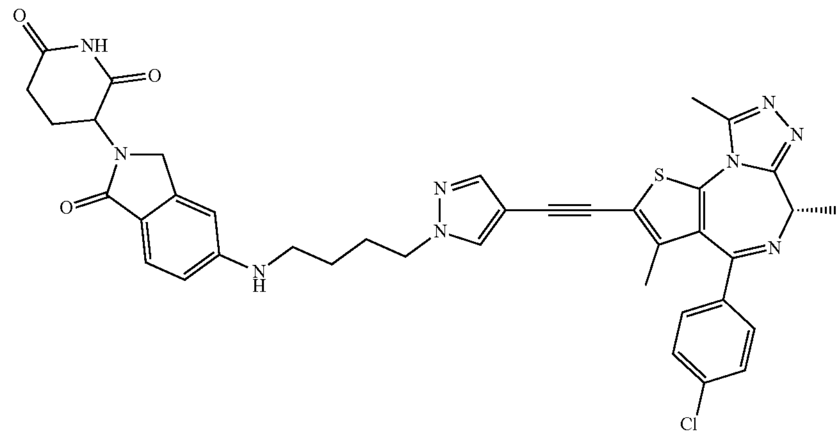 [SMILES: Cc1c(C#Cc2cnn(CCCCNc3ccc4c(c3)CN(C3CCC(=O)NC3=O)C4=O)c2)sc2c1C(c1ccc(Cl)cc1)=N[C@@H](C)c1nnc(C)n1-2] | 3-(5-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione |
| 185 | 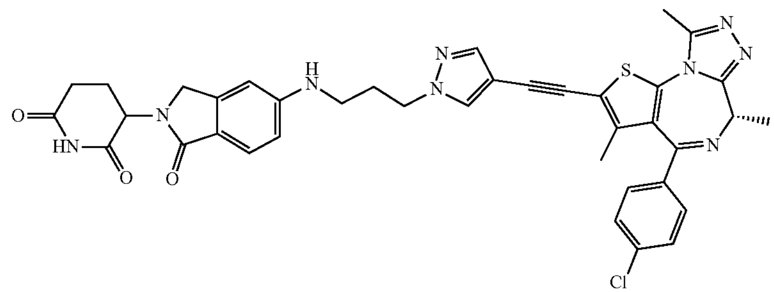 [SMILES: Cc1c(C#Cc2cnn(CCCNc3ccc4c(c3)CN(C3CCC(=O)NC3=O)C4=O)c2)sc2c1C(c1ccc(Cl)cc1)=N[C@@H](C)c1nnc(C)n1-2] | 3-(5-((3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)amino)-1-oxoisoindolin-2-yl)piperidine-2,6-dione |

TABLE 1A-continued

| Cpd. No. | Structure | Name |
|---|---|---|
| 188 | 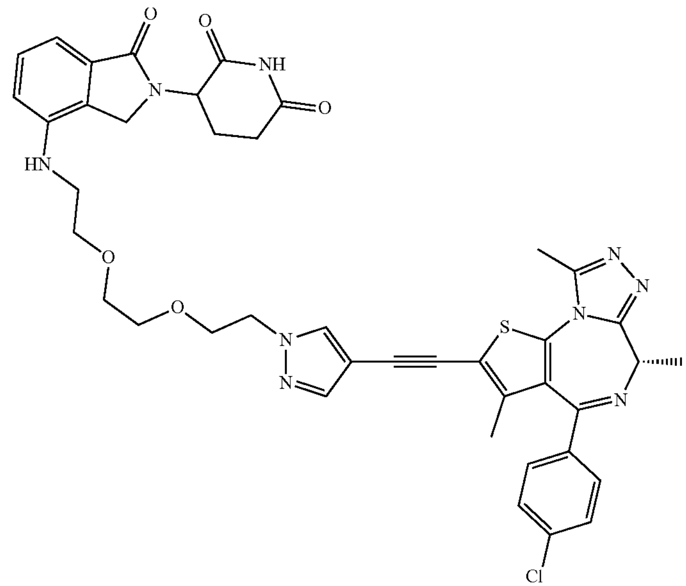 [SMILES: Cc1c(C#Cc2cnn(CCOCCOCCNc3cccc4c3CN(C3CCC(=O)NC3=O)C4=O)c2)sc2c1C(c1ccc(Cl)cc1)=N[C@@H](C)c1nnc(C)n1-2] | 3-(4-((2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)ethyl)amino)-1-oxoisoindolin-2-yl)piperidine-2,6-dione |
| 189 | 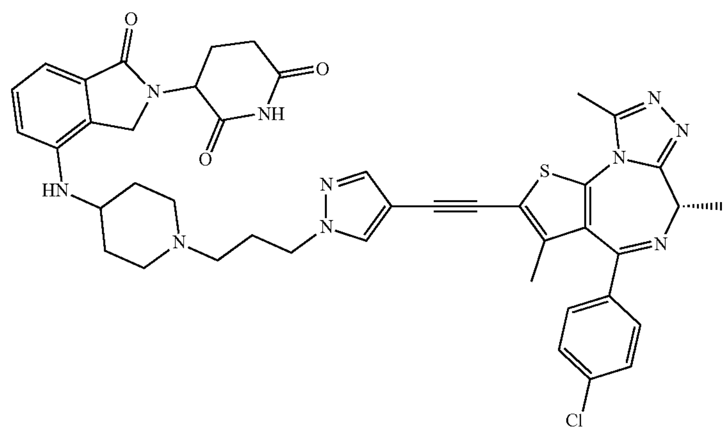 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=N[C@@H](C)c1nnc(C)n1-2] | 3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione |

TABLE 1A-continued

| Cpd. No. | Structure | Name |
|---|---|---|
| 190 | 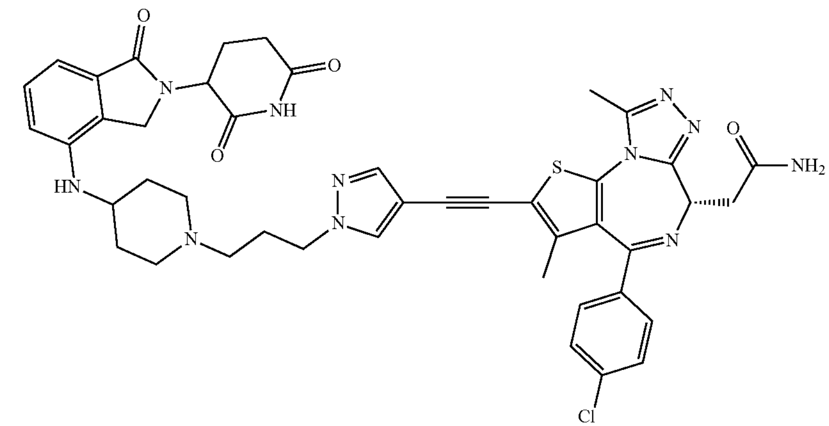 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=N[C@@H](CC(N)=O)c1nnc(C)n1-2] | 2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)acetamide |
| 191 | 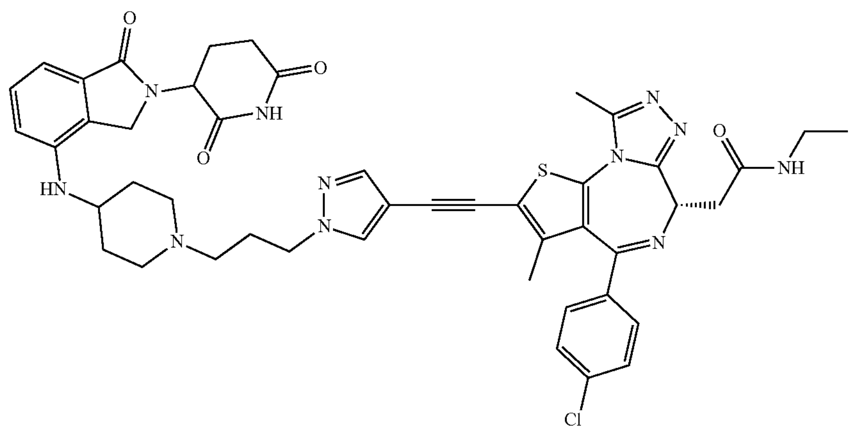 [SMILES: CCNC(=O)C[C@@H]1N=C(c2ccc(Cl)cc2)c2c(sc(C#Cc3cnn(CCCN4CCC(Nc5cccc6c5CN(C5CCC(=O)NC5=O)C6=O)CC4)c3)c2C)-n2c(C)nnc21] | 2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)-N-ethylacetamide |

TABLE 1A-continued

| Cpd. No. | Structure | Name |
|---|---|---|
| 192 | 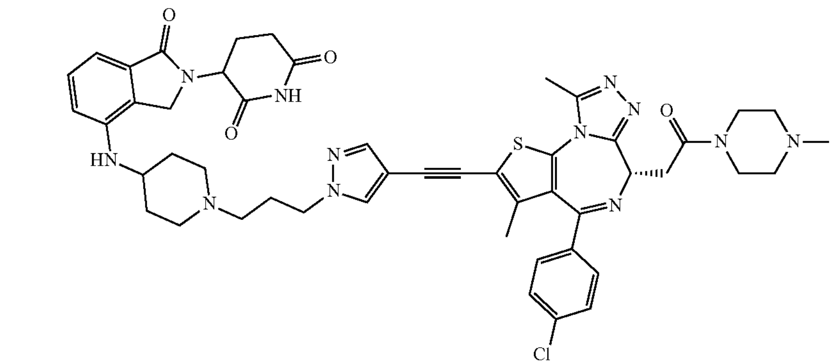 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=N[C@@H](CC(=O)N1CCN(C)CC1)c1nnc(C)n1-2] | 3-(4-((1-(3-(4-((S)-4-(4-chlorophenyl)-3,9-dimethyl-6-(2-(4-methylpiperazin-1-yl)-2-oxoethyl)-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione |
| 193 | 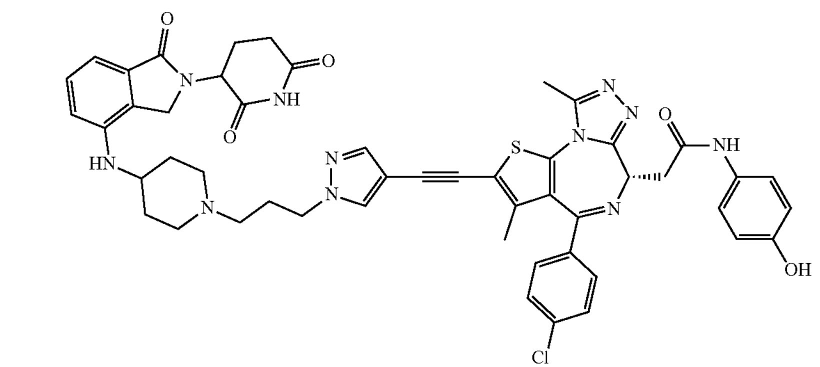 [SMILES: Cc1c(C#Cc2cnn(CCCN3CCC(Nc4cccc5c4CN(C4CCC(=O)NC4=O)C5=O)CC3)c2)sc2c1C(c1ccc(Cl)cc1)=N[C@@H](CC(=O)Nc1ccc(O)cc1)c1nnc(C)n1-2] | 2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)-N-(4-hydroxyphenyl)acetamide |
| 194 | 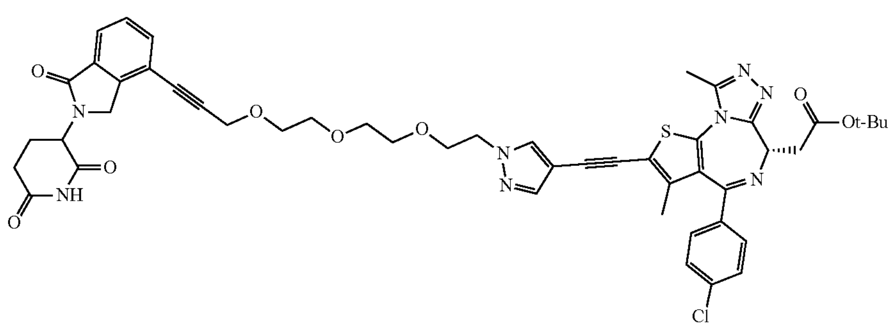 [SMILES: Cc1c(C#Cc2cnn(CCOCCOCCOCC#Cc3cccc4c3CN(C3CCC(=O)NC3=O)C4=O)c2)sc2c1C(c1ccc(Cl)cc1)=N[C@@H](CC(=O)OC(C)(C)C)c1nnc(C)n1-2] | tert-butyl 2-((6S)-4-(4-chlorophenyl)-2-((1-(2-(2-(2-((3-(2-(2,6-dioxopiperidin-3-yl)-1-oxoisoindolin-4-yl)prop-2-yn-1-yl)oxy)ethoxy)ethoxy)ethyl)-1H-pyrazol-4-yl)ethynyl)-3,9-dimethyl-6H-thieno[3,2-f][1,2,4]triazolo[4,3-a][1,4]diazepin-6-yl)acetate |

TABLE 1A-continued

| Cpd. No. | Structure | Name |
|---|---|---|
| 195 | 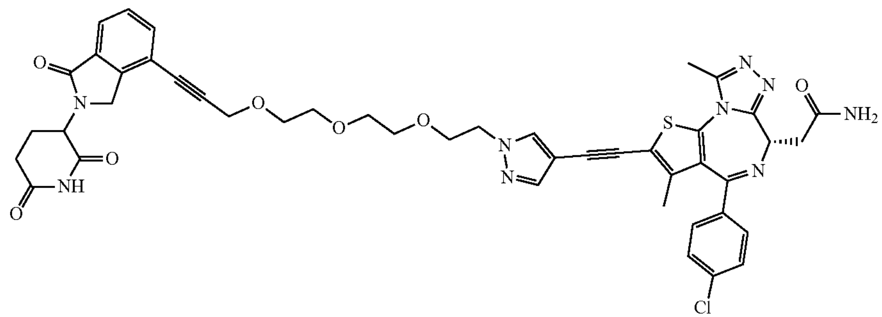 [SMILES: Cc1c(C#Cc2cnn(CCOCCOCCOCC#Cc3cccc4c3CN(C3CCC(=O)NC3=O)C4=O)c2)sc2c1C(c1ccc(Cl)cc1)=N[C@@H](CC(N)=O)c1nnc(C)n1-2] | 2-((6S)-4-(4-chlorophenyl)-2-((1-(2-(2-(2-((3-(2-(2,6-dioxopiperidin-3-yl)-1-oxoisoindolin-4-yl)prop-2-yn-1-yl)oxy)ethoxy)ethoxy)ethyl)-1H-pyrazol-4-yl)ethynyl)-3,9-dimethyl-6H-thieno[3,2-f][1,2,4]triazolo[4,3-a][1,4]diazepin-6-yl)acetamide |
| 196 | 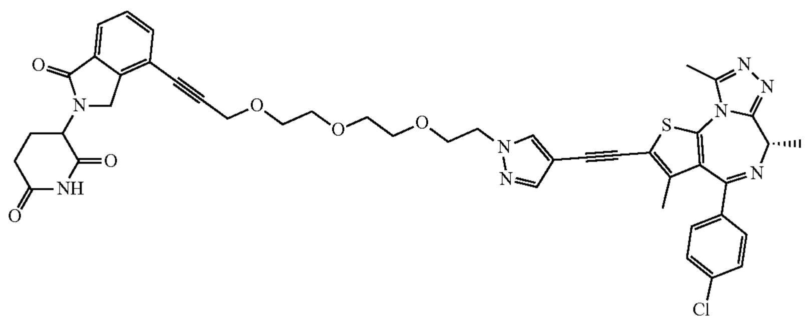 [SMILES: Cc1c(C#Cc2cnn(CCOCCOCCOCC#Cc3cccc4c3CN(C3CCC(=O)NC3=O)C4=O)c2)sc2c1C(c1ccc(Cl)cc1)=N[C@@H](C)c1nnc(C)n1-2] | 3-(4-(3-(2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)prop-1-yn-1-yl)-1-oxoisoindolin-2-yl)piperidine-2,6-dione |
| 197 | 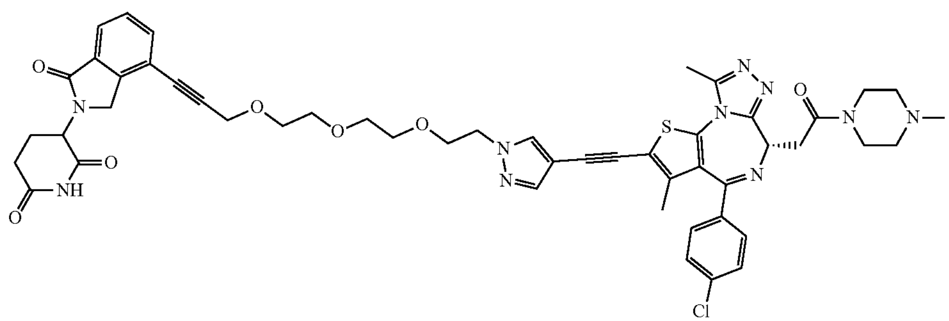 [SMILES: Cc1c(C#Cc2cnn(CCOCCOCCOCC#Cc3cccc4c3CN(C3CCC(=O)NC3=O)C4=O)c2)sc2c1C(c1ccc(Cl)cc1)=N[C@@H](CC(=O)N1CCN(C)CC1)c1nnc(C)n1-2] | 3-(4-(3-(2-(2-(2-(4-(((S)-4-(4-chlorophenyl)-3,9-dimethyl-6-(2-(4-methylpiperazin-1-yl)-2-oxoethyl)-6H-thieno[3,2-f][1,2,4]triazolo[4,3-a][1,4]diazepin-2-yl)ethynyl)-1H-pyrazol-1-yl)ethoxy)ethoxy)prop-1-yn-1-yl)-1-oxoisoindolin-2-yl)piperidine-2,6-dione |

TABLE 1A-continued

| Cpd. No. | Structure | Name |
|---|---|---|
| 198 | 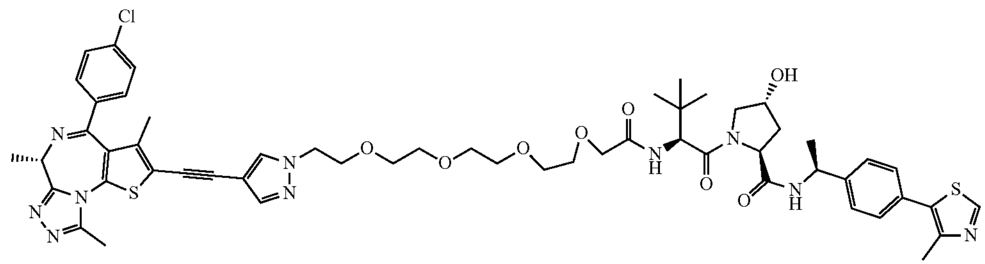 [SMILES: Cc1ncsc1-c1ccc([C@H](C)NC(=O)[C@@H]2C[C@@H](O)CN2C(=O)[C@@H](NC(=O)COCCOCCOCCOCCn2cc(C#Cc3sc4c(c3C)C(c3ccc(Cl)cc3)=N[C@@H](C)c3nnc(C)n3-4)cn2)C(C)(C)C)cc1] | (2S,4R)-1-((S)-2-(tert-butyl)-17-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide |
| 199 | 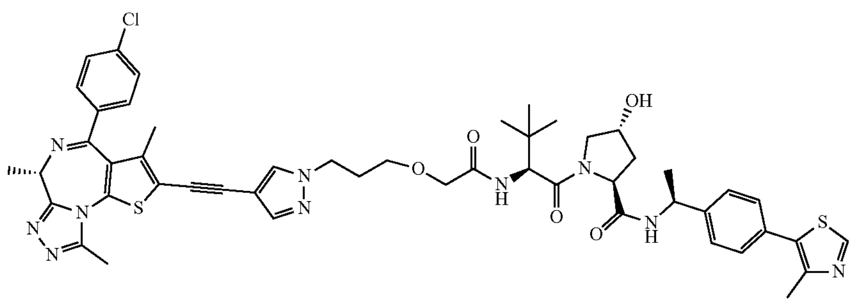 [SMILES: Cc1ncsc1-c1ccc([C@H](C)NC(=O)[C@@H]2C[C@@H](O)CN2C(=O)[C@@H](NC(=O)COCCCn2cc(C#Cc3sc4c(c3C)C(c3ccc(Cl)cc3)=N[C@@H](C)c3nnc(C)n3-4)cn2)C(C)(C)C)cc1] | (2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-N-((S)-1-(4-(4-methylthiazol-5-yl)phenyl)ethyl)pyrrolidine-2-carboxamide |
| 200 | 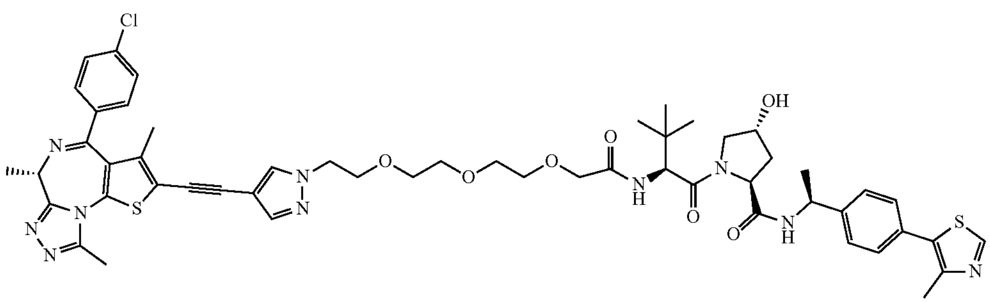 [SMILES: Cc1ncsc1-c1ccc([C@H](C)NC(=O)[C@@H]2C[C@@H](O)CN2C(=O)[C@@H](NC(=O)COCCOCCOCCn2cc(C#Cc3sc4c(c3C)C(c3ccc(Cl)cc3)=N[C@@H](C)c3nnc(C)n3-4)cn2)C(C)(C)C)cc1] | (2S,4R)-1-((S)-2-(tert-butyl)-14-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |

TABLE 1A-continued

| Cpd. No. | Structure | Name |
|---|---|---|
| 201 | 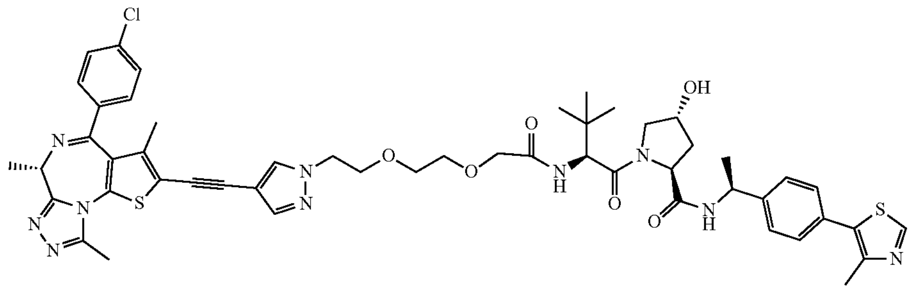 [SMILES: Cc1ncsc1-c1ccc([C@H](C)NC(=O)[C@@H]2C[C@@H](O)CN2C(=O)[C@@H](NC(=O)COCCOCCn2cc(C#Cc3sc4c(c3C)C(c3ccc(Cl)cc3)=N[C@@H](C)c3nnc(C)n3-4)cn2)C(C)(C)C)cc1] | (2S,4R)-1-((S)-2-((S)-2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 202 | 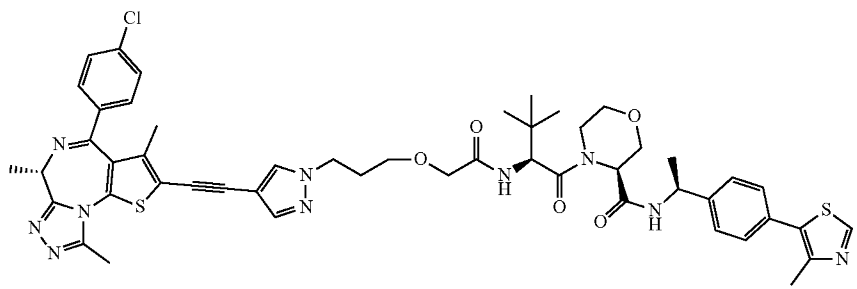 [SMILES: Cc1ncsc1-c1ccc([C@H](C)NC(=O)[C@@H]2COCCN2C(=O)[C@@H](NC(=O)COCCCn2cc(C#Cc3sc4c(c3C)C(c3ccc(Cl)cc3)=N[C@@H](C)c3nnc(C)n3-4)cn2)C(C)(C)C)cc1] | (S)-4-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-N-((S)-1-(4-(4-methylthiazol-5-yl)phenyl)ethyl)morpholine-3-carboxamide |
| 203 | 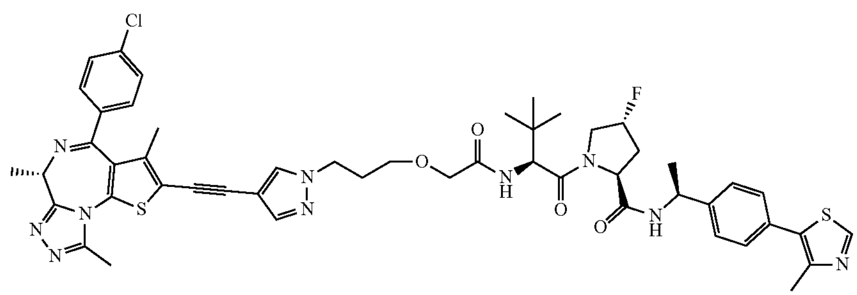 [SMILES: Cc1ncsc1-c1ccc([C@H](C)NC(=O)[C@@H]2C[C@@H](F)CN2C(=O)[C@@H](NC(=O)COCCCn2cc(C#Cc3sc4c(c3C)C(c3ccc(Cl)cc3)=N[C@@H](C)c3nnc(C)n3-4)cn2)C(C)(C)C)cc1] | (2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-fluoro-N-((S)-1-(4-(4-methylthiazol-5-yl)phenyl)ethyl)pyrrolidine-2-carboxamide |

TABLE 1A-continued

| Cpd. No. | Structure | Name |
|---|---|---|
| 204 | 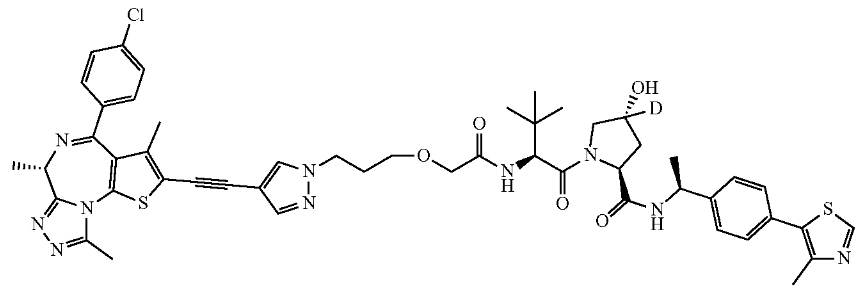 [SMILES: [2H][C@@]1(O)C[C@@H](C(=O)N[C@@H](C)c2ccc(-c3scnc3C)cc2)N(C(=O)[C@@H](NC(=O)COCCCn2cc(C#Cc3sc4c(c3C)C(c3ccc(Cl)cc3)=N[C@@H](C)c3nnc(C)n3-4)cn2)C(C)(C)C)C1] | (2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-N-((S)-1-(4-(4-methylthiazol-5-yl)phenyl)ethyl)pyrrolidine-4-d-2-carboxamide |
| 205 | 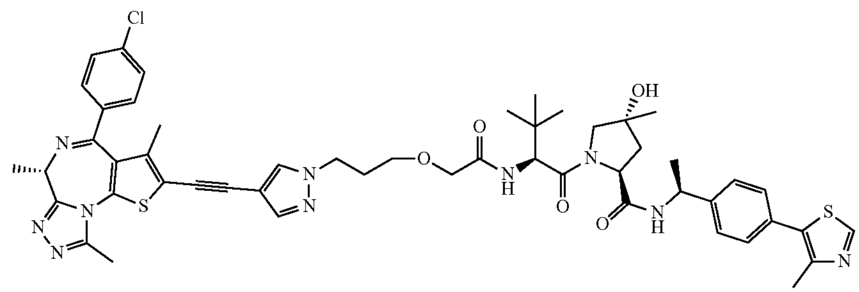 | (2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-4-methyl-N-((S)-1-(4-(4-methylthiazol-5-yl)phenyl)ethyl)pyrrolidine-2-carboxamide |

In another embodiment, Compounds of the Disclosure are compounds of Table 5, and the pharmaceutically acceptable salts and solvates thereof.

TABLE 5

| Cpd. No. | Structure | Name |
| --- | --- | --- |
| 111 | 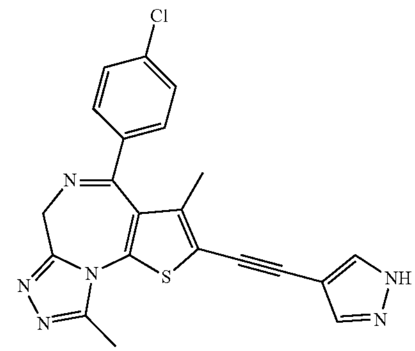 | 2-((1H-pyrazol-4-yl)ethynyl)-4-(4-chlorophenyl)-3,9-dimethyl-6H-thieno[3,2-f][1,2,4]triazolo[4,3-a][1,4]diazepine |
| 112 | 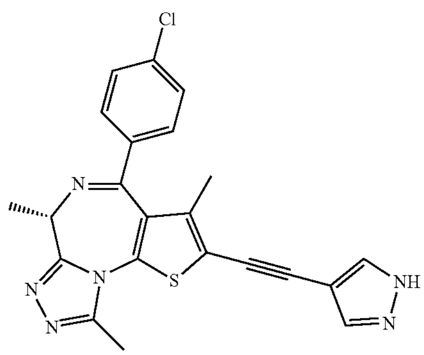 [SMILES: Cc1c(C#Cc2cn[nH]c2)sc2c1C(c1ccc(Cl)cc1)=N[C@@H](C)c1nnc(C)n1-2] | (S)-2-((1H-pyrazol-4-yl)ethynyl)-4-(4-chlorophenyl)-3,6,9-trimethyl-6H-thieno[3,2-f][1,2,4]triazolo[4,3-a][1,4]diazepine |
| 113 | 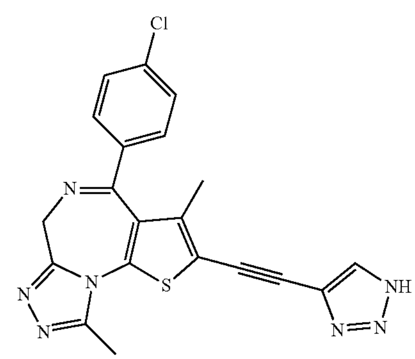 [SMILES: Cc1c(C#Cc2c[nH]nn2)sc2c1C(c1ccc(Cl)cc1)=NCc1nnc(C)n1-2] | 2-((1H-1,2,3-triazol-4-yl)ethynyl)-4-(4-chlorophenyl)-3,9-dimethyl-6H-thieno[3,2-f][1,2,4]triazolo[4,3-a][1,4]diazepine |
| 114 | 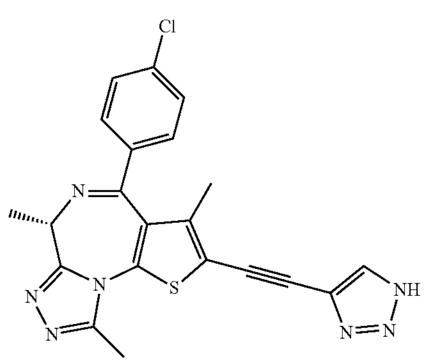 [SMILES: Cc1c(C#Cc2c[nH]nn2)sc2c1C(c1ccc(Cl)cc1)=N[C@@H](C)c1nnc(C)n1-2] | (S)-2-((1H-1,2,3-triazol-4-yl)ethynyl)-4-(4-chlorophenyl)-3,6,9-trimethyl-6H-thieno[3,2-f][1,2,4]triazolo[4,3-a][1,4]diazepine |

TABLE 5-continued

| Cpd. No. | Structure | Name |
|---|---|---|
| 115 | 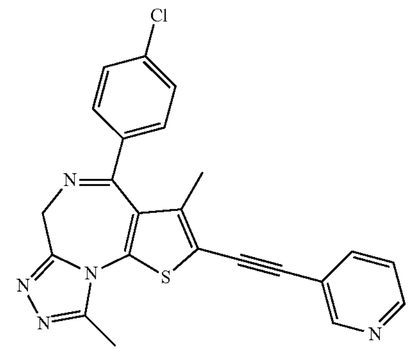 [SMILES: Cc1c(C#Cc2cccnc2)sc2c1C(c1ccc(Cl)cc1)=NCc1nnc(C)n1-2] | 4-(4-chlorophenyl)-3,9-dimethyl-2-(pyridin-3-ylethynyl)-6H-thieno[3,2-f][1,2,4]triazolo[4,3-a][1,4]diazepine |
| 116 | 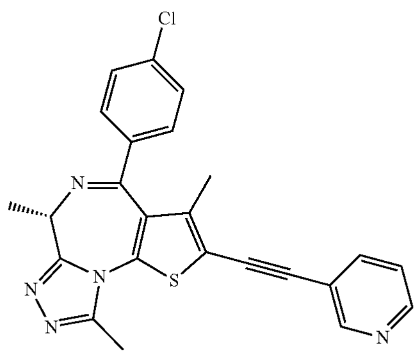 [SMILES: Cc1c(C#Cc2cccnc2)sc2c1C(c1ccc(Cl)cc1)=N[C@@H](C)c1nnc(C)n1-2] | (S)-4-(4-chlorophenyl)-3,6,9-trimethyl-2-(pyridin-3-ylethynyl)-6H-thieno[3,2-f][1,2,4]triazolo[4,3-a][1,4]diazepine |
| 117 | 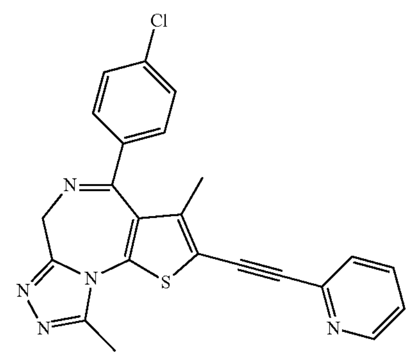 [SMILES: Cc1c(C#Cc2ccccn2)sc2c1C(c1ccc(Cl)cc1)=NCc1nnc(C)n1-2] | 4-(4-chlorophenyl)-3,9-dimethyl-2-(pyridin-2-ylethynyl)-6H-thieno[3,2-f][1,2,4]triazolo[4,3-a][1,4]diazepine |
| 118 | 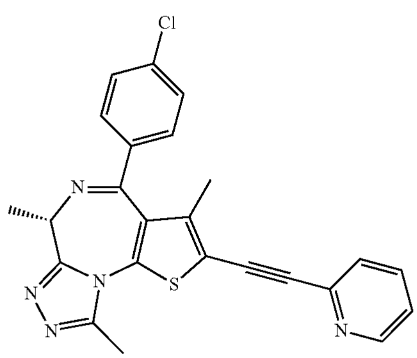 [SMILES: Cc1c(C#Cc2ccccn2)sc2c1C(c1ccc(Cl)cc1)=N[C@@H](C)c1nnc(C)n1-2] | (S)-4-(4-chlorophenyl)-3,6,9-trimethyl-2-(pyridin-2-ylethynyl)-6H-thieno[3,2-f][1,2,4]triazolo[4,3-a][1,4]diazepine |

TABLE 5-continued

| Cpd. No. | Structure | Name |
|---|---|---|
| 119 | 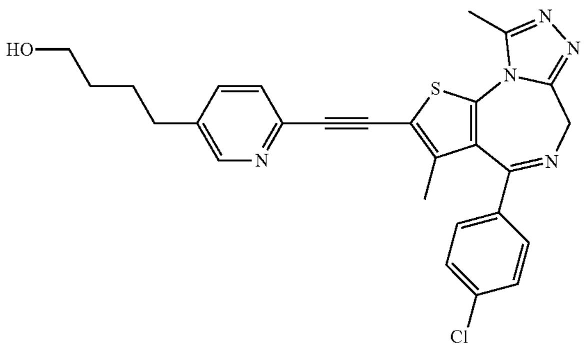 [SMILES: Cc1c(C#Cc2ccc(CCCCO)cn2)sc2c1C(c1ccc(Cl)cc1)=NCc1nnc(C)n1-2] | 4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butan-1-ol |
| 120 | 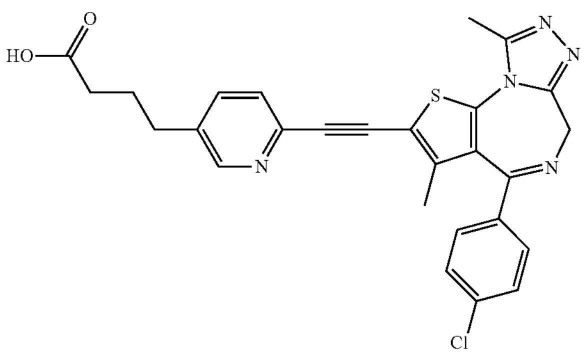 [SMILES: Cc1c(C#Cc2ccc(CCCC(=O)O)cn2)sc2c1C(c1ccc(Cl)cc1)=NCc1nnc(C)n1-2] | 4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butanal |
| 121 | 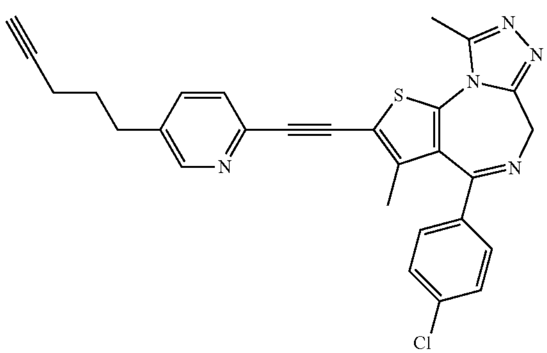 [SMILES: C#CCCCc1ccc(C#Cc2sc3c(c2C)C(c2ccc(Cl)cc2)=NCc2nnc(C)n2-3)nc1] | 4-(4-chlorophenyl)-3,9-dimethyl-2-((5-(pent-4-yn-1-yl)pyridin-2-yl)ethynyl)-6H-thieno[3,2-f][1,2,4]triazolo[4,3-a][1,4]diazepine |
| 122 | 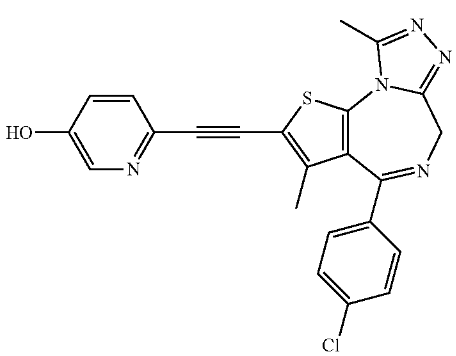 [SMILES: Cc1c(C#Cc2ccc(O)cn2)sc2c1C(c1ccc(Cl)cc1)=NCc1nnc(C)n1-2] | 6-((4-(4-chlorophenyl)-3,9-dimethyl-6H-thieno[3,2-f][1,2,4]triazolo[4,3-a][1,4]diazepin-2-yl)ethynyl)pyridin-3-ol |

TABLE 5-continued

| Cpd. No. | Structure | Name |
|---|---|---|
| 123 | 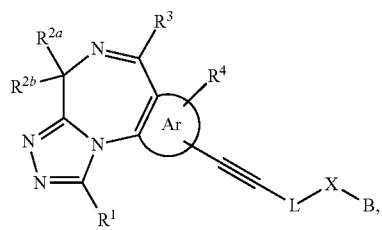 | 2-((5-(but-3-yn-1-yloxy)pyridin-2-yl)ethynyl)-4-(4-chlorophenyl)-3,9-dimethyl-6H-thieno[3,2-f][1,2,4]triazolo[4,3-a][1,4]diazepine |
| 124 | 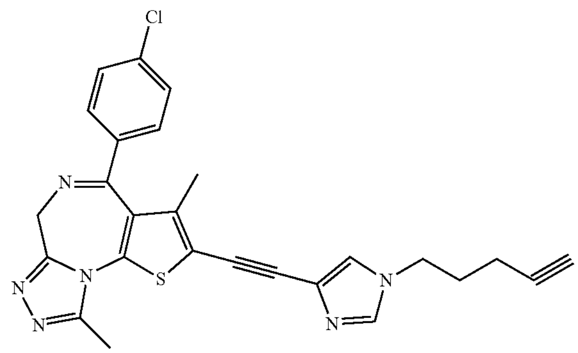 [SMILES: C#CCCCn1cnc(C#Cc2sc3c(c2C)C(c2ccc(Cl)cc2)=NCc2nnc(C)n2-3)c1] | 4-(4-chlorophenyl)-3,9-dimethyl-2-((1-(pent-4-yn-1-yl)-1H-imidazol-4-yl)ethynyl)-6H-thieno[3,2-f][1,2,4]triazolo[4,3-a][1,4]diazepine |

In another embodiment, the disclosure provides methods of making a compound having Formula I. In another embodiment, the disclosure provides a method (METHOD A) of making a compound having Formula I:

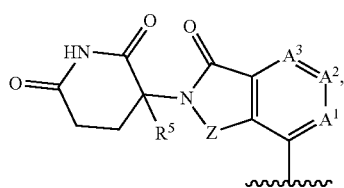

I or a pharmaceutically acceptable salt or hydrate thereof, wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, (alkoxycarbonyl)alkyl, and —$CH_2C(=O)NR^{19a}R^{19b}$, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl $R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

$R^{15}$ is selected from the group consisting of hydrogen, halogen, $C_{1-4}$ alkyl, and alkoxy;

B is a monovalent radical of a ligand for an E3 ubiquitin ligase protein, e.g., B is:

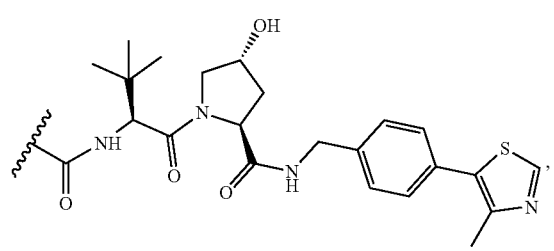

B-1

B-2

-continued

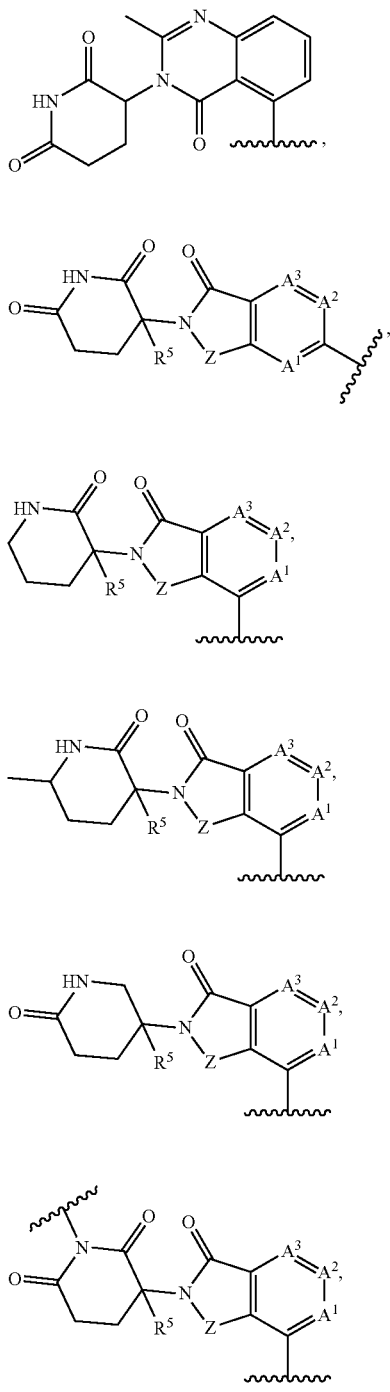

L is selected from the group consisting of alkylenyl, heteroalkylenyl, -A-$(CH_2)_m$—W—$(CH_2)_n$—, —$(CH_2)_m$—W—$(CH_2)_u$—O—$(CH_2)_v$—, and —$(CH_2)_m$—W—[$(CH_2)_w$—O]$_x$—$(CH_2)_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

each w is independently 2, 3, or 4;

x is 2, 3, or 4;

X is selected from the group consisting of —C≡C—, —$CH_2$—, —O—, —N($R^{2c}$)—, —C(=O)N($R^{2d}$)—, —N($R^{2e}$)C(=O)$CH_2$O—, and —N($R^{2f}$)C(=O)$CH_2$N($R^{2g}$)—; or X is absent;

wherein the carboxamide nitrogen atom of —N($R^{2e}$)C(=O)$CH_2$O— and —N($R^{2f}$)C(=O)$CH_2$N($R^{2g}$)—, and the carbon atom of —C(=O)N($R^{2d}$)— is attached to L;

$R^{2c}$, $R^{2d}$, $R^{2e}$, $R^{2f}$, and $R^{2g}$ are each independently selected from the group consisting of hydrogen and $C_{1-4}$ alkyl;

Z is selected from the group consisting of —CH$_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl;

$R^{16c}$ is selected from the group consisting of hydrogen, halo, and $C_{1-4}$ alkyl; and $R^{19a}$ and $R^{19b}$ are independently selected from the group consisting of hydrogen, $C_{1-6}$ alkyl and optionally substituted aryl; or $R^{19a}$ and $R^{19b}$ taken together with the nitrogen atom to which they are attached form a 4- to 8-membered optionally substituted heterocyclo, the method comprising:

(1) reacting a compound having Formula X:

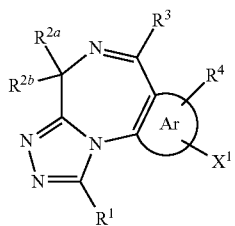

X wherein:

$X^1$ is selected from the group consisting of —Br and —I;

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, (alkoxycarbonyl)alkyl, and —CH$_2$C(=O)NR$^{19a}$R$^{19b}$, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$; and $R^{15}$ is selected from the group consisting of hydrogen, halogen, $C_{1-4}$ alkyl, and alkoxy;

$R^{19a}$ and $R^{19b}$ are independently selected from the group consisting of hydrogen, $C_{1-6}$ alkyl and optionally substituted aryl; or $R^{19a}$ and $R^{19b}$ taken together with the nitrogen atom to which they are attached form a 4- to 8-membered optionally substituted heterocyclo, with a compound having Formula XI:

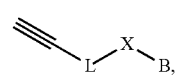

XI wherein:

B is selected from the group consisting of

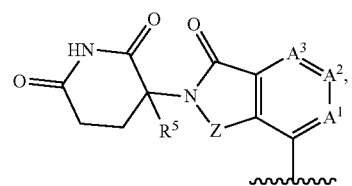

B-1

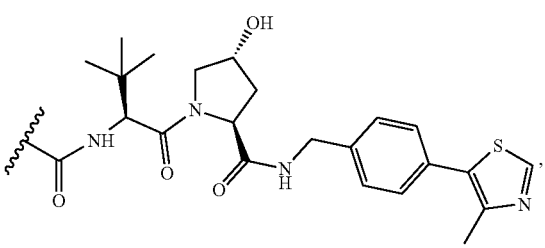

B-2

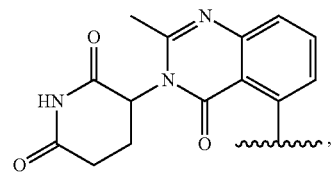

B-3

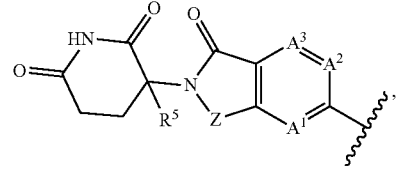

B-4

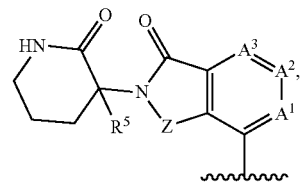

B-5

-continued

B-6

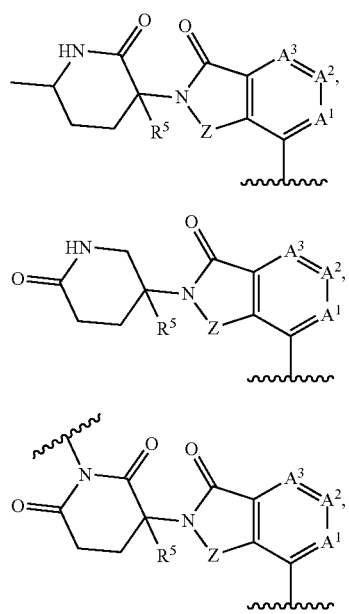

B-7

B-8

B-9

B-10

B-11

B-12

-continued

B-13

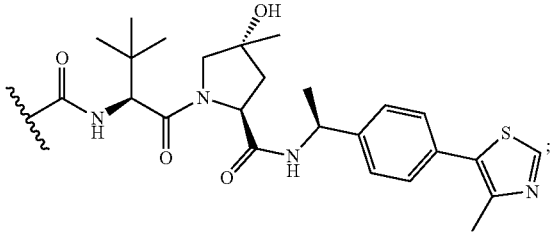

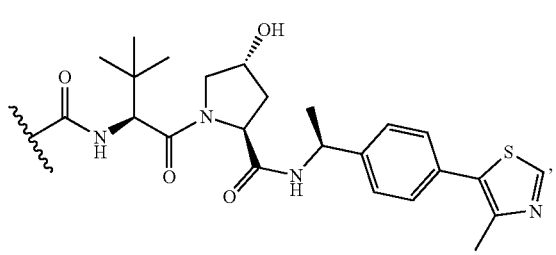

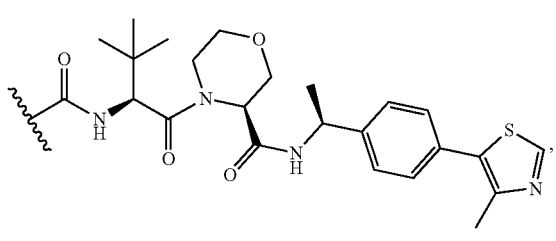

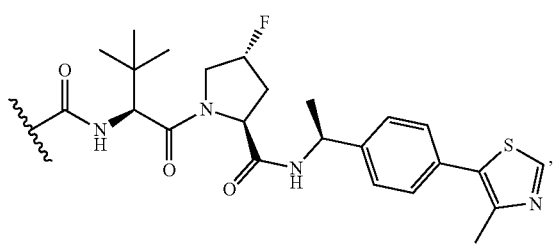

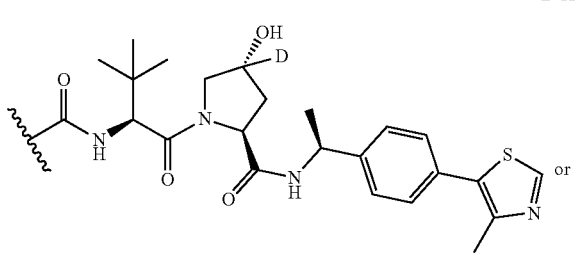

or

L is selected from the group consisting of alkylenyl, heteroalkylenyl, -A-$(CH_2)_m$—W—$(CH_2)_n$—, —$(CH_2)_m$—W—$(CH_2)_u$—O—$(CH_2)_v$—, and —$(CH_2)_m$—W—$[(CH_2)_w$—O$]_x$—$(CH_2)_v$—;

A is selected from the group consisting of 5 membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

each w is independently 2, 3, or 4;

x is 2, 3, or 4

X is selected from the group consisting of —C≡C—, —$CH_2$—, —O—, —N($R^{2c}$)—, —C(=O)N($R^{2d}$)—, —N($R^{2e}$)C(=O)$CH_2$O—, and —N($R^{2f}$)C(=O)$CH_2$N($R^{2g}$)—; or X is absent;

wherein the carboxamide nitrogen atom of —N($R^{2e}$)C(=O)$CH_2$O— and —N($R^{2f}$)C(=O)$CH_2$N($R^{2g}$)—, and the carbon atom of —C(=O)N($R^{2d}$)— is attached to L;

$R^{2c}$, $R^{2d}$, $R^{2e}$, $R^{2f}$, and $R^{2g}$ are each independently selected from the group consisting of hydrogen and $C_{1-4}$ alkyl;

Z is selected from the group consisting of —$CH_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, and (2) isolating the compound having Formula I, or a pharmaceutically acceptable salt or solvate thereof.

Non-limiting exemplary compounds having Formula XI are compounds of Table 2.

TABLE 2
| Structure |
|---|
| 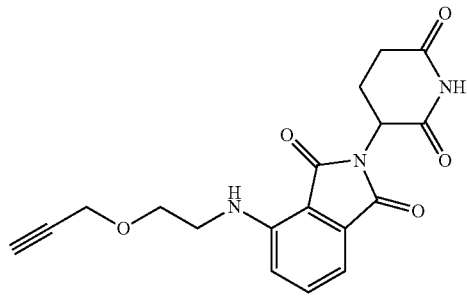 [SMILES: C#CCOCCNc1cccc2c1C(=O)N(C1CCC(=O)NC1=O)C2=O] |
| 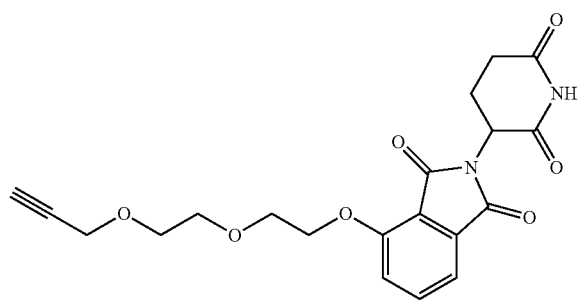 [SMILES: C#CCOCCOCCOc1cccc2c1C(=O)N(C1CCC(=O)NC1=O)C2=O] |
| 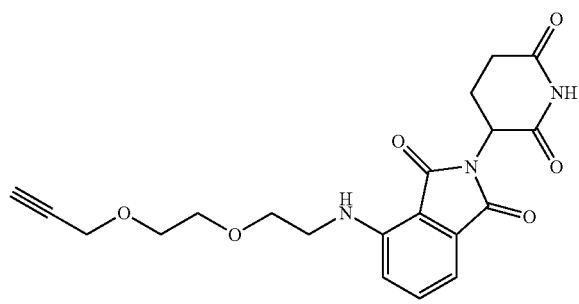 [SMILES: C#CCOCCOCCNc1cccc2c1C(=O)N(C1CCC(=O)NC1=O)C2=O] |
| 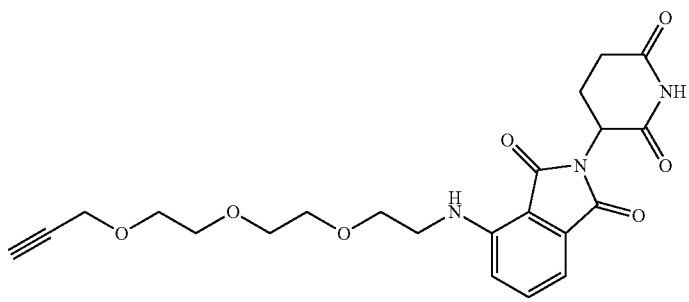 [SMILES: C#CCOCCOCCOCCNc1cccc2c1C(=O)N(C1CCC(=O)NC1=O)C2=O] |
| 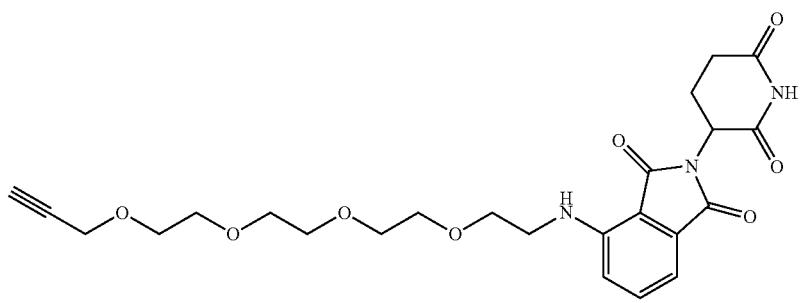 [SMILES: C#CCOCCOCCOCCOCCNc1cccc2c1C(=O)N(C1CCC(=O)NC1=O)C2=O] |

TABLE 2-continued

Structure

TABLE 2-continued
Structure
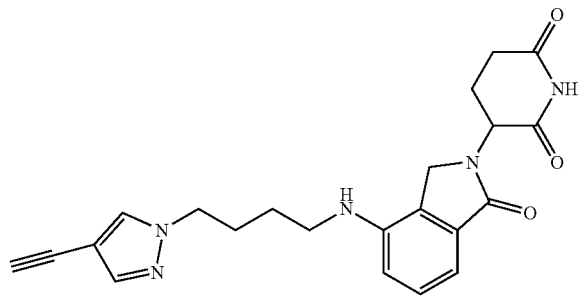 [SMILES: C#Cc1cnn(CCCCNc2cccc3c2CN(C2CCC(=O)NC2=O)C3=O)c1]
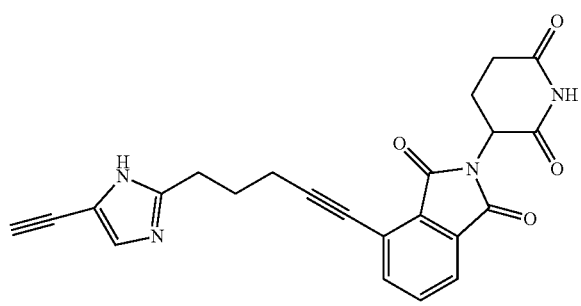 [SMILES: C#Cc1cnc(CCCC#Cc2cccc3c2C(=O)N(C2CCC(=O)NC2=O)C3=O)[nH]1]
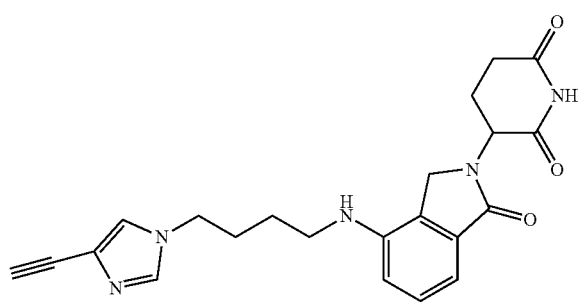 [SMILES: C#Cc1cn(CCCCNc2cccc3c2CN(C2CCC(=O)NC2=O)C3=O)cn1]
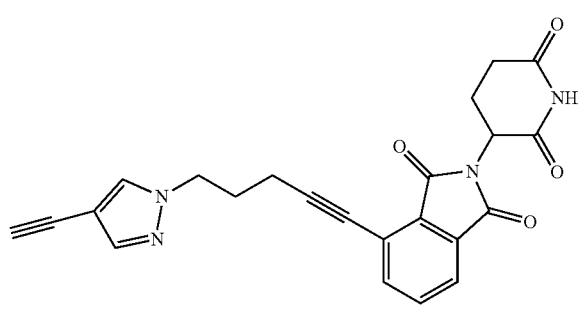 [SMILES: C#Cc1cnn(CCCC#Cc2cccc3c2C(=O)N(C2CCC(=O)NC2=O)C3=O)c1]
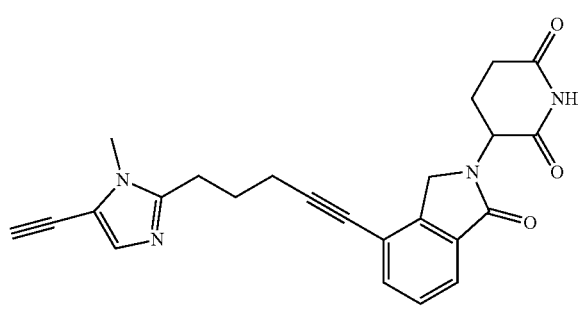 [SMILES: C#Cc1cnc(CCCC#Cc2cccc3c2CN(C2CCC(=O)NC2=O)C3=O)n1C]

TABLE 2-continued
Structure
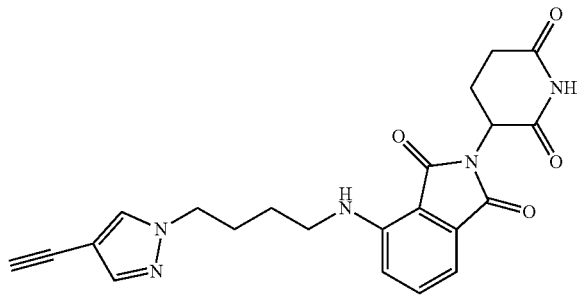 [SMILES: C#Cc1cnn(CCCCNc2cccc3c2C(=O)N(C2CCC(=O)NC2=O)C3=O)c1]
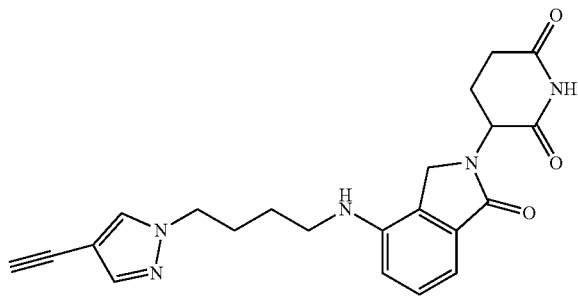 [SMILES: C#Cc1cnn(CCCCNc2cccc3c2CN(C2CCC(=O)NC2=O)C3=O)c1]
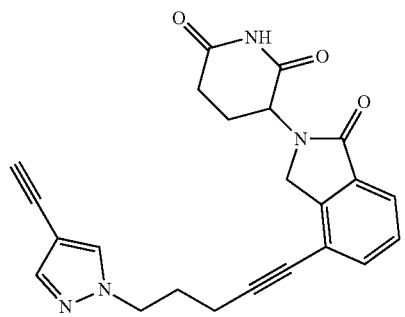 [SMILES: C#Cc1cnn(CCCC#Cc2cccc3c2CN(C2CCC(=O)NC2=O)C3=O)c1]
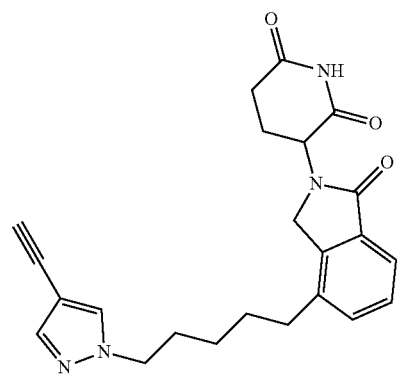 [SMILES: C#Cc1cnn(CCCCCc2cccc3c2CN(C2CCC(=O)NC2=O)C3=O)c1]
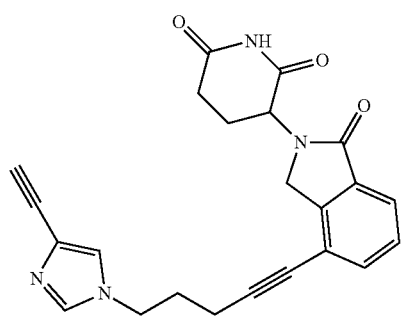 [SMILES: C#Cc1cn(CCCC#Cc2cccc3c2CN(C2CCC(=O)NC2=O)C3=O)cn1]

TABLE 2-continued

Structure

TABLE 2-continued
| Structure |
| --- |
| 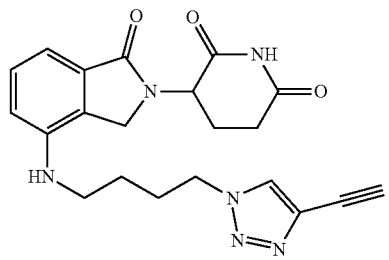 [SMILES: C#Cc1cn(CCCCCc2cccc3c2CN(C2CCC(=O)NC2=O)C3=O)nn1] |
| 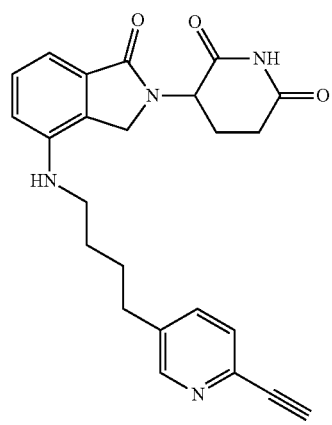 [SMILES: C#Cc1ccc(CCCCNc2cccc3c2CN(C2CCC(=O)NC2=O)C3=O)cn1] |
| 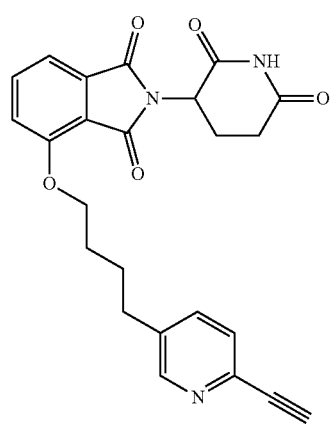 [SMILES: C#Cc1ccc(CCCCOc2cccc3c2C(=O)N(C2CCC(=O)NC2=O)C3=O)cn1] |
| 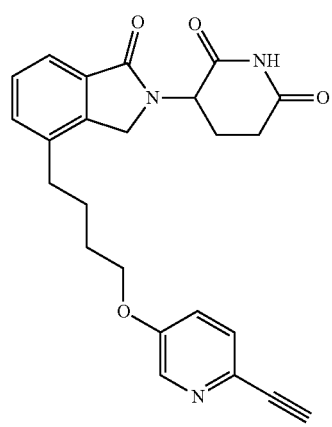 [SMILES: C#Cc1ccc(OCCCCc2cccc3c2CN(C2CCC(=O)NC2=O)C3=O)cn1] |

TABLE 2-continued
Structure
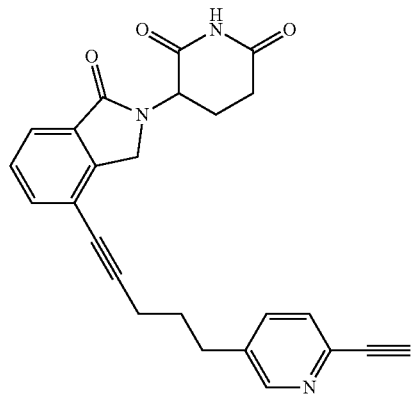
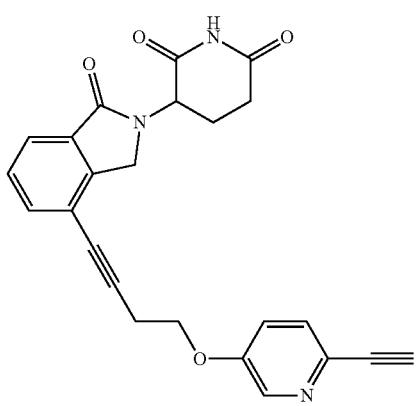
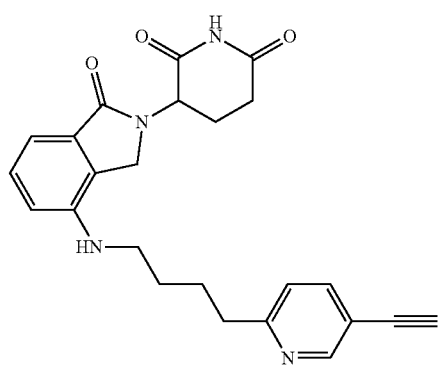 [SMILES: C#Cc1ccc(CCCCNc2cccc3c2CN(C2CCC(=O)NC2=O)C3=O)nc1]
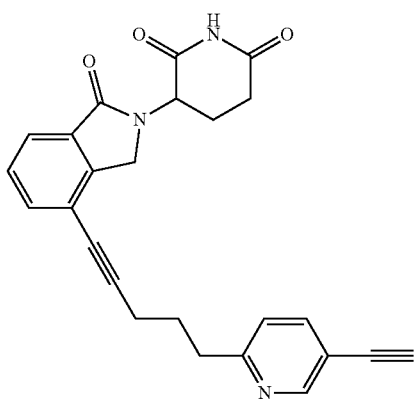 [SMILES: C#Cc1ccc(CCCC#Cc2cccc3c2CN(C2CCC(=O)NC2=O)C3=O)nc1]

TABLE 2-continued

Structure

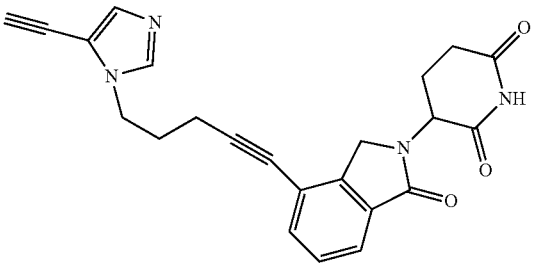 [SMILES: C#Cc1cncn1CCCC#Cc1cccc2c1CN(C1CCC(=O)NC1=O)C2=O]

In another embodiment, the disclosure provides a method (METHOD B) of making a compound of claim 1 having Formula I:

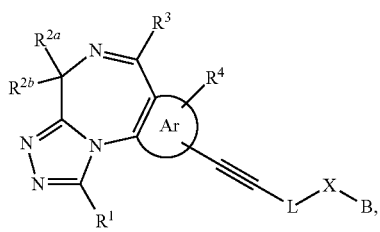

or a pharmaceutically acceptable salt or hydrate thereof, wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, and (alkoxycarbonyl)alkyl, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

$R^{15}$ is selected from the group consisting of hydrogen, halogen, $C_{1-4}$ alkyl, and alkoxy;

B is:

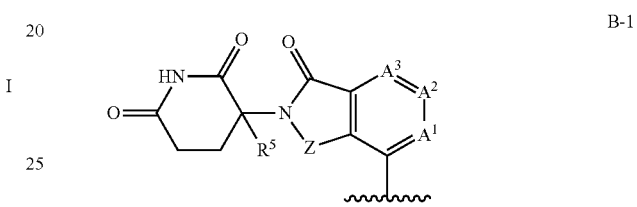

L is —W—(CH$_2$)$_n$—;

W is selected from the group consisting of phenylenyl, 5-membered heteroarylenyl, and 6-membered heteroarylenyl;

n is 1, 2, 3, 4, 5, 6, 7, or 8;

X is —N(H)—;

Z is selected from the group consisting of —CH$_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, the method comprising:

(1) condensing a compound having Formula XII:

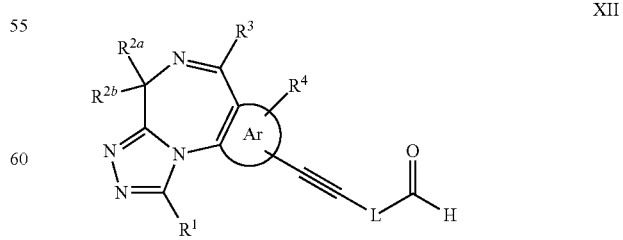

wherein:

$R^1$ is selected from the group consisting of hydrogen and optionally substituted $C_{1-4}$ alkyl;

$R^{2a}$ and $R^{2b}$ are each independently selected from the group consisting of hydrogen, optionally substituted $C_{1-4}$ alkyl, and (alkoxycarbonyl)alkyl, or $R^{2a}$ and $R^{2b}$ together with the carbon atom to which they are attached form a 3- to 6-membered cycloalkyl;

$R^3$ is selected from the group consisting of optionally substituted $C_{6-14}$ aryl and optionally substituted 5- to 14-membered heteroaryl;

$R^4$ is selected from the group consisting of hydrogen, halogen, optionally substituted $C_{1-4}$ alkyl, optionally substituted $C_{2-4}$ alkenyl, optionally substituted $C_{2-4}$ alkynyl, aralkyl, optionally substituted $C_{6-14}$ aryl, optionally substituted $C_{3-12}$ cycloalkyl, optionally substituted 3- to 14-membered heterocyclo, and optionally substituted 5- to 14-membered heteroaryl;

is a fused thienyl or fused phenyl group, wherein the fused phenyl group is additionally substituted with $R^{15}$;

$R^{15}$ is selected from the group consisting of hydrogen, halogen, $C_{1-4}$ alkyl, and alkoxy, L is —W—$(CH_2)_n$—;

W is selected from the group consisting of phenylenyl, 5-membered heteroarylenyl, and 6-membered heteroarylenyl; and n is 0, 1, 2, 3, 4, 5, 6, or 7;

with a compound having Formula XIII:

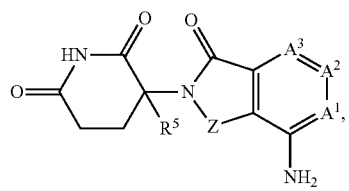

or a pharmaceutically acceptable salt or hydrate thereof, wherein:

Z is selected from the group consisting of —$CH_2$ and —C(=O)—;

$R^5$ is selected from the group consisting of hydrogen, methyl, and fluoro;

$A^1$ is selected from the group consisting of —C($R^{16a}$)= and —N=;

$A^2$ is selected from the group consisting of —C($R^{16b}$)= and —N=;

$A^3$ is selected from the group consisting of —C($R^{16c}$)= and —N=;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl, to give a compound having Formula XIV:

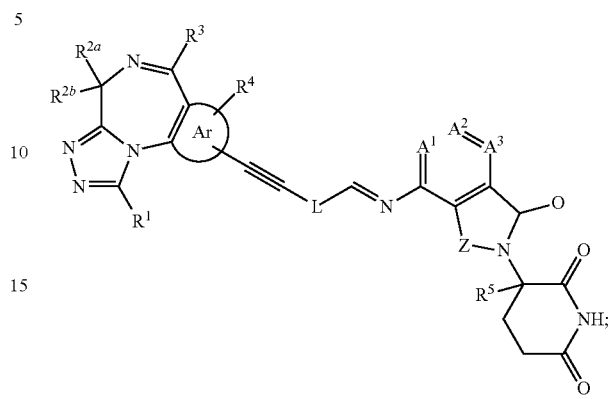

(2) reducing the compound having Formula XIV to give a compound having Formula I, or a pharmaceutically acceptable salt or solvate thereof.

In another embodiment, the disclosure provides a method, e.g., METHOD A or METHOD B, for making a compound represented by Formula II

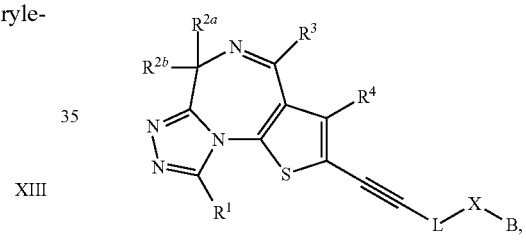

and the pharmaceutically acceptable salts or hydrates thereof, wherein $R^1$, $R^{2a}$, $R^{2b}$, $R^3$, $R^4$, L, X, and B are as defined in connection with Formula I.

In another embodiment, the disclosure provides a method, e.g., METHOD A or METHOD B, for making a compound represented by Formula I or Formula II, and the pharmaceutically acceptable salts or hydrates thereof, wherein $R^3$ is optionally substituted phenyl.

In another embodiment, the disclosure provides a method, e.g., METHOD A or METHOD B, for making a compound represented by Formula I or Formula II, and the pharmaceutically acceptable salts or hydrates thereof, wherein $R^1$ is $C_{1-4}$ alkyl. In another embodiment, $R^1$ is methyl.

In another embodiment, the disclosure provides a method, e.g., METHOD A or METHOD B, for making a compound represented by Formula I or Formula II, and the pharmaceutically acceptable salts or hydrates thereof, wherein $R^{2a}$ and $R^{2b}$ are each independently selected from the group consisting of hydrogen and $C_{1-4}$ alkyl.

In another embodiment, the disclosure provides a method, e.g., METHOD A or METHOD B, for making a compound represented by Formula m:

III

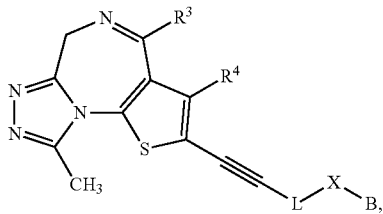

and the pharmaceutically acceptable salts or hydrates thereof, wherein $R^3$, $R^4$, L, X, and B are as defined in connection with Formula I.

In another embodiment, the disclosure provides a method, e.g., METHOD A or METHOD B, for making a compound represented by Formula IV:

IV

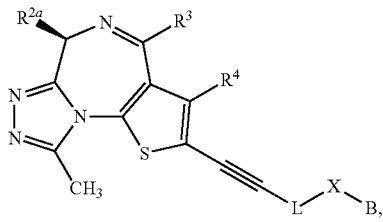

and the pharmaceutically acceptable salts or hydrates thereof, wherein $R^{2a}$ is $C_{1-4}$ alkyl, and $R^3$, $R^4$, L, X, and B are as defined in connection with Formula I.

In another embodiment, the disclosure provides a method, e.g., METHOD A or METHOD B, for making a compound represented by Formula V:

V

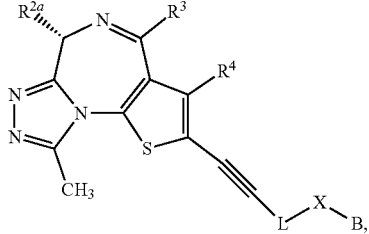

and the pharmaceutically acceptable salts or hydrates thereof, wherein $R^{2a}$ is $C_{1-4}$ alkyl, and $R^3$, $R^4$, L, X, and B are as defined in connection with Formula I.

In another embodiment, the disclosure provides a method, e.g., METHOD A or METHOD B, for making a compound represented by any one of Formula I-V, and the pharmaceutically acceptable salts or hydrates thereof, wherein $R^4$ is $C_{1-4}$ alkyl. In another embodiment, $R^4$ is methyl. In another embodiment, $R^4$ is hydrogen.

In another embodiment, the disclosure provides a method, e.g., METHOD A or METHOD B, for making a compound represented by Formula VI:

VI

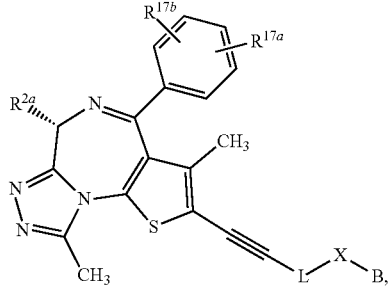

and the pharmaceutically acceptable salts and hydrates thereof, wherein $R^{2a}$ is selected from the group consisting of hydrogen and $C_{1-3}$ alkyl; $R^{17a}$ and $R^{17b}$ are each independently selected from the group consisting of hydrogen, $C_{1-4}$ alkyl, haloalkyl, $C_{1-4}$ alkoxy, and halo; and L, X, and B are as defined in connection with Formula I. In another embodiment, $R^{17a}$ and $R^{17b}$ are each independently selected from the group consisting of hydrogen and halo In another embodiment, the disclosure provides a method, e.g., METHOD A or METHOD B, for making a compound represented by any one of Formulae I-VI, and the pharmaceutically acceptable salts or solvates thereof, wherein L is $C_{1-12}$ alkylenyl. In another embodiment, L is selected from the group consisting of —$CH_2$—, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, and —$CH_2(CH_2)_6CH_2$—.

In another embodiment, the disclosure provides a method, e.g., METHOD A or METHOD B, for making a compound represented by any one of Formulae I-VI, and the pharmaceutically acceptable salts or solvates thereof, wherein, L is 3- to 12-membered heteroalkylenyl. In another embodiment, L is —$(CH_2)_oO$—$(CH_2CH_2O)_p$—$(CH_2)_q$—; o is 1, 2, or 3; p is 0, 1, 2, 3, 4, or 5; and q is 1, 2, or 3.

In another embodiment, the disclosure provides a method, e.g., METHOD A or METHOD B, for making a compound represented by any one of Formulae I-VI, and the pharmaceutically acceptable salts or solvates thereof, wherein L is selected from the group consisting of: —$CH_2OCH_2CH_2$—, —$CH_2CH_2OCH_2CH_2$—, —$CH_2O(CH_2CH_2O)CH_2CH_2$—, —$CH_2O(CH_2CH_2O)CH_2CH_2$—, —$CH_2O(CH_2CH_2O)_3CH_2CH_2$—, —$CH_2CH_2O(CH_2CH_2O)_6CH_2CH_2$—, —$CH_2CH_2O(CH_2CH_2O)_6CH_2CH_2$—, —$CH_2CH_2CH_2OCH_2CH_2OCH_2CH_2CH_2$—, —$CH_2CH_2CH_2O(CH_2CH_2O)_2CH_2CH_2CH_2$—, and —$CH_2CH_2CH_2O(CH_2)_4OCH_2CH_2CH_2$—.

In another embodiment, the disclosure provides a method, e.g., METHOD A or METHOD B, for making a compound represented by any one of Formulae I-VI, and the pharmaceutically acceptable salts or solvates thereof, wherein L is —$(CH_2)_m$—W—$(CH_2)_n$—. In another embodiment, W is phenylenyl. In another embodiment, W is 5-membered heteroarylenyl. In another embodiment, W is 6-membered heteroarylenyl. In another embodiment, wherein m is 0. In another embodiment, wherein n is 1, 2, 3, 4, or 5.

In another embodiment, the disclosure provides a method, e.g., METHOD A or METHOD B, for making a compound represented by any one of Formulae I-VI, and the pharmaceutically acceptable salts or solvates thereof, and Intermediates of the Disclosure are compounds represented by Formula XI, and the pharmaceutically acceptable salts or solvates thereof, wherein L is —$(CH_2)_m$—W—$(CH_2)_u$—

O—(CH$_2$)$_v$—. In another embodiment, W is phenylenyl. In another embodiment, W is 5-membered heteroarylenyl. In another embodiment, W is 6-membered heteroarylenyl.

In another embodiment, the disclosure provides a method, e.g., METHOD A or METHOD B, for making a compound represented by any one of Formulae I-VI, and the pharmaceutically acceptable salts or solvates thereof, wherein L is selected from the group consisting of:

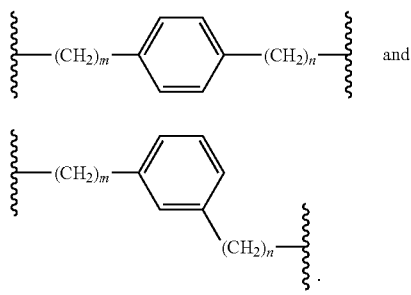

In another embodiment, m is 0. In another embodiment, n is 1, 2, 3, 4, or 5.

In another embodiment, the disclosure provides a method, e.g., METHOD A or METHOD B, for making a compound represented by any one of Formulae I-VI, and the pharmaceutically acceptable salts or solvates thereof, wherein L is selected from the group consisting of:

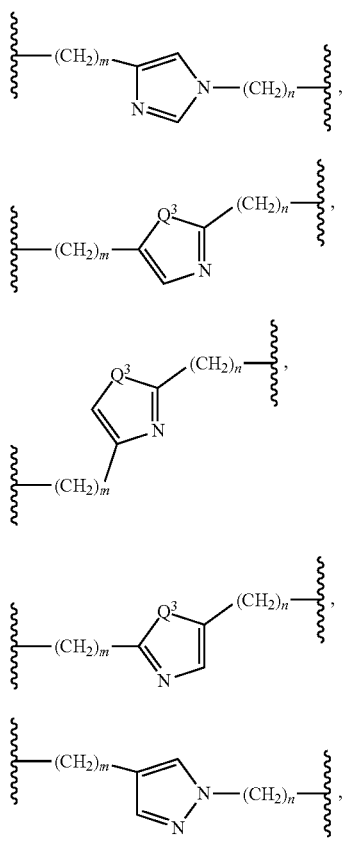

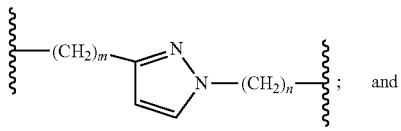

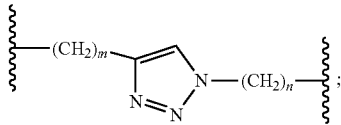

Q$^3$ is selected from the group consisting of —O—, —S—, and —N(R$^6$)—; and R$^6$ is selected from the group consisting of hydrogen and C$_{1-4}$ alkyl. In another embodiment, m is 0. In another embodiment, n is 1, 2, 3, 4, or 5. In another embodiment, n is 2, 3, or 4. In another embodiment, L is L-3. In another embodiment, L is L-4. In another embodiment, L is L-5. In another embodiment, L is L-6. In another embodiment, L is L-7. In another embodiment, L is L-8. In another embodiment, L is L-9.

In another embodiment, the disclosure provides a method, e.g., METHOD A or METHOD B, for making a compound represented by any one of Formulae I-VI, and the pharmaceutically acceptable salts or solvates thereof, wherein L is selected from the group consisting of:

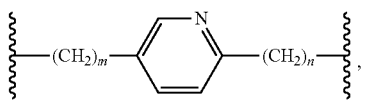

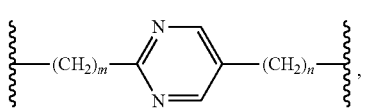

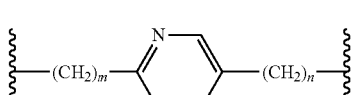

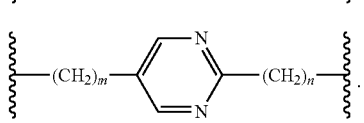

In another embodiment, m is 0. In another embodiment, n is 1, 2, 3, 4, or 5. In another embodiment, n is 2, 3, or 4. In another embodiment, L is L-10. In another embodiment, L is L-11. In another embodiment, L is L-12. In another embodiment, L is L-13.

In another embodiment, the disclosure provides a method, e.g., METHOD A or METHOD B, for making a compound represented by any one of Formulae I-VI, and the pharmaceutically acceptable salts or solvates thereof, wherein L is —(CH$_2$)$_m$—W—(CH$_2$)$_u$—O—(CH$_2$)$_v$—; W is selected from the group consisting of 5-membered heteroarylenyl and optionally substituted 6-membered heteroarylenyl; m is 0, 1, 2, 3, 4, 5, 6, or 7; u is 0; and v is 1, 2, 3, or 4. In another embodiment, m is 0.

In another embodiment, the disclosure provides a method, e.g., METHOD A or METHOD B, for making a compound represented by Formula VII:

VII

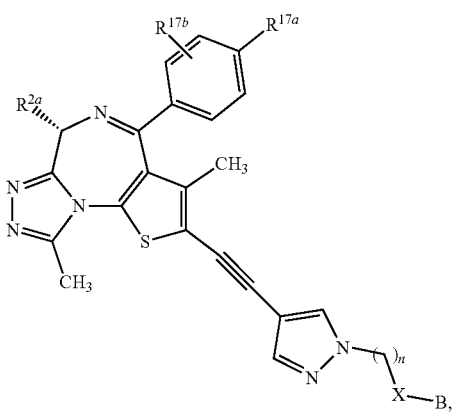

and the pharmaceutically acceptable salts or solvates thereof, wherein n is 2, 3, 4, or 5, and $R^{2a}$, $R^{17a}$, $R^{17b}$, X, B, and n are as defined in connection with Formula VI.

In another embodiment, the disclosure provides a method, e.g., METHOD A or METHOD B, for making a compound represented by Formula VIII:

VIII

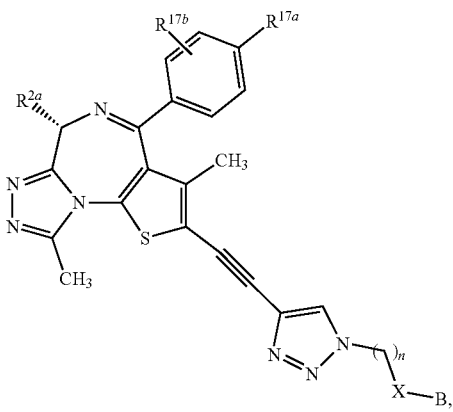

and the pharmaceutically acceptable salts or solvates thereof, wherein n is 2, 3, 4, or 5, and $R^{2a}$, $R^{17a}$, $R^{17b}$, X, B, and n are as defined in connection with Formula VI.

In another embodiment, the disclosure provides a method, e.g., METHOD A or METHOD B, for making a compound represented by Formula IX:

IX

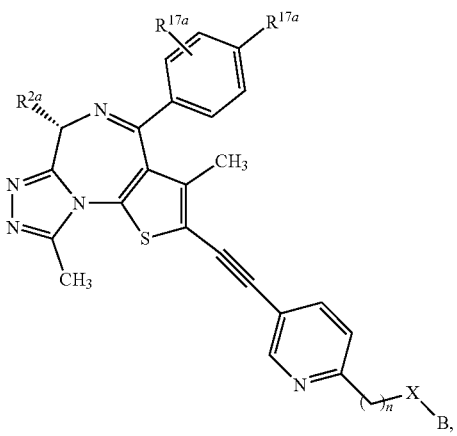

and the pharmaceutically acceptable salts or solvates thereof, wherein n is 2, 3, 4, or 5, and $R^{2a}$, $R^{17a}$, $R^{17b}$, X, B, and n are as defined in connection with Formula VI.

In another embodiment, the disclosure provides a method, e.g., METHOD A or METHOD B, for making a compound represented by any one of Formulae VII-IX, and the pharmaceutically acceptable salts or solvates thereof, wherein $R^{2a}$ is hydrogen. In another embodiment, $R^{2a}$ is methyl.

In another embodiment, the disclosure provides a method, e.g., METHOD A or METHOD B, for making a compound represented by any one of Formulae VII-IX, and the pharmaceutically acceptable salts or solvates thereof, wherein X is selected from the group consisting of —C≡C—, —CH$_2$—, —O—, and —N(H)—. In another embodiment, X is —C≡C—. In another embodiment, X is —CH$_2$—. In another embodiment, X is —O—. In another embodiment, X is —N(H)—.

In another embodiment, the disclosure provides a method, e.g., METHOD A or METHOD B, for making a compound represented by any one of Formula I-IX, and the pharmaceutically acceptable salts or solvates thereof, wherein B is B-1. In another embodiment, $A^1$ is —C($R^{16a}$)═ and $R^{16a}$ is selected from the group consisting of hydrogen and halo. In another embodiment, $A^2$ is —C($R^{16b}$)═ and $R^{16b}$ is selected from the group consisting of hydrogen and halo. In another embodiment, $A^3$ is —C($R^{16c}$)═ and $R^{16c}$ is selected from the group consisting of hydrogen and halo. In another embodiment, $A^1$ is —N═, $A^2$ is —C($R^{16b}$)═, and $A^3$ is —C($R^{16c}$)═. In another embodiment, $A^1$ is —C($R^{16a}$)═, $A^2$ is —N═, and $A^3$ is —C($R^{16c}$)═. In another embodiment, $A^1$ is —C($R^{16a}$)═, $A^2$ is —C($R^{16b}$)═ and $A^3$ is —N═. In another embodiment, Z is —CH$_2$—. In another embodiment, Z is —C(═O)—. In another embodiment, $R^5$ is hydrogen. In another embodiment, B-1 is selected from the group consisting of:

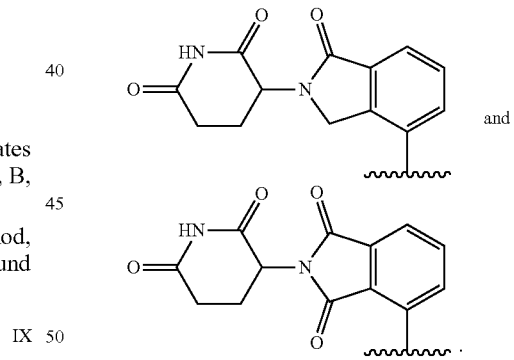

In another embodiment, the disclosure provides a method, e.g., METHOD A, for making a compound represented by any one of Formula I-IX, and the pharmaceutically acceptable salts or solvates thereof, wherein B is B-2.

In another embodiment, the disclosure provides a method, e.g., METHOD A, for making a compound represented by any one of Formula I-IX, and the pharmaceutically acceptable salts or solvates thereof, wherein B is B-3.

In another embodiment, the disclosure provides a method, e.g., METHOD A, for making a compound represented by any one of Formula I-IX, and the pharmaceutically acceptable salts or solvates thereof, wherein B is B-4. In another embodiment, $A^1$ is —C($R^{16a}$)═ and $R^{16a}$ is selected from the group consisting of hydrogen and halo. In another embodiment, $A^2$ is —C($R^{16b}$)═ and $R^{16b}$ is selected from the group consisting of hydrogen and halo. In another embodiment, $A^3$ is —C($R^{16c}$)═ and $R^{16c}$ is selected from the group consisting of hydrogen and halo. In another embodiment, $A^1$ is —N═, $A^2$ is —C($R^{16b}$)═, and $A^3$ is —C($R^{16c}$)═. In another embodiment, $A^1$ is —C($R^{16a}$)═, $A^2$ is —N═, and $A^3$ is —C($R^{16c}$)═. In another embodiment, $A^1$ is —C($R^{16a}$)═, $A^2$ is —C($R^{16b}$)═ and $A^3$ is —N═. In another embodiment, Z is —CH$_2$—. In another embodiment, Z is —C(═O)—. In another embodiment, $R^5$ is hydrogen. In another embodiment, B-4 is selected from the group consisting of:

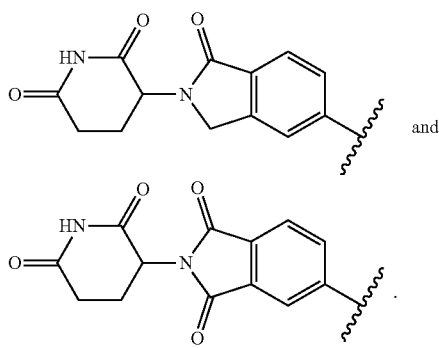

Compounds of the Disclosure inhibit or degrade BET bromodomain proteins and are useful in the treatment or prevention of a variety of diseases and conditions. In particular, Compounds of the Disclosure are useful in methods of treating or preventing a disease or condition wherein inhibition or degradation BET bromodomain proteins provides a benefit, for example, cancers and proliferative diseases. The therapeutic methods of this disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

In one embodiment, the second therapeutic agent is a MCL-1 inhibitor. In another embodiment, the second therapeutic agent is a BCL-$X_L$ inhibitor, e.g., ABT-199 (venetoclax).

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as BET bromodomain protein inhibitors or degraders for the treatment of a variety of diseases and conditions wherein inhibition or degradation of BET bromodomain proteins has a beneficial effect. Compounds of the Disclosure typically have a binding affinity ($IC_{50}$) to BET bromodomains of less than 100 μM, e.g., less than 50 μM, less than 25 μM, and less than 5 μM, less than about 1 μM, less than about 0.5 μM, or less than about 0.1 μM. In one embodiment, the present disclosure relates to a method of treating an individual suffering from a disease or condition wherein inhibition or degradation of BET bromodomain proteins provides a benefit comprising administering a therapeutically effective amount of a Compound of the Disclosure to an individual in need thereof.

Since Compounds of the Disclosure are inhibitors or degraders of one or more BET bromodomain proteins, a number of diseases and conditions mediated by BET bromodomain proteins can be treated by employing these compounds. The present disclosure is thus directed generally to a method for treating a condition or disorder responsive to inhibition or degradation of BRD2, BRD3, BRD4, BRD-t, or an isoform or mutant thereof, in an animal, e.g., a human, suffering from, or at risk of suffering from, the condition or disorder, the method comprising administering to the animal an effective amount of one or more Compounds of the Disclosure. In one embodiment, the condition or disorder is responsive to inhibition or degradation of BRD4.

The present disclosure is further directed to a method of inhibiting or degrading BET bromodomain proteins in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein inhibition or degradation of BET bromodomains provides a benefit, packaged separately or together, and an insert having instructions for using these active agents.

In one embodiment, a Compound of the Disclosure is administered in conjunction with a second therapeutic agent useful in the treatment of a disease or condition wherein inhibition or degradation of BET bromodomain proteins provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit or degrade BET bromodomain proteins in the patient.

In one embodiment, the disease to be treated or prevented by the Compound of the Disclosure is cancer. In another embodiment, the present disclosure provides a method of treating or preventing cancer in a subject in need thereof comprising administering a therapeutically effective amount of a Compound of the Disclosure to the subject. While not being limited to a specific mechanism, in some embodiments, Compounds of the Disclosure can treat or prevent cancer by inhibiting or degrading BET bromodomain proteins. Examples of treatable cancers include, but are not limited to, any one or more of the cancers of Table 3.

TABLE 3

| | |
|---|---|
| adrenal cancer | lymphoepithelioma |
| acinic cell carcinoma | lymphoma |
| acoustic neuroma | acute lymphocytic leukemia |
| acral lentigious melanoma | acute myelogeous leukemia |
| acrospiroma | chronic lymphocytic leukemia |
| acute eosinophilic leukemia | liver cancer |
| acute erythroid leukemia | small cell lung cancer |
| acute lymphoblastic leukemia | non-small cell lung cancer |
| acute megakaryoblastic leukemia | MALT lymphoma |
| acute monocytic leukemia | malignant fibrous histiocytoma |
| acute promyelocytic leukemia | malignant peripheral nerve sheath tumor |
| adenocarcinoma | malignant triton tumor |
| adenoid cystic carcinoma | mantle cell lymphoma |
| adenoma | marginal zone B-cell lymphoma |
| adenomatoid odontogenic tumor | mast cell leukemia |
| adenosquamous carcinoma | mediastinal germ cell tumor |
| adipose tissue neoplasm | medullary carcinoma of the breast |
| adrenocortical carcinoma | medullary thyroid cancer, |
| adult T-cell leukemia/lymphoma | medulloblastoma |
| aggressive NK-cell leukemia | melanoma, |
| AIDS-related lymphoma | meningioma, |
| alveolar rhabdomyosarcoma | merkel cell cancer |
| alveolar soft part sarcoma | mesothelioma |
| ameloblastic fibroma | metastatic urothelial carcinoma |
| anaplastic large cell lymphoma | mixed Mullerian tumor |
| anaplastic thyroid cancer | mucinous tumor |

TABLE 3-continued

| | |
|---|---|
| angioimmunoblastic T-cell lymphoma, | multiple myeloma |
| angiomyolipoma | muscle tissue neoplasm |
| angiosarcoma | mycosis fungoides |
| astrocytoma | myxoid liposarcoma |
| atypical teratoid rhabdoid tumor | myxoma |
| B-cell chronic lymphocytic leukemia | myxosarcoma |
| B-cell prolymphocytic leukemia | nasopharyngeal carcinoma |
| B-cell lymphoma | neurinoma |
| basal cell carcinoma | neuroblastoma |
| biliary tract cancer | neurofibroma |
| bladder cancer | neuroma |
| blastoma | nodular melanoma |
| bone cancer | ocular cancer |
| Brenner tumor | oligoastrocytoma |
| Brown tumor | oligodendroglioma |
| Burkitt's lymphoma | oncocytoma |
| breast cancer | optic nerve sheath meningioma |
| brain cancer | optic nerve tumor |
| carcinoma | oral cancer |
| carcinoma in situ | osteosarcoma |
| carcinosarcoma | ovarian cancer |
| cartilage tumor | Pancoast tumor |
| cementoma | papillary thyroid cancer |
| myeloid sarcoma | paraganglioma |
| chondroma | pinealoblastoma |
| chordoma | pineocytoma |
| choriocarcinoma | pituicytoma |
| choroid plexus papilloma | pituitary adenoma |
| clear-cell sarcoma of the kidney | pituitary tumor |
| craniopharyngioma | plasmacytoma |
| cutaneous T-cell lymphoma | polyembryoma |
| cervical cancer | precursor T-lymphoblastic lymphoma |
| colorectal cancer | primary central nervous system lymphoma |
| Degos disease | primary effusion lymphoma |
| desmoplastic small round cell tumor | preimary peritoneal cancer |
| diffuse large B-cell lymphoma | prostate cancer |
| dysembryoplastic neuroepithelial tumor, | pancreatic cancer |
| dysgerminoma | pharyngeal cancer |
| embryonal carcinoma | pseudomyxoma periotonei |
| endocrine gland neoplasm | renal cell carcinoma |
| endodermal sinus tumor | renal medullary carcinoma |
| enteropathy-associated T-cell lymphoma | retinoblastoma |
| esophageal cancer | rhabdomyoma |
| fetus in fetu | rhabdomyosarcoma |
| fibroma | Richter's transformation |
| fibrosarcoma | rectal cancer |
| follicular lymphoma | sarcoma |
| follicular thyroid cancer | Schwannomatosis |
| ganglioneuroma | seminoma |
| gastrointestinal cancer | Sertoli cell tumor |
| germ cell tumor | sex cord-gonadal stromal tumor |
| gestational choriocarcinoma | signet ring cell carcinoma |
| giant cell fibroblastoma | skin cancer |
| giant cell tumor of the bone | small blue round cell tumors |
| glial tumor | small cell carcinoma |
| glioblastoma multiforme | soft tissue sarcoma |
| glioma | somatostatinoma |
| gliomatosis cerebri | soot wart |
| glucagonoma | spinal tumor |
| gonadoblastoma | splenic marginal zone lymphoma |
| granulosa cell tumor | squamous cell carcinoma |
| gynandroblastoma | synovial sarcoma |
| gallbladder cancer | Sezary's disease |
| gastric cancer | small intestine cancer |
| hairy cell leukemia | squamous carcinoma |
| hemangioblastoma | stomach cancer |
| head and neck cancer | T-cell lymphoma |
| hemangiopericytoma | testicular cancer |
| hematological malignancy | thecoma |
| hepatoblastoma | thyroid cancer |
| hepatosplenic T-cell lymphoma | transitional cell carcinoma |
| Hodgkin's lymphoma | throat cancer |
| non-Hodgkin's lymphoma | urachal cancer |
| invasive lobular carcinoma | urogenital cancer |
| intestinal cancer | urothelial carcinoma |
| kidney cancer | uveal melanoma |
| laryngeal cancer | uterine cancer |
| lentigo maligna | verrucous carcinoma |
| lethal midline carcinoma | visual pathway glioma |
| leukemia | vulvar cancer |
| leydig cell tumor | vaginal cancer |
| liposarcoma | Waldenstrom's macroglobulinemia |
| lung cancer | Warthin's tumor |
| lymphangioma | Wilms' tumor |
| lymphangiosarcoma | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer. In another embodiment, the cancer is triple-negative breast cancer (TNBC).

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In another embodiment, the disclosure provides procedures of personalized medicine for patients having cancer, e.g., triple-negative breast cancer ("TNBC"), leukemia, castration-resistant prostate cancer ("CRPC"), and encompasses the selection of treatment options with the highest likelihood of successful outcome for individual cancer patients. In another aspect, the disclosure relates to the use of an assay(s) to predict the treatment outcome, e.g., the likelihood of favorable responses or treatment success, in patients having cancer such as TNBC, leukemia, or CRPC.

In another embodiment, the disclosure provides methods of selecting a patient, e.g., human subject for treatment of cancer with a Compound of the Disclosure, comprising obtaining a biological sample, e.g., blood cells, from the patient, testing a biological sample from the patient for the presence of a biomarker, and selecting the patient for treatment if the biological sample contains the biomarker. In another embodiment, the methods further comprise administering a therapeutically effective amount of a Compound of the Disclosure to the patient if the biological sample contains the biomarker. Examples of biomarkers include, but are not limited to, overexpression of MCL-1, overexpression of BCL-$X_L$, and co-overexpression of MCL-1 and BCL-$X_L$.

In another embodiment, the disclosure provides methods predicting treatment outcomes in a patient having cancer, e.g., TNBC, leukemia, or CRPC, comprising obtaining a biological sample from the patient, testing the biological sample from the patient for the presence of a biomarker, e.g., overexpression of MCL-1, overexpression of BCL-$X_L$, and co-overexpression of MCL-1 and BCL-$X_L$, wherein the detection of the biomarker indicates the patient will respond favorably to administration of a therapeutically effective amount of a Compound of the Disclosure. Favorable responses include, but are not limited to, hematologic responses, e.g., normalization of blood counts in the patient—white blood cells, red blood cells, and platelets (detectable by simple blood tests); cytogenetic responses, e.g., reduction or disappearance of the number of Philadelphia chromosome-positive cells in the patient (detectable by standard laboratory methods) and/or molecular responses, e.g., reduction or disappearance in quantities of the abnormal BCR-ABL protein in the patient (detectable by PCR assays).

In another embodiment, the disclosure provides methods treating cancer, e.g., TNBC, leukemia, or CRPC, comprising administering a therapeutically effective amount of a Compound of the Disclosure to a patient, e.g., a human subject, with cancer in whom the patient's cells contain a biomarker, e.g., overexpression of MCL-1, overexpression of BCL-$X_L$, and co-overexpression of MCL-1 and BCL-$X_L$. In one embodiment, the patient is selected for treatment with a Compound of the Disclosure after the patient's cells have been determined to contain a biomarker.

In another embodiment, the method of treating a patient having cancer comprises obtaining a biological sample from the patient, determining whether the biological sample contains co-overexpression of MCL-1 and BCL-$X_L$, and administering to the patient a therapeutically effective amount a Compound of the Disclosure, if the biological sample contains co-overexpression of MCL-1 and BCL-$X_L$. In another embodiment, the method further comprises administering a therapeutically effective amount of a MCL-1 inhibitor, a therapeutically effective amount of a BCL-$X_L$ inhibitor, or a therapeutically effective amount of both a MCL-1 inhibitor and BCL-$X_L$ inhibitor.

The term "biomarker" as used herein refers to any biological compound, such as a protein, a fragment of a protein, a peptide, a polypeptide, a nucleic acid, etc. that can be detected and/or quantified in a patient in vivo or in a biological sample obtained from a patient. Furthermore, a biomarker can be the entire intact molecule, or it can be a portion or fragment thereof. In one embodiment, the expression level of the biomarker is measured. The expression level of the biomarker can be measured, for example, by detecting the protein or RNA (e.g., mRNA) level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration (i.e., expression level) of the biomarker in a patient, or biological sample obtained from the patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

In one embodiment, the biomarker is MCL-1, BCL-$X_L$, or MCL-1 and BCL-$X_L$. In another embodiment, the measurable aspect of the MCL-1, BCL-$X_L$, or MCL-1 and BCL-$X_L$ is overexpression status, e.g., co-overexpression of MCL-1 and BCL-$X_L$.

Thus, in certain aspects of the disclosure, the biomarker is MCL-1, BCL-$X_L$, or MCL-1 and BCL-$X_L$ which is differentially present in a subject of one phenotypic status (e.g., a patient having cancer, e.g., TNBC, with co-overexpression of MCL-1 and BCL-$X_L$) as compared with another phenotypic status (e.g., a normal undiseased patient or a patient having cancer without mutation-bearing cells).

In addition to individual biological compounds, e.g., MCL-1, BCL-$X_L$, the term "biomarker" as used herein is meant to include groups or sets of multiple biological compounds. For example, the combination of MCL-1 and BCL-$X_L$ may comprise a biomarker. Thus, a "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting MCL-1 and/or BCL-$X_L$ overexpression in a patient or a biological sample may be used in the methods of the disclosure. Examples include, but are not limited to, PCR (polymerase chain reaction), or RT-PCR, Northern blot, Western blot, ELISA (enzyme linked immunosorbent assay), RIA (radioimmunoassay), gene chip analysis of RNA expression, immunohistochemistry or immunofluorescence (See, e.g., Slagle et al. Cancer 83:1401 (1998)). Certain embodiments of the disclosure include methods wherein biomarker RNA expression (transcription) is determined. Other embodiments of the disclosure include methods wherein protein expression in the biological sample is determined. See, for example, Harlow et al., Antibodies: A Laboratory Manual, Cold Spring Harbor Laboratory, Cold Spring Harbor, N.Y., (1988) and Ausubel et al., Current Protocols in Molecular Biology, John Wiley & Sons, New York 3rd Edition, (1995). For northern blot or RT-PCR analysis, RNA is isolated from the tumor tissue sample using RNAse free techniques. Such techniques are commonly known in the art.

When quantified in a patient in vivo, the expression level of proteins such as MCL-1 or variants thereof may be determined by administering an antibody that binds specifically to MCL-1 (See, e.g., U.S. Published Appl. No. 2006/0127945) and determining the extent of binding. The antibody may be detectably labeled, e.g., with a radioisotope such as carbon-11, nitrogen-13, oxygen-15, and fluorine-18. The label may then be detected by positron emission tomography (PET).

In one embodiment of the disclosure, a biological sample is obtained from the patient and cells in the biopsy are assayed for determination of biomarker expression or mutation status.

In one embodiment of the disclosure, PET imaging is used to determine biomarker expression.

In another embodiment of the disclosure, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is pre-hybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabeled probes and their use are well known in the art. The presence and or relative levels of expression of the biomarker being assayed can be quantified using, for example, densitometry.

In another embodiment of the disclosure, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used to determine the level of RNA encoding a biomarker of the disclosure in a tumor tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., *Cold Spring Harbor Symp. Quant. Biol.* 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligonucleotide that is hybridized to the target amplicon (biomarker gene). RT-PCR probes are oligonucleotides that have a fluorescent reporter dye attached to the 5'-end and a quencher moiety coupled to the 3'-end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In still another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In still another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In still another embodiment of the disclosure, the expression of a biomarker is evaluated by use of a gene chip or microarray. Such techniques are within ordinary skill held in the art.

The term "biological sample" as used herein refers any tissue or fluid from a patient that is suitable for detecting a biomarker, such as MCL-1 and/or BCL-$X_L$ expression status. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practitioner. In one embodiment of the disclosure, the biological sample comprises blood cells.

The present disclosure provides the following particular embodiments with respect to personalized medicine for patients having cancer:

Embodiment I

A method of treating a patient having cancer, the method comprising administering a therapeutically effective amount of a Compound of the Disclosure to the patient, wherein cells of the patient contain a biomarker, and the biomarker is overexpression of MCL-1, overexpression of BCL-$X_L$, or co-overexpression of MCL-1 and BCL-$X_L$.

Embodiment II

A method of treating a patient having cancer, the method comprising:
(a) determining the expression level of MCL-1, BCL-$X_L$, or MCL-1 and BCL-$X_L$, in a biological sample from the patient, and when the expression level is determined to be higher than that of a control sample, e.g., a sample from a normal undiseased patient or a patient having cancer without overexpression of MCL-1, BCL-$X_L$, or MCL-1 and BCL-$X_L$,
(b) administering to the patient a therapeutically effective amount of a Compound of the Disclosure.

Embodiment III

A method for treating a cancer that overexpresses MCL-1, BCL-$X_L$, or MCL-1 and BCL-$X_L$, in a patient, the method comprising administering to the patient a therapeutically effective amount of a Compound of the Disclosure.

Embodiment IV

The method of any one of Embodiments I-III, wherein at least one additional anticancer agent is administered to the patient.

Embodiment V

The method of Embodiment IV, wherein the at least one additional anticancer agent is a BCL-$X_L$ inhibitor, e.g., ABT-199.

Embodiment V

The method of Embodiment IV, wherein the at least one additional anticancer agent is a MCL-1 inhibitor.

Embodiment VI

A method of treating a human patient having TNBC, the method comprising:
(a) obtaining a biological sample from the patient;
(b) determining whether to biological sample co-overexpresses MCL-1 and BCL-$X_L$; and
(c) administering to the patient a therapeutically effective amount a Compound of the Disclosure if the biological sample indicates co-overexpression of MCL-1 and BCL-$X_L$.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the BET bromodomain protein inhibitor or degrader that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidineamine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Ax1 receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor or degrader, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor or degrader also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. In one embodiment, a pharmaceutical composition comprising a Compound of the Disclosure, or a pharmaceutically acceptable salt or hydrate thereof, and a pharmaceutically acceptable carrier, is provided. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "BET bromodomain" or "BET bromodomain protein" or "BET" as used herein means one or more of BRD2, BRD3, BRD4, and BRD-t, or an isoform or mutant thereof.

A "monovalent radical of a ligand for an E3 ubiquitin ligase protein" is derived from the removal of a hydrogen or other suitable atom, e.g., Br, I, or group, e.g., —OH, from a parent E3 ubiquitin ligase protein ligand. The removal of a hydrogen atom or other suitable atom or group facilitates the linkage of the parent E3 ubiquitin ligase protein ligand to a BET bromodomain inhibitor to give a heterobifunctional compound having Formula I. In one embodiment, a hydrogen atom is removed from any suitable —NH$_2$ group of the parent E3 ubiquitin ligase protein ligand. In another embodiment, a hydrogen atom is removed from any suitable —OH group of the parent E3 ubiquitin ligase protein ligand. In another embodiment, a hydrogen atom is removed from any suitable —N(H)— group of the parent E3 ubiquitin ligase protein ligand. In another embodiment, a hydrogen atom is removed from any suitable —CH$_3$, —CH$_2$—, —CH= group of the parent E3 ubiquitin ligase protein ligand. In another embodiment, the hydrogen atom is removed from any suitable —OH group of the parent E3 ubiquitin ligase protein ligand. In another embodiment, a Br or I atom is removed from any suitable aryl or heteroaryl group of the parent E3 ubiquitin ligase protein ligand. Exemplary non-limiting monovalent radicals of E3 ubiquitin ligase protein ligands include:

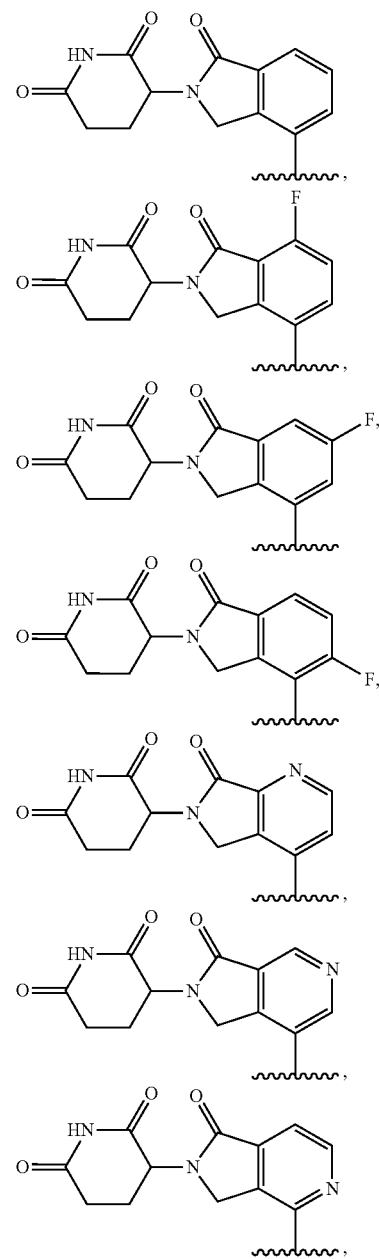

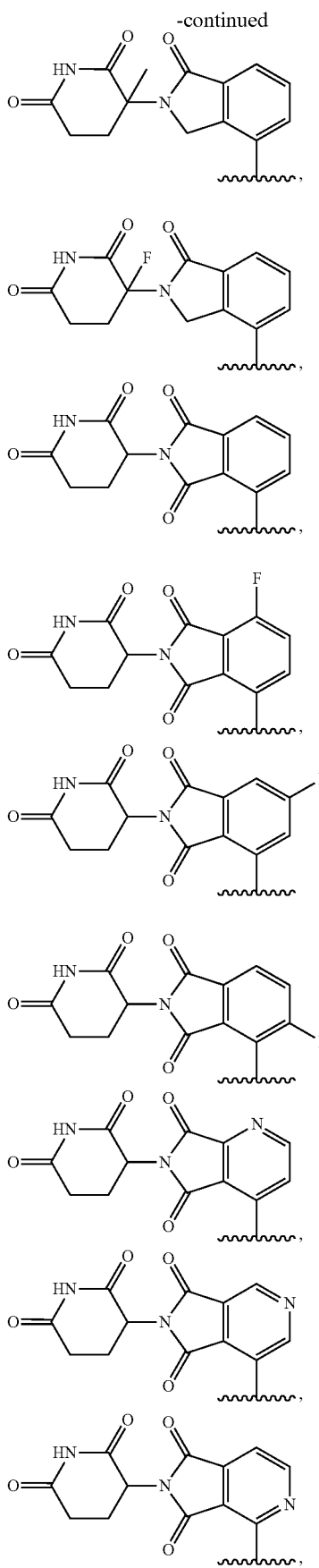

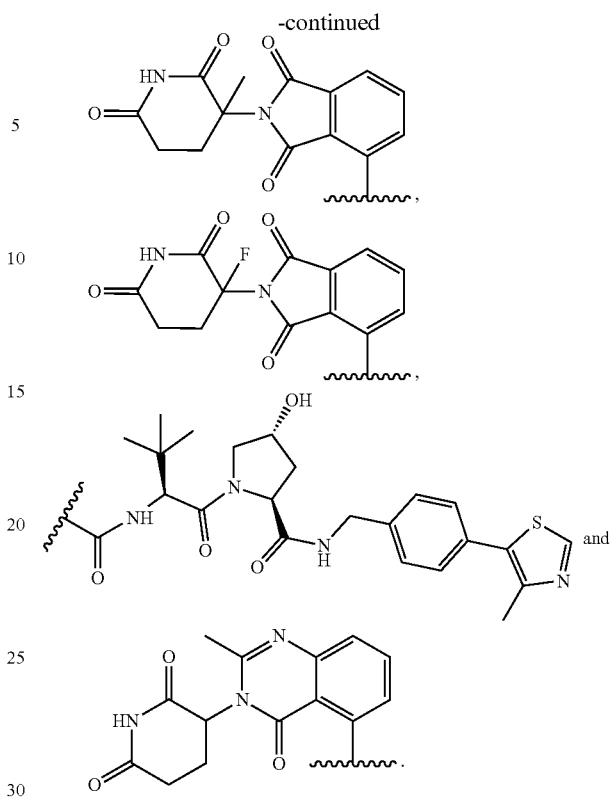

A "ligand for an E3 ubiquitin ligase protein" or "parent ligand for an E3 ubiquitin ligase protein" or "E3 ubiquitin ligase protein ligand" refers to a compound that binds, e.g., inhibits, an E3 ubiquitin ligase protein, including the von Hippel-Lindau protein (VHL). Ligands for E3 ubiquitin ligase proteins are known to those of ordinary skill in the art. Exemplary non-limiting ligands for an E3 ubiquitin ligase protein include phthalimide-based drugs such as thalidomide.

The term "a disease or condition wherein inhibition or degradation of BET bromodomain proteins provides a benefit" pertains to a disease or condition in which at least one of BRD2, BRD3, BRD4, and BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain inhibitor or degrader. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a BET bromodomain for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors or degraders of BET bromodomain proteins and can be used in treating or preventing diseases and conditions wherein inhibition or degradation of BET bromodomains provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number±10%. Thus, "about 10" means 9 to 11.

In the present disclosure, the term "halo" as used by itself or as part of another group refers to —Cl, —F, —Br, or —I.

In the present disclosure, the term "nitro" as used by itself or as part of another group refers to —$NO_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-20}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "heteroalkyl" as used by itself or part of another group refers to unsubstituted straight- or branched-chain aliphatic hydrocarbons containing from three to thirty chain atoms, i.e., 3- to 30-membered heteroalkyl, or the number of chain atoms designated, wherein at least one —$CH_2$— is replaced with at least one —O—, —N(H)—, or —S—. The —O—, N(H)—, or —S— can independently be placed at any interior position of the aliphatic hydrocarbon chain so long as each —O—, N(H)—, or —S— group is separated by at least two —$CH_2$— groups. In one embodiment, one —$CH_2$— group is replaced with one —O— group. In another embodiment, two —$CH_2$— groups are replaced with two —O— groups. In another embodiment, three —$CH_2$— groups are replaced with three —O— groups. In another embodiment, four —$CH_2$— groups are replaced with four —O— groups. Non-limiting exemplary heteroalkyl groups include:
—$CH_2OCH_3$;
—$CH_2OCH_2CH_2CH_3$;
—$CH_2CH_2CH_2OCH_3$;
—$CH_2OCH_2CH_2OCH_3$; and
—$CH_2OCH_2CH_2OCH_2CH_2OCH_3$.

In the present disclosure, the term "alkylenyl" as used herein by itself or part of another group refers to a divalent form of an alkyl group. In one embodiment, the alkylenyl is a divalent form of a $C_{1-12}$ alkyl. In one embodiment, the alkylenyl is a divalent form of a $C_{1-10}$ alkyl. In one embodiment, the alkylenyl is a divalent form of a $C_{1-8}$ alkyl. In one embodiment, the alkylenyl is a divalent form of a $C_{1-6}$ alkyl. In another embodiment, the alkylenyl is a divalent form of a $C_{1-4}$ alkyl. Non-limiting exemplary alkylenyl groups include:
—$CH_2$—,
—$CH_2CH_2$—,
—$CH_2CH_2CH_2$—,
—$CH_2(CH_2)_2CH_2$—,
—$CH(CH_2)_3CH_2$—,
—$CH_2(CH_2)_4CH_2$—,
—$CH_2(CH_2)_5CH_2$—,
—$CH_2CH(CH_3)CH_2$—, and
—$CH_2C(CH_3)_2CH_2$—.

In the present disclosure, the term "heteroalkylenyl" as used herein by itself or part of another group refers to a divalent form of a heteroalkyl group. In one embodiment, the heteroalkylenyl is a divalent form of a 3- to 12-membered heteroalkyl. In another embodiment, the heteroalkylenyl is a divalent form of a 3- to 10-membered heteroalkyl. In another embodiment, the heteroalkylenyl is a divalent form of a 3- to 8-membered heteroalkyl. In another embodiment, the heteroalkylenyl is a divalent form of a 3- to 6-membered heteroalkyl. In another embodiment, the heteroalkylenyl is a divalent form of a 3- to 4-membered heteroalkyl. In another embodiment, the heteroalkylenyl is a radical of the formula: —$(CH_2)_oO$—$(CH_2CH_2O)_p$—$(CH_2)_q$—, wherein o is 2 or 3; p is 0, 1, 2, 3, 4, 5, 6, or 7; and q is 2 or 3. In another embodiment, the heteroalkylenyl is a radical of the formula: —$(CH_2)_rO$—$(CH_2)_s$—$O(CH_2)_t$—, wherein r is 2, 3, or 4; s is 3, 4, or 5; and t is 2 or 3. Non-limiting exemplary heteroalkylenyl groups include:
—$CH_2OCH_2$—;
—$CH_2CH_2OCH_2CH_2$—;
—$CH_2OCH_2CH_2CH_2$—;
—$CH_2CH_2OCH_2CH_2CH_2$—;
—$CH_2CH_2OCH_2CH_2OCH_2CH_2$—; and
—$CH_2CH_2OCH_2CH_2OCH_2CH_2O$—.

In the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In another embodiment, the optionally substituted alkyl is substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and —CHO. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2SO_2CH_3$, —$CH_2CH_2CO_2H$, —$CH_2CH_2SO_2CH_3$, —$CH_2CH_2COPh$, and —$CH_2C_6H_{11}$. Non-limiting exemplary substituted alkyl groups also include —$CH_2CH_2CHO$, —$CH_2CH_2CH_2CHO$, and —$CH_2CH_2CH_2CH_2CHO$.

In the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

In the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

In the present disclosure, the term "cycloalkylenyl" as used herein by itself or part of another group refers to a divalent form of an optionally substituted cycloalkyl group. In one embodiment, the heterocyclenyl is a 4-membered cycloalkylenyl. In another embodiment, the heterocyclenyl is a 5-membered cycloalkylenyl. In another embodiment, the heterocyclenyl is a 6-membered cycloalkylenyl. Non-limiting exemplary heterocyclenyl groups include:

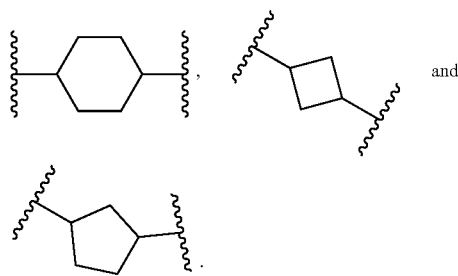
and

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

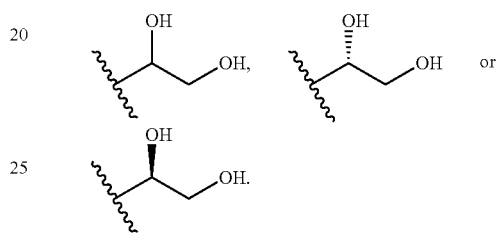
or

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, tert-butoxy, —OCH$_2$CH$_2$C≡CH, and —OCH$_2$CH$_2$CH$_2$C≡CH.

In the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —SCH$_3$, and —SCH$_2$CH$_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

In the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

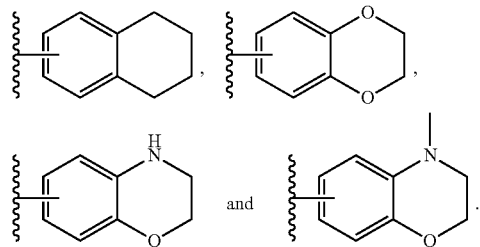

In the present disclosure, the term "phenylenyl" as used herein by itself or part of another group refers to a divalent form of an optionally substituted phenyl group. Non-limiting examples include:

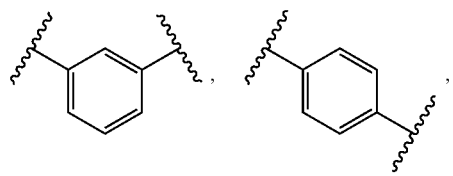

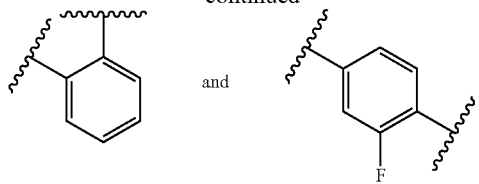

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is $PhCH_2O$—.

In the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted. Non-limiting exemplary optionally substituted 5-membered heteroaryl groups include, but are not limited to:

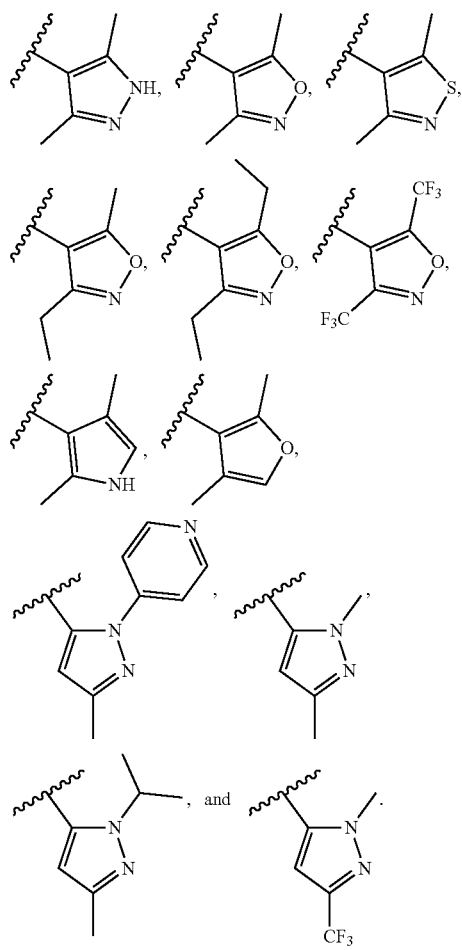

The term optionally substituted heteroaryl is also meant to include groups having fused optionally substituted cycloalkyl and fused optionally substituted heterocyclo rings. Non-limiting examples include:

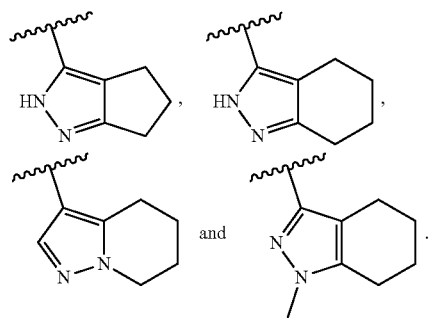

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl include:

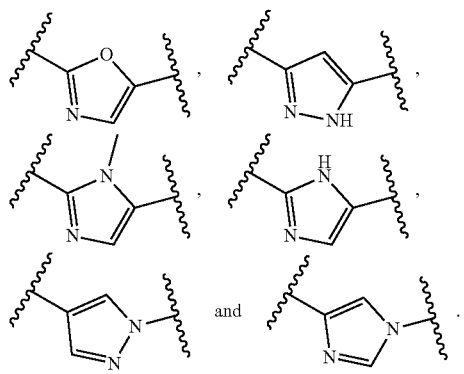

In one embodiment, the heteroarylenyl is a 6-membered heteroarylenyl. Non-limiting examples of a 6-membered heteroarylenyl include:

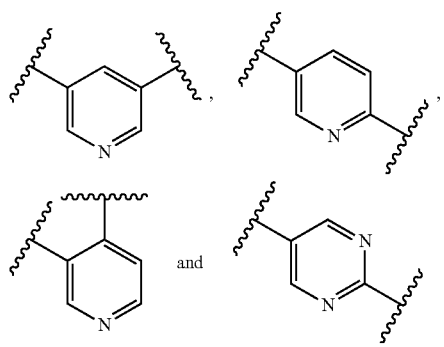

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH₂— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, CF₃C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

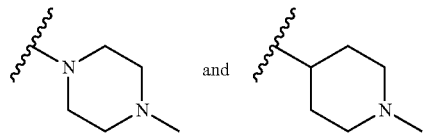

In the present disclosure, the term "heterocyclenyl" as used herein by itself or part of another group refers to a divalent form of an optionally substituted heterocyclo group. Substitution may occur at any available carbon atom or nitrogen atom. In one embodiment, the heterocyclenyl is a 4-membered heterocyclenyl. In another embodiment, the heterocyclenyl is a 5-membered heterocyclenyl. In another embodiment, the heterocyclenyl is a 6-membered heterocyclenyl. Non-limiting exemplary heterocyclenyl groups include:

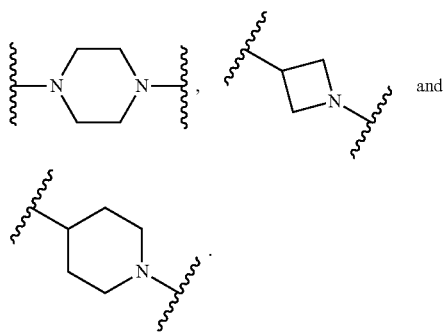

In the present disclosure, the term "amino" as used by itself or as part of another group refers to —NR¹⁰ᵃR¹⁰ᵇ, wherein R¹⁰ᵃ and R¹⁰ᵇ are each independently hydrogen, optionally substituted alkyl, alkynyl, haloalkyl, hydroxyalkyl, optionally substituted cycloalkyl, optionally substituted aryl, optionally substituted heterocyclo, or optionally substituted heteroaryl, or R¹⁰ᵃ and R¹⁰ᵇ are taken together to form a 3- to 8-membered optionally substituted heterocyclo. Non-limiting exemplary amino groups include —NH₂ and —N(H)(CH₃).

In the present disclosure, the term "(amino)alkyl" as used by itself or as part of another group refers to an alkyl group substituted with an amino group. Non-limiting exemplary amino alkyl groups include —CH₂CH₂NH₂, and —CH₂CH₂N(H)CH₃, —CH₂CH₂N(CH₃)₂, and —CH₂N(H) cyclopropyl.

In the present disclosure, the term "carboxamido" as used by itself or as part of another group refers to a radical of formula —C(=O)NR⁹ᵃR⁹ᵇ, wherein R⁹ᵃ and R⁹ᵇ are each independently hydrogen, optionally substituted alkyl, hydroxyalkyl, optionally substituted cycloalkyl, optionally substituted aryl, optionally substituted heterocyclo, or optionally substituted heteroaryl, or R⁹ᵃ and R⁹ᵇ taken together with the nitrogen to which they are attached form a 3- to 8-membered optionally substituted heterocyclo group. In one embodiment, R⁹ᵃ and R⁹ᵇ are each independently hydrogen or optionally substituted alkyl. In one embodiment, R⁹ᵃ and R⁹ᵇ are taken together to taken together with the nitrogen to which they are attached form a 3- to 8-membered optionally substituted heterocyclo group. Non-limiting exemplary carboxamido groups include, but are not limited to, —CONH₂, —CON(H)CH₃, —CON(CH₃)₂, —CON(H)Ph,

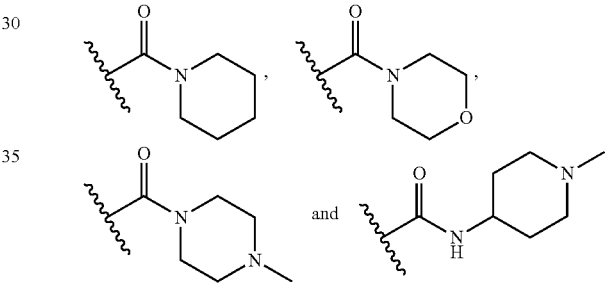

In the present disclosure, the term "sulfonamido" as used by itself or as part of another group refers to a radical of the formula —SO₂NR⁸ᵃR⁸ᵇ, wherein R⁸ᵃ and R⁸ᵇ are each independently hydrogen, optionally substituted alkyl, or optionally substituted aryl, or R⁸ᵃ and R⁸ᵇ taken together with the nitrogen to which they are attached from a 3- to 8-membered heterocyclo group. Non-limiting exemplary sulfonamido groups include —SO₂NH₂, —SO₂N(H)CH₃, and —SO₂N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH₃.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

In the present disclosure, the term "alkylsulfonyl" as used by itself or as part of another group refers to a sulfonyl group, i.e., —SO₂—, substituted by any of the above-mentioned optionally substituted alkyl groups. A non-limiting exemplary alkylsulfonyl group is —SO₂CH₃.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl group substituted with an optionally substituted heterocyclo group. In one embodiment, the (heterocyclo)alkyl is a C$_{1-4}$ alkyl substituted with one optionally substituted heterocyclo group. Non-limiting exemplary (heterocyclo)alkyl groups include:

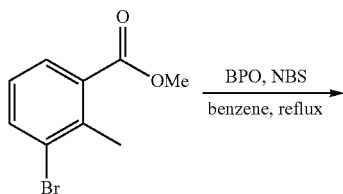
and

EXAMPLES

Example 1

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione (Cpd. No. 1)

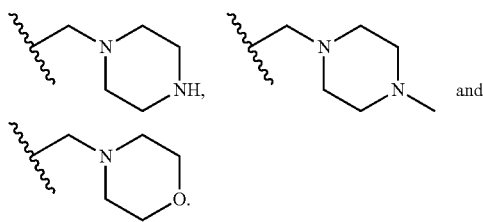

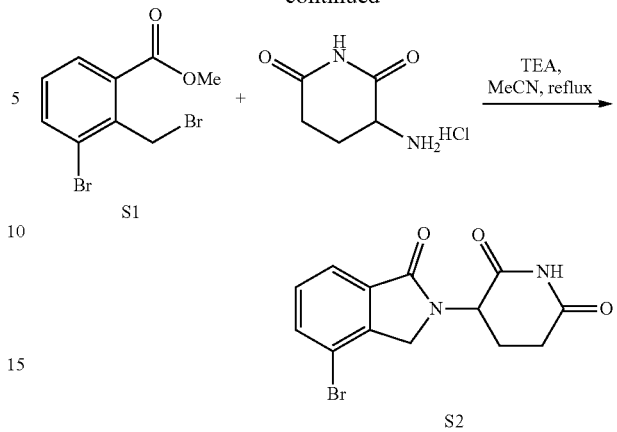

To a round-bottomed flask, methyl 3-bromo-2-methylbenzoate (18.3 g, 80 mmol, 1.0 eq), N-bromosuccinimide (17.1 g, 96 mmol, 1.2 eq) and benzoyl peroxide (1.9 g, 8.0 mmol, 0.1 eq) were mixed in 150 mL of benzene. The reaction mixture was stirred at 80° C. for 12 h. After cooling to room temperature, the reaction mixture was evaporated to remove most of the solvent. The resulting residue was purified by flash column chromatography with hexane/ethyl acetate to give the desired product S1 as colorless oil (23.4 g, 95% yield).

To a round-bottomed flask, compound S1 (23.4 g, 76 mmol, 1.0 eq) and 3-aminopiperidine-2,6-dione hydrochloride (13.8 g, 83.6 mmol, 1.1 eq) were mixed in 150 mL of acetonitrile. The resulting reaction mixture was stirred at 85° C. for 12 h. After cooling to room temperature, the reaction mixture was poured into 200 mL of cooled water. The resulting mixture was filtrated and the solid was washed with water and ethyl acetate sequentially. After drying, a slightly purple solid was obtained, which was used directly in the following reactions without further purification (19.6 g, 80% yield). UPLC-MS calculated for C$_{13}$H$_{12}$BrN$_2$O$_3$ [M+1]$^+$: 323.00, found 322.96.

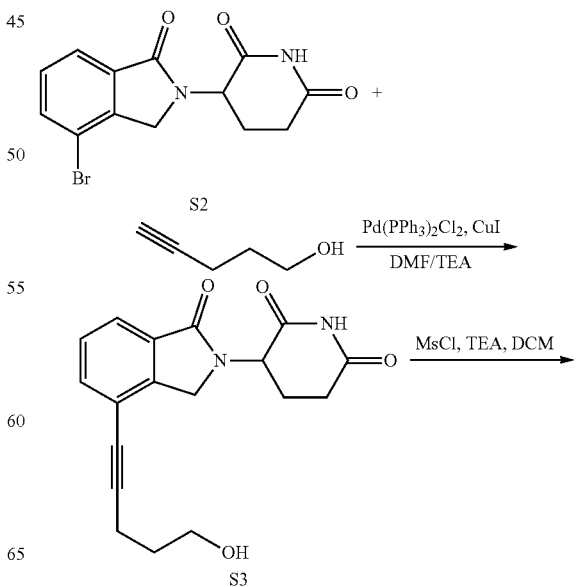

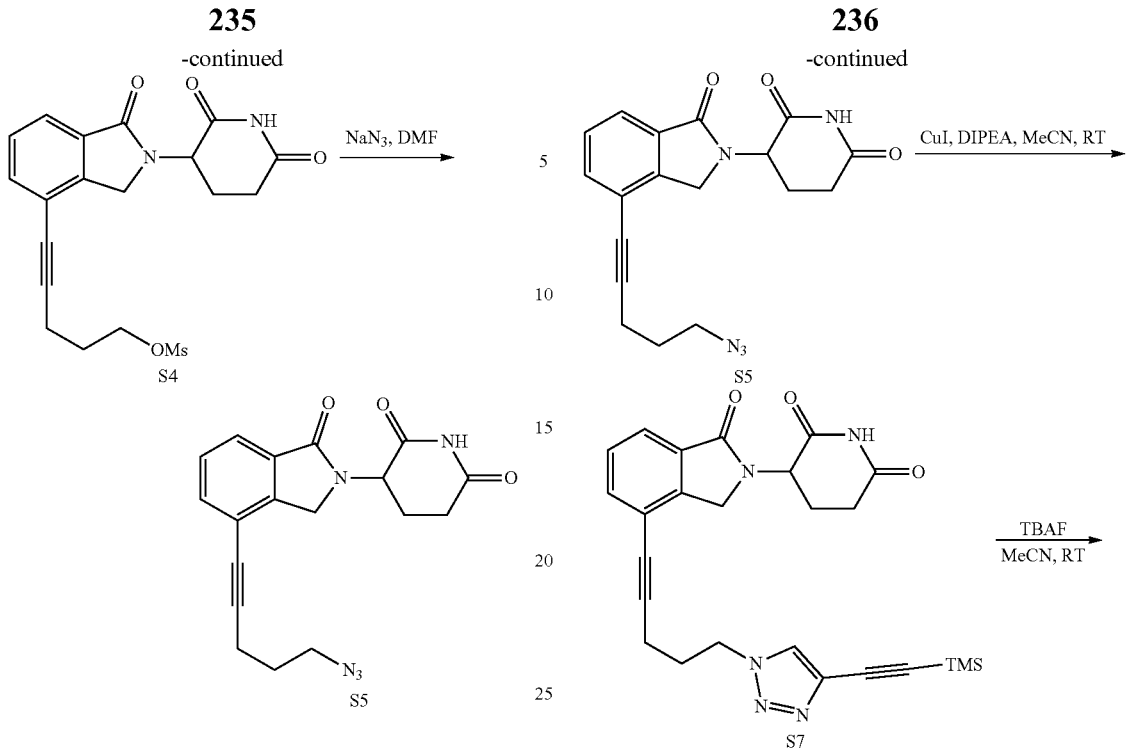

To a round-bottomed flask, compound S2 (2.59 g, 8.0 mmol, 1.0 eq), 4-pentyn-1-ol (1.01 g, 12.0 mmol, 1.5 eq), Pd(PPh$_3$)$_2$Cl$_2$ (421 mg, 0.6 mmol, 0.075 eq) and CuI (228 mg, 1.2 mmol, 0.15 eq) were mixed in 24 mL of DMF. The reaction mixture was sealed and filled with nitrogen. 10 mL of triethylamine was added and the reaction mixture was heated to 80° C. to stir for 8 h. After cooling to room temperature, the reaction mixture was evaporated to remove most of the solvent to give the dark residue, which was purified by flash column chromatography with DCM/MeOH to afford the final compound S3 as a white solid (2.08 g, 80% yield). UPLC-MS calculated for C$_{18}$H$_{19}$N$_2$O$_4$ [M+1]$^+$: 327.13, found 327.15.

To a round-bottomed flask, compound S3 (1.04 g, 3.2 mmol, 1.0 eq) was suspended in 100 mL of dichloromethane. Mesyl chloride (495 µL, 6.4 mmol, 2.0 eq) was added dropwise to the upper solution at 0° C. Then triethylamine (1.33 mL, 9.6 mmol, 3.0 eq) was added. The suspended solution turned clear within 1 min. The reaction mixture was stirred at room temperature for 1 h. Then the solvent was evaporated to give crude product S4, which was used in the next step reaction without further purification. UPLC-MS calculated for C$_{19}$H$_{21}$N$_2$O$_6$S [M+1]$^+$: 405.11, found 405.14.

Crude S4 was dissolved in 15 mL of DMF. Then sodium azide (416 mg, 6.4 mmol, 2.0 eq) was added and the solution was stirred at 60° C. for 1 h. After cooling to room temperature, the reaction mixture was diluted with water and purified by HPLC with MeCN/H$_2$O (0.1% TFA) as the eluent to afford the desired compound S5 as a white solid (690 mg, 61% yield). UPLC-MS calculated for C$_{18}$H$_{18}$N$_5$O$_3$ [M+1]$^+$: 352.14, found 352.15.

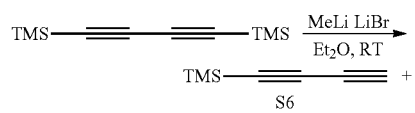

To a solution of 1,4-bis(trimethylsilyl)-buta-1,3-diyne (1.0 g, 5.14 mmol) in 15 mL of dry ethyl ether, MeLi LiBr (1.5 M in ether, 6.68 mmol, 4.45 mL) was added and the reaction mixture was stirred at room temperature for 12 h. The reaction was quenched with saturated NH$_4$Cl (aq) at 0° C. and the product was extracted with ethyl ether. The combined organic layer was dried over anhydrous Na$_2$SO$_4$. After filtration, the solution was carefully evaporated in vacuum to give the crude S6 as slightly dark oil, which was diluted in 5 mL of t-BuOH and stored below 0° C.

To a solution of azide S5 (690 mg, 1.97 mmol, 1.0 eq), S6 (0.5 M in t-BuOH, 4.7 mL, 2.36 mmol, 1.2 eq) in 30 mL of acetonitrile was added CuI (74 mg, 0.39 mmol, 0.2 eq) and DIPEA (1.7 mL, 9.83 mmol, 5.0 eq). The reaction mixture was stirred at room temperature for 12 h. After evaporation to remove the solvent, the crude residue was purified by reverse flash column with MeCN/H$_2$O (0.1% TFA) to give the product S7 as a white solid (338 mg, 36% yield). UPLC-MS calculated for C$_{25}$H$_{28}$N$_5$O$_3$Si [M+1]$^+$: 474.20, found 474.23.

To suspended solution of S7 (338 mg, 0.71 mmol, 1.0 eq) in 10 mL of acetonitrile was added TBAF (1.0 M in THF, 1.42 mL, 1.42 mmol, 2.0 eq). The solution turned clear within 1 min. After 1 h, the reaction mixture was diluted with water and purified by HPLC with MeCN/H$_2$O (0.1%

TFA) to afford the desired product S8 as a white solid (270 mg, 95% yield). UPLC-MS calculated for $C_{22}H_{20}N_5O_3$ [M+1]$^+$: 402.16, found 402.21.

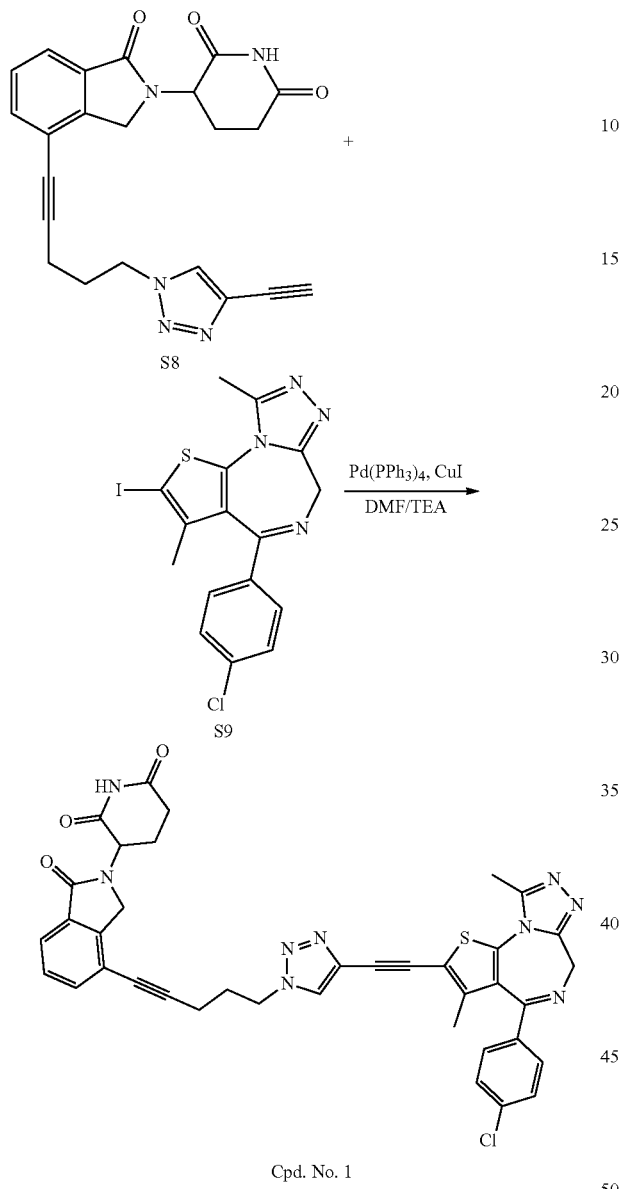

Cpd. No. 1

To a solution of S9 (13.6 mg, 0.03 mmol, 1.0 eq, see Compound 06 in Example 21), S8 (18.1 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 1 as a white solid (15 mg, 68% yield). $^1$H NMR (400 MHz, CD$_3$OD) δ (ppm) 8.36 (s, 1H), 7.72 (d, J=7.2 Hz, 1H), 7.60 (d, J=7.2 Hz, 1H), 7.53-7.46 (m, 5H), 5.36 (d, J=13.2 Hz, 1H), 5.16 (dd, J=13.2 Hz, J=4.8 Hz, 1H), 4.65 (t, J=6.4 Hz, 2H), 4.53 (d, J=17.2 Hz, 1H), 4.46 (d, J=17.2 Hz, 1H), 4.35 (d, J=12.8 Hz, 1H), 2.96-2.87 (m, 1H), 2.82-2.76 (m, 4H), 2.59 (t, J=6.4 Hz, 2H), 2.61-2.54 (m, 1H), 2.30-2.24 (m, 2H), 2.22-2.18 (m, 1H), 1.85 (s, 3H); UPLC-MS calculated for $C_{38}H_{31}ClN_9O_3S$ [M+1]$^+$: 728.20, found 728.19.

Example 2

Synthesis of 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione (Cpd. No. 2)

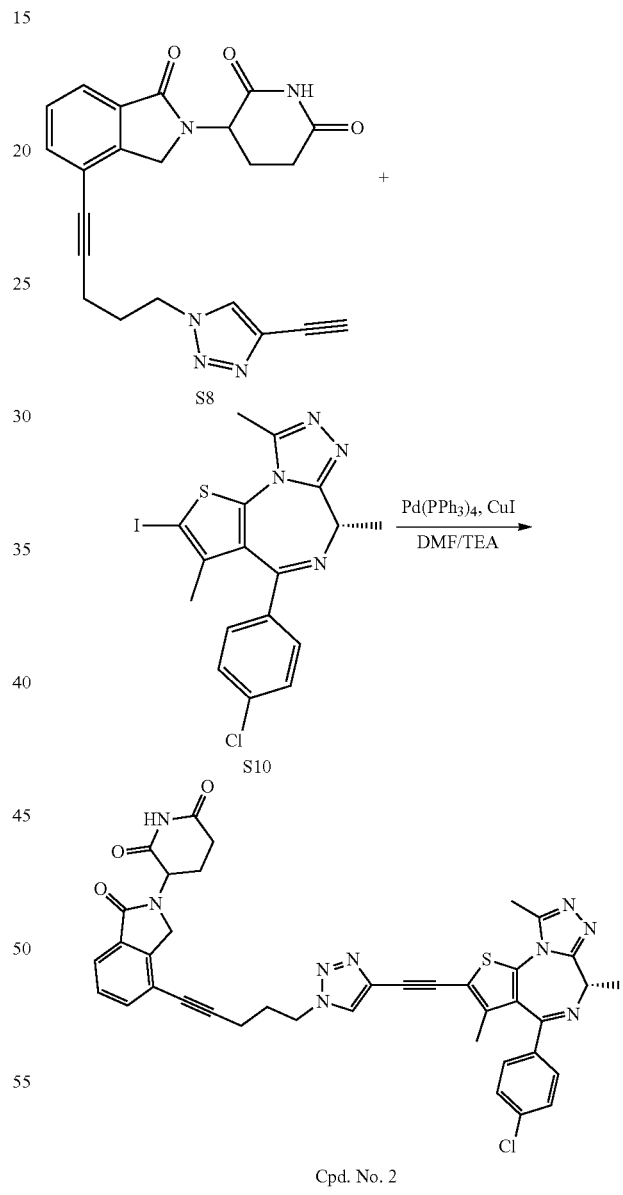

Cpd. No. 2

To a solution of S10 (14.1 mg, 0.03 mmol, 1.0 eq, see compound N6 of Example 20), S8 (18.1 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 2 as a white solid (16 mg, 70% yield). $^1$H NMR (400 MHz, CD$_3$OD) δ (ppm) 8.35 (s, 1H), 7.71 (d, J=7.2 Hz, 1H), 7.59 (d, J=7.6 Hz, 1H), 7.52-7.44 (m, 5H), 5.15 (dd, J=13.2 Hz, J=5.2 Hz, 1H), 4.65 (t, J=7.2 Hz, 2H), 4.53 (d, J=17.6 Hz, 1H), 4.46 (d, J=17.6 Hz, 1H), 4.39 (q, J=6.7 Hz, 1H), 2.95-2.86 (m, 1H), 2.81-2.75 (m, 1H), 2.75 (s, 3H), 2.58 (t, J=6.8 Hz, 2H), 2.57-2.50 (m, 1H), 2.30-2.21 (m, 2H), 2.20-2.17 (m, 1H), 2.01 (d, J=6.8 Hz, 3H), 1.86 (s, 3H); UPLC-MS calculated for C$_{39}$H$_{33}$ClN$_9$O$_3$S [M+1]$^+$: 742.21, found 742.17.

Example 3

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione (Cpd. No. 3)

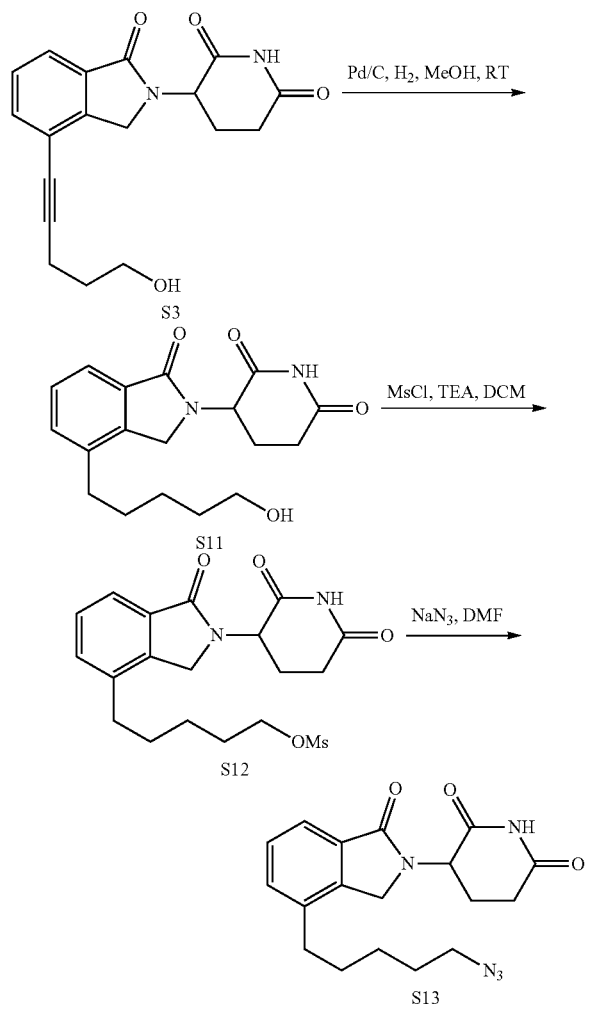

To a suspended solution of S3 (684 mg) in 100 mL of MeOH under nitrogen atmosphere was added 70 mg of Pd/C (10 wt %). Hydrogen was filled/evacuated into the flask three times. The solution was stirred at room temperature under 1 atm hydrogen atmosphere for 12 h. After consumption of the starting material, the solvent was evaporated and the residue was purified by flash column chromatography with DCM/MeOH to afford the desired product S11 as a white solid (693 mg, 90% yield). UPLC-MS calculated for C$_{18}$H$_{23}$N$_2$O$_4$ [M+1]$^+$: 331.17, found 331.13.

To a suspended solution of S11 (693 mg, 2.1 mmol, 1.0 eq) in 30 mL of DCM was added mesyl chloride (325 μL, 4.2 mmol, 2.0 eq) at 0° C. Then trimethylamine (0.88 mL, 6.3 mmol, 3.0 eq) was added dropwise. The solution turned clear within 1 min. After 1 h, the solvent was evaporated to give crude compound S12, which was used in the next step reaction without further purification.

The above obtained crude compound S12 was dissolved in 10 mL of DMF, and sodium azide (275 mg, 4.2 mmol, 2.0 eq) was added. Then the reaction mixture was stirred at 60° C. for 5 h. After cooling to room temperature, the reaction was diluted in water and purified by HPLC with MeCN/H$_2$O (0.1% TFA) to afford the compound S13 as a white solid (682 mg, 91% yield). UPLC-MS calculated for C$_{18}$H$_{22}$N$_5$O$_3$ [M+1]$^+$: 356.17, found 356.29.

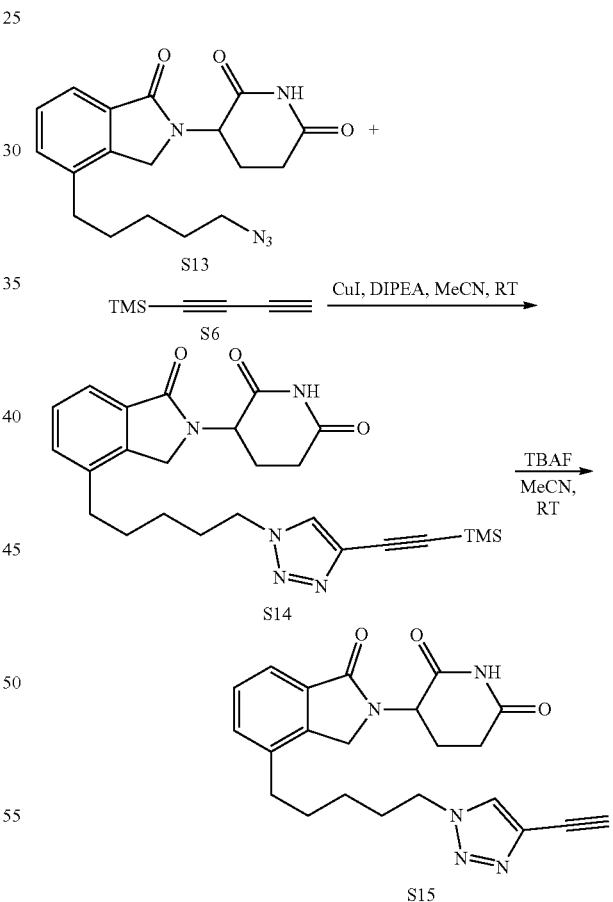

Following the procedure for the synthesis of S7, 513 (682 mg, 1.92 mmol, 1.0 eq) was used in the reaction. Finally compound 514 was obtained as a white solid (704 mg, 76% yield). UPLC-MS calculated for C$_{25}$H$_{32}$N$_5$O$_3$Si [M+1]$^+$: 478.23, found 478.24.

Following the procedure for the synthesis of S8, compound 514 (704 mg, 1.47 mmol, 1.0 eq) was used in the reaction. Finally compound S15 was obtained as a white solid (565 mg, 95% yield). UPLC-MS calculated for $C_{22}H_{24}N_5O_3$ [M+1]$^+$: 406.19, found 406.26.

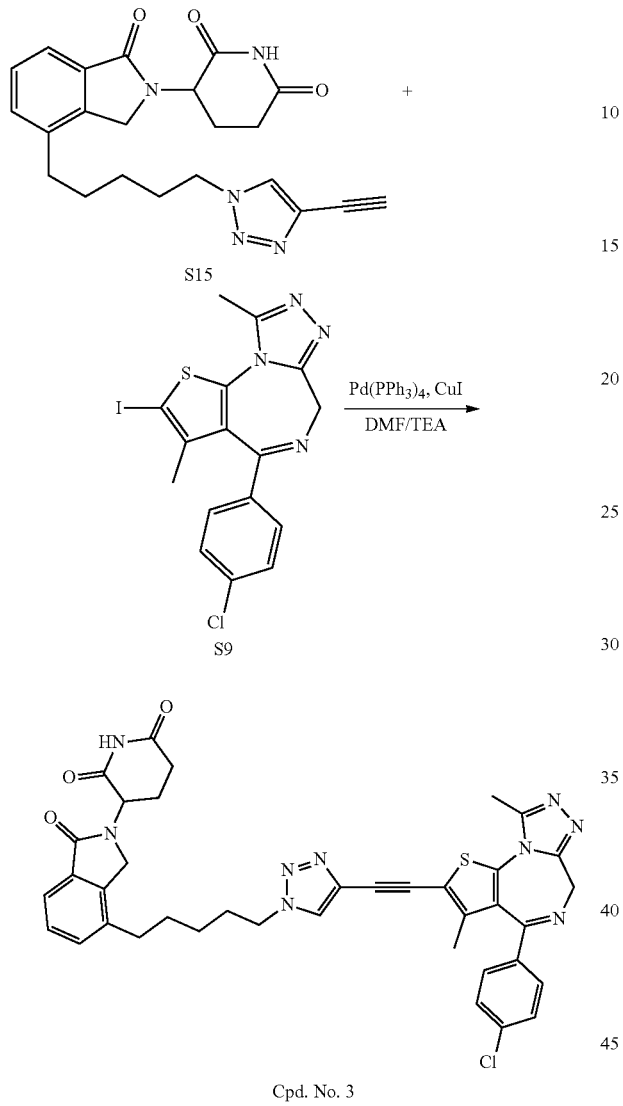

Cpd. No. 3

To a solution of S9 (14.1 mg, 0.03 mmol, 1.0 eq), S15 (18.2 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 3 as a white solid (14 mg, 63% yield). $^1$H NMR (400 MHz, CD$_3$OD) δ (ppm) 8.26 (s, 1H), 7.65-7.63 (m, 1H), 7.53 (d, J=8.4 Hz, 2H), 7.48-7.44 (m, 4H), 5.36 (d, J=13.2 Hz, 1H), 5.16 (dd, J=13.6 Hz, J=5.2 Hz, 1H), 4.52-4.42 (m, 4H), 4.35 (d, J=13.2 Hz, 1H), 2.96-2.87 (m, 1H), 2.82-2.80 (m, 1H), 2.76 (s, 3H), 2.71 (t, J=7.6 Hz, 2H), 2.59-2.48 (m, 1H), 2.23-2.17 (m, 1H), 1.99-1.96 (m, 2H), 1.92 (s, 3H), 1.76-1.68 (m, 2H), 1.40-1.30 (m, 2H); UPLC-MS calculated for $C_{38}H_{35}ClN_9O_3S$ [M+1]$^+$: 732.23, found 732.17.

Example 4

Synthesis of 3-(4-(5-(4-(((S)-4-(4-chlorophenyl)-3,6,9-trimethyl-6H-thieno[3,2 f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione (Cpd. No. 4)

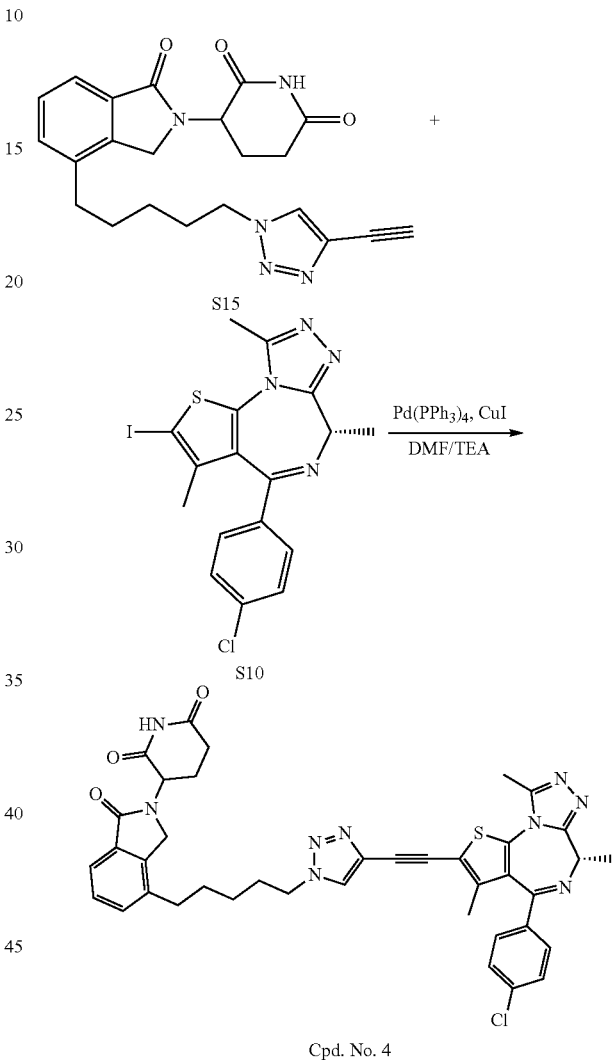

Cpd. No. 4

To a solution of S10 (14.1 mg, 0.03 mmol, 1.0 eq), S15 (18.2 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 4 as a white solid (16 mg, 72% yield). $^1$H NMR (400 MHz, CD$_3$OD) δ (ppm) 8.25 (s, 1H), 7.63 (dd, J=6.0 Hz, J=2.8 Hz, 1H), 7.51 (d, J=8.8 Hz, 2H), 7.47-7.42 (m, 4H), 5.15 (dd, J=13.2 Hz, J=5.2 Hz, 1H), 4.51-4.38 (m, 5H), 2.95-2.86 (m, 1H), 2.80-2.75 (m, 1H), 2.74 (s, 3H), 2.69 (t, J=7.6 Hz, 2H), 2.59-2.47 (m, 1H), 2.22-2.15 (m, 1H), 2.01 (d, J=6.8 Hz, 3H), 1.96 (t, J=7.6 Hz, 2H), 1.92 (s, 3H), 1.75-1.67 (m, 2H), 1.39-1.29 (m, 2H); UPLC-MS calculated for $C_{39}H_{37}ClN_9O_3S$ [M+1]$^+$: 746.24, found 746.29.

Example 5

Synthesis of 3-(4-(4-((4-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione (Cpd. No. 5)

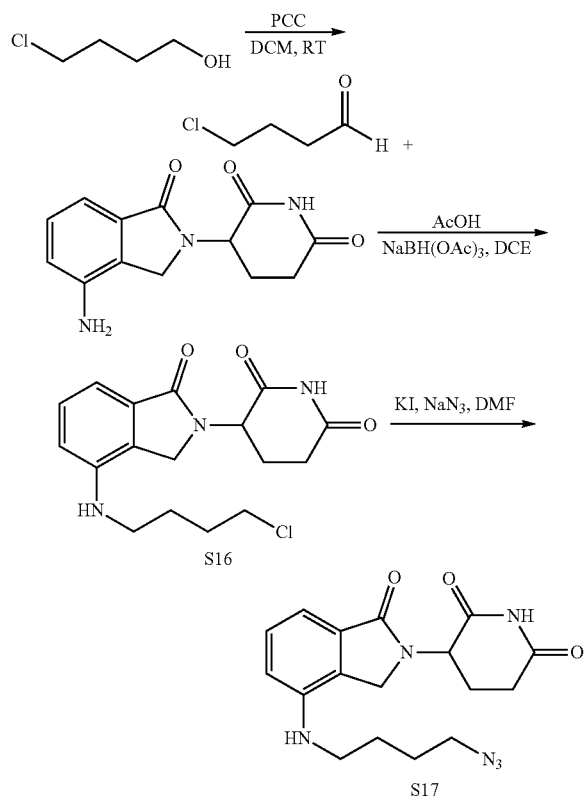

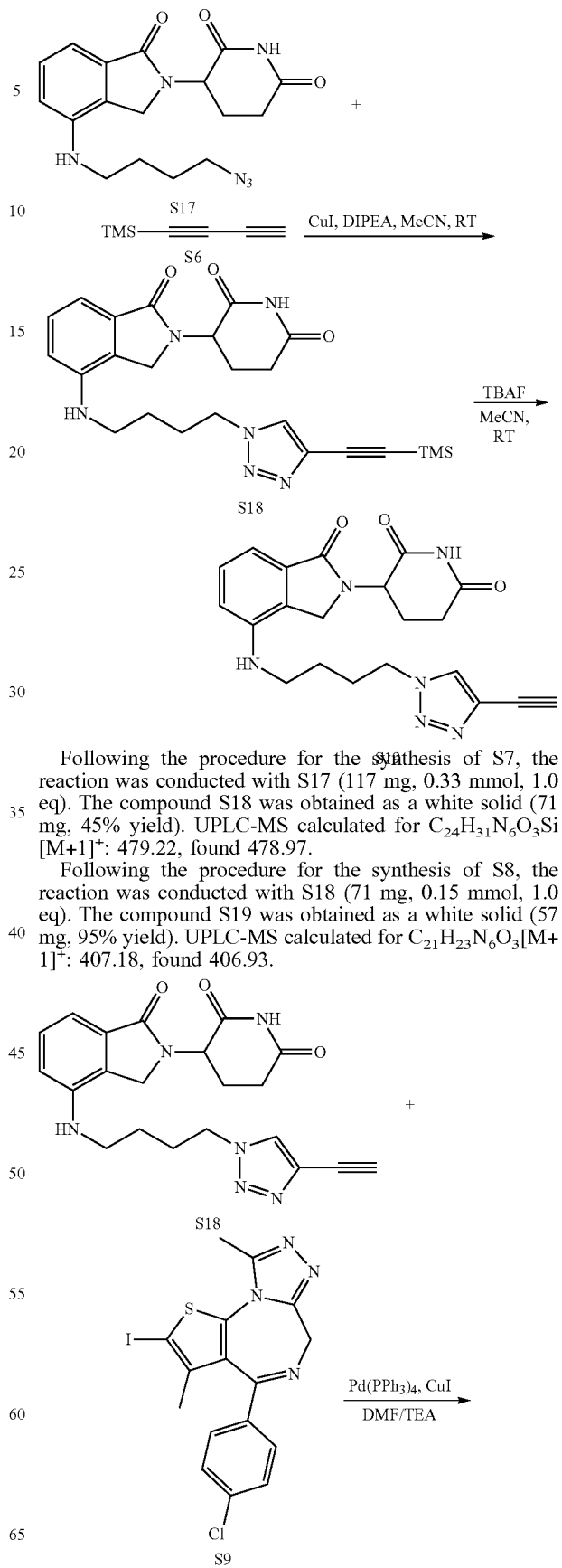

To a solution of PCC (7.29 g, 33.8 mmol, 1.2 eq) in 30 mL of DCM was added dropwise a solution of 4-chloro-1-butanol (3.06 g, 28.2 mmol, 1.0 eq) in 10 mL of DCM. The solution was stirred at room temperature for 1 h. Then the solution was filtered through celite and washed with ethyl ether. The combined organic layer was evaporated and the concentrated residue was purified by flash column chromatography with DCM to afford the desired product as colorless oil.

To a solution of lenalidomide (950 mg, 3.66 mmol, 1.0 eq) and 4-chloro-1-butanal (429 mg, 4.03 mmol, 1.1 eq) in 30 mL of DCE was added acetic acid (0.2 mL, 3.66 mmol, 1.0 eq) and sodium triacetoxyborohydride (1.55 g, 7.32 mmol, 2.0 eq). The suspended solution was stirred at room temperature for 12 h. The reaction mixture was quenched with brine and the product was extracted with DCM. The combined organic layer was dried over anhydrous $Na_2SO_4$ and the solvent was evaporated to give the crude product, which was purified by flash column chromatography with DCM/MeOH to afford the desired product S16 as a white solid (128 mg, 10% yield). UPLC-MS calculated for $C_{17}H_{21}ClN_3O_3[M+1]^+$: 350.13, found 350.11.

To a solution of S16 (128 mg, 0.366 mmol, 1.0 eq) in 3 mL of DMF was added potassium iodide (6.1 mg, 0.037 mmol, 0.1 eq) and sodium azide (47.6 mg, 0.732 mmol, 2.0 eq). The solution was heat to 60° C. to stir for 2 h. After cooling to room temperature, the solution was diluted in water and purified by HPLC with $MeCN/H_2O$ (0.1% TFA) to afford the compound S17 as a white solid (117 mg, 90% yield). UPLC-MS calculated for $C_{17}H_{21}N_6O_3$ $[M+1]^+$: 357.17, found 350.20.

Following the procedure for the synthesis of S7, the reaction was conducted with S17 (117 mg, 0.33 mmol, 1.0 eq). The compound S18 was obtained as a white solid (71 mg, 45% yield). UPLC-MS calculated for $C_{24}H_{31}N_6O_3Si$ $[M+1]^+$: 479.22, found 478.97.

Following the procedure for the synthesis of S8, the reaction was conducted with S18 (71 mg, 0.15 mmol, 1.0 eq). The compound S19 was obtained as a white solid (57 mg, 95% yield). UPLC-MS calculated for $C_{21}H_{23}N_6O_3[M+1]^+$: 407.18, found 406.93.

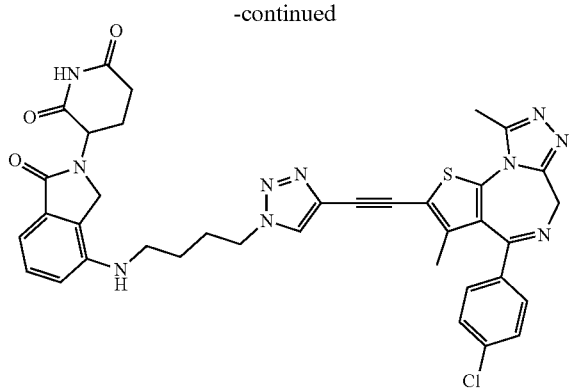

Cpd. No. 5

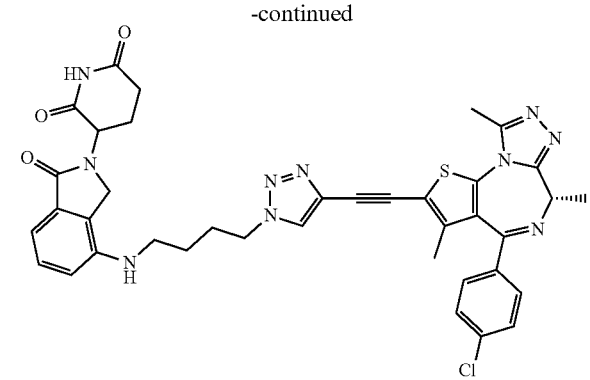

Cpd. No. 6

To a solution of S9 (14.1 mg, 0.03 mmol, 1.0 eq), S15 (18.2 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 5 as a white solid (13 mg, 60% yield). $^1$H NMR (400 MHz, CD$_3$OD) δ (ppm) 8.29 (s, 1H), 7.52 (d, J=8.4 Hz, 2H), 7.46 (d, J=8.8 Hz, 2H), 7.31 (t, J=8.0 Hz, 1H), 7.07 (dd, J=7.6 Hz, J=0.4 Hz, 1H), 6.80 (dd, J=7.6 Hz, 1H), 5.35 (d, J=12.8 Hz, 1H), 5.13 (dd, J=13.2 Hz, J=5.2 Hz, 1H), 4.50 (t, J=7.2 Hz, 2H), 4.33 (d, J=13.2 Hz, 1H), 4.29 (d, J=16.8 Hz, 1H), 4.24 (d, J=16.8 Hz, 1H), 3.28-3.23 (m, 2H), 2.95-2.86 (m, 1H), 2.81-2.79 (m, 1H), 2.74 (s, 3H), 2.51-2.40 (m, 1H), 2.21-2.14 (m, 1H), 2.10-2.03 (m, 2H), 1.90 (s, 3H), 1.70-1.62 (m, 2H); UPLC-MS calculated for C$_{37}$H$_{34}$ClN$_{10}$O$_3$S [M+1]$^+$: 733.22, found 733.14.

To a solution of S10 (14.1 mg, 0.03 mmol, 1.0 eq), S18 (18.2 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 6 as a white solid (20 mg, 90% yield). $^1$H NMR (400 MHz, CD$_3$OD) δ (ppm) 8.28 (s, 1H), 7.51 (d, J=8.4 Hz, 2H), 7.45 (d, J=8.8 Hz, 2H), 7.31 (t, J=8.0 Hz, 1H), 7.07 (dd, J=7.6 Hz, J=0.4 Hz, 1H), 6.80 (d, J=7.6 Hz, 1H), 5.13 (dd, J=13.2 Hz, J=5.2 Hz, 1H), 4.50 (t, J=7.2 Hz, 2H), 4.38 (q, J=6.8 Hz, 1H), 4.29 (d, J=16.4 Hz, 1H), 4.24 (d, J=16.8 Hz, 1H), 3.26 (t, J=7.2 Hz, 2H), 2.95-2.86 (m, 1H), 2.80-2.75 (m, 1H), 2.73 (s, 3H), 2.51-2.40 (m, 1H), 2.20-2.14 (m, 1H), 2.07 (m, 2H), 2.01 (d, J=6.8 Hz, 2H), 1.91 (s, 3H), 1.70-1.63 (m, 2H); UPLC-MS calculated for C$_{38}$H$_{36}$ClN$_{10}$O$_3$S [M+1]$^+$: 747.24, found 747.15.

Example 6

Synthesis of 3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione (Cpd. No. 6)

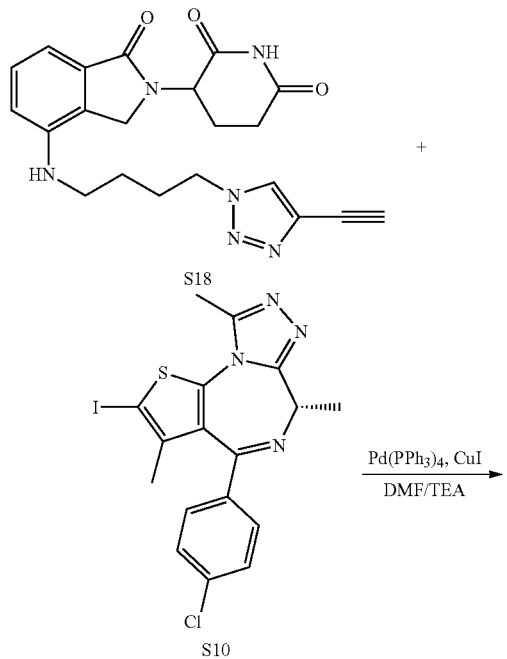

Example 7

Synthesis of 3-(4-(((4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione (Cpd. No. 7)

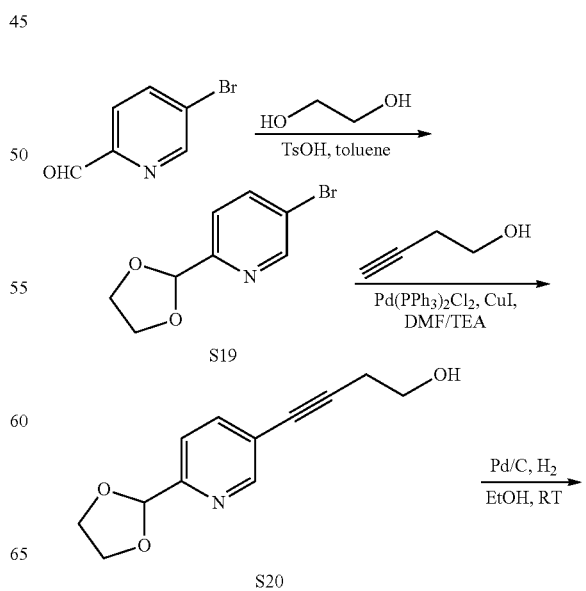

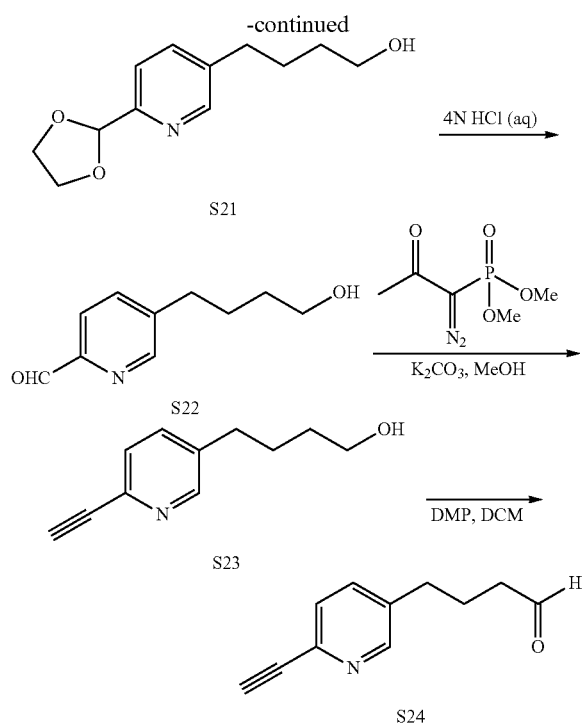

To a solution of 5-bromopyridine-2-aldehyde (13.24 g, 71.2 mmol, 1.0 eq) in 200 ml of toluene was added TsOH monohydrate (677 mg, 3.56 mmol, 0.05 eq) and ethyleneglycol (8.0 mL, 142.4 mmol, 2.0 eq). The solution was heated to reflux with a Dean-Stark trap for 12 h. After cooling to room temperature, the solvent was evaporated and the residue was purified by flash column chromatography with DCM/MeOH to afford the compound S19 as colorless oil (14.74 g, 90% yield).

To a round-bottomed flask, compound S19 (5.95 g, 25.9 mmol, 1.0 eq), 4-butyn-1-ol (2.36 g, 33.6 mmol, 1.3 eq), Pd(PPh$_3$)$_2$Cl$_2$ (909 mg, 1.295 mmol, 0.05 eq) and CuI (494 mg, 2.59 mmol, 0.1 eq) were mixed in 24 mL of DMF. The reaction mixture was sealed and filled with Nitrogen. 24 mL of triethylamine was added and the reaction mixture was heated to 80° C. to stir for 5 h. After cooling to room temperature, most of the solvent was evaporated and the residue was diluted in DCM and brine. The combined organic layer was dried and purified by flash column chromatography with DCM/MeOH to afford the final compound S20 as colorless oil (4.54 g, 80% yield). UPLC-MS calculated for C$_{12}$H$_{14}$NO$_3$ [M+1]$^+$: 220.10, found 220.09.

To the solution of S20 (4.54 g) in 100 mL of EtOH under nitrogen atmosphere was added 500 mg of Pd/C (10 wt %). Hydrogen was filled into the flask with three times. The solution was stirred at room temperature under 1 atm hydrogen atmosphere for 12 h. After consumption of the starting material, the solvent was evaporated and the residue was purified by flash column chromatography with DCM/MeOH to afford the desired product S21 as colorless oil (3.93 g, 85% yield). UPLC-MS calculated for C$_{12}$H$_{18}$NO$_3$ [M+1]$^+$: 224.13, found 224.14.

To the solution of S21 (1.84 g, 8.25 mmol, 1.0 eq) in 30 mL of THF was added 30 mL of 4N HCl (aq). The solution was heated to reflux for 6 h. After cooling to room temperature, the solvent was evaporated and diluted in ethyl acetate and saturated NaHCO$_3$ aqueous solution. After extraction several times, the combined organic layer was dried and the concentrated residue was purified by flash column chromatography with DCM/MeOH to afford the compound S22 as colorless oil (3.0 g, 95% yield). UPLC-MS calculated for C$_{10}$H$_{14}$NO$_2$ [M+1]$^+$: 180.10, found 180.05.

To the solution of dimethyl (1-diazo-2-oxopropyl)phosphonate (25.14 mmol, 1.5 eq) and K$_2$CO$_3$ (2.0 eq) in 80 mL of methanol was added dropwise a solution of S22 (3.0 g, 16.76 mmol, 1.0 eq) in 20 mL of methanol. The resulting solution was stirred at room temperature for 2 h. The solvent was evaporated and the residue was diluted in ethyl acetate and brine. The combined organic layer was dried over anhydrous Na$_2$SO$_4$. After filtration and evaporation, the crude product was purified by flash column chromatography to afford the desired compound S23 as colorless oil (2.1 g, 72% yield). UPLC-MS calculated for C$_{10}$H$_{14}$NO [M+1]$^+$: 176.11, found 176.01.

To a solution of S23 (1.1 g, 6 mmol, 1.0 eq) in 100 mL of DCM was added Dess-Martin Periodinane (4.6 g, 10.8 mmol, 1.8 eq). The reaction was stirred at room temperature for 2 h. 10 mL of water and 20 mL of saturated Na$_2$S$_2$O$_8$ aqueous solution was added. After being stirred for 10 min, the reaction solution was filtered through celite and washed with DCM. After extraction for 3 times, the combined organic layer was dried over anhydrous Na$_2$SO$_4$. After filtration and evaporation, the crude product was purified by flash column chromatography to afford the desired compound S24 as colorless oil (680 mg, 65% yield). UPLC-MS calculated for C$_{11}$H$_{12}$NO [M+1]$^+$: 174.09, found 174.08.

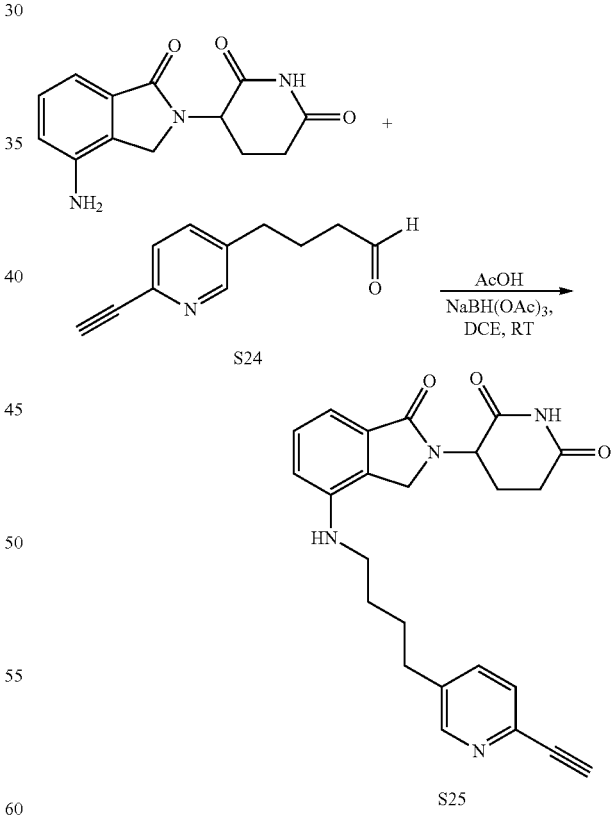

To a solution of lenalidomide (1.01 g, 3.9 mmol, 1.0 eq) and compound S24 (680 mg, 3.9 mmol, 1.0 eq) in 50 mL of DCE was added acetic acid (0.23 mL, 3.9 mmol, 1.0 eq) and sodium triacetoxyborohydride (1.66 g, 3.9 mmol, 2.0 eq). The suspended solution was stirred at room temperature for 12 h. DCM and saturated NaHCO$_3$ aqueous solution was added. After extraction, the combined organic layer was dried 974 mg, 60% yield). UPLC-MS calculated for $C_{24}H_{25}N_4O_3$ [M+1]$^+$: 417.19, found 416.98.

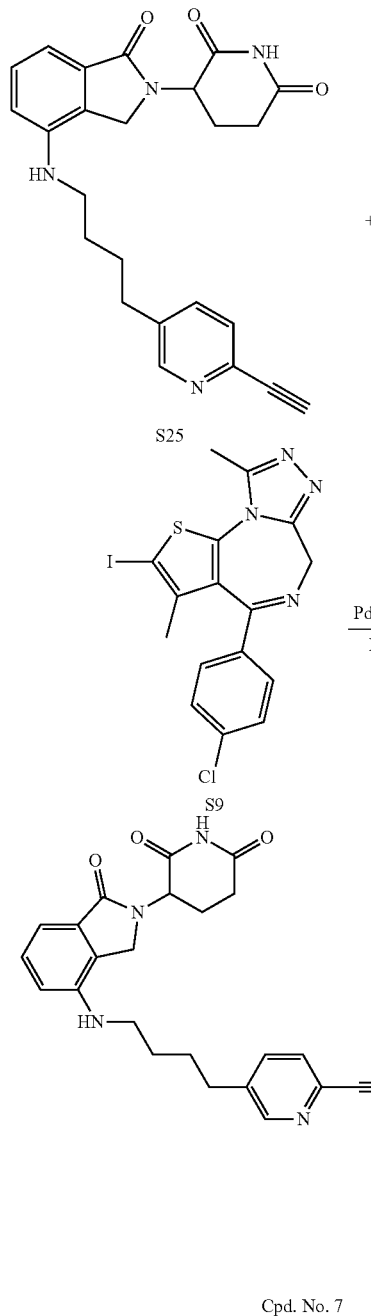

Cpd. No. 7

To a solution of S9 (14.1 mg, 0.03 mmol, 1.0 eq), S25 (18.7 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 7 as a white solid (11 mg, 50% yield). $^1$H NMR (400 MHz, CD$_3$OD) δ (ppm) 8.44 (s, 1H), 7.75 (dd, J=8.0 Hz, J=2.0 Hz, 1H), 7.58-7.52 (m, 3H), 7.46 (d, J=8.8 Hz, 2H), 7.31 (t, J=8.0 Hz, 1H), 7.07 (d, J=7.2 Hz, 1H), 6.80 (d, J=8.0 Hz, 1H), 5.36 (d, J=12.8 Hz, 1H), 5.14 (dd, J=13.2 Hz, J=5.2 Hz, 1H), 4.34 (d, J=13.2 Hz, 1H), 4.29 (d, J=16.8 Hz, 1H), 4.23 (d, J=16.8 Hz, 1H), 3.26 (t, J=6.8 Hz, 2H), 2.96-2.87 (m, 1H), 2.81-2.74 (m, 6H), 2.51-2.40 (m, 1H), 2.21-2.15 (m, 1H), 1.96 (s, 3H), 1.84-1.76 (m, 2H), 1.74-1.67 (m, 2H); UPLC-MS calculated for $C_{40}H_{36}ClN_8O_3S$ [M+1]$^+$: 743.23, found 743.22.

Example 8

Synthesis of 3-(4-((4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione (Cpd. No. 8)

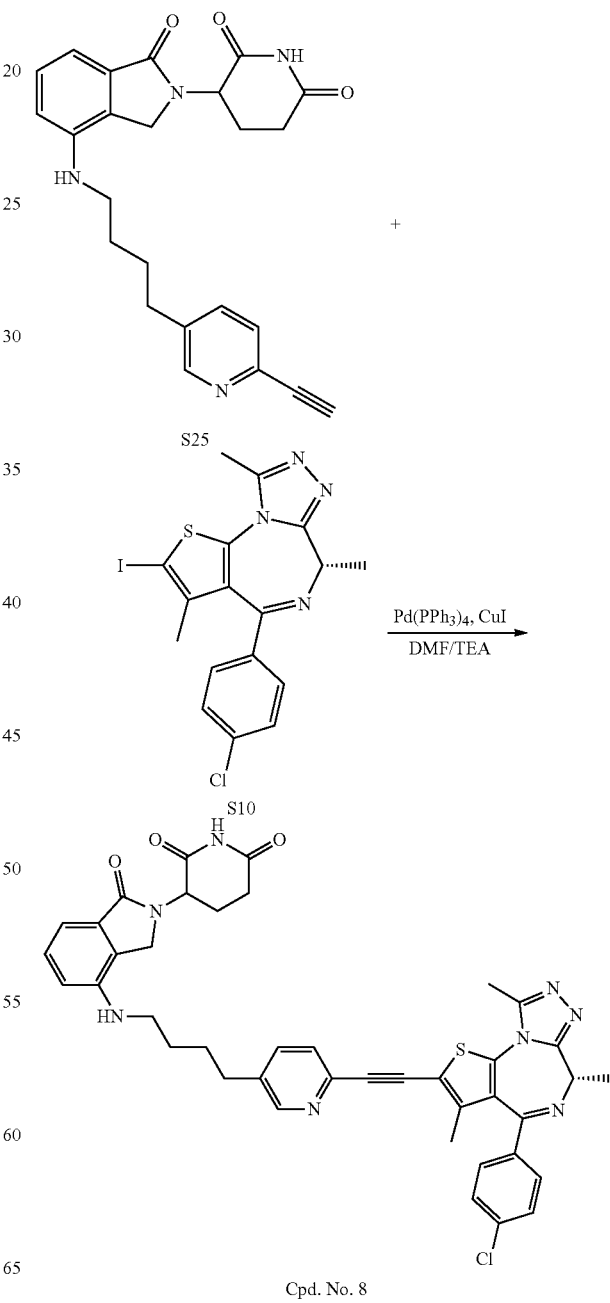

Cpd. No. 8

To a solution of S10 (14.1 mg, 0.03 mmol, 1.0 eq), S25 (18.7 mg, 0.045 mmol, 1.5 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 8 as a white solid (10 mg, 45% yield). $^1$H NMR (400 MHz, CD$_3$OD) δ (ppm) 8.43 (s, 1H), 7.74 (dd, J=8.0 Hz, J=2.0 Hz, 1H), 7.57 (d, J=7.6 Hz, 1H), 7.51 (d, J=8.8 Hz, 2H), 7.45 (d, J=8.8 Hz, 2H), 7.30 (t, J=8.0 Hz, 1H), 7.06 (d, J=7.2 Hz, 1H), 6.79 (d, J=7.6 Hz, 1H), 5.13 (dd, J=13.2 Hz, J=5.2 Hz, 1H), 4.39 (q, J=6.8 Hz, 1H), 4.28 (d, J=16.8 Hz, 1H), 4.23 (d, J=16.8 Hz, 1H), 3.25 (t, J=6.8 Hz, 2H), 2.95-2.86 (m, 1H), 2.80-2.73 (m, 3H), 2.74 (s, 3H), 2.50-2.39 (m, 1H), 2.20-2.14 (m, 1H), 2.01 (d, J=6.4 Hz, 3H), 1.96 (s, 3H), 1.83-1.75 (m, 2H), 1.73-1.66 (m, 2H); UPLC-MS calculated for C$_{41}$H$_{38}$ClN$_8$O$_3$S [M+1]$^+$: 757.25, found 757.34.

Example 9

Synthesis of 4-(4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione (Cpd. No. 9)

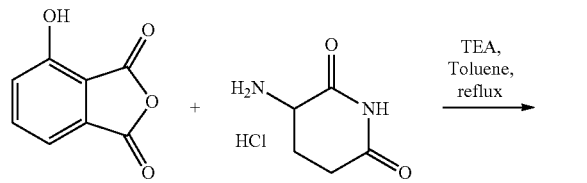

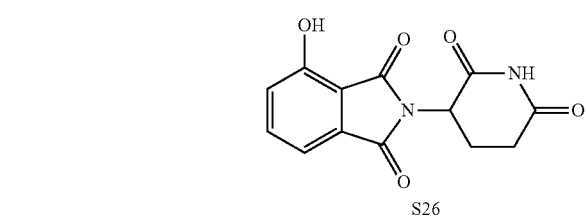

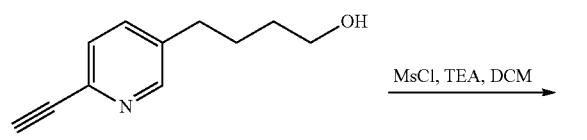

S26 + S27 $\xrightarrow{\text{KI, KHCO}_3\text{, DMF}}$ -continued

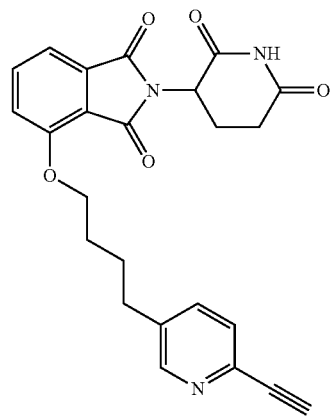

S28

To a round-bottom flask, 3-hydroxyphthalic anhydride (1 g, 6.09 mmol) and 3-aminoperidine-2,6-dione hydrochloride (1.0 g, 6.09 mmol) were mixed in 50 mL of toluene. Triethyl amine (0.93 mL, 6.7 mmol) was added. The resulting reaction mixture was heated to reflux for 12 h with Dean-Stark trap equipment. After cooling to ambient temperature, evaporation of most of the solvent to give a crude product, which was purified by flash column chromatography with DCM: ethyl acetate to get the desired product as a slightly yellow solid S26 (1.5 g, 90% yield). $^1$H NMR (400 MHz, DMSO-d$^6$) δ (ppm) 11.16 (s, 1H), 11.08 (s, 1H), 7.65 (t, J=7.6 Hz, 1H), 7.32 (d, J=7.2 Hz, 1H), 7.25 (d, J=8.4 Hz, 1H), 5.07 (dd, J=12.8 Hz, J=5.2 Hz, 1H), 2.93-2.84 (m, 1H), 2.61-2.46 (m, 1H), 2.05-2.01 (m, 1H).

To a solution of compound S23 (210 mg, 1.2 mmol, 1.0 eq) in 10 mL of DCM at 0° C. was added mesyl chloride (0.14 mL, 1.8 mmol, 1.5 eq) and triethyl amine (0.34 mL, 2.4 mmol, 2.0 eq) sequentially. The resulting solution was stirred at room temperature for 1 h. After evaporation of the solvent, the residue was purified by flash column chromatography with DCM/MeOH to afford the compound S27 as colorless oil (224 mg, 74% yield). UPLC-MS calculated for C$_{12}$H$_{16}$NO$_3$S [M+1]$^+$: 254.09, found 253.92.

To a solution of compound S27 (224 mg, 0.89 mmol, 1.0 eq) and S26 (243 mg, 0.89 mmol, 1.0 eq) in 4 mL of DMF was added KI (15 mg, 0.09 mmol, 0.1 eq) and KHCO$_3$ (178 mg, 1.78 mmol, 2.0 eq). The resulting solution was stirred at room temperature for 5 h. After cooling to room temperature, the solution was diluted in water and purified by HPLC with MeCN/H$_2$O (0.1% TFA) to afford the compound S28 as a white solid (290 mg, 75% yield). UPLC-MS calculated for C$_{24}$H$_{22}$N$_3$O$_5$[M+1]$^+$: 432.16, found 431.92.

253

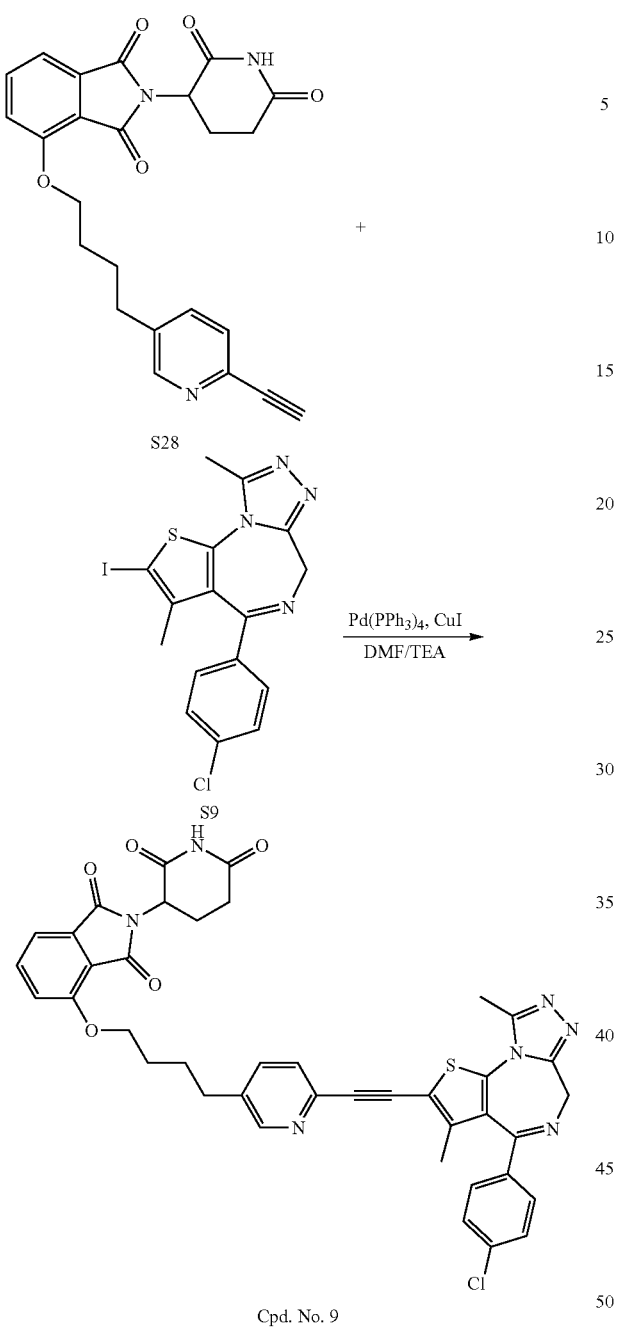

Cpd. No. 9

To a solution of S9 (14.1 mg, 0.03 mmol, 1.0 eq), S28 (26 mg, 0.06 mmol, 2.0 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 9 as a white solid (19 mg, 85% yield). $^1$H NMR (400 MHz, CD$_3$OD) δ (ppm) 8.47 (s, 1H), 7.79 (dd, J=8.0 Hz, J=2.4 Hz, 1H), 7.73 (dd, J=8.4 Hz, J=7.2 Hz, 1H), 7.58 (d, J=8.0 Hz, 1H), 7.52 (d, J=8.4 Hz, 2H), 7.45 (d, J=8.4 Hz, 2H), 7.41 (d, J=6.8 Hz, 1H), 7.38 (d, J=8.4 Hz, 1H), 5.36 (d, J=13.2 Hz, 1H), 5.08 (dd, J=12.4 Hz, J=5.6 Hz, 1H), 4.34 (d, J=13.2 Hz, 1H), 4.24 (t, J=5.6 Hz, 2H), 2.91-2.66 (m, 5H), 2.75 (s, 3H), 2.16-2.09 (m, 1H), 1.95 (s, 3H), 1.94-1.89 (m, 4H); UPLC-MS calculated for C$_{40}$H$_{33}$ClN$_7$O$_5$S [M+1]$^+$: 758.20, found 757.71.

254

Example 10

Synthesis of 4-(4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione (Cpd. No. 10)

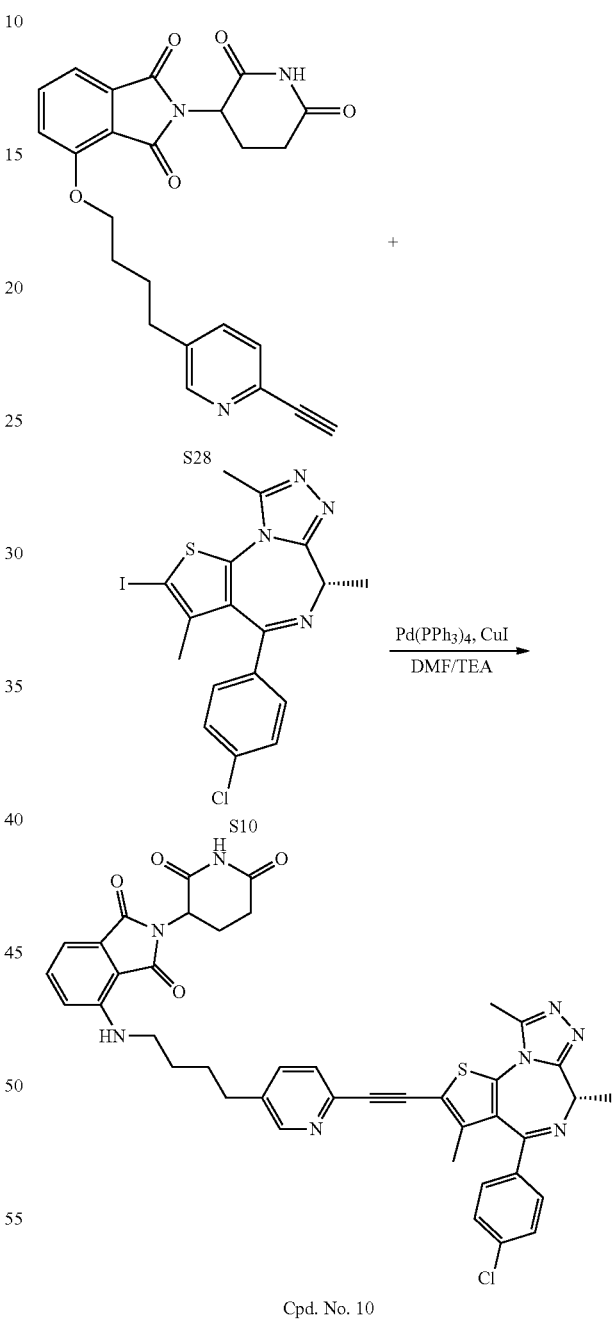

Cpd. No. 10

To a solution of S10 (14.1 mg, 0.03 mmol, 1.0 eq), S25 (26 mg, 0.06 mmol, 2.0 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 10 as a white solid (20 mg, 87% yield). $^1$H NMR (400 MHz, CD$_3$OD) δ (ppm) 8.47 (s, 1H), 7.80 (dd, J=8.0 Hz, J=2.4 Hz, 1H), 7.73 (dd, J=8.4 Hz, J=7.2 Hz, 1H), 7.59 (d, J=8.0 Hz, 1H), 7.52 (d, J=8.8 Hz, 2H), 7.45 (d, J=8.8 Hz, 2H), 7.41 (d, J=7.2 Hz, 1H), 7.38 (d, J=8.4 Hz, 1H), 5.08 (dd, J=12.8 Hz, J=5.6 Hz, 1H), 4.39 (q, J=6.8 Hz, 1H), 4.24 (t, J=5.6 Hz, 2H), 2.90-2.80 (m, 3H), 2.77-2.65 (m, 2H), 2.75 (s, 3H), 2.15-2.09 (m, 1H), 2.01 (d, J=6.8 Hz, 3H), 1.96 (s, 3H), 1.95-1.90 (m, 4H); UPLC-MS calculated for $C_{41}H_{35}ClN_7O_5S$ [M+1]$^+$: 772.21, found 771.70.

Example 11

Synthesis of 3-(4-(4-(((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperidine-2,6-dione (Cpd. No. 11)

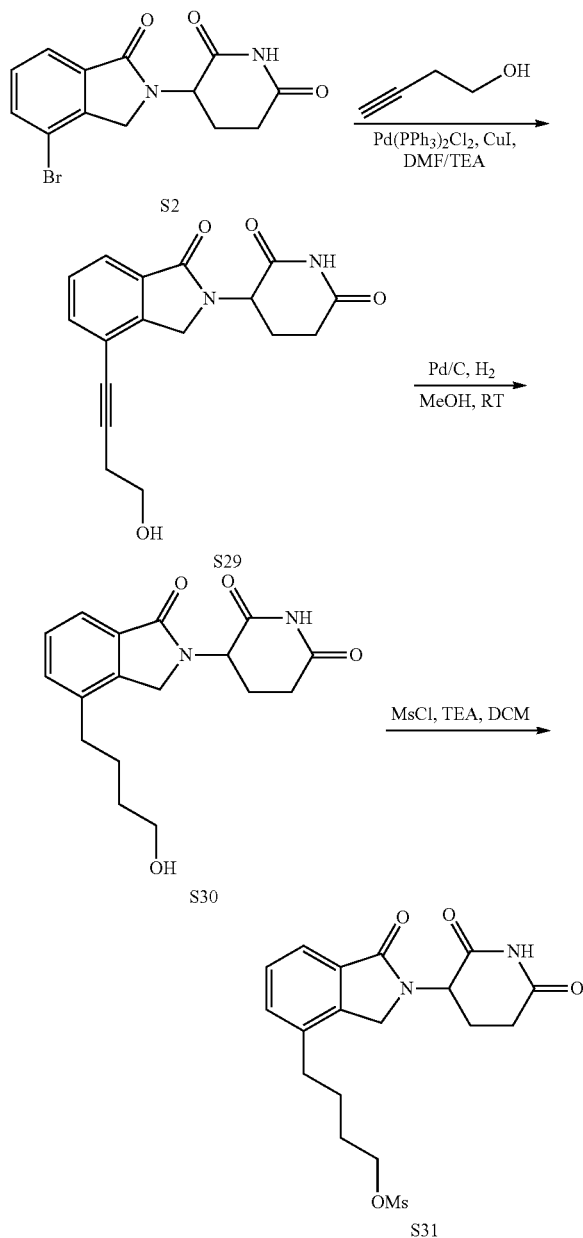

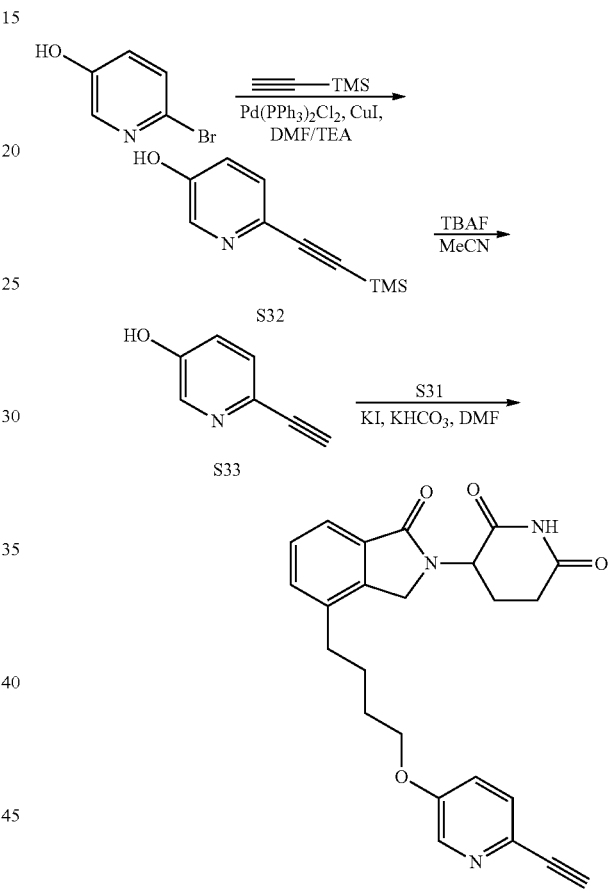

Following the procedure for the synthesis of compound S3, the reaction was conducted with S2 (1.29 g, 4.0 mmol, 1.0 eq). Finally, compound S29 was obtained as a slightly yellow solid (1.12 g, 90% yield). UPLC-MS calculated for $C_{17}H_{17}N_2O_4$ [M+1]$^+$: 313.12, found 313.13.

Following the procedure for the synthesis of compound S11, the reaction was conducted with S29 (157 mg, 0.50 mmol, 1.0 eq). Finally, compound S30 was obtained as a white solid (148 mg, 94% yield). UPLC-MS calculated for $C_{17}H_{21}N_2O_4$ [M+1]$^+$: 317.15, found 317.15.

Following the procedure for the synthesis of compound S4, the reaction was conducted with S30 (148 mg, 0.468 mmol, 1.0 eq). Finally, compound S31 was obtained as a white solid (175 mg, 95% yield). UPLC-MS calculated for $C_{18}H_{23}N_2O_6S$ [M+1]$^+$: 395.13, found 395.17.

To a solution of 2-bromo-5-hydroxypyridine (1.04 g, 6.0 mmol, 1.0 eq) and trimethylsilylacetylene (1.7 mL, 12.0 mmol, 2.0 eq) in 30 mL of anhydrous THF were added Pd(PPh$_3$)$_2$Cl$_2$ (420 mg, 0.6 mmol, 0.1 eq) and CuI (228 mg, 1.2 mmol, 0.2 eq) under nitrogen atmosphere. Then 8 mL of triethylamine was injected. The reaction flask was sealed and the reaction solution was stirred at 60° C. for 5 h. After cooling to room temperature, the solvent was evaporated and the residue was purified by flash column chromatography with DCM/MeOH to afford the compound S32 as colorless oil (803 mg, 70% yield). UPLC-MS calculated for $C_{10}H_{14}NOSi$ [M+1]$^+$: 192.08, found 191.98.

Following the procedure for the synthesis of compound S8, the reaction was conducted with S32 (803 mg, 4.2 mmol, 1.0 eq). Finally, the compound S33 was obtained as a white solid (400 mg, 80% yield). UPLC-MS calculated for $C_7H_6NO$ [M+1]$^+$: 120.04, found 119.93.

To a solution of compound S31 (175 mg, 0.44 mmol, 1.0 eq) and S33 (79 mg, 0.66 mmol, 1.5 eq) in 5.0 mL of DMF were added KI (7.3 mg, 0.044 mmol, 0.1 eq) and KHCO$_3$ (88 mg, 0.88 mmol, 2.0 eq) sequentially. The resulted solution was stirred at 70° C. for 6 h. After cooling to room temperature, the reaction mixture was diluted in water and ethyl acetate. After extraction for 3 times, the combined organic layer was dried over Na$_2$SO$_4$. The concentrated residue was purified by reverse flash column chromatography with MeCN/H$_2$O (0.1% TFA) to afford the compound S34 as a white solid (156 mg, 85% yield). UPLC-MS calculated for C$_{24}$H$_{24}$N$_3$O$_4$ [M+1]$^+$: 418.18, found 418.20.

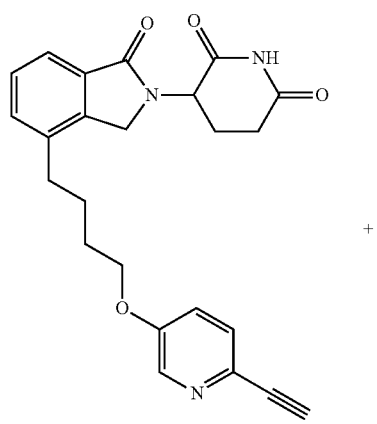

S34

+

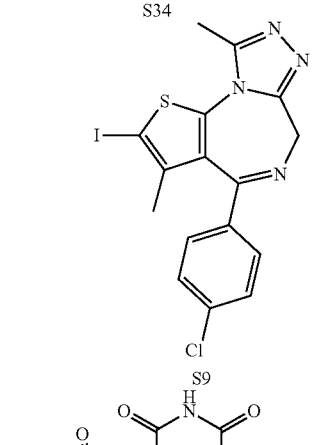

S9

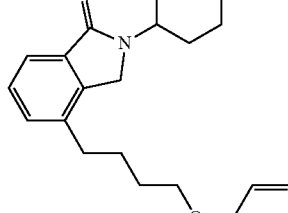

Cpd. No. 11

To a solution of S9 (14.1 mg, 0.03 mmol, 1.0 eq), S34 (25 mg, 0.06 mmol, 2.0 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 11 as a white solid (X mg, X yield). $^1$H NMR (400 MHz, CD$_3$OD) δ (ppm) 8.25 (d, J=2.4 Hz, 1H), 7.64 (dd, J=7.2 Hz, J=1.6 Hz, 1H, 7.59 (d, J=8.8 Hz, 1H), 7.53-7.48 (m, 4H), 7.45 (d, J=8.8 Hz, 2H), 7.41 (dd, J=8.8 Hz, J=2.8 Hz, 1H), 5.35 (d, J=13.2 Hz, 1H), 5.16 (dd, J=13.2 Hz, J=5.2 Hz, 1H), 4.50 (d, J=17.2 Hz, 1H), 4.45 (d, J=16.8 Hz, 1H), 4.34 (d, J=13.2 Hz, 1H), 4.14 (t, J=6.0 Hz, 2H), 2.96-2.86 (m, 1H), 2.81-2.76 (m, 3H), 2.74 (s, 3H), 2.52-2.41 (m, 1H), 2.20-2.14 (m, 1H), 1.93 (s, 3H), 1.92-1.84 (m, 4H); UPLC-MS calculated for C$_{40}$H$_{35}$ClN$_7$O$_4$S [M+1]$^+$: 744.22, found 744.20.

Example 12

Synthesis of 3-(4-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperidine-2,6-dione (Cpd. No. 12)

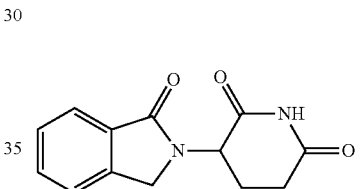

+

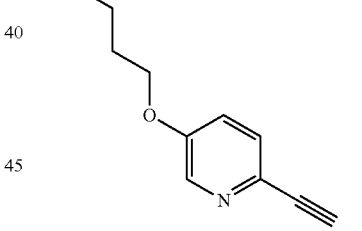

S34

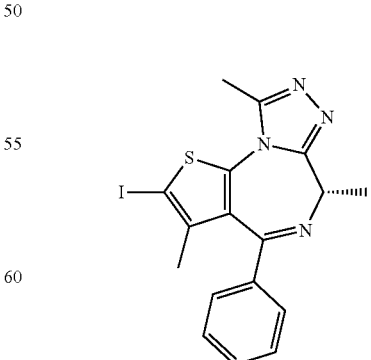

S10

259

-continued

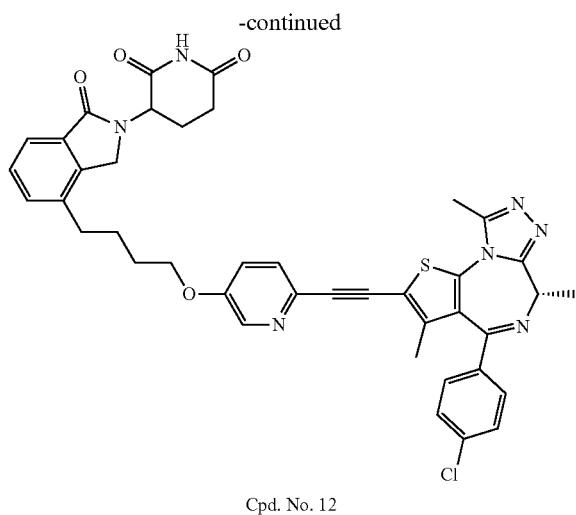

Cpd. No. 12

To a solution of S10 (14.1 mg, 0.03 mmol, 1.0 eq), S34 (25 mg, 0.06 mmol, 2.0 eq), Pd(PPh$_3$)$_4$ (3.5 mg, 0.003 mmol, 0.1 eq) and CuI (1.2 mg, 0.006 mmol, 0.2 eq) in 2 mL of DMF under nitrogen was added 1.0 mL of trimethylamine. The resulting reaction mixture was stirred at 60° C. for 5 h. After cooling to room temperature, the mixture was purified by HPLC to afford Cpd. No. 12 as a white solid. $^1$H NMR (400 MHz, CD$_3$OD) δ (ppm) 8.25 (d, J=2.4 Hz, 1H), 7.64 (dd, J=7.2 Hz, J=1.6 Hz, 1H), 7.59 (d, J=8.8 Hz, 1H), 7.53-7.40 (m, 7H), 5.15 (dd, J=13.2 Hz, J=5.2 Hz, 1H), 4.50 (d, J=16.8 Hz, 1H), 4.45 (d, J=17.2 Hz, 1H), 4.39 (q, J=6.8 Hz, 1H), 4.14 (t, J=5.6 Hz, 2H), 2.95-2.86 (m, 1H), 2.81-2.75 (m, 3H), 2.74 (s, 3H), 2.52-2.41 (m, 1H), 2.20-2.13 (m, 1H), 2.01 (d, J=6.8 Hz, 3H), 1.94 (s, 3H), 1.89-1.84 (m, 4H); UPLC-MS calculated for C$_{41}$H$_{37}$ClN$_7$O$_4$S [M+1]$^+$: 758.23, found 758.23.

Example 13

Synthesis of 3-(4-(5-(6-((4-(4-chlorophenyl)-3,9-dimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione (Cpd. No. 13)

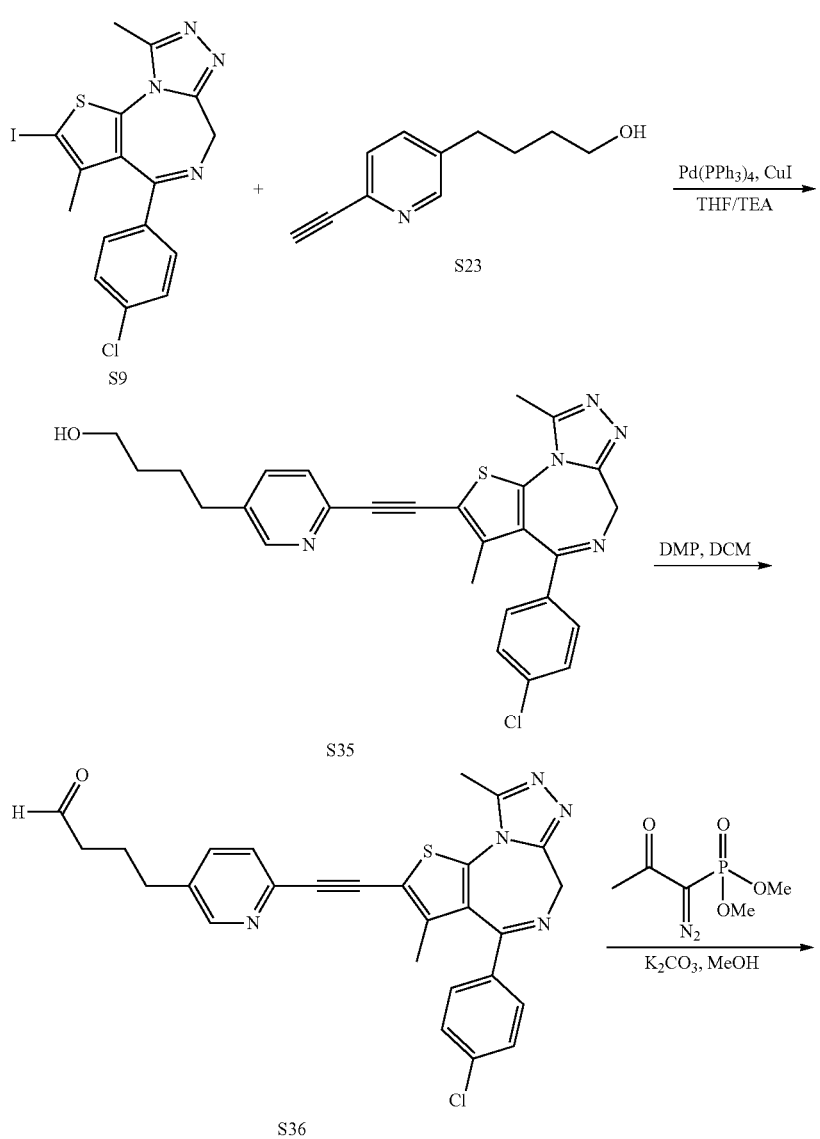

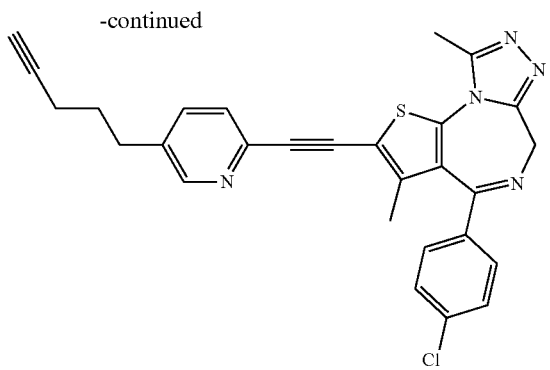

S37

To a solution of S9 (455 mg, 1.0 mmol, 1.0 eq), S23 (263 mg, 1.5 mmol, 1.5 eq), Pd(PPh$_3$)$_2$Cl$_2$ (70 mg, 0.1 mmol, 0.1 eq) and CuI (38 mg, 0.2 mmol, 0.2 eq) in 18 mL of THF under nitrogen was added 6.0 mL of trimethylamine. The resulting reaction mixture was stirred at 60° C. for 5 h. After cooling to room temperature, the mixture was purified by flash column chromatography with DCM/MeOH to afford the compound S35 as slightly yellow oil (216 mg, 43% yield). UPLC-MS calculated for C$_{27}$H$_{25}$ClN$_5$OS [M+1]$^+$: 502.15, found 502.16.

To a solution of S35 (216 mg, 0.43 mmol, 1.0 eq) in 10 mL of DCM was added Dess-Martin periodinane (365 mg, 0.86 mmol, 2.0 eq). The reaction mixture was stirred at room temperature for 2 h. Then 2 mL of water and 2 mL of saturated Na$_2$S$_2$O$_8$ aqueous solution were added to quench the reaction. The solution was filtered through celite and washed with DCM. After extraction for 3 times, the combined organic layer was dried over anhydrous Na$_2$SO$_4$. The concentrated residue was purified by flash column chromatography with DCM/MeOH to afford the compound S36 as colorless oil (167 mg, 78% yield). UPLC-MS calculated for C$_{27}$H$_{23}$ClN$_5$OS [M+1]$^+$: 500.13, found 500.09.

To a solution of S36 (167 mg, 0.33 mmol, 1.0 eq) in 5 mL of methanol was added K$_2$CO$_3$ (93 mg, 0.67 mmol, 2.0 eq) and dimethyl (1-diazo-2-oxopropyl)phosphonate (129 mg, 0.67 mmol, 2.0 eq) sequentially. The reaction mixture was stirred at room temperature for 2 h. The solvent was evaporated and the residue was diluted in MeCN/H$_2$O and purified by HPLC with MeCN/H$_2$O (0.1% TFA) to afford the compound S37 as a white solid (147 mg, 90% yield). UPLC-MS calculated for C$_{28}$H$_{23}$ClN$_5$S [M+1]$^+$: 496.14, found 496.10.

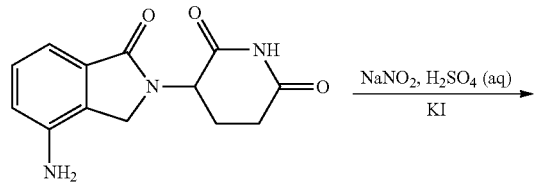

$$\xrightarrow{\text{NaNO}_2, \text{H}_2\text{SO}_4 \text{ (aq)}}_{\text{KI}}$$

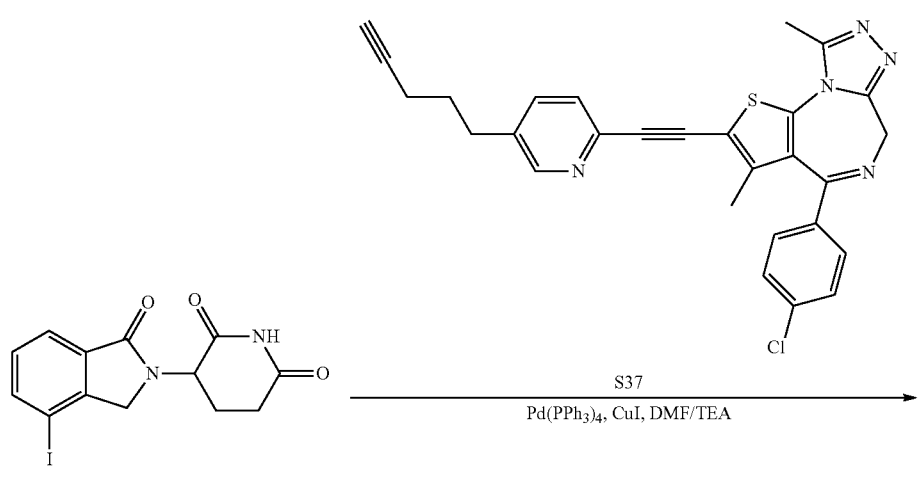

S38 $\xrightarrow[\text{Pd(PPh}_3)_4, \text{CuI, DMF/TEA}]{\text{S37}}$

-continued

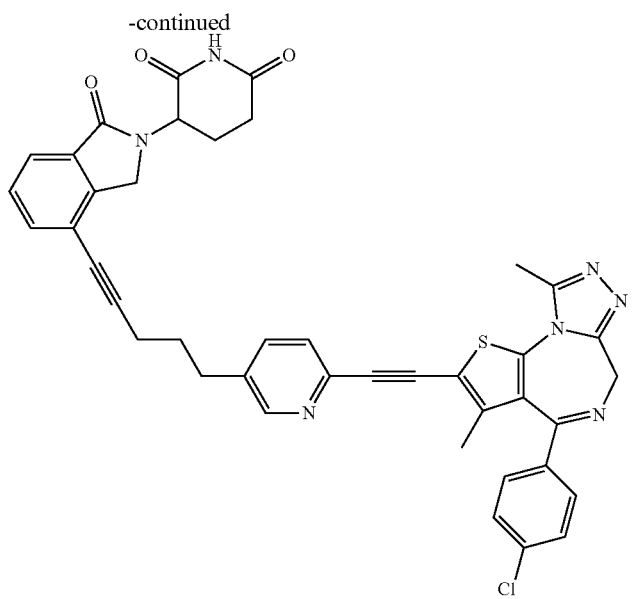

Cpd. No. 13

To a suspended solution of lenalidomide (1.04 g, 4.0 mmol, 1.0 eq) and NaNO$_2$ (0.83 g, 12.0 mmol, 3.0 eq) in 40 mL of water at 0° C. was added diluted sulfuric acid (4.0 mL in 10 mL of water). Then the solution was stirred at room temperature for 20 min. Then a solution of KI (3.32 g, 20.0 mmol, 5.0 eq) in 20 mL of water was added and the solution was heated to 80° C. to stir for 3 h. After cooling to room temperature, NaOH (aq) was added to neutralize the solution and the concentrated residue was purified by flash column chromatography with DCM/MeOH to afford the compound S38 as a slightly yellow solid (1.26 g, 85% yield). UPLC-MS calculated for C$_{13}$H$_{12}$IN$_2$O$_3$[M+1]$^+$: 370.99, found 370.95.

To a solution of S37 (25 mg, 0.05 mmol, 1.0 eq), S38 (18 mg, 0.05 mmol, 1.0 eq), Pd(PPh$_3$)$_4$ (5.7 mg, 0.005 mmol, 0.1 eq) and CuI (1.9 mg, 0.01 mmol, 0.2 eq) in 1.5 mL of DMF under nitrogen was added 1.0 mL of trimethylamine. The resulting reaction mixture was stirred at 60° C. for 7 h. After cooling to room temperature, the mixture was purified by HPLC to afford Cpd. No. 13 as a white solid (30 mg, 82% yield). $^1$H NMR (400 MHz, CD$_3$OD) δ (ppm) 8.50 (s, 1H), 7.80 (dd, J=8.4 Hz, J=2.0 Hz, 1H), 7.72 (d, J=7.6 Hz, 1H), 7.60-7.48 (m, 5H), 7.46 (d, J=8.4 Hz, 2H), 5.36 (d, J=13.2 Hz, 1H), 5.15 (dd, J=13.6 Hz, J=5.2 Hz, 1H), 4.50 (d, J=17.6 Hz, 1H), 4.45 (d, J=17.6 Hz, 1H), 4.34 (d, J=12.8 Hz, 1H), 2.94-2.85 (m, 3H), 2.80-2.74 (m, 4H), 2.58-2.45 (m, 3H), 2.21-2.15 (m, 1H), 2.02-1.94 (m, 2H), 1.93 (s, 3H); UPLC-MS calculated for C$_{41}$H$_{33}$ClN$_7$O$_3$S [M+1]$^+$: 738.21, found 738.13.

Example 14

Synthesis of 3-(4-(5-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione (Cpd. No. 14)

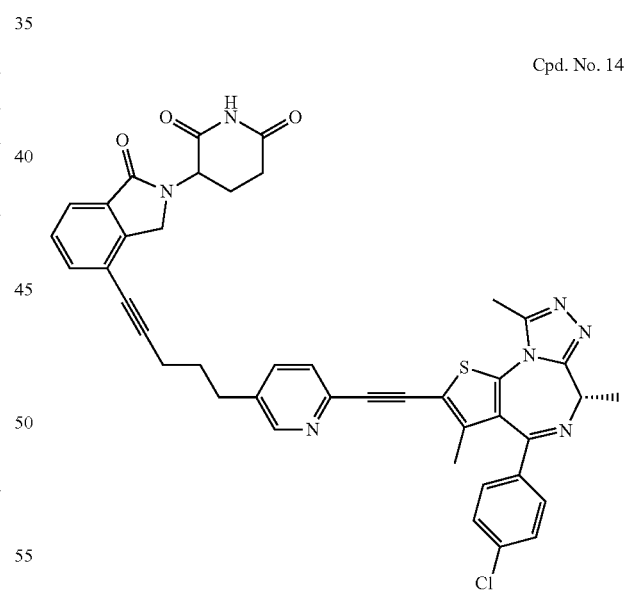

Cpd. No. 14

Cpd. No. 14 was prepared as described for Cpd. No. 13. $^1$H NMR (400 MHz, CD$_3$OD) δ (ppm) 8.49 (s, 1H), 7.79 (dd, J=8.0 Hz, J=2.0 Hz, 1H), 7.72 (d, J=7.2 Hz, 1H), 7.60-7.37 (m, 2H), 7.53-7.44 (m, 5H), 5.15 (dd, J=13.2 Hz, J=5.2 Hz, 1H), 4.50 (d, J=17.2 Hz, 1H), 4.45 (d, J=17.2 Hz, 1H), 4.39 (q, J=6.8 Hz, 1H), 2.94-2.85 (m, 3H), 2.80-2.78 (m, 1H), 2.74 (s, 3H), 2.56-2.45 (m, 3H), 2.21-2.15 (m, 1H), 2.08-1.96 (m, 2H), 2.01 (d, J=6.89 Hz, 3H), 1.94 (s, 3H); UPLC-MS calculated for C$_{42}$H$_{35}$ClN$_7$O$_3$S [M+1]$^+$: 752.22, found 752.20.

Example 15
Synthesis of 3-(4-(4-(((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione (Cpd. No. 15)
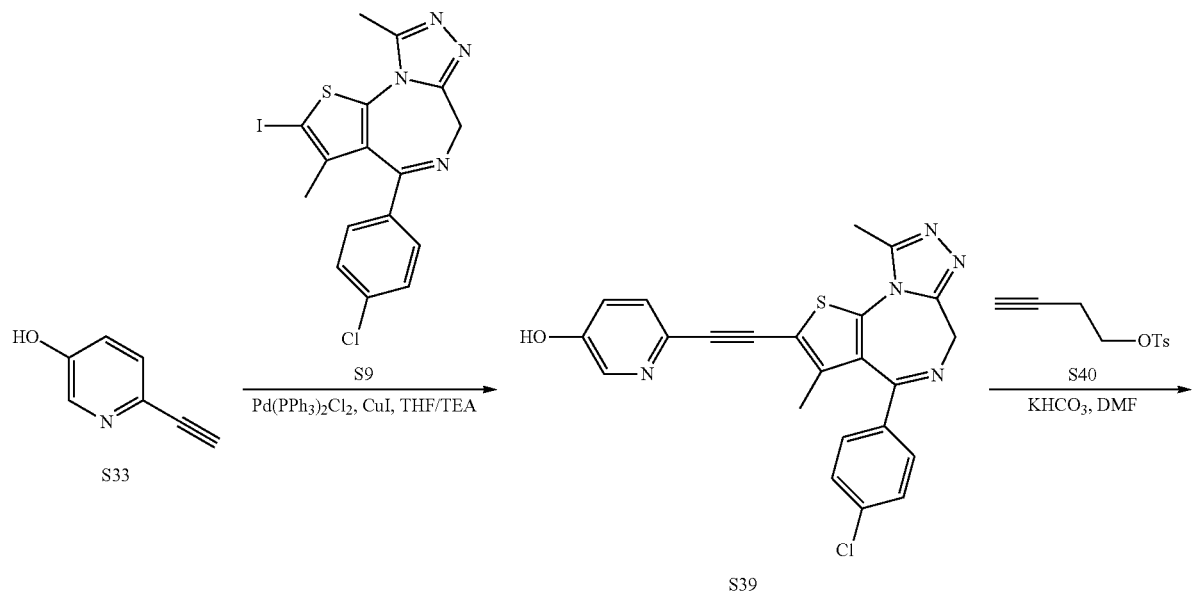
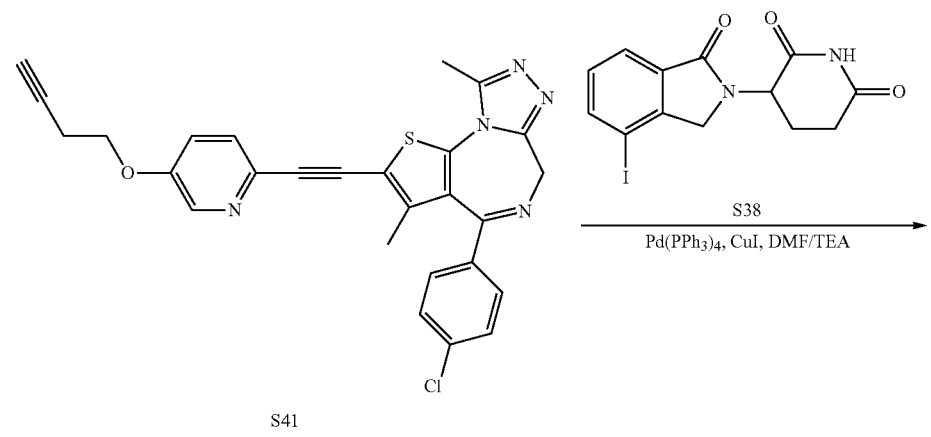

-continued

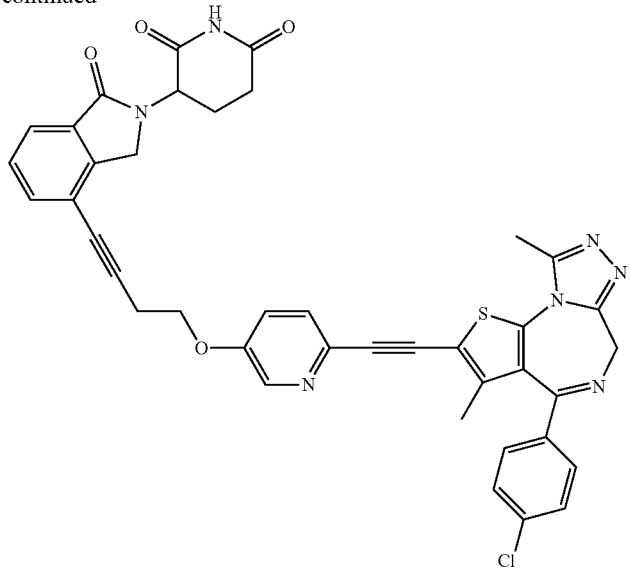

Cpd. No. 15

To a solution of S33 (155 mg, 1.3 mmol, 1.3 eq), S9 (455 mg, 1.0 mmol, 1.0 eq), Pd(PPh$_3$)$_2$Cl$_2$ (70.2 mg, 0.1 mmol, 0.1 eq) and CuI (38.1 mg, 0.2 mmol, 0.2 eq) in 20 mL of THF under nitrogen was added 3.0 mL of trimethylamine. The resulting reaction mixture was stirred at 60° C. for 6 h. After cooling to room temperature, the mixture was diluted with ethyl acetate and filtered through celite. The solvent was evaporated and the residue was purified by flash column chromatography with DCM/MeOH to afford the compound S39 as a slightly yellow solid (267 mg, 60% yield). UPLC-MS calculated for C$_{23}$H$_{17}$ClN$_5$OS [M+1]$^+$: 446.08, found 446.05.

To a solution of compound S39 (45 mg, 0.1 mmol, 1.0 eq) and S40 (67 mg, 0.3 mmol, 3.0 eq) in 2.0 mL of DMF was added KHCO$_3$ (11 mg, 0.3 mmol, 3.0 eq). The solution was heated to 70° C. to stir for 12 h. After cooling to room temperature, the solution was diluted in water and ethyl acetate. Normal workup was performed to remove most of DMF. The combined organic layer was concentrated and purified by HPLC with MeCN/H$_2$O to afford the compound S41 as yellow solid (20 mg, 40% yield). UPLC-MS calculated for C$_{27}$H$_{21}$ClN$_5$OS [M+1]$^+$: 498.12, found 498.05.

To a solution of S41 (20 mg, 0.04 mmol, 1.0 eq) and S38 (18 mg, 0.048 mmol, 1.2 eq) in 1.5 mL of DMF were added Pd(PPh$_3$)$_4$ (4.6 mg, 0.004 mmol, 0.1 eq) and CuI (1.5 mg, 0.008 mmol, 0.2 eq) sequentially. Nitrogen was purged into the solution for 10 min. The solution was heated to 60° C. for 2 h. After cooling to room temperature, the solution was diluted in ethyl acetate and filtered through celite. Normal workup was conducted and the concentrated residue was purified by HPLC with MeCN/H$_2$O to afford Cpd. No. 15 as an white solid (20 mg, 70% yield). $^1$H NMR (400 MHz, CD$_3$OD) δ (ppm) 8.34 (s, 1H), 7.75 (dd, J=7.6 Hz, J=0.8 Hz, 1H), 7.63-7.60 (m, 2H), 7.53-7.44 (m, 6H), 5.36 (d, J=12.8 Hz, 1H), 5.15-5.09 (m, 1H), 4.42-4.32 (m, 5H), 3.01 (t, J=6.4 Hz, 2H), 2.94-2.85 (m, 1H), 2.80-2.78 (m, 1H), 2.75 (s, 3H), 2.44-2.32 (m, 1H), 2.20-2.10 (m, 1H), 1.94 (s, 3H); UPLC-MS calculated for C$_{40}$H$_{31}$ClN$_7$O$_4$S [M+1]$^+$: 740.18, found 740.11.

Example 16

Synthesis of 3-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione (Cpd. No. 16)

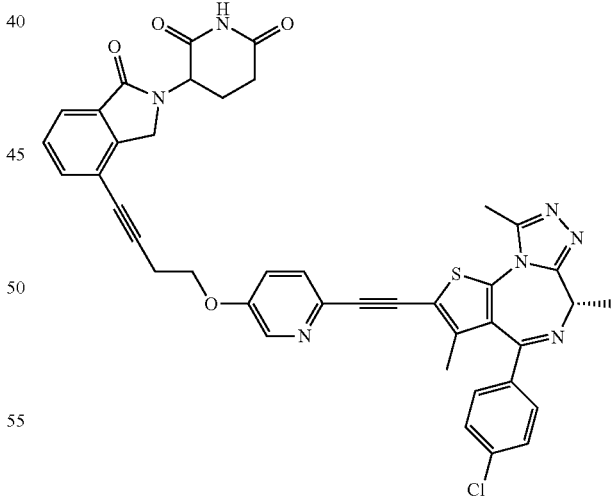

Cpd. No. 16 was prepared as described for Cpd. No. 15 using S10 instead of S9. $^1$H NMR (400 MHz, CD$_3$OD) δ (ppm) 8.33 (s, 1H), 7.74 (dd, J=7.6 Hz, J=0.8 Hz, 1H), 7.62-7.59 (m, 2H), 7.53-7.43 (m, 6H), 5.14-5.09 (m, 1H), 4.42-4.33 (m, 5H), 3.00 (t, J=6.4 Hz, 2H), 2.95-2.85 (m, 1H), 2.80-2.73 (m, 4H), 2.44-2.33 (m, 1H), 2.18-2.11 (m, 1H), 2.01 (d, J=6.8 Hz, 3H), 1.94 (s, 3H); UPLC-MS calculated for C$_{41}$H$_{33}$ClN$_7$O$_4$S [M+1]$^+$: 754.20, found 754.14.

Example 17

Synthesis of 3-(4-((4-(5-((4-(4-chlorophenyl)-3,9-dimethyl-6H-thieno[3,2-f][1,2,4]triazolo[4,3-a][1,4]diazepin-2-yl)ethynyl)pyridin-2-yl)butyl)amino)-1-oxoisoindolin-2-yl)piperidine-2,6-dione (Cpd. No. 17)

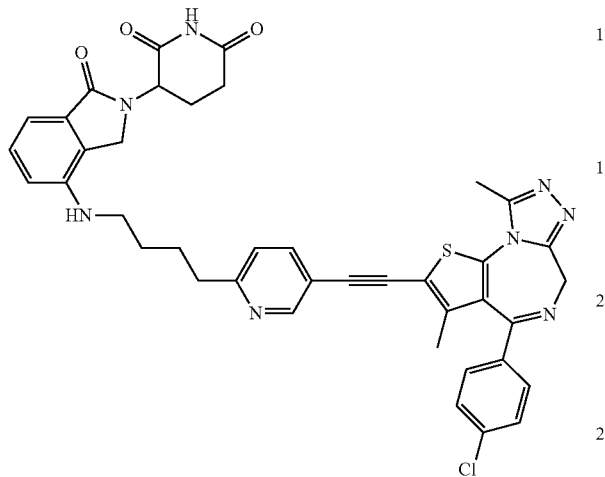 [SMILES: Cc1c(C#Cc2ccc(CCCCNc3cccc4c3CN(C3CCC(=O)NC3=O)C4=O)nc2)sc2c1C(c1ccc(Cl)cc1)=N[C@@H](C)c1nnc(C)n1-2]

Cpd. No. 17 was prepared following the procedure described for the synthesis of Cpd. No. 7 using 6-bromonicotinaldehyde. $^1$H NMR (400 MHz, CD$_3$OD) δ (ppm) 8.59 (d, J=1.6 Hz, 1H), 7.87 (dd, J=8.0 Hz, J=2.0 Hz, 1H), 7.53 (d, J=8.4 Hz, 2H), 7.47 (d, J=8.4 Hz, 2H), 7.38 (d, J=7.6 Hz, 1H), 7.30 (t, J=8.0 Hz, 1H), 7.07 (d, J=7.2 Hz, 1H), 6.79 (d, J=7.6 Hz, 1H), 5.36 (d, J=13.2 Hz, 1H), 5.15 (dd, J=13.2 Hz, J=5.2 Hz, 1H), 4.33 (d, J=13.2 Hz, 1H), 4.29 (d, J=16.8 Hz, 1H), 4.24 (d, J=16.8 Hz, 1H), 3.28-3.23 (m, 2H), 2.95-2.86 (m, 3H), 2.82-2.75 (m, 4H), 2.52-2.41 (m, 1H), 2.21-2.16 (m, 1H), 1.93 (s, 3H), 1.90-1.84 (m, 2H), 1.75-1.67 (m, 2H); UPLC-MS calculated for C$_{40}$H$_{36}$ClN$_8$O$_3$S [M+1]$^+$: 743.23, found 743.27.

Example 18

Synthesis of 3-(4-((4-(5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)butyl)amino)-1-oxoisoindolin-2-yl)piperidine-2,6-dione (Cpd. No. 18)

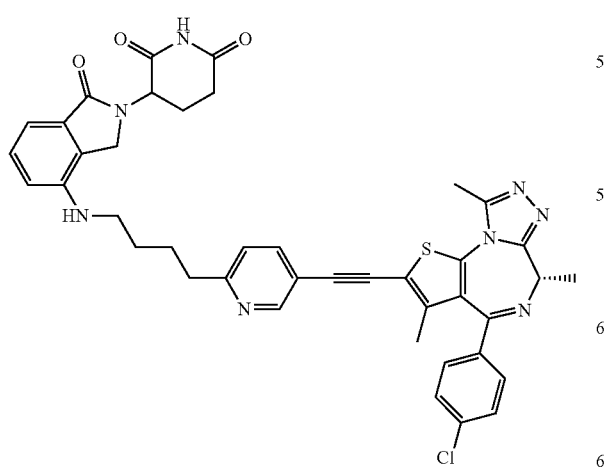

Cpd. No. 18 was prepared following the procedure described for the synthesis of Cpd. No. 8 using 6-bromonicotinaldehyde. $^1$H NMR (400 MHz, CD$_3$OD) δ (ppm) 8.60 (d, J=1.6 Hz, 1H), 7.89 (dd, J=8.0 Hz, J=2.0 Hz, 1H), 7.51 (d, J=8.4 Hz, 2H), 7.44 (d, J=8.4 Hz, 2H), 7.39 (d, J=8.0 Hz, 1H), 7.28 (t, J=8.0 Hz, 1H), 7.05 (d, J=7.2 Hz, 1H), 6.76 (d, J=8.0 Hz, 1H), 5.12 (dd, J=13.2 Hz, J=5.2 Hz, 1H), 4.37 (q, J=6.8 Hz, 1H), 4.27 (d, J=16.8 Hz, 1H), 4.22 (d, J=16.8 Hz, 1H), 3.24 (t, J=6.8 Hz, 2H), 2.93-2.84 (m, 3H), 2.78-2.68 (m, 4H), 2.49-2.34 (m, 1H), 2.18-2.13 (m, 1H), 2.01 (d, J=6.8 Hz, 3H), 1.93 (s, 3H), 1.90-1.82 (m, 2H), 1.73-1.65 (m, 2H); UPLC-MS calculated for C$_{41}$H$_{38}$ClN$_8$O$_3$S [M+1]$^+$: 757.25, found 757.29.

Example 19

Synthesis of 3-(4-(5-(5-((4-(4-chlorophenyl)-3,9-dimethyl-6H-thieno[3,2-f][1,2,4]triazolo[4,3-a][1,4]diazepin-2-yl)ethynyl)pyridin-2-yl)pent-1-yn-1-yl)-1-oxoisoindolin-2-yl)piperidine-2,6-dione (Cpd. No. 19)

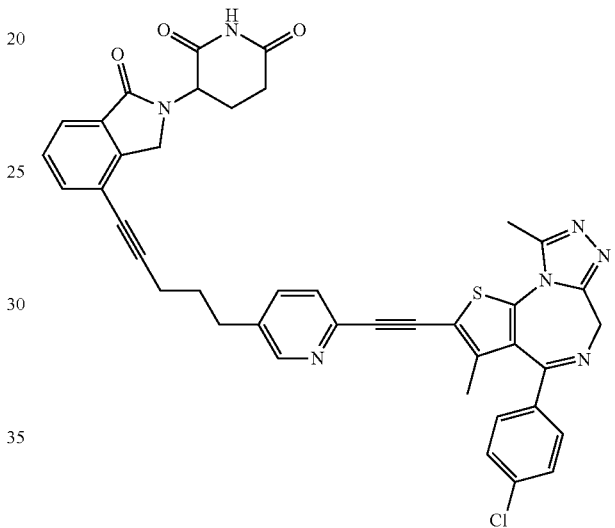

Cpd. No. 19 was prepared following the procedure described for the synthesis of Cpd. No. 13 using 6-bromonicotinaldehyde. $^1$H NMR (400 MHz, CD$_3$OD) δ (ppm) 8.60 (s, 1H), 7.86 (dd, J=8.0 Hz, J=2.0 Hz, 1H), 7.71 (d, J=7.6 Hz, 1H), 7.58-7.42 (m, 7H), 5.36 (d, J=12.8 Hz, 1H), 5.16 (dd, J=13.2 Hz, J=5.2 Hz, 1H), 4.49 (d, J=13.2 Hz, 1H), 4.43 (d, J=13.6 Hz, 1H), 4.33 (d, J=12.8 Hz, 1H), 3.02 (t, J=7.6 Hz, 2H), 2.95-2.86 (m, 1H), 2.81-2.75 (m, 4H), 2.58-2.46 (m, 3H), 2.20-2.15 (m, 1H), 2.11-2.04 (m, 2H), 1.90 (s, 3H); UPLC-MS calculated for C$_{41}$H$_{33}$ClN$_7$O$_3$S [M+1]$^+$: 738.21, found 738.09.

Example 20

Synthesis of (S)-4-(4-chlorophenyl)-2-iodo-3,6,9-trimethyl-6H-thieno[3,2-f][1,2,4]triazolo[4,3-a][1,4]diazepine (N6 or S10)

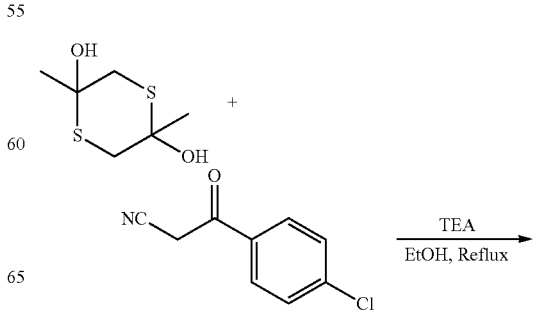

271

-continued

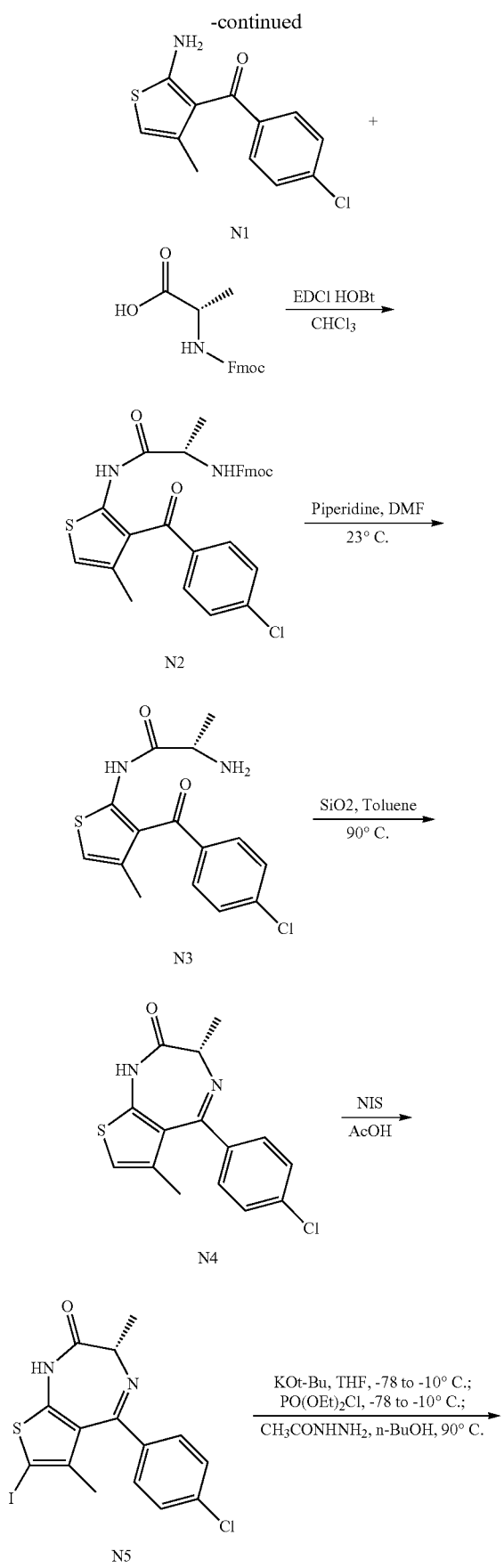

N1

N2

N3

N4

N5

272

-continued

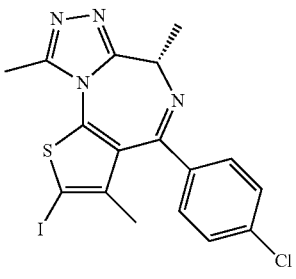

N6 or S10

Step 1: Synthesis of (2-amino-4-methylthiophen-3-yl)(4-chlorophenyl)methanone (Compound N1)

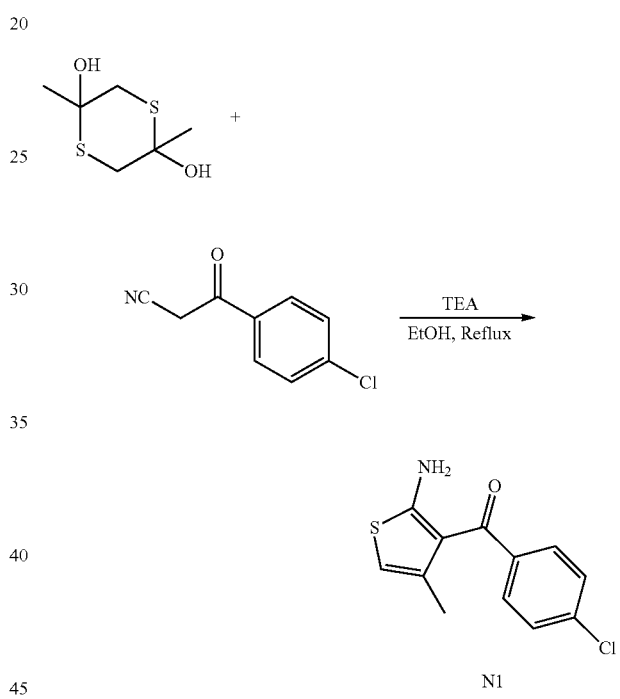

N1

To a suspension of 3-(4-chloro-phenyl)-3-oxo-propionitrile (900 mg, 5 mmol) and 2,5-dimethyl-[1,4]dithiane-2,5-diol (450 mg, 2.5 mmol) in absolute EtOH (10 mL), cooled in a bath of water/ice, was added TEA (5 mmol, 0.7 mL). After stirring for 10 min at r.t., the mixture was refluxed for 2 h. The red-brown solution was evaporated and the residue dissolved in EtOAc (10 mL) and the organic phase subsequently washed with 1% w/v HCl (5 mL), a saturated solution of NaHCO$_3$ (5 mL), water (5 mL), brine (5 mL), dried (Na$_2$SO$_4$) and concentrated to give a brown residue. This latter was suspended in ethyl ether (15 mL), the suspension stirred for 30 min and filtered. The filtrate was concentrated, suspended with petroleum ether and the resulting suspension stirred for 30 min and filtered. The residue was purified by column chromatography using a mixture of EtOAc-petroleum ether as eluent, to give 440 mg of compound N1 as an orange solid, 35% yield. ESI-MS m/z 252.03 [M+H]$^+$.

Step 2: Synthesis of (9H-fluoren-9-yl)methyl (S)-(1-((3-(4-chlorobenzoyl)-4-methylthiophen-2-yl)amino)-1-oxopropan-2-yl)carbamate (Compound N2)

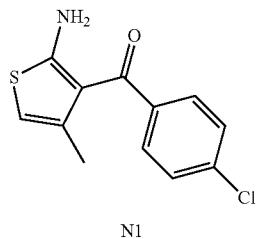

N1

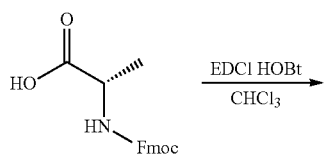

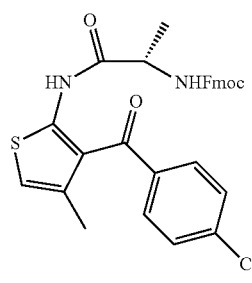

N2

To the solution of Fmoc-Ala-OH (3.0 g, 9.7 mmol) in chloroform (40 mL) was added EDC.HCl (2.2 g, 11.5 mmol) and HOBt (540 mg, 4.0 mmol). Then Compound N1 (2.2 g, 8.8 mmol) was added to above solution. The resulting mixture was stirred at 40° C. for 24 h. The reaction was quenched by addition of water (80 mL). The organic phase was taken, washed with saturated ammonium chloride solution, brine and dried with sodium sulfate, purified with flash column chromatography to give 2.0 g of the desired Compound N2, 42% yield. ESI-MS m/z 567.09 [M+Na]⁺.

Step 3: Synthesis of (S)-2-amino-N-(3-(4-chlorobenzoyl)-4-methylthiophen-2-yl)propanamide (Compound N3)

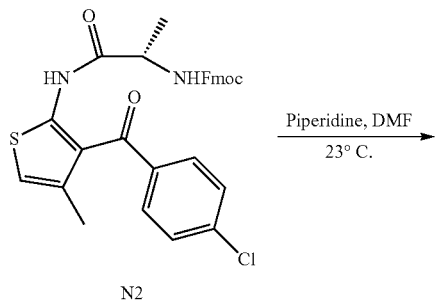

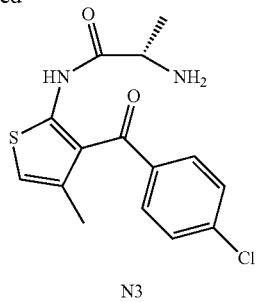

N3

Compound N2 (256 mg, 0.47 mmol, 1 equiv) was dissolved into 20% piperidine in DMF solution (2.2 ml, 0.22 M) at 23° C. After 1 h, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (24 gram silica gel, gradient 0 to 100% ethyl acetate-hexane) to afford free amine Compound N3 (129 mg, 85%) as yellow solid. ESI-MS m/z 322.81 [M+H]⁺.

Step 4: Synthesis of (S)-5-(4-chlorophenyl)-3,6-dimethyl-1,3-dihydro-2H-thieno[2,3-e][1,4]diazepin-2-one (Compound N4)

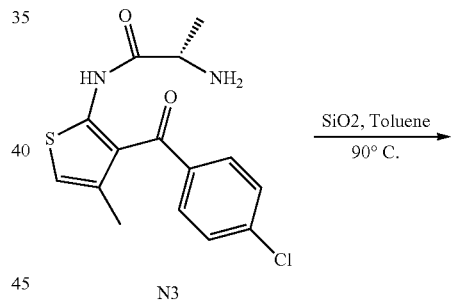

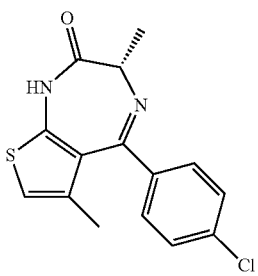

N4

Amino ketone (Compound N3) (136 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography (12 gram silica gel, gradient 0 to 100% ethyl acetate-hexanes) to afford compound N4 (77 mg, 60%). ESI-MS m/z 305.05 [M+H]⁺.

Step 5: Synthesis of (S)-5-(4-chlorophenyl)-7-iodo-3,6-dimethyl-1,3-dihydro-2H-thieno[2,3-e][1,4]diazepin-2-one (Compound N5)

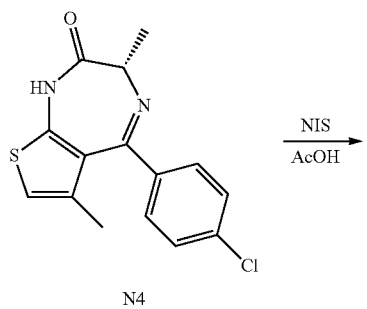

305 mg (1 mmol) of Compound N4 was dissolved in 5 mL glacial acetic acid and then added with a solution of 450 mg (2.0 mmol) of NIS in 2 mL of glacial acetic acid within 5 min. After the addition was complete, the solution was still stirred for 2 h at room temperature. Then the reaction mixture was poured into water, neutralized with sodium bicarbonate under addition of methylene chloride, the organic layer was separated, dried over sodium sulfate and evaporated to give the crude product. The residue was purified by flash column chromatography to afford Compound N5 (215 mg, 50%). ESI-MS m/z 431.03 [M+H]$^+$.

Step 6: Synthesis of (S)-4-(4-chlorophenyl)-2-iodo-3,6,9-trimethyl-6H-thieno[3,2-f][1,2,4]triazolo[4,3-a][1,4]diazepin (Compound N6)

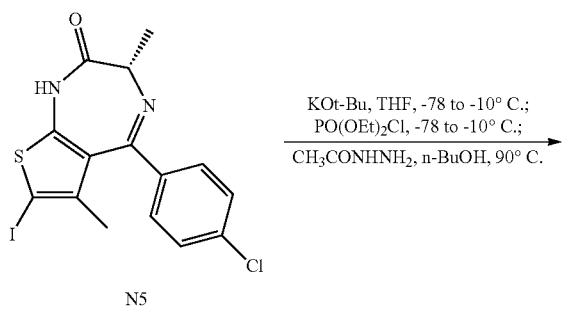

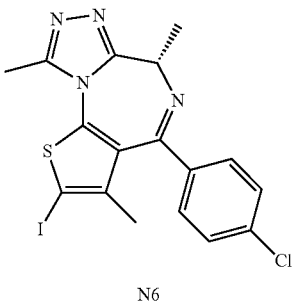

Potassium tert-butoxide (1.0 M solution in THF, 0.3 mL, 0.30 mmol, 1.10 equiv) was added to a solution Compound N5 (116 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 mL, 0.32 mmol, 1.20 equiv) was added to reaction mixture. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 2 h, all solvents were removed under reduced pressure. The residue was purified with flash column chromatography (4 g silica gel, gradient 0 to 100% ethyl acetate-hexanes) to afford 73 mg of Compound N6, 58% yield. ESI-MS m/z 469.66 [M+H]$^+$.

Example 21

Synthesis of 4-(4-chlorophenyl)-2-iodo-3,9-dimethyl-6H-thieno[3,2-f][1,2,4]triazolo[4,3-a][1,4]diazepine

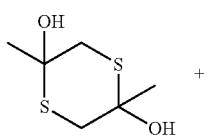

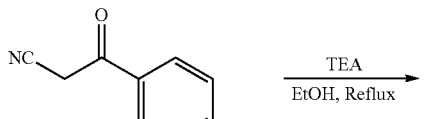

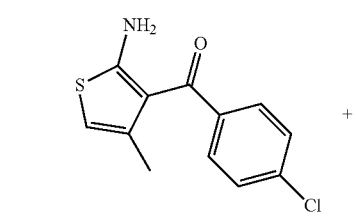

277
-continued
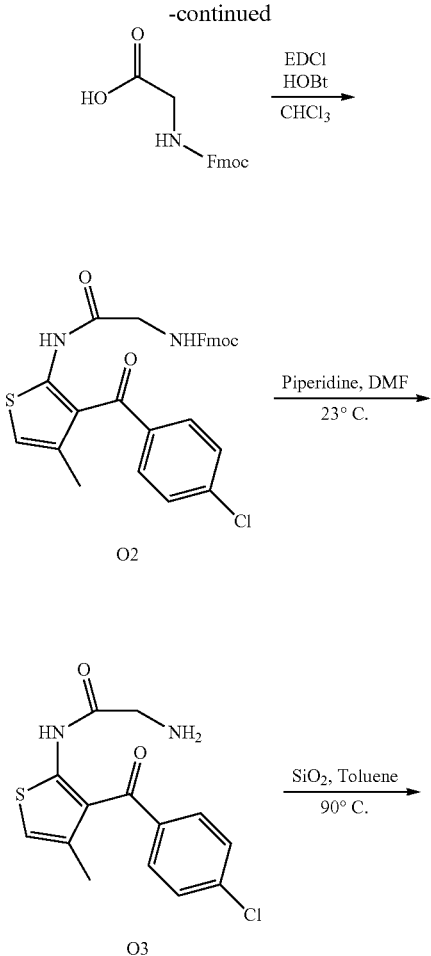
278
-continued
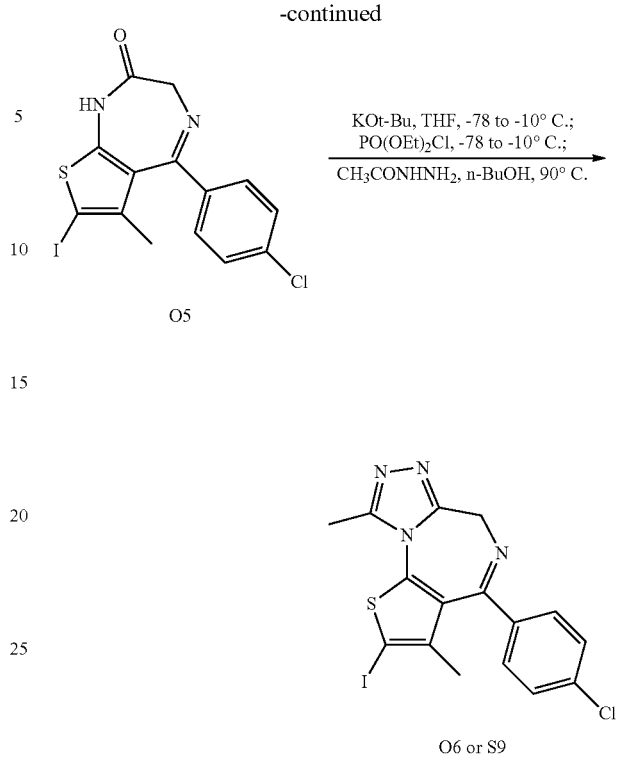
Following the same synthetic procedure as in Example 1, O6 was obtained using N1 and Fmoc-Gly-OH as starting materials. ESI-MS m/z 455.65 [M+H]$^+$.
Example 22
Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione (Cpd. No. 20)
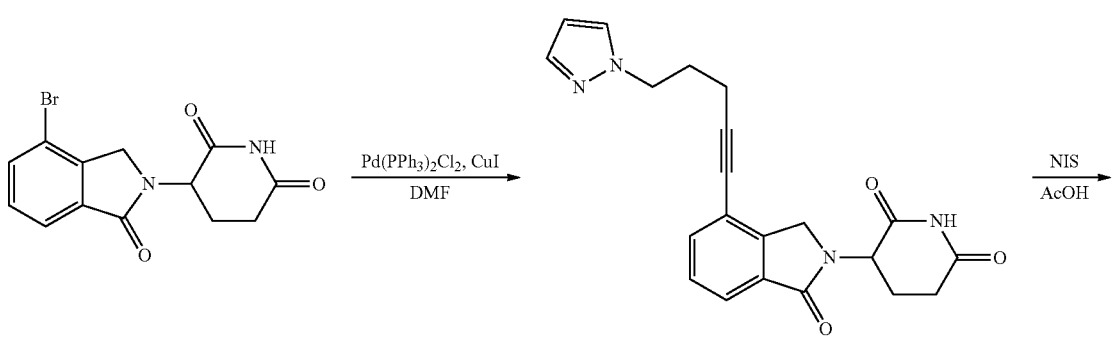

-continued

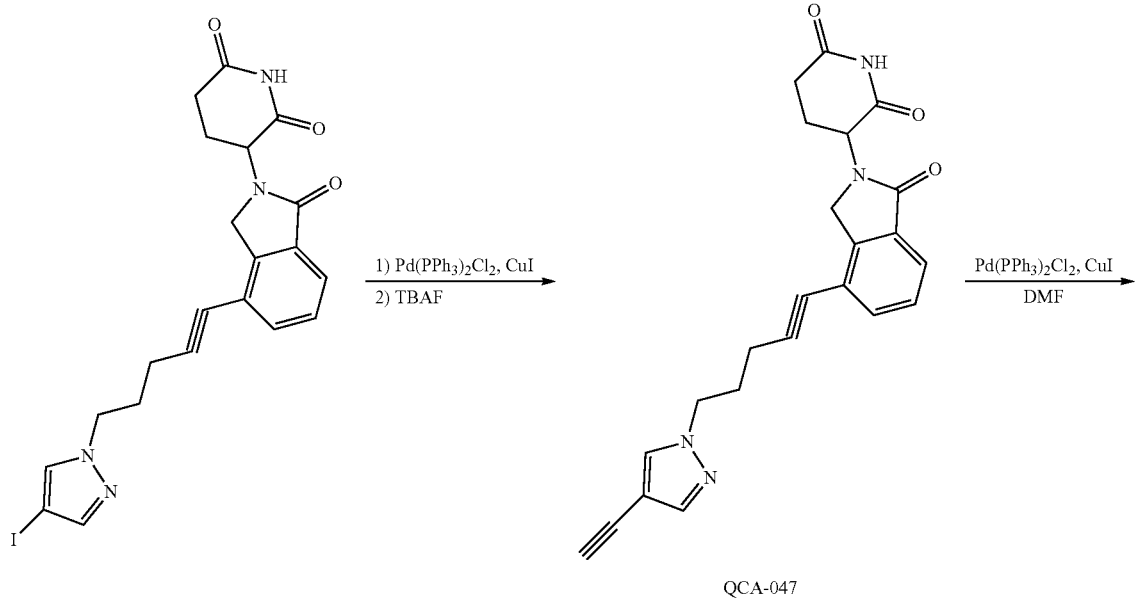

QCA-047

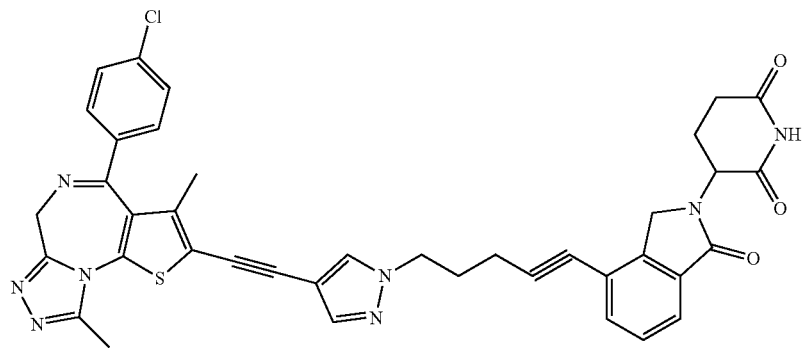

Cpd. No. 20

Step 1: To a Schlenk tube was added CuI (5.3 mg), Pd(Ph₃P)₂Cl₂ (20 mg), 3-(4-bromo-1-oxoisoindolin-2-yl)piperidine-2,6-dione (100 mg, 0.31 mmol), and 1-(pent-4-yn-1-yl)-1H-imidazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford 3-(4-(5-(1H-imidazol-1-yl)pent-1-yn-1-yl)-1-oxoisoindolin-2-yl)piperidine-2,6-dione (42 mg, 36% yield). ESI-MS: 377.22.

Step 2: 3-(4-(5-(1H-imidazol-1-yl)pent-1-yn-1-yl)-1-oxoisoindolin-2-yl)piperidine-2,6-dione (100 mg, 0.26 mmol) in acetic acid (2 mL) was added NIS (56 mg). The reaction was stirred for 1 h prior to being concentrated. The residue was purified by HPLC to afford 3-(4-(5-(4-iodo-1H-imidazol-1-yl)pent-1-yn-1-yl)-1-oxoisoindolin-2-yl)piperidine-2,6-dione (39 mg, 30%). ESI-MS: 503.11.

Step 3: To a Schlenk tube was added CuI (5.3 mg), Pd(Ph₃P)₂Cl₂ (20 mg), 3-(4-(5-(4-iodo-1H-imidazol-1-yl)pent-1-yn-1-yl)-1-oxoisoindolin-2-yl)piperidine-2,6-dione (101 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford Cpd. No. 42 (50 mg, 63% yield). ESI-MS: 401.17.

Step 4: To a Schlenk tube was added CuI (3.8 mg), Pd(Ph₃P)₂Cl₂ (7 mg), 06 (23 mg, 0.05 mmol), and QCA-047 (40 mg, 0.1 mmol), THF (2 mL) and Et₃N (0.5 mL). The reaction mixture was heated at 70° C. for 12 hours. The reaction mixture was cooled and treated with EtOAc and brine. The organic layer was separated, dried, and evaporated. The residue was subjected to HPLC purification to afford the title compound (6.3 mg, 15% yield). ESI-MS m/z 728.05 [M+H]$^+$.

Example 23

Synthesis of 4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(2,6-dioxopiperidin-3-yl)isoindoline-1,3-dione (Cpd. No. 21)

tert-butyl (4-hydroxybutyl)carbamate (1.89 g, 10 mmol) and Cs$_2$CO$_3$ (3.9 g, 12 mmol) was added. The reaction mixture was heated to reflux for 12 h. After the reaction was cooled, the mixture was filtered and the filtrate was evaporated. The residue was taken up in EtOAc and water. The organic layer was separated, washed with brine, dried, and evaporated. The residue was purified by chromatography (EtOAc/Hexanes: 1:2) to afford crude tert-butyl (4-(4-iodo-1H-pyrazol-1-yl)butyl)carbamate (2.3 g, 53%), which was treated with DCM (5 mL) and TFA (5 mL). The reaction mixture was stirred for 12 hours. All the volatiles were removed under vacuum and the residue was subjected to HPLC purification to afford 4-(4-iodo-1H-pyrazol-1-yl)butan-1-amine.

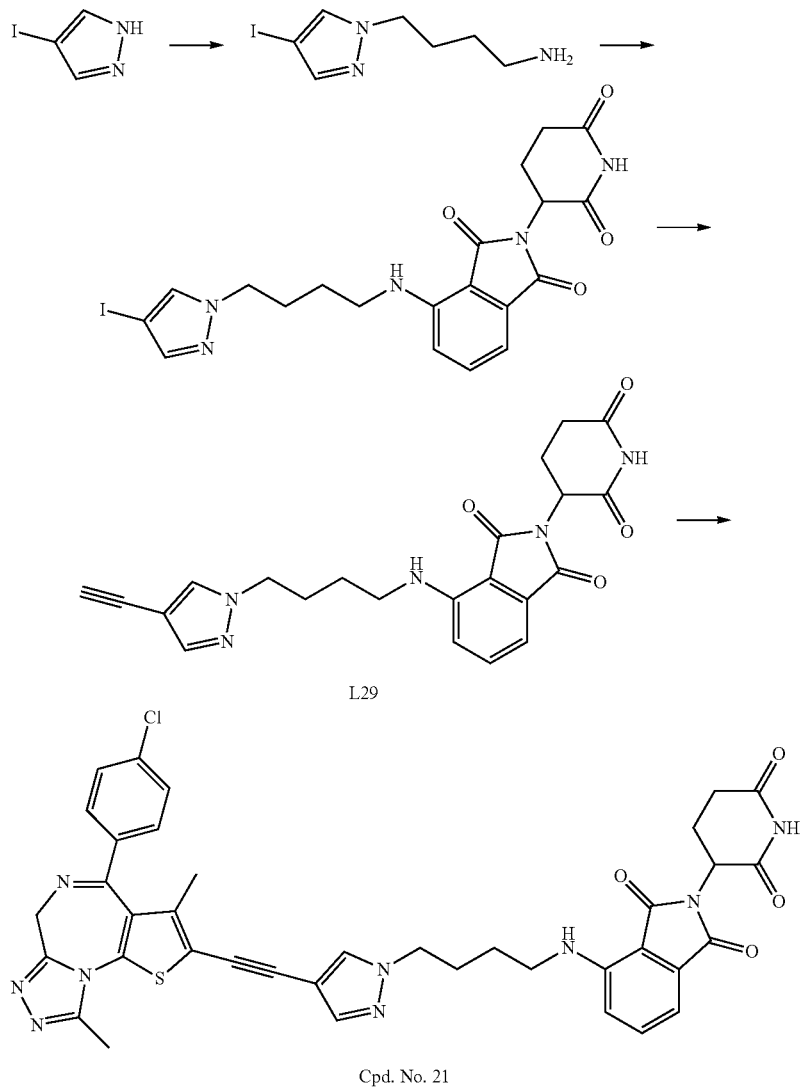

Cpd. No. 21

Step 1: To a solution of 4-iodo-1H-pyrazole (2.4 g, 12 mmol) and triethylamine (1.85 mL, 13 mmol) in DCM (20 mL) at 0° C. was added MsCl (1 mL, 12.6 mmol). The reaction mixture was allowed to warm to r.t. and stirred for another 1 hour. The reaction mixture was quenched with saturated NH$_4$Cl solution, extracted with DCM. The organic layer was separated, washed with brine, dried, and evaporated. The residue was dissolved in CH$_3$CN (70 mL) and Step 2: To a solution of TFA salt of 4-(4-iodo-1H-pyrazol-1-yl)butan-1-amine (378 mg, 1 mmol) and 2-(2,6-dioxopiperidin-3-yl)-4-fluoroisoindoline-1,3-dione (276 mg, 1 mmol) in DMF (1 mL) was added DIPEA (0.52 mL, 3 mmol). The reaction mixture was heated at 90° C. for 12 hours. The reaction mixture was cooled and treated with EtOAc and brine. The organic layer was separated, dried, and evaporated. The residue was subject to HPLC purification to afford 2-(2,6-dioxopiperidin-3-yl)-4-((4-(4-iodo-1H-pyrazol-1-yl)butyl)amino)isoindoline-1,3-dione (122 mg, 23% yield).

Step 3: To a Schlenk tube was added CuI (5.3 mg), Pd(Ph₃P)₂Cl₂ (20 mg), 2-(2,6-dioxopiperidin-3-yl)-4-((4-(4-iodo-1H-pyrazol-1-yl)butyl)amino)isoindoline-1,3-dione (100 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford compound L29 (50 mg, 60% yield). ESI-MS: 420.13.

Step 4: To a Schlenk tube was added CuI (3.8 mg), Pd(Ph₃P)₂Cl₂ (7 mg), O6 (23 mg, 0.05 mmol), and L29 (42 mg, 0.1 mmol), THF (2 mL) and Et₃N (0.5 mL). The reaction mixture was heated at 70° C. for 12 hours. The reaction mixture was cooled and treated with EtOAc and brine. The organic layer was separated, dried, and evaporated. The residue was subjected to HPLC purification to afford the title compound (15 mg, 35% yield). ESI-MS m/z 746.33 [M+H]⁺.

Example 24

Synthesis of 4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-2-(2,6-dioxopiperidin-3-yl)isoindoline-1,3-dione (Cpd. No. 22)

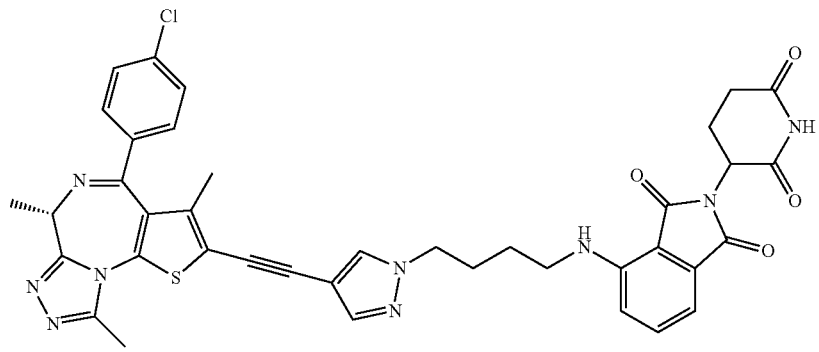

Cpd. No. 22

Cpd. No. 22 was prepared following the procedure described for the synthesis of Cpd. No. 21 in Example 23. ESI-MS m/z 760.55 [M+H]⁺.

Example 25

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione (Cpd. No. 23)

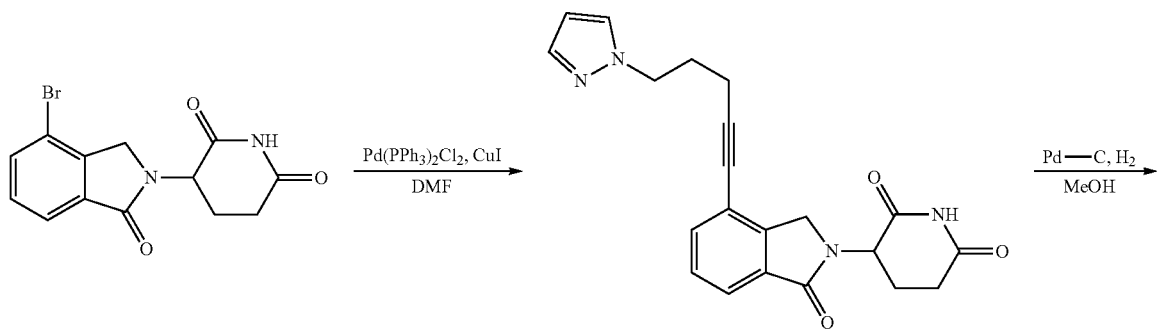

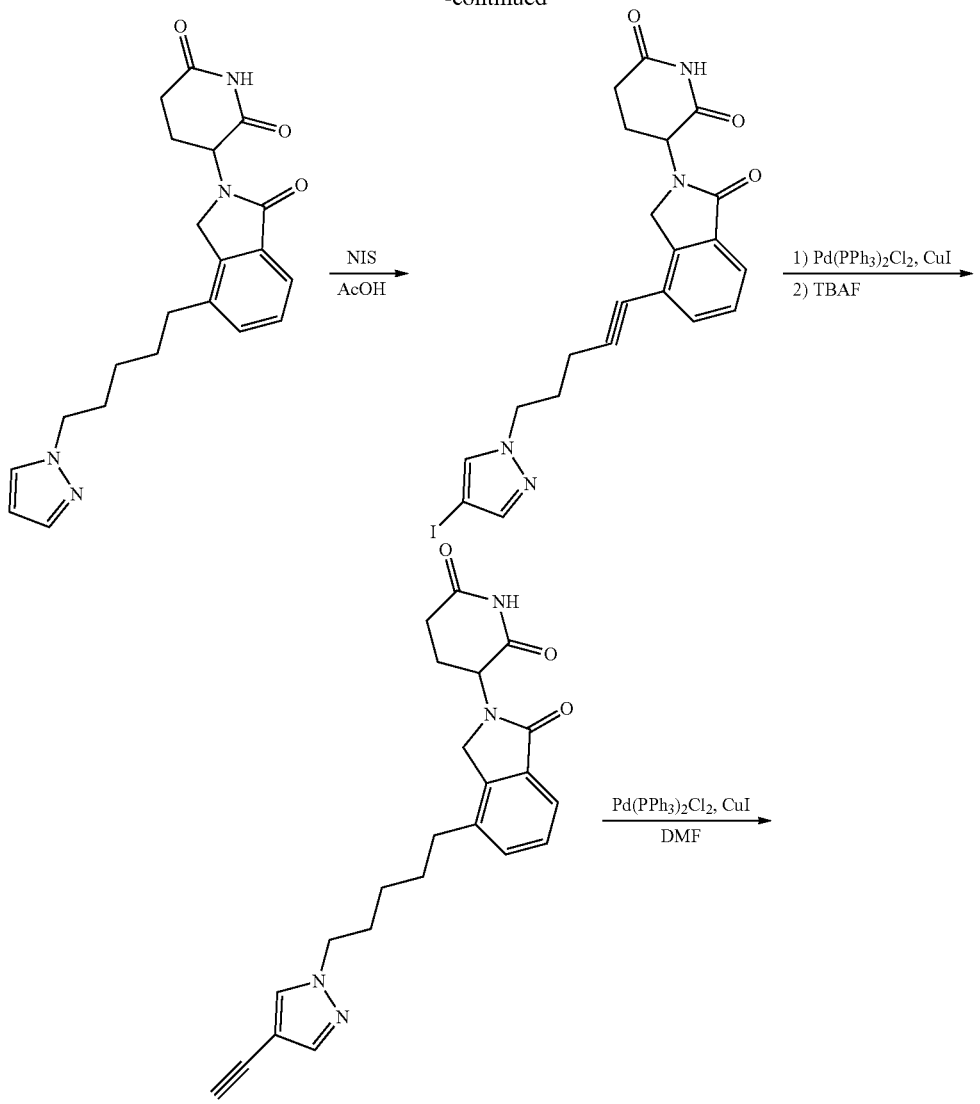

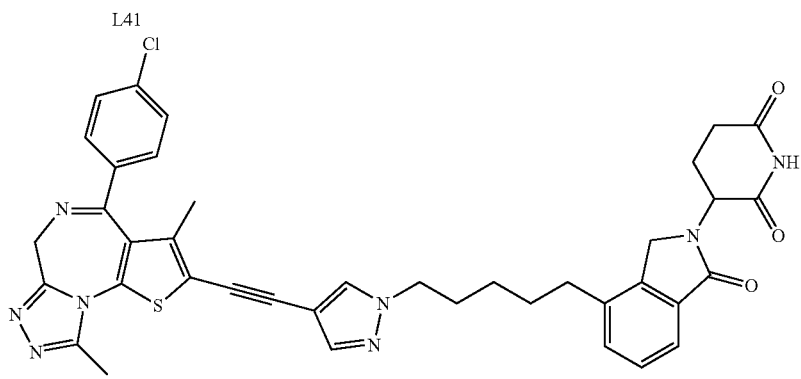

Cpd. No. 23

Step 1: To a Schlenk tube was added CuI (5.3 mg), Pd(Ph₃P)₂Cl₂ (20 mg), 3-(4-bromo-1-oxoisoindolin-2-yl)piperidine-2,6-dione (100 mg, 0.31 mmol), and 1-(pent-4-yn-1-yl)-1H-pyrazole (50 mg, 0.37 mmol), DMF (4 mL) and Et₃N (1 mL). The reaction mixture was heated at 80° C. for 12 hours. The reaction mixture was cooled and treated with EtOAc and brine. The organic layer was separated, dried, and evaporated. The residue was purified by chromatography (MeOH/DCM) to afford the desired product (82 mg, 70% yield). ESI-MS: 377.15.

Step 2: To a solution of the product from step 1 (100 mg, 0.266 mmol) in MeOH (2 mL) was added 10% Pd/C. The reaction was stirred under H₂ balloon for 4 h prior to being filtered. The organic solvent was removed to afford 3-(4-(5-(1H-pyrazol-1-yl)pentyl)-1-oxoisoindolin-2-yl)piperidine-2,6-dione (97 mg, 95%).

Step 3: 3-(4-(5-(1H-pyrazol-1-yl)pentyl)-1-oxoisoindolin-2-yl)piperidine-2,6-dione (100 mg, 0.26 mmol) in acetic acid (2 mL) was added NIS (56 mg). The reaction was stirred for 6 h prior to being concentrated. The residue was purified by HPLC to afford 3-(4-(5-(4-iodo-1H-pyrazol-1-yl)pentyl)-1-oxoisoindolin-2-yl)piperidine-2,6-dione (118 mg, 90%). ESI-MS: 507.19.

Step 4: To a Schlenk tube was added CuI (5.3 mg), Pd(Ph₃P)₂Cl₂ (20 mg), 3-(4-(5-(4-iodo-1H-pyrazol-1-yl)pentyl)-1-oxoisoindolin-2-yl)piperidine-2,6-dione (101 mg, 0.2 mmol), and ethynyltrimethylsilane (39.2 mg, 0.4 mmol), THF (4 mL) and Et₃N (1 mL). The reaction mixture was heated at 40° C. for 12 hours. The reaction mixture was cooled and treated with EtOAc and brine. The organic layer was separated, dried, and evaporated. The residue was purified by chromatography (EtOAc) to afford crude product, which was dissolved in THF and a solution of TBAF in THF (1M, 0.2 mL) was added. After 5 minutes, the reaction mixture was evaporated and the residue was subjected to HPLC purification to afford compound L41 (44 mg, 55% yield). ESI-MS: 405.19.

Step 5: To a Schlenk tube was added CuI (3.8 mg), Pd(Ph₃P)₂Cl₂ (7 mg), 06 (23 mg, 0.05 mmol), and L41 (40 mg, 0.1 mmol), THF (2 mL) and Et₃N (0.5 mL). The reaction mixture was heated at 70° C. for 12 hours. The reaction mixture was cooled and treated with EtOAc and brine. The organic layer was separated, dried, and evaporated. The residue was subjected to HPLC purification to afford the title compound (21.1 mg, 50% yield). ESI-MS m/z 731.19 [M+H]⁺.

Example 26

Synthesis of 3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione (Cpd. No. 24)

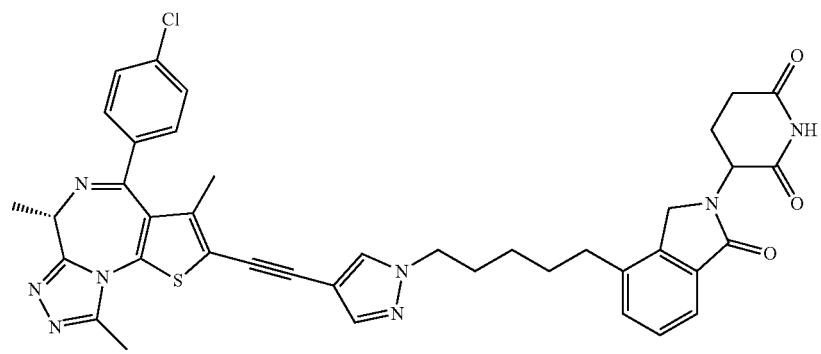

Cpd. No. 24

Cpd. No. 24 was prepared following the procedure described for the synthesis of Cpd. No. 23 in Example 25. ESI-MS m/z 745.23 [M+H]⁺.

Example 27

Synthesis of 4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione (Cpd. No. 25)

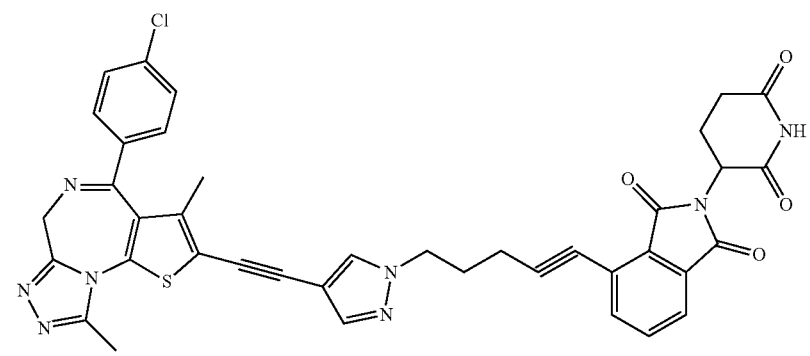

Cpd. No. 29

Cpd. No. 25 was prepared following the procedure described for the synthesis of Cpd. No. 23 in Example 25. ESI-MS m/z 741.07 [M+H]+.

Example 28

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione (Cpd. No. 26)

reaction mixture was heated at 80° C. for 6 hours. The reaction mixture was cooled and treated with EtOAc and brine. The organic layer was separated, dried, and evaporated. The residue was purified by chromatography (MeOH/DCM) to afford 2-((1H-imidazol-4-yl)ethynyl)-4-(4-chlorophenyl)-3,9-dimethyl-6H-thieno[3,2-f][1,2,4]triazolo[4,3-a][1,4]diazepine (65 mg, 50% yield). ESI-MS m/z 420.97 [M+H]+.

Step 2: To a suspension of 2-((1H-imidazol-4-yl)ethynyl)-4-(4-chlorophenyl)-3,9-dimethyl-6H-thieno[3,2-f][1,2,4]triazolo[4,3-a][1,4]diazepine (419 mg, 1 mmol) and 5-chloro-

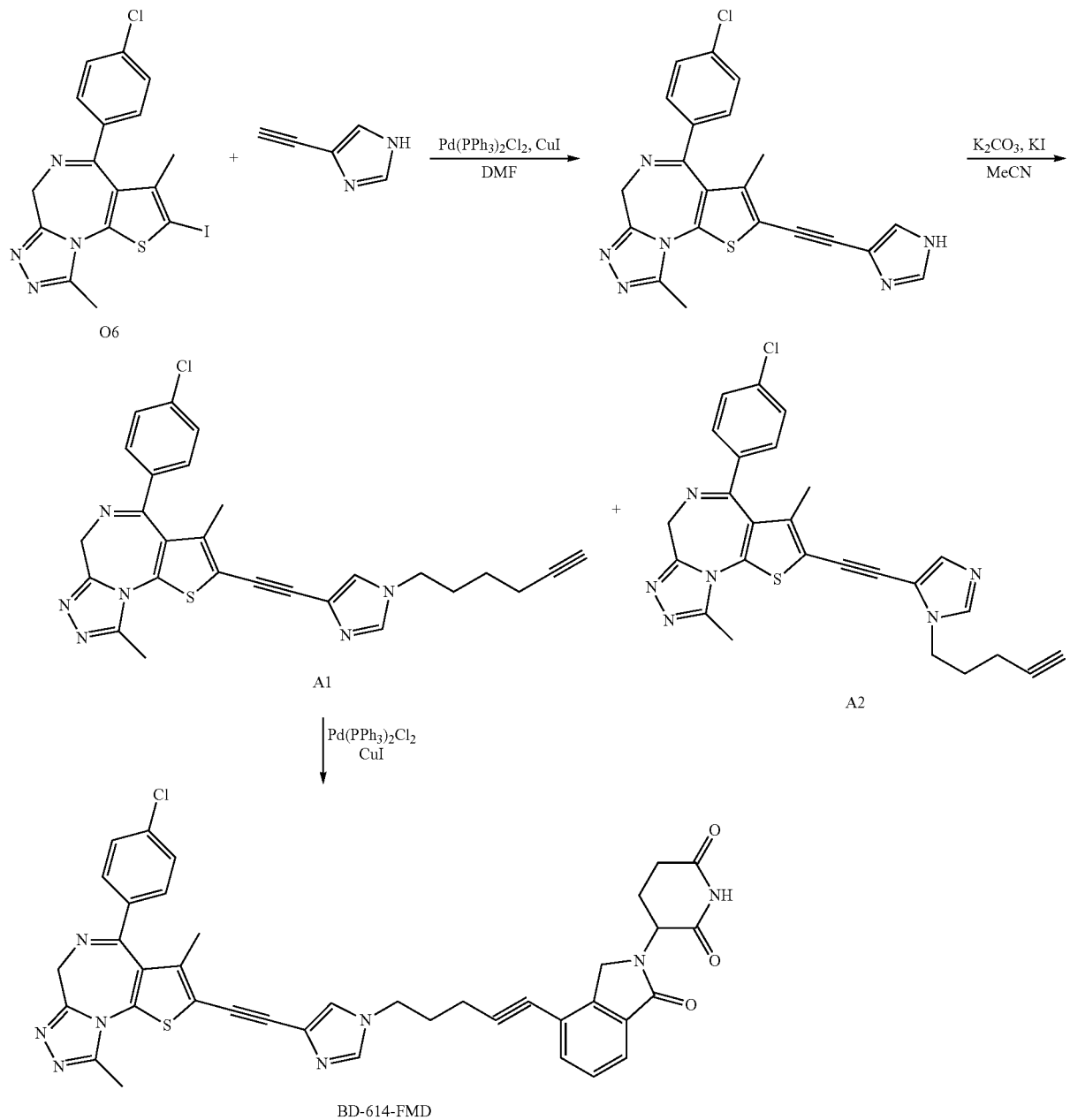

Step 1: To a Schlenk tube was added CuI (5.3 mg), Pd(Ph₃P)₂Cl₂ (20 mg), 4-(4-chlorophenyl)-2-iodo-3,9-dimethyl-6H-thieno[3,2-f][1,2,4]triazolo[4,3-a][1,4]diazepine O6 (141 mg, 0.31 mmol), and 4-ethynyl-1H-imidazole (34 mg, 0.37 mmol), DMF (4 mL) and Et₃N (1 mL). The pent-1-yne (204 mg, 2 mmol) in acetonitrile (15 mL) was added K₂CO₃ (415 mg, 3 mmol, 3 eq) and KI (17 mg, 0.1 mmol, 0.1 eq). The mixture was stirred for 6 hours at 85° C. under N₂ protection. The reaction mixture was quenched with water and extracted with EtOAc. The residue was purified by HPLC to afford 145 mg of the intermediate A1, 4-(4-chlorophenyl)-3,9-dimethyl-2-((1-(pent-4-yn-1-yl)-1H-imidazol-4-yl)ethynyl)-6H-thieno[3,2-f][1,2,4]triazolo[4,3-a][1,4]diazepine with 30% yield. ESI-MS m/z 484.84 [M+H]+.

Step 3: To a Schlenk tube was added CuI (3.8 mg, 0.02 mmol), Pd(Ph$_3$P)$_2$Cl$_2$ (14 mg, 0.02 mmol), A1 (48 mg, 0.1 mmol), and 3-(4-iodo-1-oxoisoindolin-2-yl)piperidine-2,6-dione (111 mg, 0.3 mmol), DMF (4 mL) and Et$_3$N (1 mL). The reaction mixture was heated at 80° C. under N$_2$ protection for 6 hours. The reaction mixture was cooled and treated with EtOAc and brine. The organic layer was separated, dried, and evaporated. The residue was purified by HPLC to afford Cpd. No. 26 (67 mg, 80% yield). ESI-MS m/z 726.64 [M+H]+.

Example 29

Synthesis of 4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-2-(2,6-dioxopiperidin-3-yl)isoindoline-1,3-dione (Cpd. No. 27)

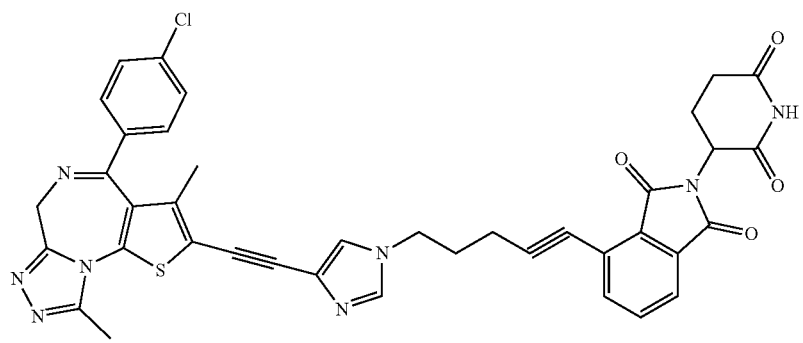

Cpd. No. 27

Cpd. No. 27 was prepared following the procedure described for the synthesis of Cpd. No. 26 in Example 28. ESI-MS m/z 740.70 [M+H]+.

Example 30

Synthesis of 3-(4-(5-(5-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione (Cpd. No. 28)

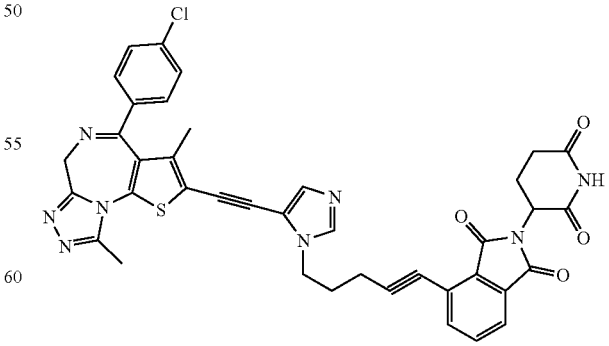

Cpd. No. 28

Cpd. No. 28 was prepared following the procedure described for the synthesis of Cpd. No. 26 in Example 28. ESI-MS m/z 726.64 [M+H]+.

Example 31

Synthesis of 4-(5-(5-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-2-(2,6-dioxopiperidin-3-yl)isoindoline-1,3-dione (Cpd. No. 29)

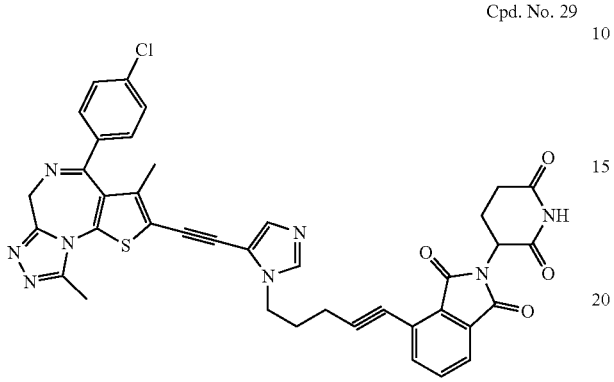

Cpd. No. 29

Cpd. No. 29 was prepared following the procedure described for the synthesis of Cpd. No. 26 in Example 28. ESI-MS m/z 742.15 [M+H]⁺.

Example 32

Synthesis of 4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione (Cpd. No. 30)

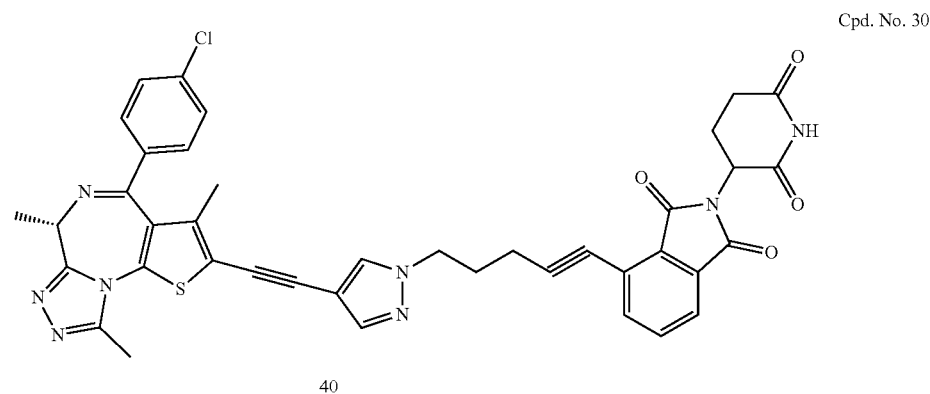

Cpd. No. 30

Cpd. No. 30 was prepared following the procedure described for the synthesis of Cpd. No. 23 in Example 25. ESI-MS m/z 755.35 [M+H]⁺.

Example 33

Synthesis of 3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione (Cpd. No. 31)

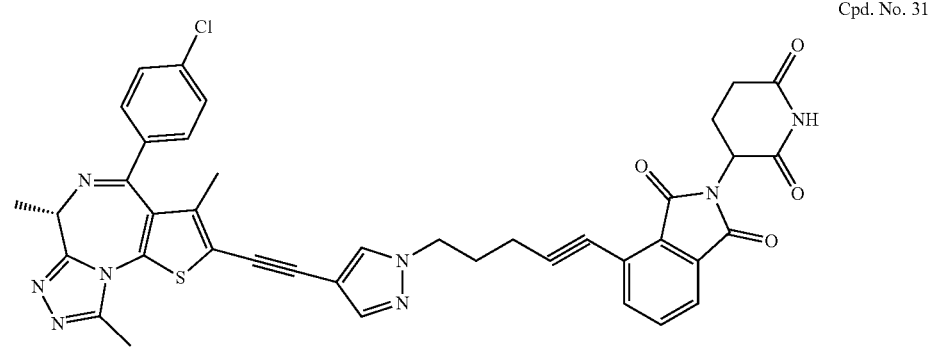 [SMILES: Cc1c(C#Cc2cnn(CCCC#Cc3cccc4c3C(=O)N(C3CCC(=O)NC3=O)C4=O)c2)sc2c1C(c1ccc(Cl)cc1)=N[C@@H](C)c1nnc(C)n1-2]

Cpd. No. 31

Cpd. No. 31 was prepared following the procedure described for the synthesis of Cpd. No. 20 in Example 22. ESI-MS m/z 741.92 [M+H]⁺.

Example 34

Synthesis of 4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione (Cpd. No. 32)

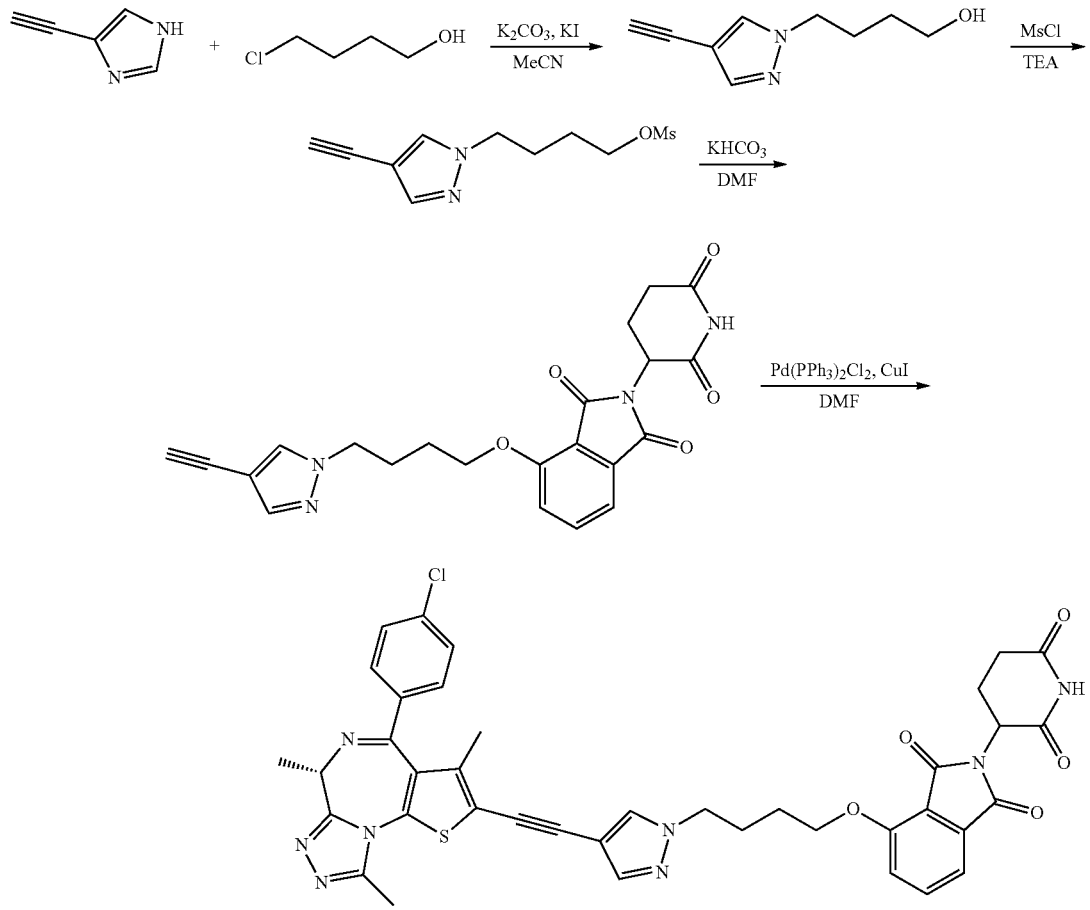

Cpd. No. 32

Step 1: To a suspension of 4-ethynyl-1H-pyrazole (920 mg, 10 mmol) and 4-chlorobutan-1-ol (216 mg, 20 mmol) in acetonitrile (25 mL) was added K₂CO₃ (4.1 g, 30 mmol, 3 eq) and KI (166 mg, 1 mmol, 0.1 eq). The mixture was stirred for 6 hours at 85° C. under N₂ protection. The reaction mixture was quenched with water and extracted with EtOAc. The residue was purified by chromatography (DCM:MeOH 10:1) to afford to afford 1.3 g of 4-(4-ethynyl-1H-pyrazol-1-yl)butan-1-ol with 80% yield. ESI-MS m/z 165.02 [M+H]⁺.

Step 2: To a suspended solution of 4-(4-ethynyl-1H-pyrazol-1-yl)butan-1-ol (328 mg, 2 mmol, 1.0 eq) in 30 mL of DCM was added mesyl chloride (310 μL, 4 mmol, 2.0 eq) at 0° C. Then trimethylamine (0.77 mL, 6 mmol, 3.0 eq) was added dropwise. The solution turned clear within 1 min. After 1 h, the solvent was evaporated to give crude 4-(4-ethynyl-1H-pyrazol-1-yl)butyl methanesulfonate, which was used in the next step reaction without further purification.

Step 3: To a solution of 2-(2,6-dioxopiperidin-3-yl)-4-hydroxyisoindoline-1,3-dione (137 mg, 0.5 mmol), 4-(4-ethynyl-1H-pyrazol-1-yl)butyl methanesulfonate (61 mg, 0.25 mmol) in DMF (2 mL) was added KHCO₃ (50 mg) and KI (10 mg). The reaction mixture was stirred at 70° C. for 12 hour prior to being taken up in ethyl acetate and water. The organic layer was separated, dried, and evaporated. The residue was purified by HPLC to afford 2-(2,6-dioxopiperidin-3-yl)-4-(4-(4-ethynyl-1H-pyrazol-1-yl)butoxy)isoindoline-1,3-dione (80 mg, 60%).

Step 4: To a Schlenk tube was added CuI (3.8 mg), Pd(Ph₃P)₂Cl₂ (7 mg), N6 (23.4 mg, 0.05 mmol), and 2-(2,6-dioxopiperidin-3-yl)-4-(4-(4-ethynyl-1H-pyrazol-1-yl)butoxy)isoindoline-1,3-dione (40 mg, 0.075 mmol), DMF (2 mL) and Et₃N (0.5 mL). The reaction mixture was heated at 70° C. for 6 hours. The reaction mixture was cooled and treated with EtOAc and brine. The organic layer was separated, dried, and evaporated. The residue was subjected to HPLC purification to afford the title compound in 65% yield. ESI-MS m/z 761.09 [M+H]⁺.

Example 35

Synthesis of 4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione (Cpd. No. 33)

Cpd. No. 33

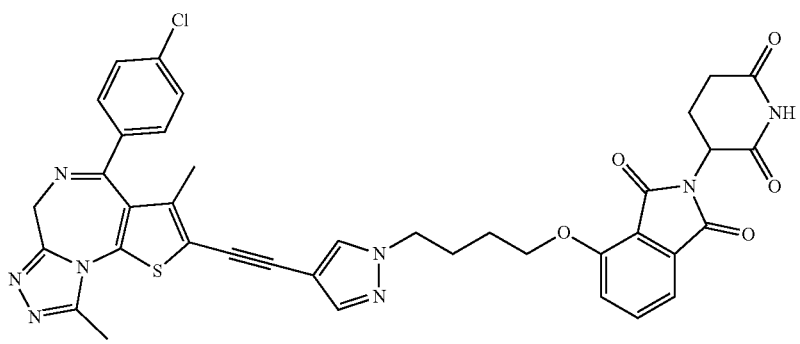

Cpd. No. 33 was prepared following the procedure described for the synthesis of Cpd. No. 32 in Example 34. ESI-MS m/z 747.23 [M+H]⁺.

Example 36

In Vitro Activity

Cell growth inhibitory activity of representative Compounds of the Disclosure was determined in various cell lines using CellTiter-Glo® Luminescent Cell Viability Assay. See Table 4. Cells were seeded in 384-well white opaque cell culture plates at a density of 2,000 cells/well with serially diluted compounds and incubated at 37° C. in an atmosphere of 95% air and 5% $CO_2$ for 4 days. Cell viability was determined using the CellTiter-Glo® Luminescent Cell Viability Assay Kit (Promega, Madison, Wis.) according to the manufacture's instruction. Briefly, a volume of CellTiter-Glo® Reagent equal to the volume of cell culture medium was added to each well, and then the plates were incubated at room temperature for 10-20 minutes. The luminescent signal was measured using a Tecan Infinite M1000 multimode microplate reader (Tecan, Morrisville, N.C.). The half maximal inhibitory concentration ($IC_{50}$) was calculated using the GraphPad Prism 5 software (GraphPad Software, La Jolla, Calif.).

TABLE 4

| Cpd. No. | $IC_{50}$ (nM) | | | |
|---|---|---|---|---|
| | RS4; 11 | MOLM-13 | MDA-MB-231 | MDA-MB-468 |
| 1 | 0.25 | 1.16 | 8.1 | 10.0 |
| 2 | <0.0015 | 0.40 | 0.19 | 0.27 |
| 3 | 0.27 | 1.0 | 3.5 | 3.1 |
| 4 | <0.0015 | 0.30 | <0.015 | <0.015 |
| 5 | 0.29 | 3.6 | 22.8 | 26.1 |
| 6 | <0.0015 | 0.77 | 2.3 | 1.7 |
| 7 | 0.81 | 4.2 | 6.08 | 10.7 |
| 8 | 0.19 | 0.26 | 0.17 | 0.65 |
| 9 | 2.3 | 19 | 20.4 | 33 |
| 10 | 0.26 | 2.5 | 1.6 | 5.2 |
| 11 | N.T. | 11.4 | 18.1 | 51 |
| 12 | N.T. | 1.2 | 0.86 | 3.0 |
| 13 | N.T. | 6.4 | 7.4 | 32.4 |
| 14 | N.T. | 0.24 | 0.18 | 1.1 |
| 15 | N.T. | 82.6 | 39.1 | N.T. |
| 16 | N.T. | 1.1 | 1.7 | N.T. |
| 17 | N.T. | 10.3 | 11.1 | N.T. |
| 18 | N.T. | 0.23 | 0.43 | N.T. |
| 19 | N.T. | 10.4 | 10.8 | N.T. |
| 20 | 0.1 | 0.8 | 0.08 | 0.2 |
| 21 | 0.3 | 1.1 | 3.8 | 6.5 |
| 22 | 0.2 | 0.9 | 0.9 | 1.8 |
| 23 | 0.3 | 1.9 | 1.7 | 4.2 |
| 24 | <0.015 | <0.015 | <0.015 | <0.015 |
| 25 | 1.0 | 9.1 | 24.2 | 34.9 |
| 26 | >10 | 39.2 | >100 | >100 |
| 27 | >10 | 32.0 | >100 | >100 |
| 28 | >10 | 66.1 | >100 | >100 |
| 29 | 7.0 | 22.8 | >100 | >100 |
| 30 | N.T. | N.T. | 3.7 | 3.6 |
| 31 | N.T. | N.T. | <0.015 | <0.015 |
| 32 | N.T. | N.T. | 2.5 | 3.5 |
| 33 | N.T. | N.T. | N.T. | N.T. |
| 142 | 1.0 | 6.4 | 30.4 | 32.9 |
| 144 | N.T. | 6.8 | 10.1 | N.T. |
| 145 | 0.13 | N.T. | 0.39 | N.T. |
| 146 | N.T. | 1.0 | 1.2 | N.T. |
| 147 | 0.05 | N.T. | 0.08 | N.T. |
| 148 | N.T. | 0.24 | 0.4 | N.T. |
| 149 | N.T. | 0.42 | 0.67 | N.T. |
| 150 | N.T. | >100 | >100 | N.T. |
| 151 | N.T. | >100 | >100 | N.T. |
| 152 | N.T. | 8.7 | 12.2 | N.T. |
| 153 | N.T. | >100 | >100 | N.T. |
| 154 | N.T. | >100 | >100 | N.T. |
| 155 | N.T. | >100 | >100 | N.T. |
| 156 | N.T. | 12.8 | 17.6 | N.T. |
| 157 | N.T. | 18.6 | 52.7 | N.T. |
| 158 | N.T. | 2.5 | 7.2 | N.T. |
| 159 | N.T. | >100 | >100 | N.T. |
| 160 | N.T. | 42.6 | 58.8 | N.T. |
| 161 | 20.4 | N.T. | 71.8 | N.T. |
| 162 | 2.4 | N.T. | 22.0 | N.T. |
| 163 | 216 | N.T. | 284 | N.T. |
| 164 | 74 | N.T. | 78.5 | N.T. |
| 165 | 3.7 | N.T. | 12.7 | N.T. |
| 166 | N.T. | 0.9 | 0.6 | N.T. |

TABLE 4-continued

| Cpd. No. | IC$_{50}$ (nM) | | | |
|---|---|---|---|---|
| | RS4; 11 | MOLM-13 | MDA-MB-231 | MDA-MB-468 |
| 167 | N.T. | 6.2 | 7.2 | N.T. |
| 168 | N.T. | 0.8/2.0 | 0.9/0.5 | N.T. |
| 168 | N.T. | 0.8/1.0 | 0.8/0.2 | N.T. |
| 170 | N.T. | 0.5/2.3 | 1.2/0.5 | N.T. |
| 171 | N.T. | 0.6/0.8 | 0.9/1.0 | N.T. |
| 172 | N.T. | 2.3 | 4.4 | N.T. |
| 173 | N.T. | 3.3 | 4.6 | N.T. |
| 174 | N.T. | 0.1/0.3 | 0.2/0.02 | N.T. |
| 175 | N.T. | 0.35 | 1.5 | N.T. |
| 176 | N.T. | 0.07/0.6 | 0.6/0.2 | N.T. |
| 177 | N.T. | 0.6 | 0.02/0.5 | N.T. |
| 178 | N.T. | 1.0 | 0.6 | N.T. |
| 179 | N.T. | 0.9 | 0.2 | N.T. |
| 180 | N.T. | 0.2 | 0.04 | N.T. |
| 181 | N.T. | >1000 | 531.6 | N.T. |
| 182 | N.T. | 2.8 | 1.7 | N.T. |
| 183 | N.T. | 0.8 | 0.3 | N.T. |
| 184 | N.T. | 0.5 | 0.1 | N.T. |
| 185 | N.T. | 0.2 | 0.1 | N.T. |
| 188 | N.T. | N.T. | 1.7 | N.T. |
| 189 | N.T. | N.T. | N.T. | N.T. |
| 190 | N.T. | 0.05 | 0.1 | N.T. |
| 191 | N.T. | 0.04 | 0.2 | N.T. |
| 192 | N.T. | 0.07 | 0.08 | N.T. |
| 193 | N.T. | 0.03 | 0.06 | N.T. |
| 194 | N.T. | 0.8 | 0.7 | N.T. |
| 195 | N.T. | 2.4 | 5.4 | N.T. |
| 196 | N.T. | 0.2 | 0.4 | N.T. |
| 197 | N.T. | 1.1 | 2.5 nM | N.T. |
| 198 | N.T. | 0.24 ± 0.06 | 1.5 | N.T. |
| 199 | N.T. | 0.5 ± 0.06 | 6.7 | N.T. |
| 200 | N.T. | 0.34 ± 0.03 | 3.1 | N.T. |
| 201 | N.T. | 2.1 ± 0.32 | 24.9 | N.T. |
| 202 | N.T. | 91.6 | N.T. | N.T. |
| 203 | N.T. | N.T. | 37.5 | N.T. |
| 204 | N.T. | N.T. | N.T. | N.T. |
| 205 | N.T. | 42.3 | 93.0 | N.T. |

It is to be understood that the foregoing embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:
1. A compound having Formula I:

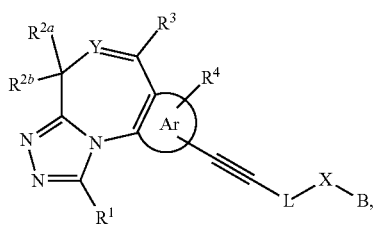

I or a pharmaceutically acceptable salt or hydrate thereof, wherein:
$R^1$ is selected from the group consisting of hydrogen and $C_{1-4}$ alkyl;
$R^{2a}$ and $R^{2b}$ are each independently selected from the group consisting of hydrogen, $C_{1-4}$ alkyl, (alkoxycarbonyl)alkyl, and $-CH_2C(=O)NR^{19a}R^{19b}$, or $R^{2a}$ and $R^{2b}$ together with the carbon atom to which they are attached form a 3- to 6-membered cycloalkyl;
$R^3$ is selected from the group consisting of optionally substituted $C_{6-14}$ aryl and optionally substituted 5- to 14-membered heteroaryl;
$R^4$ is selected from the group consisting of hydrogen, halogen, $C_{1-4}$ alkyl, $C_{2-4}$ alkenyl, $C_{2-4}$ alkynyl, aralkyl, optionally substituted $C_{6-14}$ aryl, $C_{3-12}$ cycloalkyl, optionally substituted 4- to 8-membered-membered heterocyclo, and optionally substituted 5- to 14-membered heteroaryl;

is a fused thienyl or fused phenyl group, wherein the fused phenyl group is additionally substituted with $R^{15}$;
Y is $-N=$;
$R^{15}$ is selected from the group consisting of hydrogen, halogen, $C_{1-4}$ alkyl, and alkoxy;
B is selected from the group consisting of:

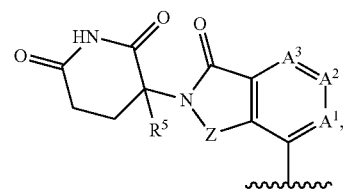

B-1

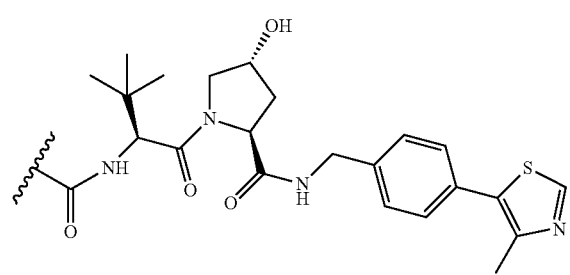

B-2

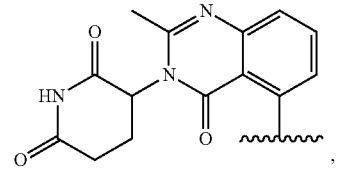

B-3

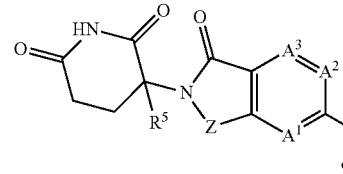

B-4

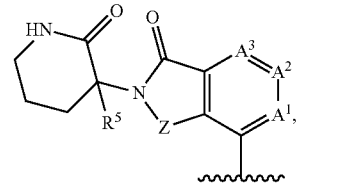

B-5

-continued

B-6
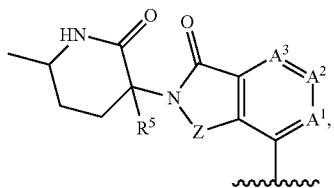

B-7
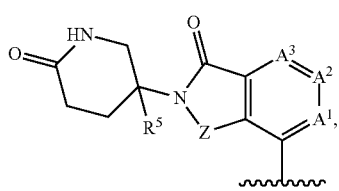

B-8
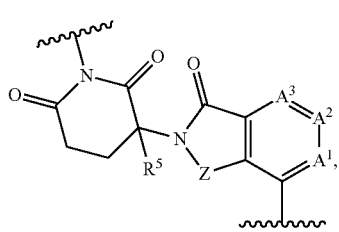

B-9
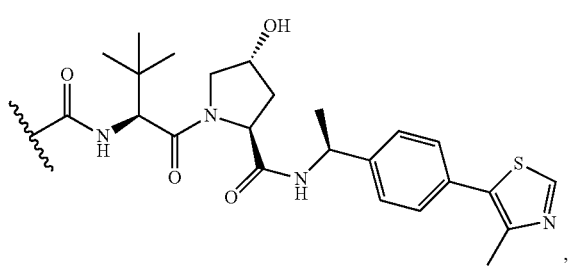

B-10
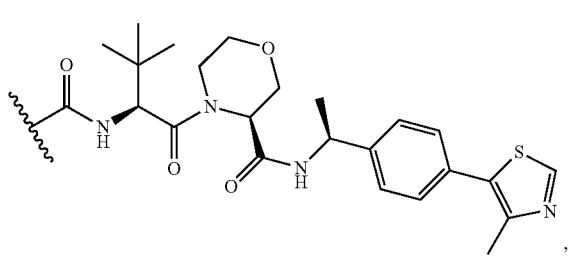

B-11
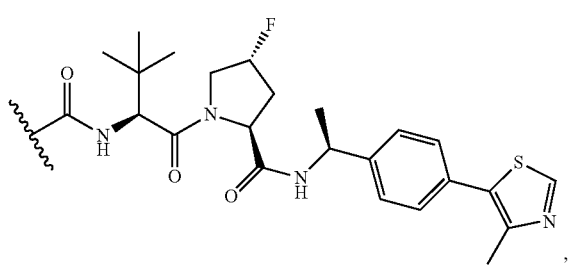

-continued

B-12
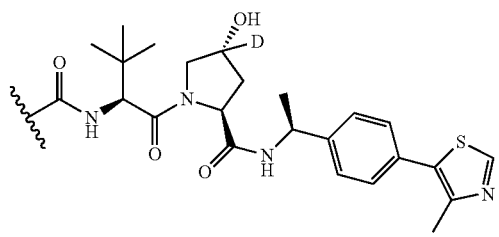

and

B-13
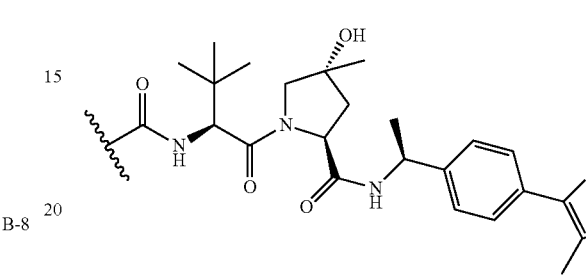

L is selected from the group consisting of alkylenyl, heteroalkylenyl, -A-(CH$_2$)$_m$—W—(CH$_2$)$_n$—, —(CH$_2$)$_m$—W—(CH$_2$)$_u$—O—(CH$_2$)$_m$—, and —(CH$_2$)$_m$—W—[(CH$_2$)$_w$—O]—(CH$_2$)$_v$—;

A is selected from the group consisting of 5-membered heteroarylenyl and 6-membered heteroarylenyl; or A is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

each w is independently 2, 3, or 4;

x is 2, 3, or 4;

X is selected from the group consisting of —C≡C—, —CH$_2$—, —O—, —N(R$^{2c}$)—, —C(=O)N(R$^{2d}$)—, —N(R$^{2e}$)C(=O)CH$_2$O—, and —N(R$^{2f}$)C(=O)CH$_2$N(R$^{2g}$)—; or X is absent;

wherein the carboxamide nitrogen atom of —N(R$^{2e}$)C(=O)CH$_2$O— and —N(R$^{2f}$)C(=O)CH$_2$N(R$^{2g}$)—, and the carbon atom of —C(=O)N(R$^{2d}$)— is attached to L;

R$^{2c}$, R$^{2d}$, R$^{2e}$, R$^{2f}$, and R$^{2g}$ are each independently selected from the group consisting of hydrogen and C$_{1-4}$ alkyl;

Z is selected from the group consisting of —CH$_2$ and —C(=O)—;

R$^5$ is selected from the group consisting of hydrogen, methyl, and fluoro;

A$^1$ is selected from the group consisting of —C(R$^{16a}$)= and —N=;

A$^2$ is selected from the group consisting of —C(R$^{16b}$)= and —N=;

A$^3$ is selected from the group consisting of —C(R$^{16c}$)= and —N=;

R$^{16a}$ is selected from the group consisting of hydrogen, halo, and C$_{1-4}$ alkyl;

R$^{16b}$ is selected from the group consisting of hydrogen, halo, and C$_{1-4}$ alkyl;

R$^{16c}$ is selected from the group consisting of hydrogen, halo, and C$_{1-4}$ alkyl; and $R^{19a}$ and $R^{19b}$ are independently selected from the group consisting of hydrogen, $C_{1-6}$ alkyl and optionally substituted aryl; or $R^{19a}$ and $R^{19b}$ taken together with the nitrogen atom to which they are attached form a 4- to 8-membered optionally substituted heterocyclo, wherein each optionally substituted $C_{6-14}$ aryl is independently either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted 5- to 14-membered heteroaryl heteroaryl, heterocyclo, alkoxyalkyl, (amino)alkyl, (carboxamido)alkyl, mercaptoalkyl, and (heterocyclo)alkyl;

each optionally substituted 5- to 14-membered heteroaryl is independently either unsubstituted or substituted with one or two substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, substituted cycloalkyl, alkenyl, alkynyl, optionally substituted aryl, optionally substituted 5- to 14-membered heteroaryl, heterocyclo, alkoxyalkyl, (amino)alkyl, (carboxamido)alkyl, mercaptoalkyl, and (heterocyclo)alkyl; and each optionally substituted 4- to 8-membered heterocyclo independently either unsubstituted or substituted with one to four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, $CF_3C(=O)-$, arylcarbonyl, alkylsulfonyl, arylsulfonyl, carboxy, carboxyalkyl, alkyl, cycloalkyl, alkenyl, alkynyl, optionally substituted aryl, optionally substituted 5- to 14-membered heteroaryl, heterocyclo, alkoxyalkyl, (amino)alkyl, (carboxamido)alkyl, mercaptoalkyl, and (heterocyclo)alkyl.

2. The compound of claim 1 having Formula V:

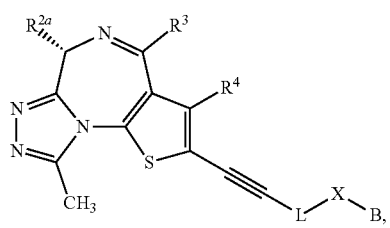

or a pharmaceutically acceptable salt or hydrate thereof, wherein $R^{2a}$ is $C_{1-4}$ alkyl.

3. The compound of claim 1 having Formula VI:

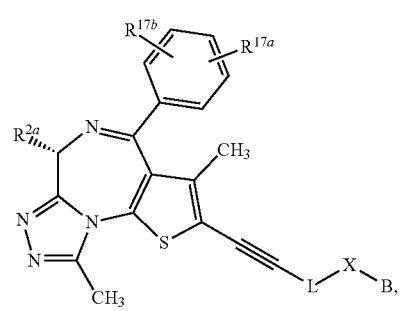

or a pharmaceutically acceptable salt or hydrate thereof, wherein:

$R^{2a}$ is selected from the group consisting of hydrogen and $C_{1-3}$ alkyl; and $R^{17a}$ and $R^{17b}$ are each independently selected from the group consisting of hydrogen, $C_{1-4}$-alkyl, haloalkyl, $C_{1-4}$ alkoxy, and halo.

4. The compound of claim 1, or a pharmaceutically acceptable salt or solvate thereof, wherein L is $C_{1-12}$ alkylenyl.

5. The compound of claim 1, or a pharmaceutically acceptable salt or solvate thereof, wherein L is 3- to 12-membered heteroalkylenyl.

6. The compound of claim 1, or a pharmaceutically acceptable salt or solvate thereof, wherein L is $-(CH_2)_m-W-(CH_2)_n-$.

7. The compound of claim 1, or a pharmaceutically acceptable salt or solvate thereof, wherein L is $-(CH_2)_m-W-(CH_2)_u-O-(CH_2)_v-$.

8. The compound of claim 3, or a pharmaceutically acceptable salt or solvate thereof, having Formula VII:

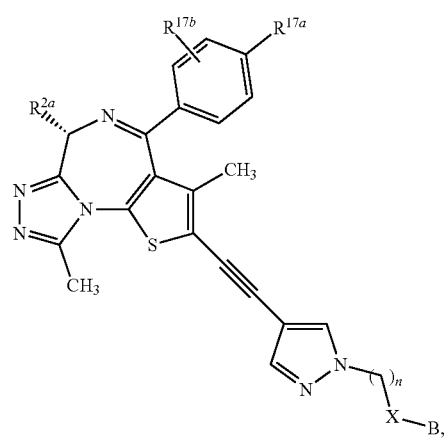

wherein n is 2, 3, 4, or 5.

9. The compound of claim 3, or a pharmaceutically acceptable salt or solvate thereof, having Formula VIII:

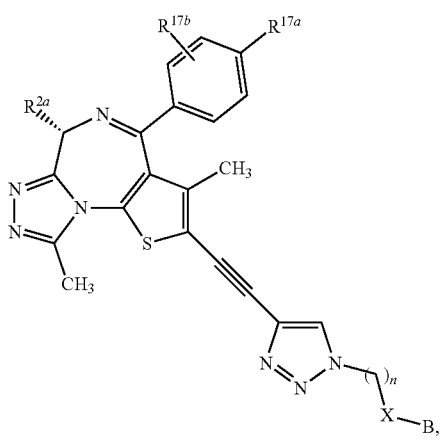

VIII wherein n is 2, 3, 4, or 5.

10. The compound of claim 3, or a pharmaceutically acceptable salt or solvate thereof, having Formula IX:

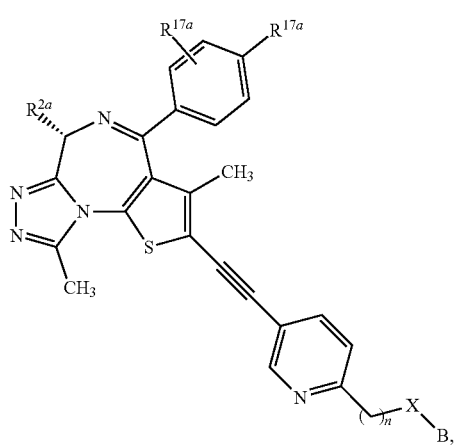

IX wherein n is 2, 3, 4, or 5.

11. The compound of claim 3, or a pharmaceutically acceptable salt or solvate thereof, wherein X is selected from the group consisting of —C≡C—, —CH$_2$—, —O—, and —N(H)—.

12. The compound of claim 1, or a pharmaceutically acceptable salt or hydrate thereof, wherein B is B-1.

13. The compound of claim 1, or a pharmaceutically acceptable salt or hydrate thereof, selected from the group consisting of:

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione;

3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pent-1-yn-1-yl)-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione;

3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)pentyl)-1-oxoisoindolin-2-yl)piperidine-2,6-dione;

3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione;

3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-1,2,3-triazol-1-yl)butyl)amino)-1-oxoisoindolin-2-yl)piperidine-2,6-dione;

3-(4-((4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione;

3-(4-((4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butyl)amino)-1-oxoisoindolin-2-yl)piperidine-2,6-dione;

4-(4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione;

4-(4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)butoxy)-2-(2,6-dioxopiperidin-3-yl)isoindoline-1,3-dione;

3-(4-(4-((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperidine-2,6-dione;

3-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)butyl)-1-oxoisoindolin-2-yl)piperidine-2,6-dione;

3-(4-(5-(6-((4-(4-chlorophenyl)-3,9-dimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione;

3-(4-(5-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)pent-1-yn-1-yl)-1-oxoisoindolin-2-yl)piperidine-2,6-dione;

3-(4-((6-((4-(4-chlorophenyl)-3,9-dimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione;

3-(4-(4-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)oxy)but-1-yn-1-yl)-1-oxoisoindolin-2-yl)piperidine-2,6-dione;

3-(4-((4-(5-((4-(4-chlorophenyl)-3,9-dimethyl-6H-thieno[3,2-f][1,2,4]triazolo[4,3-a][1,4]diazepin-2-yl)ethynyl)pyridin-2-yl)butyl)amino)-1-oxoisoindolin-2-yl)piperidine-2,6-dione;

3-(4-((4-(5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)butyl)amino)-1-oxoisoindolin-2-yl)piperidine-2,6-dione;

3-(4-(5-(5-((4-(4-chlorophenyl)-3,9-dimethyl-6H-thieno[3,2-f][1,2,4]triazolo[4,3-a][1,4]diazepin-2-yl)ethynyl)pyridin-2-yl)pent-1-yn-1-yl)-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione;

4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(2,6-dioxopiperidin-3-yl)isoindoline-1,3-dione;

4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-2-(2,6-dioxopiperidin-3-yl)isoindoline-1,3-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione;

3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione;

4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione;

4-(5-(4-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-2-(2,6-dioxopiperidin-3-yl)isoindoline-1,3-dione;

3-(4-(5-(5-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-1-oxoisoindolin-2-yl)piperidine-2,6-dione;

4-(5-(5-((4-(4-chlorophenyl)-3,9-dimethyl-6H-thieno[3,2-f][1,2,4]triazolo[4,3-a][1,4]diazepin-2-yl)ethynyl)-1H-imidazol-1-yl)pent-1-yn-1-yl)-2-(2,6-dioxopiperidin-3-yl)isoindoline-1,3-dione;

4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione;

3-(4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione;

4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione;

4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-2-(2,6-dioxopiperidin-3-yl)isoindoline-1,3-dione;

3-(4-(4-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperazin-1-yl)-1-oxoisoindolin-2-yl)piperidine-2,6-dione;

4-(4-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione;

3-(4-(4-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-1-oxoisoindolin-2-yl)piperidine-2,6-dione;

4-(4-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione;

3-(4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methoxy)-1-oxoisoindolin-2-yl)piperidine-2,6-dione;

3-(4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione;

3-(4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)ethyl)-1-oxoisoindolin-2-yl)piperidine-2,6-dione 4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methoxy)-2-(2,6-dioxopiperidin-3-yl)isoindoline-1,3-dione;

4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)methyl)amino)-2-(2,6-dioxopiperidin-3-yl)isoindoline-1,3-dione;

4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)azetidin-3-yl)ethyl)-2-(2,6-dioxopiperidin-3-yl)isoindoline-1,3-dione;

3-(4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methoxy)-1-oxoisoindolin-2-yl)piperidine-2,6-dione;

3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione;

3-(4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)ethyl)-1-oxoisoindolin-2-yl)piperidine-2,6-dione;

4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methoxy)-2-(2,6-dioxopiperidin-3-yl)isoindoline-1,3-dione;

4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-2-(2,6-dioxopiperidin-3-yl)isoindoline-1,3-dione;

4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)ethyl)-2-(2,6-dioxopiperidin-3-yl)isoindoline-1,3-dione;

3-(4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methoxy)-1-oxoisoindolin-2-yl)piperidine-2,6-dione;

3-(4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione;

3-(4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)ethyl)-1-oxoisoindolin-2-yl)piperidine-2,6-dione;

4-((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methoxy)-2-(2,6-dioxopiperidin-3-yl)isoindoline-1,3-dione;

4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-2-(2,6-dioxopiperidin-3-yl)isoindoline-1,3-dione;

4-(2-(1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)ethyl)-2-(2,6-dioxopiperidin-3-yl)isoindoline-1,3-dione;

3-(4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methoxy)-1-oxoisoindolin-2-yl)piperidine-2,6-dione;

3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione;

3-(4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)ethyl)-1-oxoisoindolin-2-yl)piperidine-2,6-dione;

4-((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methoxy)-2-(2,6-dioxopiperidin-3-yl)isoindoline-1,3-dione;

4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-2-(2,6-dioxopiperidin-3-yl)isoindoline-1,3-dione;

4-(2-(1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)ethyl)-2-(2,6-dioxopiperidin-3-yl)isoindoline-1,3-dione;

3-(4-((4-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-1-oxoisoindolin-2-yl)piperidine-2,6-dione;

4-((4-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-2-(2,6-dioxopiperidin-3-yl)isoindoline-1,3-dione;

3-(4-((4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-1-oxoisoindolin-2-yl)piperidine-2,6-dione;

4-((4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)methyl)-2-(2,6-dioxopiperidin-3-yl)isoindoline-1,3-dione;

3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione;

3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione;

3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-1-oxoisoindolin-2-yl)piperidine-2,6-dione;

4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione;

4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione;

4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-2-(2,6-dioxopiperidin-3-yl)isoindoline-1,3-dione;

3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione;

3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione;

3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-1-oxoisoindolin-2-yl)piperidine-2,6-dione;

4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione;

4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione;

4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)-2-(2,6-dioxopiperidin-3-yl)isoindoline-1,3-dione;

3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione;

3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione;

3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione;

3-(4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-5-fluoro-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-6-fluoro-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-7-fluoro-1-oxoisoindolin-2-yl)piperidine-2,6-dione;

3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-5-fluoro-1-oxoisoindolin-2-yl)piperidine-2,6-dione;

3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-6-fluoro-1-oxoisoindolin-2-yl)piperidine-2,6-dione;
3-(4-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-7-fluoro-1-oxoisoindolin-2-yl)piperidine-2,6-dione;
3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-5-fluoro-1-oxoisoindolin-2-yl)piperidine-2,6-dione;
3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-6-fluoro-1-oxoisoindolin-2-yl)piperidine-2,6-dione;
3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-7-fluoro-1-oxoisoindolin-2-yl)piperidine-2,6-dione;
3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-1-oxoisoindolin-2-yl)piperidine-2,6-dione;
4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)amino)-2-(2,6-dioxopiperidin-3-yl)isoindoline-1,3-dione;
3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-1-oxoisoindolin-2-yl)piperidine-2,6-dione;
4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione;
3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione;
3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione;
4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-2-(2,6-dioxopiperidin-3-yl)isoindoline-1,3-dione;
4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-2-(2,6-dioxopiperidin-3-yl)isoindoline-1,3-dione;
3-(4-((4-((4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)oxy)-1-oxoisoindolin-2-yl)piperidine-2,6-dione;
3-(4-((4-((4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)amino)-1-oxoisoindolin-2-yl)piperidine-2,6-dione;
4-((4-((4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)oxy)-2-(2,6-dioxopiperidin-3-yl)isoindoline-1,3-dione;
4-((4-((4-(4-(4-chlorophenyl)-3,9-dimethyl-6H-thieno[3,2-f][1,2,4]triazolo[4,3-a][1,4]diazepin-2-yl)ethynyl)-1H-pyrazol-1-yl)methyl)benzyl)amino)-2-(2,6-dioxopiperidin-3-yl)isoindoline-1,3-dione;
3-(5-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-2-methyl-4-oxoquinazolin-3(4H)-yl)piperidine-2,6-dione;
3-(5-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-2-methyl-4-oxoquinazolin-3(4H)-yl)piperidine-2,6-dione;
3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-2-methyl-4-oxoquinazolin-3(4H)-yl)piperidine-2,6-dione;
3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-methyl-4-oxoquinazolin-3(4H)-yl)piperidine-2,6-dione;
3-(5-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-2-methyl-4-oxoquinazolin-3(4H)-yl)piperidine-2,6-dione;
3-(5-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-methyl-4-oxoquinazolin-3(4H)-yl)piperidine-2,6-dione;
3-(5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pentyl)-2-methyl-4-oxoquinazolin-3(4H)-yl)piperidine-2,6-dione;
3-(5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-methyl-4-oxoquinazolin-3(4H)-yl)piperidine-2,6-dione;
3-(4-(((1-((5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)methyl)piperidin-4-yl)methyl)amino)-1-oxoisoindolin-2-yl)piperidine-2,6-dione;
3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione;
4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)piperidin-4-yl)oxy)-2-(2,6-dioxopiperidin-3-yl)isoindoline-1,3-dione;
3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione;
3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione;
4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)oxy)-2-(2,6-dioxopiperidin-3-yl)isoindoline-1,3-dione;
3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methoxy)-1-oxoisoindolin-2-yl)piperidine-2,6-dione;
3-(4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)amino)-1-oxoisoindolin-2-yl)piperidine-2,6-dione;

4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)oxy)-2-(2,6-dioxopiperidin-3-yl)isoindoline-1,3-dione;

3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione;

3-(4-(((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methyl)amino)-1-oxoisoindolin-2-yl)piperidine-2,6-dione;

3-(4-(((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)-1H-imidazol-4-yl)methyl)amino)-1-oxoisoindolin-2-yl)piperidine-2,6-dione;

3-(4-((4-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione 3-(4-(3-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclobutyl)amino)-1-oxoisoindolin-2-yl)piperidine-2,6-dione;

3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)amino)-1-oxoisoindolin-2-yl)piperidine-2,6-dione;

3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)methyl)amino)-1-oxoisoindolin-2-yl)piperidine-2,6-dione;

3-(4-((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)amino)-1-oxoisoindolin-2-yl)piperidine-2,6-dione;

3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)amino)-1-oxoisoindolin-2-yl)piperidine-2,6-dione;

3-(4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-7-fluoro-1-oxoisoindolin-2-yl)piperidine-2,6-dione;

3-(4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione;

4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(3-fluoro-2,6-dioxopiperidin-3-yl)isoindoline-1,3-dione;

3-(4-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione;

3-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione;

3-(4-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butoxy)-1-oxoisoindolin-2-yl)piperidine-2,6-dione;

3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione;

3-(4-((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)piperidin-4-yl)amino)-1-oxoisoindolin-2-yl)piperidine-2,6-dione;

3-(4-(((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methyl)amino)-1-oxoisoindolin-2-yl)piperidine-2,6-dione;

3-(4-(((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methyl)amino)-1-oxoisoindolin-2-yl)piperidine-2,6-dione;

3-(4-(((1-(4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)-1H-imidazol-4-yl)methyl)amino)-1-oxoisoindolin-2-yl)piperidine-2,6-dione;

4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-2-(2,6-dioxopiperidin-3-yl)isoindoline-1,3-dione;

3-(4-((1-(2-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)ethyl)-1H-imidazol-4-yl)methoxy)-1-oxoisoindolin-2-yl)piperidine-2,6-dione;

4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methoxy)-2-(2,6-dioxopiperidin-3-yl)isoindoline-1,3-dione;

3-(4-((1-(3-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)propyl)-1H-imidazol-4-yl)methoxy)-1-oxoisoindolin-2-yl)piperidine-2,6-dione;

5-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione;

5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2,6-dioxopiperidin-3-yl)isoindoline-1,3-dione;

4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(2-oxopiperidin-3-yl)isoindoline-1,3-dione;

4-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-2-(2-oxopiperidin-3-yl)isoindoline-1,3-dione;

4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(6-methyl-2-oxopiperidin-3-yl)isoindolin-1-one;

4-(5-(4-(((S)-4-(4-chlorophenyl)-3,6,9-trimethyl-6H-thieno[3,2-f][1,2,4]triazolo[4,3-a][1,4]diazepin-2-yl)

ethynyl)-1H-pyrazol-1-yl)pent-1-yn-1-yl)-2-(6-methyl-2-oxopiperidin-3-yl)isoindolin-1-one;

4-(5-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)pent-1-yn-1-yl)-2-(6-oxopiperidin-3-yl)isoindoline-1,3-dione;

4-((4-(4-((4-(4-chlorophenyl)-3,9-dimethyl-6H-thieno[3,2-f][1,2,4]triazolo[4,3-a][1,4]diazepin-2-yl)ethynyl)-1H-pyrazol-1-yl)butyl)amino)-2-(6-oxopiperidin-3-yl)isoindoline-1,3-dione;

3-(4-amino-1-oxoisoindolin-2-yl)-1-(4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)piperidine-2,6-dione;

3-(4-(5-(5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)pent-1-yn-1-yl)-1-oxoisoindolin-2-yl)piperidine-2,6-dione;

3-(4-(((1-((6-((4-(4-chlorophenyl)-3,9-dimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione;

3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)piperidin-4-yl)methyl)amino)-1-oxoisoindolin-2-yl)piperidine-2,6-dione;

3-(4-(((1-((5-(((S)-4-(4-chlorophenyl)-3,6,9-trimethyl-6H-thieno[3,2-f][1,2,4]triazolo[4,3-a][1,4]diazepin-2-yl)ethynyl)pyridin-2-yl)methyl)piperidin-4-yl)methyl)amino)-1-oxoisoindolin-2-yl)piperidine-2,6-dione;

3-(4-(((1-((6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)methyl)azetidin-3-yl)methyl)amino)-1-oxoisoindolin-2-yl)piperidine-2,6-dione;

3-(4-(((1S,4r)-4-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione;

3-(4-(((1R,4s)-4-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclohexyl)amino)-1-oxoisoindolin-2-yl)piperidine-2,6-dione;

3-(4-(((1S,3r)-3-((4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)methyl)cyclobutyl)amino)-1-oxoisoindolin-2-yl)piperidine-2,6-dione;

3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperidin-4-yl)methyl)amino)-1-oxoisoindolin-2-yl)piperidine-2,6-dione;

3-(4-(((1-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)azetidin-3-yl)methyl)amino)-1-oxoisoindolin-2-yl)piperidine-2,6-dione;

3-(4-(((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)methyl)amino)-1-oxoisoindolin-2-yl)piperidine-2,6-dione;

3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)azetidin-3-yl)amino)-1-oxoisoindolin-2-yl)piperidine-2,6-dione;

4-(4-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperazin-1-yl)-2-(2,6-dioxopiperidin-3-yl)isoindoline-1,3-dione;

3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pent-1-yn-1-yl)-1-oxoisoindolin-2-yl)piperidine-2,6-dione;

3-(5-(5-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)pentyl)-1-oxoisoindolin-2-yl)piperidine-2,6-dione;

3-(4-(4-(6-((4-(4-chlorophenyl)-3,9-dimethyl-6H-thieno[3,2-f][1,2,4]triazolo[4,3-a][1,4]diazepin-2-yl)ethynyl)pyridin-3-yl)but-1-yn-1-yl)-1-oxoisoindolin-2-yl)piperidine-2,6-dione;

3-(4-(4-(6-(((S)-4-(4-chlorophenyl)-3,6,9-trimethyl-6H-thieno[3,2-f][1,2,4]triazolo[4,3-a][1,4]diazepin-2-yl)ethynyl)pyridin-3-yl)but-1-yn-1-yl)-1-oxoisoindolin-2-yl)piperidine-2,6-dione;

4-(4-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethyl)piperazin-1-yl)-2-(2,6-dioxopiperidin-3-yl)isoindoline-1,3-dione;

3-(5-((4-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butyl)amino)-1-oxoisoindolin-2-yl)piperidine-2,6-dione;

3-(5-((3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)amino)-1-oxoisoindolin-2-yl)piperidine-2,6-dione;

3-(4-((2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)ethyl)amino)-1-oxoisoindolin-2-yl)piperidine-2,6-dione;

3-(4-((1-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione;

2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)acetamide;

2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)-N-ethylacetamide;

3-(4-((1-(3-(4-(((S)-4-(4-chlorophenyl)-3,9-dimethyl-6-(2-(4-methylpiperazin-1-yl)-2-oxoethyl)-6H-thieno[3,2-f][1,2,4]triazolo[4,3-a][1,4]diazepin-2-yl)ethynyl)-1H-pyrazol-1-yl)propyl)piperidin-4-yl)amino)-1-oxoisoindolin-2-yl)piperidine-2,6-dione;

2-((6S)-4-(4-chlorophenyl)-2-((1-(3-(4-((2-(2,6-dioxopiperidin-3-yl)-1-oxoisoindolin-4-yl)amino)piperidin-1-yl)propyl)-1H-pyrazol-4-yl)ethynyl)-3,9-dimethyl-6H-thieno[3,2-f][1,2,4]triazolo[4,3-a][1,4]diazepin-6-yl)-N-(4-hydroxyphenyl)acetamide;

tert-butyl 2-((6S)-4-(4-chlorophenyl)-2-((1-(2-(2-(2-((3-(2-(2,6-dioxopiperidin-3-yl)-1-oxoisoindolin-4-yl)prop-2-yn-1-yl)oxy)ethoxy)ethoxy)ethyl)-1H-pyrazol- 4-yl)ethynyl)-3,9-dimethyl-6H-thieno[3,2-f][1,2,4]triazolo[4,3-a][1,4]diazepin-6-yl)acetate;

2-((6S)-4-(4-chlorophenyl)-2-((1-(2-(2-(2-((3-(2-(2,6-dioxopiperidin-3-yl)-1-oxoisoindolin-4-yl)prop-2-yn-1-yl)oxy)ethoxy)ethoxy)ethyl)-1H-pyrazol-4-yl)ethynyl)-3,9-dimethyl-6H-thieno[3,2-f][1,2,4]triazolo[4,3-a][1,4]diazepin-6-yl)acetamide;

3-(4-(3-(2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)ethoxy)prop-1-yn-1-yl)-1-oxoisoindolin-2-yl)piperidine-2,6-dione;

3-(4-(3-(2-(2-(2-(4-(((S)-4-(4-chlorophenyl)-3,9-dimethyl-6-(2-(4-methylpiperazin-1-yl)-2-oxoethyl)-6H-thieno[3,2-f][1,2,4]triazolo[4,3-a][1,4]diazepin-2-yl)ethynyl)-1H-pyrazol-1-yl)ethoxy)ethoxy)ethoxy)prop-1-yn-1-yl)-1-oxoisoindolin-2-yl)piperidine-2,6-dione;

(2S,4R)-1-((S)-2-(tert-butyl)-17-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)-4-oxo-6,9,12,15-tetraoxa-3-azaheptadecanoyl)-4-hydroxy-N—((S)-1-(4-(4-methylthiazol-5-yl)phenyl)ethyl)pyrrolidine-2-carboxamide;

(2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(tert-butyl)-14-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide;

(2S,4R)-1-((S)-2-(2-(2-(2-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(S)-4-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-N—((S)-1-(4-(4-methylthiazol-5-yl)phenyl)ethyl)morpholine-3-carboxamide;

(2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-fluoro-N—((S)-1-(4-(4-methylthiazol-5-yl)phenyl)ethyl)pyrrolidine-2-carboxamide;

(2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-N—((S)-1-(4-(4-methylthiazol-5-yl)phenyl)ethyl)pyrrolidine-4-d-2-carboxamide; and (2S,4R)-1-((S)-2-(2-(3-(4-(((S)-4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propoxy)acetamido)-3,3-dimethylbutanoyl)-4-hydroxy-4-methyl-N—((S)-1-(4-(4-methylthiazol-5-yl)phenyl)ethyl)pyrrolidine-2-carboxamide.

14. A pharmaceutical composition comprising the compound of claim 1, or a pharmaceutically acceptable salt or hydrate thereof, and a pharmaceutically acceptable carrier.

15. A method of treating a patient, the method comprising administering to the patient a therapeutically effective amount of the compound of claim 1, or a pharmaceutically acceptable salt, hydrate, or solvate thereof, wherein the patient has cancer, a chronic autoimmune disorder, an inflammatory condition, a proliferative disorder, sepsis, or a viral infection.

16. The method claim 15, wherein the patient has cancer.

17. A kit comprising the compound of claim 1, or a pharmaceutically acceptable salt, hydrate, or solvate thereof, and instructions for administering the compound, or a pharmaceutically acceptable salt, hydrate, or solvate thereof, to a patient having cancer, a chronic autoimmune disorder, an inflammatory condition, a proliferative disorder, sepsis, or a viral infection.

18. The method of claim 16, wherein cells of the patient contain a biomarker, wherein the biomarker is co-overexpression of MCL-1 and BCL-$X_L$.

19. A method of reducing BET bromodomain protein within a cell of a patient in need thereof, the method comprising administering to the patient a compound of claim 1, or a pharmaceutically acceptable salt, hydrate, or solvate thereof.

* * * * *

UNITED STATES PATENT AND TRADEMARK OFFICE
CERTIFICATE OF CORRECTION

PATENT NO. : 10,975,093 B2
APPLICATION NO. : 16/332544
DATED : April 13, 2021
INVENTOR(S) : Shaomeng Wang et al.

Page 1 of 1

It is certified that error appears in the above-identified patent and that said Letters Patent is hereby corrected as shown below:

In the Claims

At Column 302, Line 27, "$(CH_2)_m$—," should be -- $(CH_2)_v$—, --.

At Column 302, Line 28, "—O]" should be -- —O]$_x$ --.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*